(12) United States Patent
Milanov et al.

(10) Patent No.: US 7,750,160 B2
(45) Date of Patent: Jul. 6, 2010

(54) ISOXAZOLYL UREA DERIVATIVES AS KINASE MODULATORS

(75) Inventors: Zdravko V. Milanov, San Diego, CA (US); Hitesh K. Patel, Encinitas, CA (US); Robert M. Grotzfeld, Carlsbad, CA (US); Shamal A. Mehta, San Diego, CA (US); Andiliy G. Lai, San Diego, CA (US); David J. Lockhart, Del Mar, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 1223 days.

(21) Appl. No.: 10/989,824

(22) Filed: Nov. 15, 2004

(65) Prior Publication Data

US 2005/0165024 A1   Jul. 28, 2005

Related U.S. Application Data

(60) Provisional application No. 60/520,273, filed on Nov. 13, 2003, provisional application No. 60/527,094, filed on Dec. 3, 2003, provisional application No. 60/531,243, filed on Dec. 18, 2003, provisional application No. 60/531,082, filed on Dec. 18, 2003.

(51) Int. Cl.
| | |
|---|---|
| C07D 221/04 | (2006.01) |
| C07D 471/04 | (2006.01) |
| C07D 413/12 | (2006.01) |
| C07D 261/14 | (2006.01) |
| C07D 277/20 | (2006.01) |
| C07D 277/32 | (2006.01) |
| C07D 513/14 | (2006.01) |
| A61K 31/47 | (2006.01) |
| A61K 31/4375 | (2006.01) |
| A61K 31/422 | (2006.01) |
| A61K 31/4353 | (2006.01) |
| A61K 31/426 | (2006.01) |
| A61K 31/4402 | (2006.01) |
| A61K 31/4412 | (2006.01) |
| A61K 31/443 | (2006.01) |
| A61K 31/429 | (2006.01) |

(52) U.S. Cl. .................. 546/112; 546/123; 546/94; 546/272.1; 548/204; 548/151; 548/246; 514/299; 514/300; 514/378; 514/294; 514/365; 514/340; 514/366

(58) Field of Classification Search .................. 544/112; 546/123, 94, 272.1; 548/204, 151; 514/299, 514/300, 294, 365, 340, 366
See application file for complete search history.

(56) References Cited

U.S. PATENT DOCUMENTS

| | | | |
|---|---|---|---|
| 3,991,071 A | 11/1976 | Brookes et al. | |
| 4,062,861 A * | 12/1977 | Yukinaga et al. | ............ 548/246 |
| 5,773,459 A | 6/1998 | Tang et al. | |
| 6,605,617 B2 | 8/2003 | Renhowe et al. | |
| 6,645,990 B2 | 11/2003 | Askew et al. | |
| 7,238,813 B2 * | 7/2007 | Cheung et al. | ........... 548/307.4 |
| 2001/0002195 A1 | 5/2001 | Cruz | |
| 2003/0028018 A1 | 2/2003 | Renhowe et al. | |
| 2003/0158224 A1 | 8/2003 | Renhowe et al. | |
| 2003/0207883 A1 | 11/2003 | Renhowe et al. | |
| 2005/0002413 A1 | 1/2005 | Lauther | |
| 2005/0004142 A1 * | 1/2005 | Adams et al. | ............ 514/260.1 |

FOREIGN PATENT DOCUMENTS

| | | | |
|---|---|---|---|
| EP | 1 185 044 A2 | | 3/2002 |
| FR | 2 245 645 | | 4/1975 |
| JP | 53-101372 | | 4/1978 |
| JP | 53 086033 | | 7/1978 |
| WO | WO 99/32106 | | 7/1999 |
| WO | WO 99/32111 | | 7/1999 |
| WO | WO 99/32455 | | 7/1999 |
| WO | WO 99/32463 | | 7/1999 |
| WO | WO 9932106 | * | 7/1999 |
| WO | WO 9932111 | * | 7/1999 |
| WO | WO 00/43384 | | 7/2000 |
| WO | WO 01/57008 | | 8/2001 |
| WO | WO 02/062763 | | 8/2002 |
| WO | WO 02/100023 A2 | | 12/2002 |
| WO | WO 03/013517 | | 2/2003 |
| WO | WO 03/013540 A1 | | 2/2003 |
| WO | WO 03/014064 | | 2/2003 |
| WO | WO 03/031438 A1 | | 4/2003 |
| WO | WO 03/031608 A2 | | 4/2003 |
| WO | WO 03/037347 | | 5/2003 |
| WO | WO 03/039082 A1 | | 5/2003 |

(Continued)

OTHER PUBLICATIONS

Vivona et. al. (J. Chem. Soc. Perk. Trans., 1977, 14, 1616-1619).*

(Continued)

*Primary Examiner*—James O Wilson
*Assistant Examiner*—Susanna Moore
(74) *Attorney, Agent, or Firm*—Jones Day

(57) ABSTRACT

The invention provides methods and compositions for treating conditions mediated by various kinases wherein derivatives of urea compounds are employed. The invention also provides methods of using the compounds and/or compositions in the treatment of a variety of diseases and unwanted conditions in subjects.

31 Claims, No Drawings

FOREIGN PATENT DOCUMENTS

| | | |
|---|---|---|
| WO | WO 03/077892 A2 | 9/2003 |
| WO | WO 03/093250 | 11/2003 |
| WO | WO 03/099771 A2 | 12/2003 |

OTHER PUBLICATIONS

STN printout, downloaded Jan. 4, 2008, pp. 1-244.*
STN Columbus Search Report dated Nov. 4, 2005.
Lowinger, et al., Current Pharm. Design, (2002), vol. 8, pp. 2269-2278.
Smith et al., Bioorg Med. Chem Lett. (2001), vol. 11, pp. 2775-2778.
Dumas, et al., "1-Phenyl-5-pyrazolyl ureas: potent and selective p38 kinase inhibitors,"*Bioorganic & Medicinal Chemistry Letters*, 10 (18), 2051-2054, (2000).
Dumas, et al.. "Discovery of a new class of p38 kinase inhibitors," *Bioorganic & Medicinal Chemistry Letters*, 10 (18), 247-2050, (2000).
Khire, et al., "Omega-carboxypyridyl substituted ureas as Raf kinase inhibitors: SAR of the amide substituent," *Bioorganic & Medicinal Chemistry Letters*, 14 (3), 783-786 (2004).
Tiiaimattam, et al., "3D-QSAR CoMFA, CoMSIA studies on substituted ureas as Raf-1 kinase inhibitors and its confirmation with structure-based studies," *Bioorganic & Medicinal Chemistry*, 12 (24), 6415-6425, (2004).
European Search Report under Article 153(7) EPC dated May 18, 2009, for European Patent Application No. 04811122.3-1211/1684762.
Ravinda K. Ahuja, Thomas L. Magnanti, James B. Orlin: "Network Flows", Theory, Algorithms and Applictions, 1993, pp. v-x, pp. 43-46, pp. 176-180, pp. 308-315, Prentice Hall, Englewood Cliffs, New Jersey. /S.M./ I/ Susanna Moore /I.
Peng, Bin, et al., "Pharmacokinetics and pharmacodynamics of imatinib in a Phase I trial with chronic myeloid leukemia patients", *Journal of Clinical Oncology* (2004), vol. 22, No. 5, pp. 935-942.
Salomon, Arthur R, et al., "Profiling of tyrosine phosphorylation pathways in human cells using mass spectrometry", *Proc. Natl. Acad. Sci.* (2003), vol. 100, No. 2, pp. 443-448.
Le Coutre, Philipp et al., "In vivo eradication of human BCR/ABL-positive leukemia cells with an ABL kinase inhibitor", *Journal of the National Cancer Institute* (1999), vol. 91, No. 2, pp. 163-168.
Carroll, Martin et al., "CGP 57148, a tyrosine kinase inhibitor, inhibits the growth of cells expressing BCR-ABL, TEL_ABL, and TEL-PDGFR fusion proteins", *Blood* (1997), vol. 90, No. 12, pp. 4947-4952.
Zimmermann, Jürg, et al., "Potent and Selective inhibitors of the ABL-Kinase: phenylamino-pyrimidine (PAP) derivatives", *Bioorganic and Medicinal Chemistry Letters* (1997), vol. 7, No. 2, pp. 187-192.
Arvanitis, Elena A. et al., "Solid-phase synthesis of 2,4-diaminopyrimidines via Lewis acid-mediated aromatic nucleophilic substitution", *Journal of Combinatorial Chemistry*, Feb. 16, 2004.
Zimmermann, Jürg, et al, "Phenylamino-pyrimidine (PAP)-derivatives: a new class of potent and highly selective PDGF-receptor autophosphorylation inhibitors", *Bioorganic and Medicinal Chemistry Letters* (1996), vol. 6, No. 11, pp. 1221-1226.
Heinrich, Michael C., et al., "Inhibition of c-kit receptor tyrosine kinase activity by STI571, a selective tyrosine kinase inhibitor", *Blood* (2000), vol. 96, No. 3, pp. 925-932.
Buchdunger, Elisabeth, et al, "Abl protein-tyrosine kinase inhibitor STI571 inhibits in vitro signal transduction mediated by c-kit and platelet-derived growth factor receptors", *Journal of Pharmacology and Experimental Therapeutics* (2000), vol. 295, No. 1, pp. 139-145.
Sjöblom, Tobias, et al., "Growth inhibition of dermatofibrosarcoma protuberans tumors by the platelet-derived growth factor receptor antagonist STI571 through induction of apoptosis", *Cancer Research* (2001), vol. 61, pp. 5778-5783.
Tuvenson, David, et al., "STI571 inactivation of the gastrointestinal stromal tumor c-kit oncoprotein: biological and clinical implications", *Oncogene* (2001), vol. 20, pp. 5054-5058.

Mol, Clifford et al., "Structural basis for the autoinhibition and STI571 inhibition of c-kit tyrosine kinase", JBC Papers in Press, Published Apr. 29, 2004 as Manuscript No. M403319200.
Gazit, Aviv et al., "Tricyclic Quinoxalines as potent kinase inhibitors of PDGFR kinase, flt3 and kit", *Bioorganic and Medicinal Chemistry* (2003), vol. 11, pp. 2007-2018.
Gianni, Maurizio, et al., "Tyrosine kinase inhibitor STI571 potentiates the pharmacologic activity of retinoic acid in acute promyelocytic leukemia cells: effects on the degradation of RARα and PML-RARα", *Blood* (2001), vol. 97, No. 10, pp. 3234-3243.
Wisniewski, David et al., "Characterization of Potent inhibitors of the Bcr-abl and the c-kit receptor tyrosine kinase", *Cancer Research* (2002), vol. 62, pp. 4244-4255.
Nagar, Bhushan et al., "Crystal structures of the kinase domain of c-abl in complex with the small molecule inhibitors PD173955 and Imatinib (STI-571)", *Cancer Research* (2002), vol. 62, pp. 4236-4243.
Manley, P.W. et al., "Imatinib: a selective tyrosine kinase inhibitor", *European Journal of Cancer* (2002), vol. 38, Suppl. 5, pp. 519-527.
Böhmer, Frank D. et al., "A single amino acid exchange inverts susceptibility of related Receptor tyrosine kinases for the ATP site inhibitor STI-571", *Journal of Biological Chemistry* (2003), vol. 278, No. 7, pp. 5148-5155.
Hantschel, Oliver et al., "A myristoyl/phosphotyrosine switch regulates c-abl", *Cell* (2003), vol. 112, pp. 845-857.
Nagar, Bhushan, et al., "Structural basis for the autoinhibition of c-ABL tyrosine kinase", *Cell* (2003), vol. 112, pp. 859-871.
Azam, Mohammad et al., "Mechanisms of autoinhibition and STI-571/Imatinib resistance revealed by mutagenesis of BCR-ABL", *Cell* (2003), vol. 112, pp. 831-843.
Capdeville, Renaud et al., "Glivec (STI571, Imatinib), a rationally developed, targeted anticancer drug", *Nature Reviews* (2002), vol. 1, pp. 493-502.
Buchdunger, Elisabeth et al., "4,5-dianilinophthalimide: a protein-tyrosine kinase inhibitor with selectivity for the epidermal growth factor receptor signal transduction pathway and potent in vivo antitumor activity", *Proc. Natl. Acad. Sci.* (1994), vol. 91, pp. 2334-2338.
Kantarjian, Hagop et al., "High-dose imatinib mesylate therapy in newly diagnosed Philadelphia chromosome-positive chronic phase chronic myeloid leukemia", *Blood* (2004), vol. 103, No. 8, pp. 2873-2878.
Schindler, Thomas et al., "Structural Mechanism for STI-571 inhibition of Abelson tyrosine kinase", *Science* (2000), vol. 289, pp. 1938-1942.
Buchdunger, Elisabeth et al., "Selective inhibition of the platelet-derived growth factor signal transduction pathway by a protein-tyrosine kinase inhibitor of the 2- phenylaminopyrimidine class", *Proc Natl. Acad. Sci.* (1995), vol. 92, pp. 2558-2562.
Traxler, Peter et al., "Strategies toward the design of novel and selective protein tyrosine kinase inhibitors", *Pharmacol. Ther.* (1999), vol. 82, pp. 195-206.
Shah, Neil P. et al., "Overriding Imatinib resistance with a novel ABL Kinase inhibitor", *Science* (2004), vol. 305, pp. 399-401.
Sausville, Edward, "Is Another Bcr-abl inhibitor needed for Chronic Myelogenous Leukemia?", *Clinical Cancer Research* (2003), vol. 9, pp. 1233-1234.
Huron, David R. et al., "A novel pyridopyrimidine Inhibitor of Abl Kinase is a picomolar inhibitor of Bcr-abl-driven K562 cells and is effective against STI571-resistant Bcr-abl mutants", *Clinical Cancer Research* (2003), vol. 9, pp. 1267-1273.
Warmuth, Markus et al., "Dual-specific Src and Abl kinase inhibitors, PP1 and CGP76030, inhibit growth and survival of cells expressing imatinib mesylate-resistant Bcr-abl kinases", *Blood* (2003), vol. 101, No. 2, pp. 664-672.
Von Bubnoff, Nikolas et al., "Inhibition of wild-type and Mutant Bcr-abl by pyrido-pyrimidine-type small molecule kinase inhibitors", *Cancer Research* (2003), vol. 63, pp. 6395-6404.
Dorsey, Jay F. et al., "The pyrido[2,3-*d*]pyrimidine derivative PD 180970 Inhibits p210$^{Bcr-Abl}$ Tyrosine Kinase and induces apoptosis of K562 leukemic cells", *Cancer Research* (2000), vol. 60, pp. 3127-3131.
La Rosee, Paul et al., "Activity of the Bcr-abl kinase inhibitor PD180970 against clinically relevant Bcr-abl isoforms that cause resistance to Imatinib Mesylate (Gleevec, STI571)", *Cancer Research* (2002), vol. 62, pp. 7149-7153.

Tipping, A.J. et al., "Efficacy of dual-specific Bcr-abl and Src-family kinase inhibitors in cells sensitive and resistant to imatinib mesylate", *Leukemia* (2004), vol. 18, pp. 1352-1356.

Gorre, Mercedes E. et al., "Clinical Resistance to STI-571 Cancer Therapy Caused by Bcr-Abl Gene Mutation or Amplification", *Science* (2001), vol. 293, pp. 876-880.

Shah, Neil P. et al., "Multiple BCR-ABL kinase domain mutations confer polyclonal resistance to the tyrosine kinase inhibitor imatinib (STI571) in chronic phase and blast crisis chronic myeloid leukemia", *Cancer Cell* (2002), vol. 2, pp. 117-125.

CAS Search Report dated Aug. 18, 2004.

CAS Search Report dated Aug. 25, 2004.

CAS Search Report dated May 18, 2004.

CAS Search Report dated Sep. 27, 2004.

Kindler, T et al., "BCR-ABL as a target for novel therapeutic interventions", *Expert Opin. Ther. Targets* (2002), vol. 6, No. 1, pp. 85-101.

Deininger, Michael W. N. et al., "Specific targeted therapy of chronic myelogenous leukemia with Imatinib", *Pharmacological Reviews* (2003), vol. 55, No. 3, pp. 401-423.

Druker, Brian J. et al., "Chronic Myelogenous Leukemia", *Hematology* (2001), pp. 87-112.

Druker, Brian J. et al., "Chronic Myelogenous Leukemia", *Hematology* (2002), pp. 111-135.

Druker, Brian J. et al., "Activity of specific inhibitor of the Bcr-abl tyrosine kinase in the Blast Crisis of Chronic Myeloid Leukemia and Acute Lymphoblastic Leukemia with the Philadelphia chromosome", *New England Journal of Medicine* (2001), vol. 344, No. 14, pp. 1038-1042.

Goldman, John M. et al., "Chronic Myeloid Leukemia — Advances in Biology and New Approaches to Treatment", *New England Journal of Medicine* (2003), vol. 349, pp. 1451-1464.

Weisberg, Ellen et al., "Mechanism of resistance imatinib (STI571) in preclinical models and in leukemia pateints", *Drug Resistance Updates* (2001), vol. 4, pp. 22-28.

\* cited by examiner

ISOXAZOLYL UREA DERIVATIVES AS KINASE MODULATORS

This application claims priority to U.S. Provisional Application No. 60/520,273, filed Nov. 13, 2003, U.S. Provisional Application No. 60/527,094, filed Dec. 3, 2003, U.S. Provisional Application No. 60/531,243, filed Dec. 18, 2003, and U.S. Provisional Application No. 60/531,082, filed Dec. 18, 2003, the contents of which are incorporated herein by reference in their entirety.

BACKGROUND

Protein kinases (PKs) play a role in signal transduction pathways regulating a number of cellular functions, such as cell growth, differentiation, and cell death. PKs are enzymes that catalyze the phosphorylation of hydroxy groups on tyrosine, serine and threonine residues of proteins, and can be conveniently broken down into two classes, the protein tyrosine kinases (PTKs) and the serine-threonine kinases (STKs). Growth factor receptors with PTK activity are known as receptor tyrosine kinases. Protein receptor tyrosine kinases are a family of tightly regulated enzymes, and the aberrant activation of various members of the family is one of the hallmarks of cancer. The protein-tyrosine kinase family, which includes Bcr-Abl tyrosine kinase, can be divided into subgroups that have similar structural organization and sequence similarity within the kinase domain. The members of the type III group of receptor tyrosine kinases include the platelet-derived growth factor (PDGF) receptors (PDGF receptors α and β), colony-stimulating factor (CSF-1) receptor (CSF-1R, c-Fms), FLT-3, and stem cell or steel factor receptor (c-kit). A more complete listing of the known Protein receptor tyrosine kinases subfamilies is described in Plowman et al., DN&P, 7(6):334-339 (1994), which is incorporated by reference, including any drawings, as if fully set forth herein. Furthermore, for a more detailed discussion of "non-receptor tyrosine kinases", see Bolen, Oncogene, 8:2025-2031 (1993), which is incorporated by reference, including any drawings, as if fully set forth herein.

Hematologic cancers, also known as hematologic or hematopoietic malignancies, are cancers of the blood or bone marrow; including leukemia and lymphoma. Acute myelogenous leukemia (AML) is a clonal hematopoietic stem cell leukemia that represents ~90% of all acute leukemias in adults. See e.g., Lowenberg et al., *N. Eng. J. Med.* 341:1051-62 (1999). While chemotherapy can result in complete remissions, the long term disease-free survival rate for AML is about 14% with about 7,400 deaths from AML each year in the United States. The single most commonly mutated gene in AML is FLT3 kinase. See e.g., Abu-Duhier et al., *Br. J. Haemotol.* 111:190-05 (2000); Kiyoi et al., *Blood* 93:3074-80 (1999); Kottaridis et al., *Blood* 98:1752-59 (2001); Stirewalt et al., *Blood* 97:3589-95 (2001). Such mutations also indicate a poor prognosis for the patient.

The compounds provided by the present invention are urea derivatives of substituted aryls and hetroaryls, e.g., isoxazoles, pyrazoles and isothiazoles. Urea derivatives of pyrazoles have been reported to be selective p38 kinase inhibitors by Dumas, J., et al., *Bioorg. Medic. Chem. Lett.* 10:2051-2054 (2000). Oxazoles and isopyrazoles are suggested as blockers of cytokine production in WO 00/43384 published 27 Jul. 2000. Urea derivatives of isoxazole and pyrazoles are described as inhibitors of RAF kinase in WO 99/32106 published 1 Jul. 1999. Such compounds are also described as p38 kinase inhibitors by Dumas, J., et al., *Bioorg. Medic. Chem. Lett.* 10:2047-2050 (2000). These compounds are also suggested as p38 kinase inhibitors in PCT publication WO 99/32111 published 1 Jul. 1999.

There remains a need for additional compounds that are effective in inhibiting kinase activity. Given the complexities of signal transduction with the redundancy and crosstalk between various pathways, the identification of specific kinase inhibitors permits accurate targeting with limited inhibition of other pathways, thus reducing the toxicity of such inhibitory compounds.

SUMMARY OF THE INVENTION

The present invention provides compounds which modulate kinase activity, and in some embodiments inhibit protein tyrosine kinases or a specific kinase or kinase class. In some embodiments, the compositions and methods for treating and preventing conditions and diseases, such as cancer, hematologic malignancies, cardiovascular disease, inflammation or multiple sclerosis. The compounds of the invention can be delivered alone or in combination with additional agents, and are used for the treatment and/or prevention of conditions and diseases. As used throughout the specification, unless otherwise stated, each of the substituents is as previously defined.

Provided herein are compositions and methods for treating a disease comprising administering to a subject in need thereof an effective amount of a kinase modulating compound having the structure:

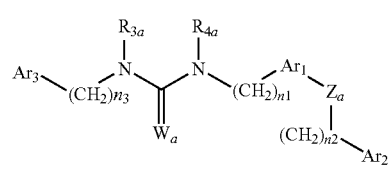

Formula A wherein:

(a) $R_{3a}$ and $R_{4a}$ are each a suitable substituent independently selected from hydrogen, or an alkyl, alkenyl, heteroalkyl, haloalkyl, alkynyl, aryl, cycloalkyl, heterocycloalkyl, heteroaryl group unsubstituted or substituted with one or more suitable substituents independently selected from the group consisting of: halogens; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer, preferably from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more suitable substituents independently selected from the group consisting of halogens, =O, —NO$_2$, —CN, —(CH$_2$)$_z$—CN where z is a whole integer, preferably from 0 to 4, —OR$_c$, —NR$_c$OR$_c$, —NR$_c$R$_c$, —C(O)NR$_c$R$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group, where each $R_c$ is independently selected from hydrogen, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more $R_c$ groups together cyclize to form part of a heteroaryl or heterocycloalkyl group unsubstituted or substituted with an unsubstituted alkyl group;

or where $R_{3a}$ and $R_{4a}$ together cyclize to form part of a heteroaryl or heterocycloalkyl group unsubstituted or substituted with one or more suitable substituents selected from halogen, =O; =S; —CN; —NO$_2$, or an alkyl, alkenyl, heteroalkyl, haloalkyl, alkynyl, aryl, cycloalkyl, heterocycloalkyl, heteroaryl group unsubstituted or substituted with one or more suitable substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer, preferably from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —NHCS(O$_2$)H, —NHC(SO)H, —NHC(S)H, and —SH groups unsubstituted or substituted with one or more suitable substituents independently selected from the group consisting of halogens, =O, —NO$_2$, —CN, —(CH$_2$)$_z$—CN where z is a whole integer, preferably from 0 to 4, —OR$_c$, —NR$_c$R$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group, where each $R_c$ is independently selected from hydrogen, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more $R_c$ groups together cyclize to form part of a heteroaryl or heterocycloalkyl group unsubstituted or substituted with an unsubstituted alkyl group;

(b) Ar$_1$, Ar$_2$ and Ar$_3$ are each independently an aryl, heteroaryl, cycloalkyl or heterocycloalkyl group unsubstituted or substituted with one or more suitable substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer, preferably from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —NHCS(O$_2$)H, —NHC(SO)H, —NHC(S)H, and —SH groups unsubstituted or substituted with one or more suitable substituents independently selected from the group consisting of halogens, =O, —NO$_2$, —CN, —(CH$_2$)$_z$—CN where z is a whole integer, preferably from 0 to 4, —OR$_c$, —NR$_c$OR$_c$, —NR$_c$R$_c$, —C(O)NR$_c$, —C(O)R$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group, where each $R_c$ is independently selected from hydrogen, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more $R_c$ groups together cyclize to form part of a heteroaryl or heterocycloalkyl group unsubstituted or substituted with an unsubstituted alkyl group;

(c) $n_1$ is 0, 1, 2, 3 or 4;

(d) $n_2$ is 0, 1, 2, 3 or 4;

(e) $n_3$ is 0, 1, 2, 3 or 4;

(f) $Z_a$ is a bond or is selected from S, O, N, NR$_c$, C(O)NR$_c$, NR$_c$C(O), and CR$_c$, wherein $R_c$ is a suitable substituent selected from hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl group; and (g) $W_a$ is S or O;

or a pharmaceutically acceptable salt, pharmaceutically acceptable N-oxide, pharmaceutically active metabolite, pharmaceutically acceptable prodrug, isomer derivative, or pharmaceutically acceptable solvate thereof.

Provided herein are compositions and methods for treating a disease comprising administering to a subject in need thereof an effective amount of a kinase modulating compound having the structure:

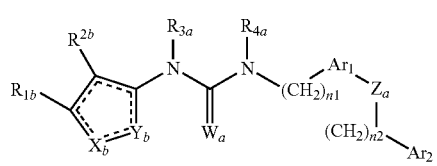

Formula B wherein:

(a) $X_b$ and $Y_b$ are independently selected from O, N, NR$_{c1}$, and CR$_c$, wherein $R_{c1}$ is a suitable substituent selected from hydrogen; alkyl, alkenyl, alkynyl, aryl, cycloalkyl, heterocycloalkyl, or heteroaryl unsubstituted or substituted with one, two, or three suitable substituents, wherein $X_b$ and $Y_b$ are not both oxygen;

(b) $R_{1b}$ and $R_{2b}$ are each a suitable substituent independently selected from hydrogen, halogen, =O; =S; —CN; —NO$_2$, or an alkyl, alkenyl, heteroalkyl, haloalkyl, alkynyl, aryl, cycloalkyl, heterocycloalkyl, heteroaryl group unsubstituted or substituted with one, two or three suitable substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one, two or three suitable substituents independently selected from the group consisting of halogens, =O, —NO$_2$, —CN, —(CH$_2$)$_z$—CN where z is a whole integer from 0 to 4, —NR$_c$, —NR$_c$R$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group, where each R$_c$ is independently selected from hydrogen, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more R$_c$ groups together cyclize to form part of a heteroaryl or heterocycloalkyl group unsubstituted or substituted with an unsubstituted alkyl group, or a pharmaceutically acceptable salt, pharmaceutically acceptable N-oxide, pharmaceutically active metabolite, pharmaceutically acceptable prodrug, or pharmaceutically acceptable solvate thereof.

Provided herein are compositions and methods for treating a disease by administering an effective amount of kinase modulating compound having the structure:

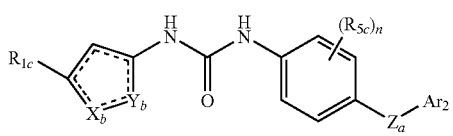

Formula C wherein:

(a) R$_{1c}$ is unsubstituted C$_1$-C$_5$ alkyl or unsubstituted C$_3$-C$_6$ cycloalkyl;

(b) n is 0, 1 or 2; and (c) Each R$_{5c}$ is a suitable substituent independently selected from the group consisting of halogens; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one, two or three suitable substituents independently selected from the group consisting of halogens, O, —NO$_2$, —CN, —(CH$_2$)$_z$—CN where z 0, 1, 2, 3, or 4, —OR$_c$, —NR$_c$R$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group, where each R$_c$ is independently selected from hydrogen, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more R$_c$ groups together cyclize to form part of a heteroaryl or heterocycloalkyl group unsubstituted or substituted with an unsubstituted alkyl group.

Provided herein are compositions and methods for treating a disease by administering an effective amount of kinase modulating compound having the structure:

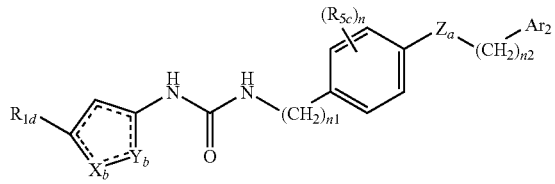

Formula D wherein:

(a) R$_{1d}$ is unsubstituted C$_1$-C$_5$ alkyl or unsubstituted C$_3$-C$_5$ cycloalkyl;

(b) n is 0, 1 or 2;

(c) n$_1$ is 0, 1 or 2; and wherein n$_2$ is 0, 1 or 2; wherein n$_1$ and n$_2$ are not both 0.

Provided herein are compositions and methods for treating a disease by administering an effective amount of a kinase modulating compound having the structure:

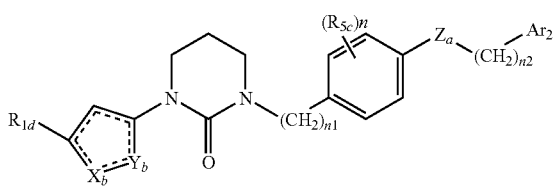

Formula E wherein:

(a) n is 0, 1 or 2;

Provided herein are compositions and methods for treating a disease by administering an effective amount of a kinase modulating compound having the structure:

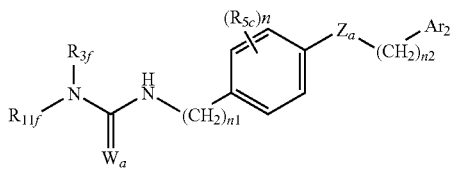

Formula F wherein:

(a) $R_{3f}$ and $R_{11f}$ cyclize to form a heteroaryl or heterocycloalkyl group substituted or unsubstituted with one, two or three suitable substituents selected from the group consisting of halogen, =O; =S; —CN; —NO$_2$, or an alkyl, alkenyl, heteroalkyl, haloalkyl, alkynyl, aryl, cycloalkyl, heterocycloalkyl, heteroaryl group unsubstituted or substituted with one, two or three suitable substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one, two or three suitable substituents independently selected from the group consisting of halogens, =O, —NO$_2$, —CN, —(CH$_2$)$_z$—CN where z is a whole integer from 0 to 4, —NR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group, where each R$_c$ is independently selected from hydrogen, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more R$_c$ groups together cyclize to form part of a heteroaryl or heterocycloalkyl group unsubstituted or substituted with an unsubstituted alkyl group.

Provided herein are compositions and methods for treating a disease comprising administering to a subject in need thereof an effective amount of a kinase modulating compound having the following structure:

Formula G wherein:

(a) $R_{2g}$, $R_{3g}$ and $R_{4g}$ are each independently selected from hydrogen, unsubstituted alkyl, unsubstituted aryl, and unsubstituted heteroaryl;

(b) n is 0, 1 or 2;

(c) $n_1$ is 0, 1 or 2;

(d) $n_2$ is 0, 1 or 2;

(e) Ar$_2$ is:

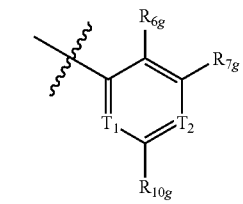

wherein:

$R_{6g}$ and $R_{7g}$ cyclize to form a 5- or 6-membered aryl, heteroaryl, heterocycloalkyl or cycloalkyl group unsubstituted or substituted with one, two or three suitable substituents independently selected from the group consisting of: halogens; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one, two or three suitable substituents independently selected from the group consisting of halogens, =O, —NO$_2$, —CN, —(CH$_2$)$_z$—CN where z is a whole integer from 0 to 4, —OR$_c$, —NR$_c$R$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group, where each is independently selected from hydrogen, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more $R_c$ groups together cyclize to form part of a heteroaryl or heterocycloalkyl group unsubstituted or substituted with an unsubstituted alkyl group;

(ii) $R_{10g}$ is a suitable substituent selected from hydrogen; halogens; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$), —NHC(SO)H, —NHC(S)H, and —SH groups unsubstituted or substituted with one, two or three suitable substituents independently selected from the group consisting of halogens, =O, —NO$_2$, —CN, —(CH$_2$)$_z$—CN where z is a whole integer from 0 to 4, —OR$_c$, —C(O)NR$_c$, —C(O)OR$_c$, —C(O)NR$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group, where each $R_c$ is independently selected from hydrogen, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more $R_c$ groups together cyclize to form part of a heteroaryl or heterocycloalkyl group unsubstituted or substituted with an unsubstituted alkyl group; and (iii) $T_1$ and $T_2$ are each independently selected from $CR_w$ and N, where $R_w$ is a suitable substituent selected from hydrogen; halogens; —CN; and —NO$_2$; and unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group;

or a pharmaceutically acceptable salt, pharmaceutically acceptable N-oxide, pharmaceutically active metabolite, pharmaceutically acceptable prodrug, or pharmaceutically acceptable solvate thereof.

Compositions and methods of Formulas A-G are provided wherein $X_b$ is O and $Y_b$ is N and/or $X_b$ is N and $Y_b$ is O; and/or $R_{2a}$, $R_{2g}$, $R_{3a}$, $R_{3g}$, $R_{4a}$ and $R_{4g}$ are each hydrogen; and/or $R_{1b}$, $R_{1c}$, and $R_{1d}$ are each an unsubstituted or substituted t-butyl and $R_{2b}$ and $R_{2g}$ are hydrogen; and/or $W_a$ is O; and/or $Z_a$ is C(O)NH or NHC(O); and/or n is 0. In various embodiments, $T_1$ is N and $T_2$ is N or $T_1$ is N and $T_2$ is CH. In other embodiments, Ar$_2$ is:

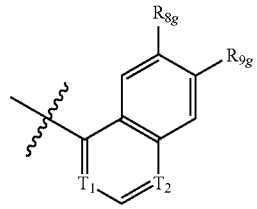

wherein:

(i) $R_{8g}$ and $R_{9g}$ are suitable substituents each independently selected from the group consisting of hydrogen; halogens; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one, two or three suitable substituents independently selected from the group consisting of halogens, =O, —NO$_2$, —CN, —(CH$_2$)$_z$—CN where z is a whole integer from 0 to 4, —OR$_c$, —NR$_c$R$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group, where each $R_c$ is independently selected from hydrogen, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more & groups together cyclize to form part of a heteroaryl or heterocycloalkyl group unsubstituted or substituted with an unsubstituted alkyl group; and (ii) $T_1$ is N and $T_2$ is CH or N.

Compositions and methods of Formulas A-G are provided herein wherein $R_{8g}$ and $R_{9g}$ are each independently selected from the group consisting of hydrogen; halogens; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, —OH, —C(O)H, —OC(O)H, —C(O)OH, —NH$_2$, —C(O)NH$_2$, —NHC(O), —OC(O)NH$_2$, —NHC(O)H, —NHC(O)OH groups unsubstituted or substituted with one, two or three suitable substituents independently selected from the group consisting of halogens, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group.

Compositions and methods of Formulas A-G are provided herein wherein each $R_{5C}$ is a suitable substituent independently selected from the group consisting of halogens; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, —OH, —C(O)H, —OC(O)H, —C(O)OH, —NH$_2$, —C(O)NH$_2$, —NHC(O), —OC(O)NH$_2$, —NHC(O)H, —NHC(O)OH groups unsubstituted or substituted with one, two or three suitable substituents independently selected from the group consisting of halogens, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, or two or more substituents cyclize to form a fused or spiro polycyclic cycloalkyl, heterocycloalkyl, aryl, or heteroaryl group.

Compositions and methods of Formula A are provided herein wherein Ar$_3$ is a 5-membered aryl, heteroaryl, heterocycloalkyl or cycloalkyl group unsubstituted or substituted with one, two or three suitable substituents. In some embodiments, Ar$_3$ is a 5- or 6-membered aryl or heteroaryl group unsubstituted or substituted with one, two or three suitable substituents.

Compositions and methods of Formula A-G are provided herein wherein n$_3$ is 0 or 1, and/or wherein n$_1$ is 0, 1 or 2, and/or n$_2$ is 0, 1 or 2. In some embodiments, R$_{3a}$/R$_{3g}$ and R$_{4a}$/R$_{4g}$ are each hydrogen. In other embodiments, R$_{3a}$/R$_{3g}$ and R$_{4a}$/R$_{4g}$ are not both substituted.

Compositions and methods of Formula A are provided herein wherein Ar$_3$ a substituted or unsubstituted 5-membered heteroaryl group and R$_2$ is hydrogen. In some embodiments, Ar$_1$ is an unsubstituted or substituted 6-membered aryl group or an unsubstituted or substituted 6-membered heteroaryl group. In other embodiments, W$_a$ is O.

Compositions and methods of Formulas A-G wherein Z$_a$ is not carbon are described herein. In some embodiments, Z$_a$ is selected from S, O, N, NR$_{c2}$, C(O)NR$_{c2}$, and NR$_{c2}$C(O), wherein R$_{c2}$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl group. In other embodiments, Z$_a$ is C(O)NH, NHC(O), or NH.

Compositions and methods of Formulas A-G wherein W$_a$ is S, O, or NH are described herein.

Compositions and methods of Formulas A-G are described herein wherein Ar$_1$ is an aryl or heteroaryl group unsubstituted or substituted with one, two or three suitable substituents independently selected from the group consisting of halogens; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, —OH, —C(O)H, —OC(O)H, —C(O)OH, —NH$_2$, —C(O)NH$_2$, —NHC(O), —OC(O)NH$_2$, —NHC(O)H, —NHC(O)OH groups unsubstituted or substituted with one, two or three suitable substituents independently selected from the group consisting of halogens, unsubstituted alkyl, unsubstituted alkenyl, unsubstituted alkynyl, unsubstituted aryl, unsubstituted cycloalkyl, unsubstituted heterocycloalkyl, and unsubstituted heteroaryl.

Compositions and methods of Formulas A-G are described herein wherein Ar$_2$ is an aryl, heteroaryl, heterocycloalkyl or cycloalkyl group unsubstituted or substituted with one, two or three suitable substituents independently selected from the group consisting of halogens; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is a whole integer from 0 to 4, —OH, —C(O)H, —OC(O)H, —C(O)OH, —NH$_2$, —C(O)NH$_2$, —NHC(O), —OC(O)NH$_2$, —NHC(O)H, —NHC(O)OH groups unsubstituted or substituted with one, two or three suitable substituents independently selected from the group consisting of halogens, unsubstituted alkyl, unsubstituted alkenyl, unsubstituted alkynyl, unsubstituted aryl, unsubstituted cycloalkyl, unsubstituted heterocycloalkyl, and unsubstituted heteroaryl. In some embodiments, Ar$_2$ is an unsubstituted or substituted pyridinyl. In other embodiments, Ar$_2$ is an unsubstituted or substituted quinazolinyl.

Compositions and methods of Formulas A-G are provided herein wherein X$_b$ and Y$_b$ are each independently selected from O, N, and NR$_{c1}$ wherein R$_{c1}$ is unsubstituted alkyl or unsubstituted aryl. In some embodiments, X$_b$ is N and Y$_b$ is NR$_{c1}$. In other embodiments, X$_b$ is O and Y$_b$ is N. In other embodiments, X$_b$ is O and Y$_b$ is N, or X$_b$ is N and Y$_b$ is O.

Compositions and methods of Formulas A-G are provided herein wherein R$_1$ is unsubstituted t-butyl or unsubstituted cyclopropyl.

Compositions and methods are provided herein wherein R$_{5c}$ is independently selected from the group consisting of halogens, —CN, —NO$_2$, unsubstituted alkyl, unsubstituted alkenyl, unsubstituted heteroalkyl, unsubstituted haloalkyl, unsubstituted alkynyl, unsubstituted aryl, unsubstituted cycloalkyl, unsubstituted heterocycloalkyl, and unsubstituted heteroaryl group.

Compositions and methods of Formulas A-G are provided herein wherein R$_{10g}$ is hydrogen or lower alkyl.

Provided herein are compositions and methods for treating a disease comprising administering to a subject in need thereof an effective amount of a kinase modulating compound having the following structure:

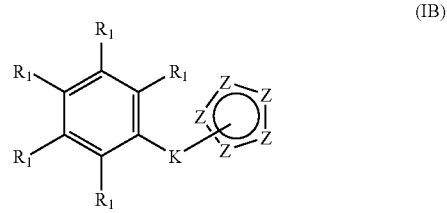

(IB)

wherein:
  each Z is independently C, CR$_3$, N, NR$_3$, O, or S, provided that no more than two Z's are heteroatoms and wherein no two adjacent Z's are O or S,
    where R$_3$ is H, substituted or unsubstituted alkyl, substituted or unsubstituted cycloalkyl, substituted or unsubstituted heteroaryl, or substituted or unsubstituted aryl; and
  each R$_1$ is independently H, halogen, substituted or unsubstituted alkyl, substituted or unsubstituted alkoxy, substituted or unsubstituted cycloalkyl, substituted or unsubstituted heterocyclyl, substituted or unsubstituted aryl, substituted or unsubstituted heteroaryl, —OR$_c$, —OC(O)R$_c$, —NO$_2$, —N(R$_c$)$_2$, S(O)$_j$R$_c$ where j is 1 or 2, —NR$_c$C(O)R$_c$, —C(O)N(R$_c$)$_2$, —C(O)$_2$R$_c$, or —C(O)R$_c$; or two adjacent R$_1$'s, are taken together to form a substituted or unsubstituted aryl or heteroaryl, where
    each R$_c$ is independently H, substituted or unsubstituted alkyl, substituted or unsubstituted cycloalkyl, substituted or unsubstituted aryl, or substituted or unsubstituted heteroaryl.

K is

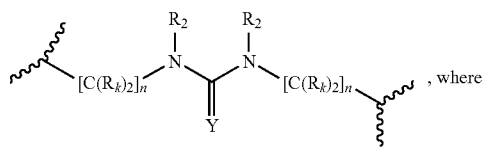, where

Y is O or S;

each $R_k$ is independently H, halogen, substituted or unsubstituted alkyl, —$OR_2$, substituted or unsubstituted alkoxy, —$OC(O)R_2$, —$NO_2$, —$N(R_2)_2$, —$SR_2$, —$C(O)R_2$, —$C(O)_2R_2$, —$C(O)N(R_2)_2$, or —$N(R_2)C(O)R_2$;

each $R_2$ is independently H, substituted or unsubstituted alkyl, substituted or unsubstituted cycloalkyl, substituted or unsubstituted heterocyclyl, substituted or unsubstituted aryl, or substituted or unsubstituted heteroaryl; or wherein two $R_2$ groups are linked together by an optionally substituted alkylene; and each n is independently 0, 1, 2, 3 or 4;

or an active metabolite, or a pharmaceutically acceptable prodrug, isomer, pharmaceutically acceptable salt or solvate thereof.

Provided herein are compositions and methods for treating a disease comprising administering to a subject in need thereof an effective amount of a kinase modulating compound having the following structure:

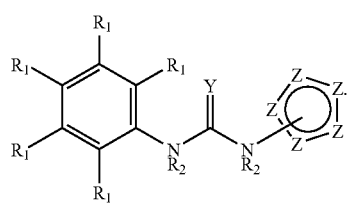

(I)

Provided herein are compositions and methods for treating a disease comprising administering to a subject in need thereof an effective amount of a kinase modulating compound having the following structure:

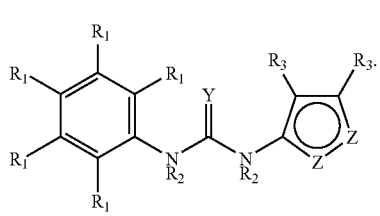

(II)

Provided herein are compositions and methods for treating a disease comprising administering to a subject in need thereof an effective amount of a kinase modulating compound having the following structure:

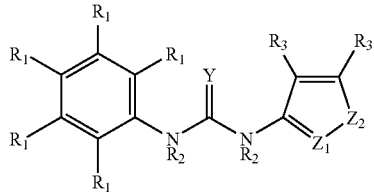

(III)

wherein:
$Z_1$ is $CR_3$ or N; and
$Z_2$ is O or S.

Provided herein are compositions and methods for treating a disease comprising administering to a subject in need thereof an effective amount of a kinase modulating compound having the following structure:

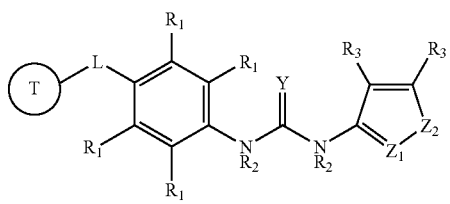

(IV)

wherein:
L is a linker selected from the group consisting of a covalent bond, -(substituted or unsubstituted alkylene)-, -(substituted or unsubstituted alkenylene)-, —O—, —O(substituted or unsubstituted alkylene)-, —C(O)—, —C(O)(substituted or unsubstituted alkylene)-, —C(O)(substituted or unsubstituted alkenylene)-, —NH—, —NH(substituted or unsubstituted alkylene)-, —NH(substituted or unsubstituted alkenylene)-, —C(O)NH—, —C(O)NH(substituted or unsubstituted alkylene), —C(O)NH(substituted or unsubstituted alkenylene)-, —NHC(O)(substituted or unsubstituted alkylene)-, —NHC(O)(substituted or unsubstituted alkenylene)-, —S—, —S(substituted or unsubstituted alkylene)-, and —NHC(O)(substituted or unsubstituted alkylene)S(substituted or unsubstituted alkylene)C(O)NH—; and T is a mono-, bi-, or tricyclic, substituted or unsubstituted cycloalkyl, heterocyclyl, aryl, or heteroaryl.

In some embodiments, T is

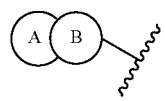

wherein A is a substituted or unsubstituted five or six-membered aryl, heterocyclyl or heteroaryl; and B is a substituted or unsubstituted five or six-membered arylene, heterocyclene or heteroarylene, wherein A and B together form a fused two-ring moiety.

Provided herein are compositions and methods for treating a disease comprising administering to a subject in need thereof an effective amount of a kinase modulating compound having the following structure:

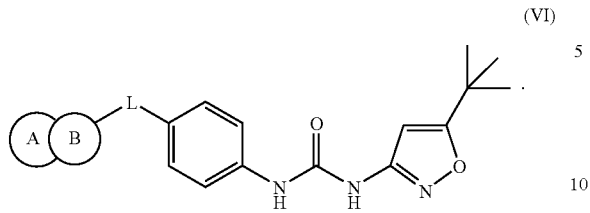
(VI)

In some embodiments, L is —C(O)NH—. In other embodiments, B is substituted or unsubstituted phenylene, pyridinylene, pyrimidinylene, pyridazinylene, thiophenylene, imidazolylene, or pyrrolylene. In still other embodiments, L is —NH—. In yet other embodiments, B is substituted or unsubstituted phenylene, pyridinylene, pyrimidinylene, pyridazinylene, thiophenylene, or imidazolylene.

Provided herein are compositions and methods for treating a disease comprising administering to a subject in need thereof an effective amount of a kinase modulating compound having the following structure:

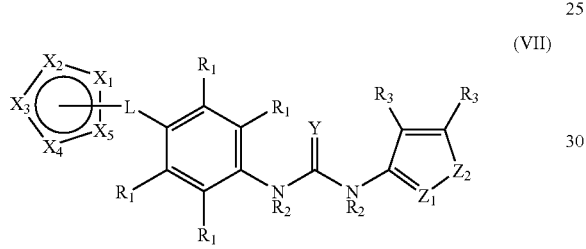
(VII)

wherein:
each of $X_1$-$X_5$ is independently C, CR, N, NR, S, or O, wherein no more than three of $X_1$-$X_5$ is a heteroatom, and no two adjacent ring atoms are O or S; where
each R is independently H, halogen, substituted or unsubstituted alkyl, —OH, substituted or unsubstituted alkoxy, —OC(O)$R_d$, —NO$_2$, —N($R_d$)$_2$, —S$R_d$, —S(O)$_j$$R_d$ where j is 1 or 2, —N$R_d$C(O)$R_d$, —C(O)$_2$$R_d$, —C(O)N($R_d$)$_2$, or —C(O)$R_d$, or two adjacent $R_d$'s are taken together to form a substituted or unsubstituted aryl or heteroaryl,
where each $R_d$ is independently H, substituted or unsubstituted alkyl, substituted or unsubstituted cycloalkyl, substituted or unsubstituted aryl, or substituted or unsubstituted heteroaryl.

Provided herein are compositions and methods for treating a disease comprising administering to a subject in need thereof an effective amount of a kinase modulating compound having the following structure:

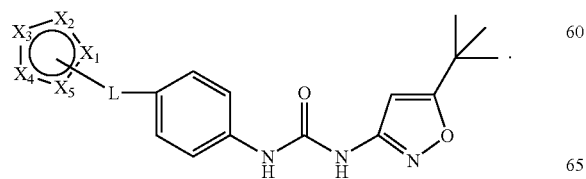
(VIII)

In some embodiments, L is a covalent bond, —C(O)NH—, —OCH$_2$—, or —OCH$_2$CH$_2$—. In other embodiments,

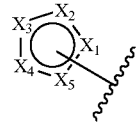

is selected from the group consisting of:

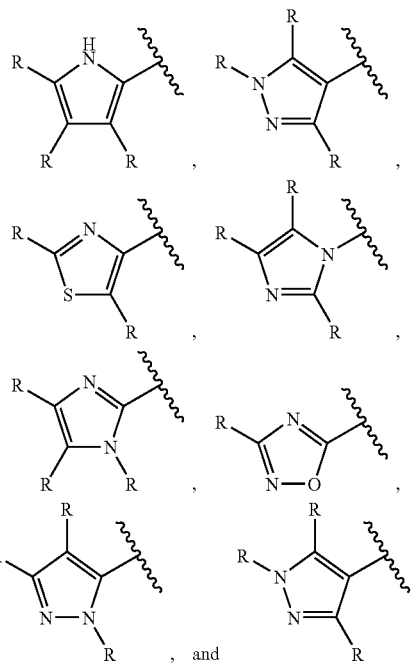
, and

Provided herein are compositions and methods for treating a disease comprising administering to a subject in need thereof an effective amount of a kinase modulating compound having the following structure:

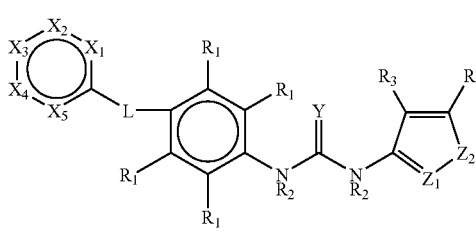
(IX)

wherein:

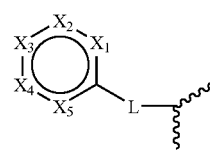

is selected from the group consisting of:
 (a) L is selected from the group consisting of —O(substituted or unsubstituted alkylene)-, and —C(O)(substituted or unsubstituted alkenylene)-; and
  each of $X_1$-$X_5$ is independently CR, N—O, or N, wherein no more than two of $X_1$-$X_5$ is N, where
   each R is independently H, halogen, substituted or unsubstituted alkyl, —OH, substituted or unsubstituted alkoxy, —OC(O)$R_d$, —NO$_2$, —N($R_d$)$_2$, —S$R_d$, —N$R_d$C(O)$R_d$, or —C(O)$R_d$,
   each $R_d$ is independently H, substituted or unsubstituted alkyl, substituted or unsubstituted cycloalkyl, substituted or unsubstituted aryl, or substituted or unsubstituted heteroaryl;
 (b) L is —NH—;
  each of $X_1$, $X_2$, $X_4$, and $X_5$ is independently CR, N—O, or N; and
  $X_3$ is independently CR$_5$ or N, wherein no more than two of $X_1$-$X_5$ is N, where
   $R_5$ is selected from the group consisting of H, halogen, substituted or unsubstituted alkyl, substituted alkoxy, —C(O)$R_d$, —OC(O)$R_d$, —NO$_2$, —N($R_d$)$_2$, and —S$R_d$, and
   each $R_d$ is independently H, substituted or unsubstituted alkyl, substituted or unsubstituted cycloalkyl, substituted or unsubstituted aryl, or substituted or unsubstituted heteroaryl;
 (c) L is —NH—;
  each of $X_1$, $X_3$, and $X_5$ is independently CR, N—O, or N; and
  each of $X_2$ and $X_4$ is independently CR$_6$ or N, wherein no more than two of $X_1$-$X_5$ is N; where
   $R_6$ is selected from the group consisting of H, halogen, unsubstituted alkyl, —OH, substituted or unsubstituted alkoxy, —C(O)$R_d$, —OC(O)$R_d$, —NO$_2$, —N($R_d$)$_2$, —S$R_d$, and alkyl substituted with alkoxy, halogen, aryl, heteroaryl, amine, —C(O)$R_d$, —OC(O)$R_d$, —NO$_2$, —N($R_d$)$_2$, and S$R_d$, and
   each $R_d$ is independently H, substituted or unsubstituted alkyl, substituted or unsubstituted cycloalkyl, substituted or unsubstituted aryl, or substituted or unsubstituted heteroaryl;
 (d) L is —C(O)NH—;
  each of $X_1$, $X_2$, $X_4$, and $X_5$ is independently CR, N—O, or N; and
  $X_3$ is independently CR$_7$ or N, wherein no more than two of $X_1$-$X_5$ is N, and when $X_3$ is N, at least one of $X_1$, $X_2$, $X_3$, or $X_5$ is not CH, where $R_7$ is selected from the group consisting of H, halogen, substituted or unsubstituted alkyl, —OH, substituted or unsubstituted alkoxy, —C(O)$R_d$, —OC(O)$R_d$, —NO$_2$, —N($R_d$)$_2$, and S$R_d$, and
   each $R_d$ is independently H, substituted or unsubstituted alkyl, substituted or unsubstituted cycloalkyl, substituted or unsubstituted aryl, or substituted or unsubstituted heteroaryl.

Provided herein are compositions and methods for treating a disease comprising administering to a subject in need thereof an effective amount of a kinase modulating compound having the following structure:

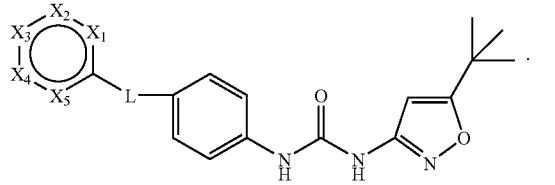

(X)

In some embodiments, L is a linker selected from the group consisting of a covalent bond, (substituted or unsubstituted alkylene), —NHC(O)—, —C(O)NH(substituted or unsubstituted alkylene), —NHC(O)(substituted or unsubstituted alkylene), —C(O)NH(substituted or unsubstituted alkenylene), —NHC(O)(substituted or unsubstituted alkenylene)-, and —O(substituted or unsubstituted alkylene)-.

Provided herein are compositions and methods for treating a disease comprising administering to a subject in need thereof an effective amount of a kinase modulating compound having the following structure:

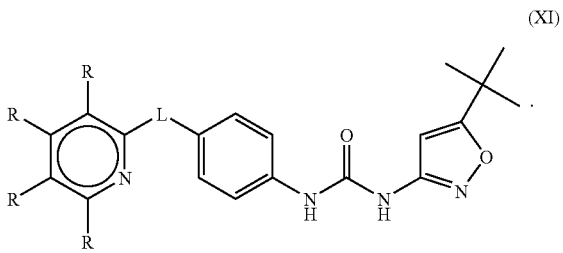

(XI)

Provided herein are compositions and methods for treating a disease comprising administering to a subject in need thereof an effective amount of a kinase modulating compound having the following structure:

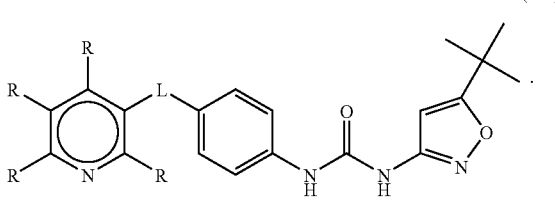

(XII)

Provided herein are compositions and methods for treating a disease comprising administering to a subject in need thereof an effective amount of a kinase modulating compound having the following structure:

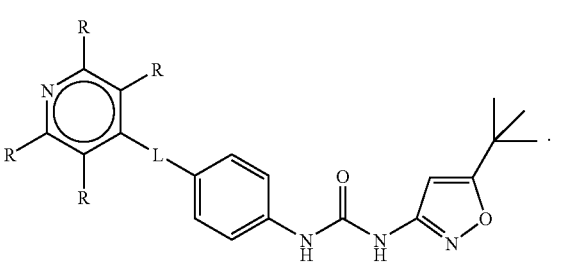

(XIII)

Provided herein are compositions and methods for treating a disease comprising administering to a subject in need thereof an effective amount of a kinase modulating compound having the following structure:

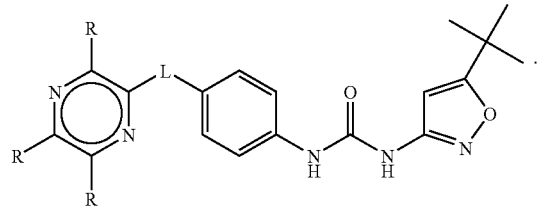

(XIV)

Provided herein are compositions and methods for treating a disease comprising administering to a subject in need thereof an effective amount of a kinase modulating compound having the following structure:

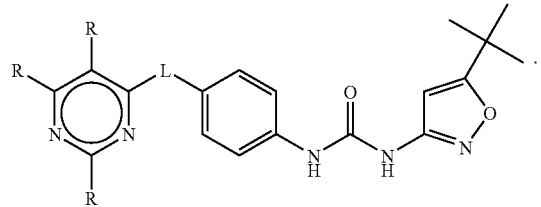

(XV)

Provided herein are compositions and methods for treating a disease comprising administering to a subject in need thereof an effective amount of a kinase modulating compound having the following structure:

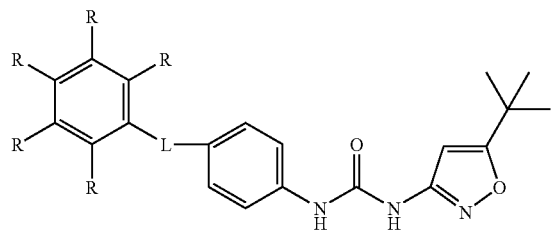

(XVI)

In some embodiments, L is a linker selected from the group consisting of —NHC(O)—, —OCH$_2$—, —OCH$_2$CH$_2$—, —NHC(O)CH$_2$SCH$_2$C(O)NH—, —CHCHC(O)NH—, —CHCHCH$_2$O—, —CH$_2$CH$_2$—, and —CH$_2$CH$_2$C(O)NH—.

Provided herein are compositions and methods for treating a disease comprising administering to a subject in need thereof an effective amount of a kinase modulating compound having the following structure:

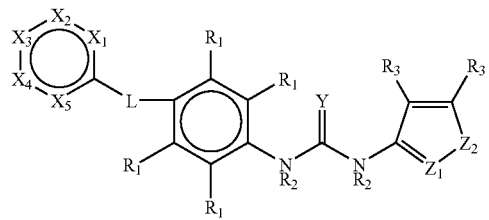

(XVII)

wherein:
each of $X_1$-$X_5$ is independently C, CR, N—O, or, wherein no more than two of $X_1$-$X_5$ is N; where
each R is independently H, halogen, substituted or unsubstituted alkyl, —OR$_d$, substituted or unsubstituted alkoxy, —OC(O)R$_d$, —NO$_2$, —N(R$_d$)$_2$, —SR$_d$, —S(O)$_j$R$_d$ where j is 1 or 2, —NR$_d$, C(O)R$_d$, —C(O)$_2$R$_d$, —C(O)N(R$_d$)$_2$ or —C(O)R$_d$; or two adjacent R's are taken together to form a substituted or unsubstituted aryl or heteroaryl, and each R$_d$ is independently H, substituted or unsubstituted alkyl, substituted or unsubstituted cycloalkyl, substituted or unsubstituted aryl, or substituted or unsubstituted heteroaryl
with a proviso that said compound is not:

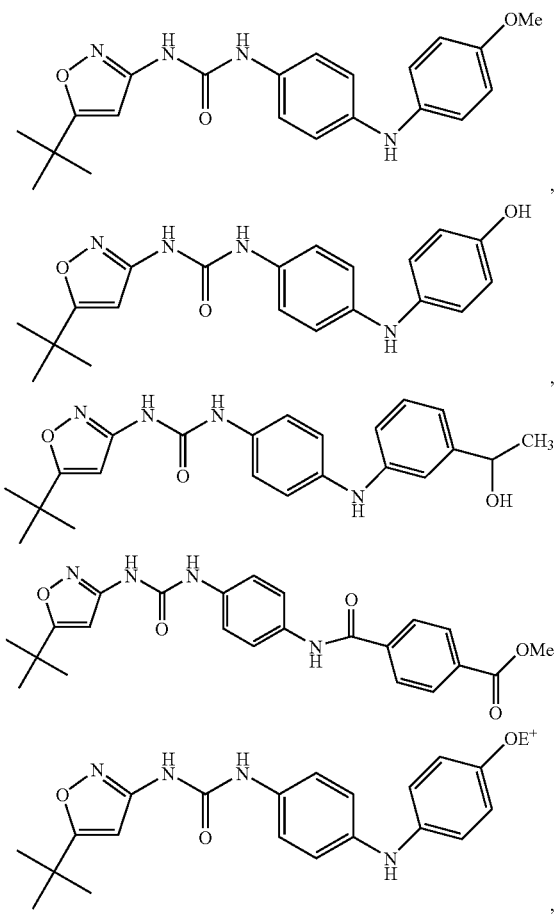

-continued

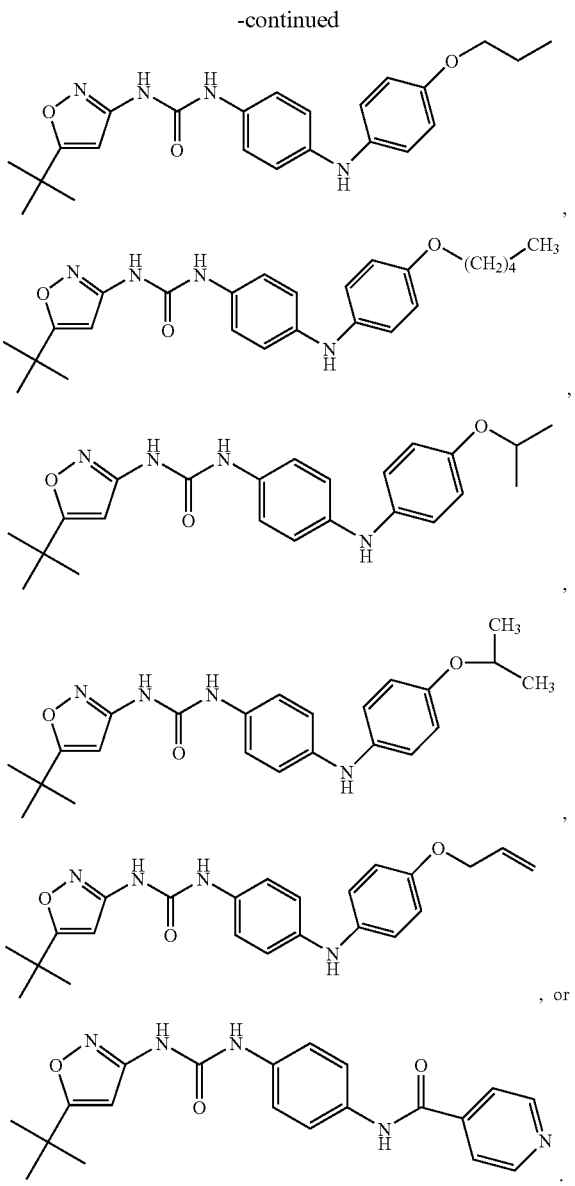

Provided herein are compositions and methods for treating a disease comprising administering to a subject in need thereof an effective amount of a kinase modulating compound having the following structure:

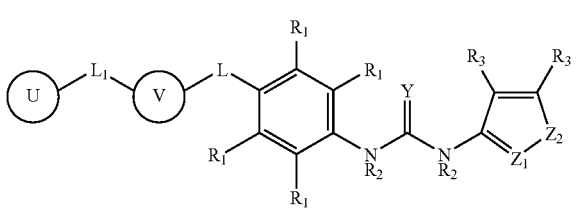

(XVIII)

wherein:

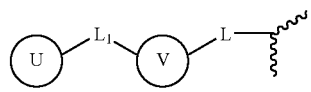

is selected from the group consisting of (a) each of L and $L_1$ is independently a linker selected from the group consisting of a covalent bond, —O(substituted or unsubstituted alkylene)-, —S—, -(substituted or unsubstituted alkylene)-, —C(O)—, and —N(substituted or unsubstituted alkylene)-;

U is a substituted or unsubstituted cycloalkyl, heterocyclyl, aryl, or heteroaryl; and V is a substituted or unsubstituted cycloalkylene, heterocyclene, arylene, or heteroarylene;

(b) L is a linker selected from the group consisting of a covalent bond, —O(substituted or unsubstituted alkylene)-, —S—, -(substituted or unsubstituted alkylene)-, —O—, —NH—, —C(O)—, —C(O)NH—, and —N(substituted or unsubstituted alkylene)-;

$L_1$ is a linker selected from the group consisting of a covalent bond, —O(substituted or unsubstituted alkylene)-, —S—, -(substituted or unsubstituted alkylene)-, —O—, —NH—, —C(O)—, and —N(substituted or unsubstituted alkylene)-;

U is selected from the group consisting of:
  (i) substituted or unsubstituted cycloalkyl;
  (ii) unsubstituted aryl;
  (iii) aryl substituted at any position with —Cl, —I, substituted or unsubstituted alkyl, —OH, substituted or unsubstituted alkoxy, —OC(O)$R_3$, —NO$_2$, —N($R_g$)$_2$, —S$R_g$, —C(O)$R_h$, where $R_h$ is H, —OH, —N($R_g$)$_2$, or substituted or unsubstituted alkoxy, and where $R_g$ is H or substituted or unsubstituted alkyl; and
  (iv) substituted or unsubstituted heteroaryl, except pyridinyl; and V is a substituted or unsubstituted cycloalkylene, heterocyclene, arylene, or heteroarylene; and (c) L is a linker selected from the group consisting of a covalent bond, —O(substituted or unsubstituted alkylene)-, —S—, -(substituted or unsubstituted alkylene)-, —O—, —NH—, —C(O)—, —C(O)NH—, and —N(substituted or unsubstituted alkylene)-;

$L_1$ is a linker selected from the group consisting of a covalent bond, —O(substituted or unsubstituted $C_2$-$C_5$ alkylene)-, —S—, -(substituted or unsubstituted alkylene)-, —O—, —NH—, —C(O)—, —C(O)NH—, and —N(substituted or unsubstituted alkylene)-;

U is selected from the group consisting of substituted or unsubstituted cycloalkyl; substituted aryl; and substituted or unsubstituted heteroaryl; and V is a substituted or unsubstituted cycloalkylene, heterocyclene, arylene, or heteroarylene.

Provided herein are compositions and methods for treating a disease comprising administering to a subject in need thereof an effective amount of a kinase modulating compound having the following structure:

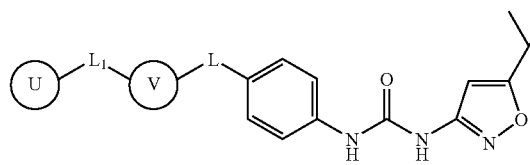

(XIX)

In some embodiments, $L_1$ is a bond; and L is a bond or —C(O)NH—. In other embodiments, U is substituted or unsubstituted phenyl, thiazolyl, or pyridinyl; and V is substituted or unsubstituted piperidinylene, thiazolylene, imidazolylene, or thiophenylene.

Provided herein are compositions and methods for treating a disease comprising administering to a subject in need thereof an effective amount of a kinase modulating compound having the following structure:

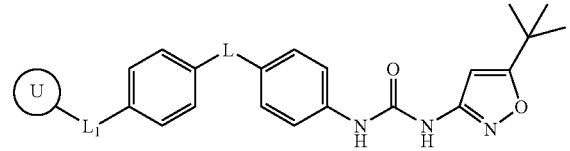

(XX)

In some embodiments, $L_1$ is a bond, —CH$_2$O—, —N(CH$_3$)—, or —O—; and L is —CH$_2$O— or —NHC(O)—. In other embodiments, U is substituted or unsubstituted phenyl, $C_3$-$C_6$ cycloalkyl, pyrimidine, or pyridine.

Provided herein are compositions and methods for treating a disease comprising administering to a subject in need thereof an effective amount of a kinase modulating compound having the following structure:

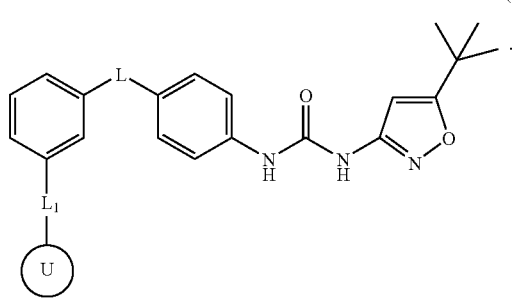

(XXI)

In some embodiments, $L_1$ is a —NH— or —O—; and L is —NHC(O)—. In other embodiments, U is substituted or unsubstituted pyrimidyl.

Provided herein are compositions and methods for treating a disease comprising administering to a subject in need thereof an effective amount of a kinase modulating compound having the following structure:

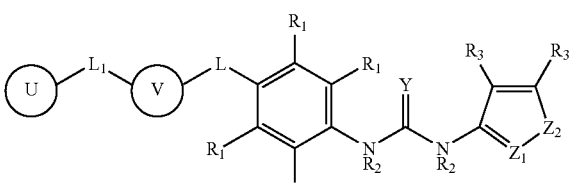

(XXII)

wherein:

L and $L_1$ is a linker selected from the group consisting of a covalent bond, substituted or unsubstituted alkenylene, substituted or unsubstituted alkylene, —C(O)NH—, —C(O)—, —NH—, —O—, —S—, —O(substituted or unsubstituted alkylene)-, —N(substituted or unsubstituted alkylene)-, C(O)NH(substituted or unsubstituted alkylene), —C(O)NH(substituted or unsubstituted alkenylene)-, —NHC(O)(substituted or unsubstituted alkylene)-, —NHC(O)(substituted or unsubstituted alkenylene)-, —C(O)(substituted or unsubstituted alkenylene)-, and —NHC(O)(substituted or unsubstituted alkylene)S(substituted or unsubstituted alkylene)C(O)NH—;

U is a substituted or unsubstituted cycloalkyl, heterocyclyl, aryl, or heteroaryl; and V is a substituted or unsubstituted cycloalkylene, heterocyclene, arylene, or heteroarylene;

with a proviso that said compound is not:

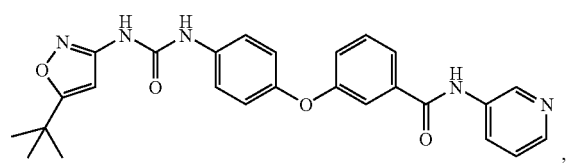

,

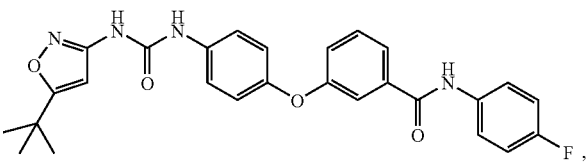

,

-continued

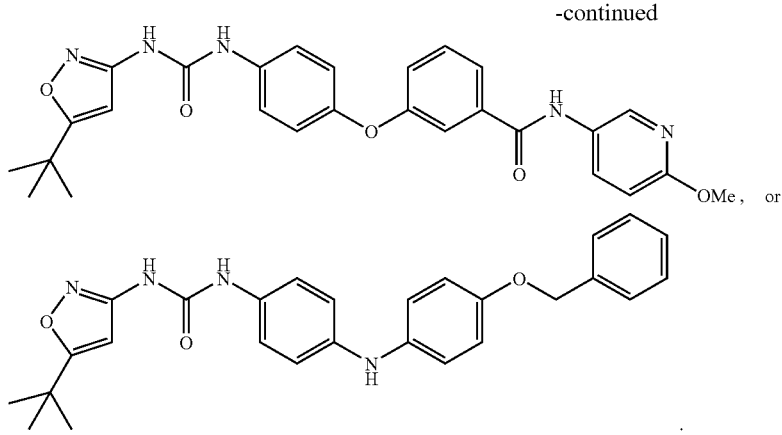

Methods for modulating p38 kinase, said method comprising administering an effective amount of a compound corresponding to Formula (IA) are provided herein:

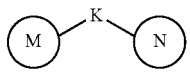
(IA)

wherein:
M is a-substituted or unsubstituted heteroaryl or substituted or unsubstituted aryl;
N is an optionally-substituted or unsubstituted aryl or substituted or unsubstituted heteroaryl; and
K is

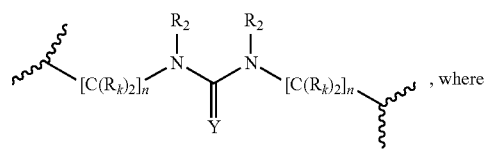
, where

Y is O or S;
each $R_k$ is independently H, halogen, substituted or unsubstituted alkyl, —OH, substituted or unsubstituted alkoxy, —OC(O)$R_2$, —NO$_2$, —N($R_2$)$_2$, —S$R_2$, or —C(O)$R_2$, —C(O)$_2R_2$, —C(O)N($R_2$)$_2$, —N($R_2$)C(O)$R_2$,
each $R_2$ is independently H, substituted or unsubstituted alkyl, substituted or unsubstituted cycloalkyl, substituted or unsubstituted heterocyclyl, substituted or unsubstituted aryl, or substituted or unsubstituted heteroaryl; or wherein two $R_2$ groups are linked together by an optionally substituted alkylene; and
each n is independently 0, 1, 2, 3 or 4;
or an active metabolite, or a pharmaceutically acceptable prodrug, isomer, pharmaceutically acceptable salt or solvate thereof.

Methods for modulating p38 kinase, said method comprising administering an effective amount of a compound, or pharmaceutically acceptable salt thereof, corresponding to Formula (I) are provided herein:

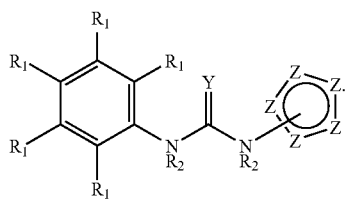
(I)

Methods for modulating p38 kinase, said method comprising administering an effective amount of a compound, or pharmaceutically acceptable salt thereof, corresponding to Formula (IV) are provided herein:

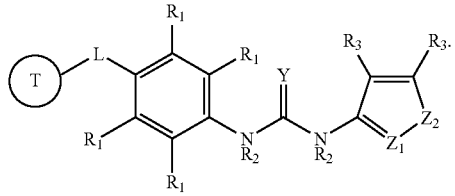
(IV)

Methods for modulating p38 kinase, said method comprising administering an effective amount of a compound, or pharmaceutically acceptable salt thereof, corresponding to Formula (VI) are provided herein:

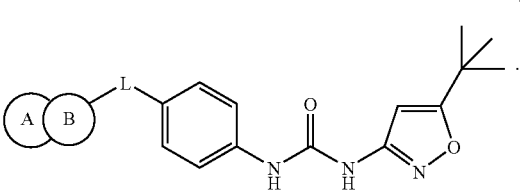
(VI)

Methods for modulating p38 kinase, said method comprising administering an effective amount of a compound, or pharmaceutically acceptable salt thereof, corresponding to Formula (XXIII) are provided herein:

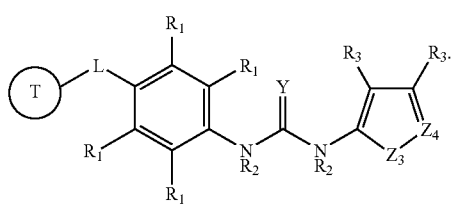
(XXIII)

Methods for modulating MKNK2 kinase, said method comprising administering an effective amount of a compound corresponding to Formula (IA) are provided herein:

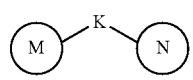
(IA)

Methods for modulating MKNK2 kinase, said method comprising administering an effective amount of a compound, or pharmaceutically acceptable salt thereof, corresponding to Formula (I) are provided herein:

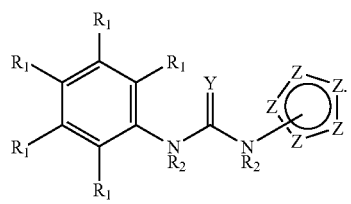
(I)

Methods for modulating MKNK2 kinase, said method comprising administering an effective amount of a compound, or pharmaceutically acceptable salt thereof, corresponding to Formula (IV) are provided herein:

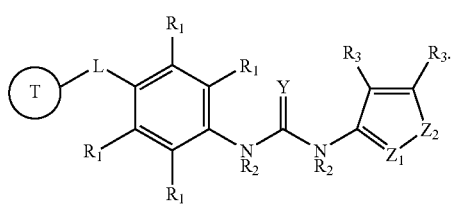
(IV)

Methods for modulating MKNK2 kinase, said method comprising administering an effective amount of a compound, or pharmaceutically acceptable salt thereof, corresponding to Formula (XVII) are provided herein:

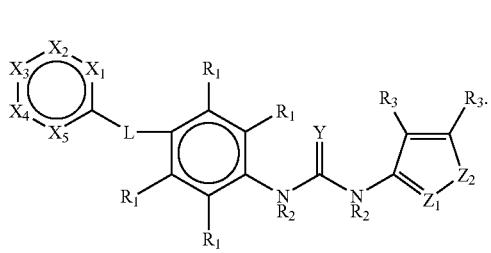
(XVII)

Methods for modulating MKNK2 kinase, said method comprising administering an effective amount of a compound, or pharmaceutically acceptable salt thereof, corresponding to Formula (X) are provided herein:

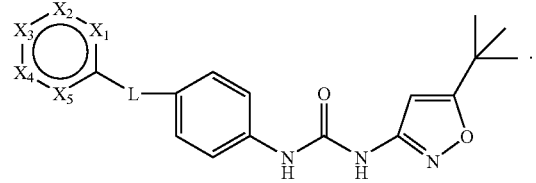
(X)

Methods for modulating STK10 kinase, said method comprising administering an effective amount of a compound corresponding to Formula (IA) are provided herein:

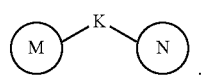
(IA)

Methods for modulating STK10 kinase, said method comprising administering an effective amount of a compound, or pharmaceutically acceptable salt thereof, corresponding to Formula (I) are provided herein:

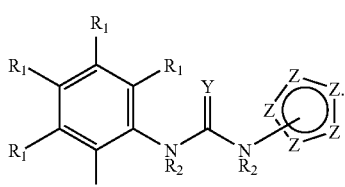
(I)

Methods for modulating STK10 kinase, said method comprising administering an effective amount of a compound, or pharmaceutically acceptable salt thereof, corresponding to Formula (IV) are provided herein:

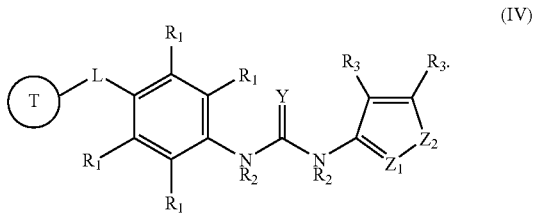

Methods for modulating STK10 kinase, said method comprising administering an effective amount of a compound, or pharmaceutically acceptable salt thereof, corresponding to Formula (VI) are provided herein:

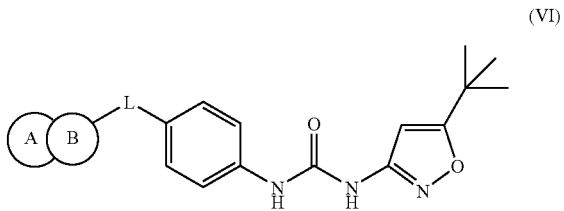

In some embodiments, the protein kinase is selected from the group comprising Step (sterile 20, sterile 11 and sterile 7); camk (calmodulin regulated kinases and related kinases); AGC (protein kinase A, protein kinase G and protein kinase C) and CMGC (cdk, map kinase, glycogen synthetase kinase and clk). The sterile 20 kinases include, for example, PAK and CZ.

In some embodiments, the protein tyrosine kinase is selected from the "HER" receptor tyrosine kinase subfamily, which includes EGFR (epithelial growth factor receptor), HER2, HER3 and HER4. In further embodiments, the protein tyrosine kinase is selected from the subfamily consisting of insulin receptor (IR), insulin-like growth factor I receptor (IGF-1R) and insulin receptor related receptor (IRR).

In some embodiments, the protein tyrosine kinase is selected from the platelet derived growth factor receptor (PDGFR) subfamily, which includes PDGFR α, PDGFR β, CSFIR, c-kit and c-fms. In another embodiment, the protein tyrosine kinase is the vascular endothelial growth factor ("VEGF") receptor subgroup.

In some embodiments, the protein tyrosine kinase is selected from the fetus liver kinase ("flk") receptor subfamily, which includes kinase insert domain-receptor fetal liver kinase-1 (KDR/FLK-1), flk-1R, flk-4 and fins-like tyrosine kinase 1 (flt-1). In further embodiments, the protein tyrosine kinase is selected from the fibroblast growth factor ("FGF") receptor subgroup, which includes the receptors FGFR1, FGFR 2, FGFR3, and FGFR4, and the ligands, FGF1, FGF2, FGF3, FGF4, FGF5, FGF6, and FGF7. In a still further embodiment, the protein tyrosine kinase is the tyrosine kinase growth factor receptor family, c-Met. In some embodiments, the protein tyrosine kinase is an fins-like tyrosine kinase 3 receptor kinase (FLT-3 kinase).

The present invention provides compounds which modulate the activity, and in some embodiments, preferentially inhibit non-receptor tyrosine kinases. In some embodiments, the non-receptor tyrosine kinases include Frk, Btk, Csk, Abl, Zap70, Fes, Fps, Fak, Jak and Ack, their respective subfamilies. In a further embodiment, the non-receptor tyrosine kinase is selected from the Src subfamily, which includes Src, Yes, Fyn, Lyn, Lck, Blk, Hck, Fgr and Yrk.

The compounds and compositions disclosed herein may be used for the prevention or treatment of cancers such as stomach, gastric, bone, ovary, colon, lung, brain, larynx, lymphatic system, genitourinary tract, ovarian, squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, leukemia, glioma, colorectal cancer, genitourinary cancer gastrointestinal cancer, or pancreatic cancer. In particular, the cancer is acute myelogenous leukemia (AML), B-precursor cell acute lymphoblastic leukemias, myelodysplastic leukemias, T-cell acute lymphoblastic leukemias, and chronic myelogenous leukemias (CMLs).

Compositions and methods for treating a disease comprising administering to a subject in need thereof an effective amount of an fms-like tyrosine kinase 3 (FLT-3) receptor modulating compound are provided herein. In one embodiment, the disease is cancer. In other embodiments, the cancer is a malignant tumor, or a hematologic malignancy such as leukemia and lymphoma. In some embodiments, the leukemia is acute myelogenous leukemia (AML), a B-precursor cell acute lymphoblastic leukemia, myelodysplastic leukemia, T-cell acute lymphoblastic leukemia or chronic myelogenous leukemia (CML).

Compositions and methods for treating a disease comprising administering to a subject in need thereof an effective amount of a Stem Cell Factor (SCF), c-kit, receptor modulating compound are provided herein. In one embodiment, the disease is cancer. In other embodiments, the cancer is a malignant tumor, or a hematologic malignancy such as leukemia and lymphoma. In some embodiments, the cancer is small-cell lung cancer, or breast cancer. In some embodiments, the leukemia is acute myelogenous leukemia (AML). In some embodiments, the malignant tumor is a germ cell tumor, a mast cell tumor, a gastrointestinal stromal tumor (GIST), melanoma, or a neuroblastoma.

Compositions and methods for treating a disease comprising administering to a subject in need thereof an effective amount of a Bcr-Abl receptor modulating compound are provided herein. In one embodiment, the disease is cancer. In other embodiments, the cancer is a malignant tumor, or a hematologic malignancy such as leukemia and lymphoma. In some embodiments, the leukemia is chronic myeloid leukemia (CML) or acute myelogenous leukemia (AML).

Compositions and methods for treating a disease comprising administering to a subject in need thereof an effective amount of a Platelet-Derived Growth Factor (PDGF) receptor modulating compound are provided herein. In one embodiment, the disease is cancer. In other embodiments, the cancer is a malignant tumor, or a hematologic malignancy such as leukemia and lymphoma. In some embodiments, the leukemia is acute lymphoblastic leukemia (ALL). In some embodiments, the lymphoma is T-cell lymphoma. In some embodiments, the malignant tumor is melanoma, or glioblastoma. In a further embodiment, the disease is a nonmalignant proliferation disease. In some embodiments, the nonmalignant proliferation disease is atherosclerosis, or restenosis. In a still further embodiment, the disease is a fibroproliferative disorder. In some embodiments, the fibroproliferative disorder is obliterative bronchiolitis.

These and other aspects of the present invention will become evident upon reference to the following detailed description. In addition, various references are set forth herein which describe in more detail certain procedures or compositions, and are incorporated by reference in their entirety.

DISCLOSURE OF THE INVENTION

To more readily facilitate an understanding of the invention and its preferred embodiments, the meanings of terms used herein will become apparent from the context of this specification in view of common usage of various terms and the explicit definitions of other terms provided in the glossary below or in the ensuing description.

Glossary of Terms

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "ADVANCED ORGANIC CHEMISTRY $3^{RD}$ ED." Vols. A and B, Plenum Press, New York. Unless otherwise indicated, conventional methods of mass spectroscopy, NMR, HPLC, protein chemistry, biochemistry, recombinant DNA techniques and pharmacology, within the skill of the art are employed.

The term "modulator" means a molecule that interacts with a target either directly or indirectly. The interactions include, but are not limited to, agonist, antagonist, and the like.

The term "agonist" means a molecule such as a compound, a drug, an enzyme activator or a hormone that enhances the activity of another molecule or the activity of a receptor site either directly or indirectly.

The term "antagonist" means a molecule such as a compound, a drug, an enzyme inhibitor, or a hormone, that diminishes or prevents the action of another molecule or the activity of a receptor site either directly or indirectly.

The terms "effective amount" or "therapeutically effective amount" refer to a sufficient amount of the agent to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective" amount in any individual case may be determined by one of ordinary skill in the art using routine experimentation.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

"Carrier materials" include any commonly used excipients in pharmaceutics and should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., Pharmaceutical Dosage Forms, Marcel Decker, New York, N.Y., 1980; and *Pharmaceutical Dosage Forms and Drug Delivery Systems*, Seventh Ed. (Lippincott Williams & Wilkins 1999).

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

The term "pharmaceutically acceptable salt" of a compound means a salt that is pharmaceutically acceptable and that possesses the desired pharmacological activity of the parent compound. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4,-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

As used herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms.

As used herein, the term "linker" means any divalent linking moiety used to connect, join, or attach two chemical groups. For example, linkers may be used to join two cyclic groups, such as to join two aryl groups (e.g., phenyl), an aryl group to a cycloalkyl group, an aryl group to a heterocyclyl group, a cycloalkyl group to a cycloalkyl group, a cycloalkyl group to a heterocyclyl group, and the like. Representative linkers include, but are not limited to, a covalent bond, -(substituted or unsubstituted alkylene)-, -(substituted or unsubstituted alkenylene)-, -(substituted or unsubstituted alkynylene)-, -(substituted or unsubstituted cycloalkylene)-, -(substituted or unsubstituted heterocyclylene)-, -(substituted or unsubstituted arylene)-, and -(substituted or unsubstituted heteroarylene)-. Exemplary linkers also include —O—, —S—, —S(O)—, —S(O)$_2$—, —S(O)$_3$—, —C(O)—, —NH—, —N=, —N=N—, =N—N—, —C(O)NH—, —S(O)NH—, and the like. Additional examples of linkers include —O(substituted or unsubstituted alkylene)-, —N(substituted or unsubstituted alkylene)-, —NHC(O)(substituted or unsubstituted alkylene)-, —C(O)(substituted or unsubstituted alkenylene)-, —NHC(O)(substituted or unsubstituted alkylene)S(substituted or unsubstituted alkylene)C (O)NH—, —NHC(O)(substituted or unsubstituted alkenylene)-, and the like. Linkers, as represented herein, embrace divalent moieties in any chemically feasible directionality. For example, compounds comprising a linker-C(O) NH— which attaches two aryl groups, Ar$_1$ to Ar$_2$, include Ar$_1$-C(O)NH—Ar$_2$ as well as Ar$_1$—NHC(O)—Ar$_2$.

As used herein, the term "halogen" includes fluorine, chlorine, bromine, and iodine.

As used herein, "alkyl" means a straight chain or branched, saturated chain having from 1 to 10 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, and n-hexyl, and longer alkyl groups, such as heptyl, and octyl. An alkyl group can be unsubstituted or substituted. Alkyl groups containing three or more carbon atoms may be straight, branched or cyclized.

As used herein, "lower alkyl" means an alkyl having from 1 to 5 carbon atoms.

As used herein, an "alkenyl group" includes a monovalent unbranched or branched hydrocarbon chain having one or more double bonds therein. The double bond of an alkenyl group can be unconjugated or conjugated to another unsaturated group. Suitable alkenyl groups include, but are not limited to, (C$_2$-C$_8$) alkenyl groups, such as vinyl, allyl, butenyl, pentenyl, hexenyl, butadienyl, pentadienyl, hexadienyl, 2-ethylhexenyl, 2-propyl-2-butenyl, (2-methyl-3-butene)-pentenyl. An alkenyl group can be unsubstituted or substituted.

As used herein, "alkynyl group" includes a monovalent unbranched or branched hydrocarbon chain having one or more triple bonds therein. The triple bond of an alkynyl group can be unconjugated or conjugated to another unsaturated group. Suitable alkynyl groups include, but are not limited to, (C$_2$-C$_6$) alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted.

The terms "trifluoromethyl," "sulfonyl," and "carboxyl" include CF$_3$, SO$_3$H, and CO$_2$H, respectively.

The term "alkoxy" as used herein includes —O-(alkyl), wherein alkyl is defined above.

As used herein, "alkoxyalkoxy" includes —O-(alkyl)-O-(alkyl), wherein each "alkyl" is independently an alkyl group defined above.

As used herein, "alkoxycarbonyl" includes —C(O)O-(alkyl), wherein alkyl is defined above.

As used herein, "alkoxycarbonylalkyl" includes -(alkyl)-C(O)O-(alkyl), wherein alkyl is defined above.

As used herein, "alkoxyalkyl" means -(alkyl)-O-(alkyl), wherein each "alkyl" is independently an alkyl group defined above.

As used herein, the term "aryl" (Ar) refers to a monocyclic, or fused or spiro polycyclic, aromatic carbocycle (ring structure having ring atoms that are all carbon) having from 3 to 12 ring atoms per ring. Illustrative examples of aryl groups include the following moieties:

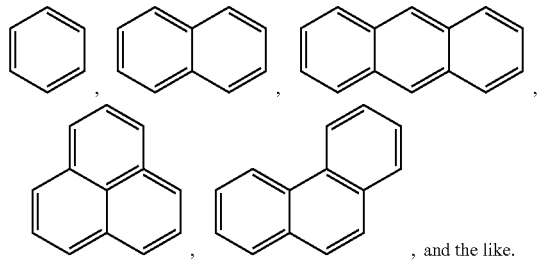

, and the like.

As used herein, the term "heteroaryl" (heteroAr) refers to a monocyclic, or fused or spiro polycyclic, aromatic heterocycle (ring structure having ring atoms selected from carbon atoms as well as nitrogen, oxygen, and sulfur heteroatoms) having from 3 to 12 ring atoms per ring. Illustrative examples of aryl groups include the following moieties:

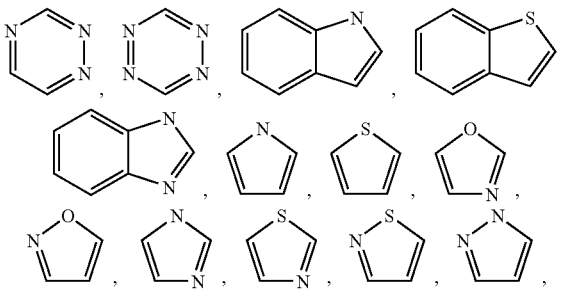

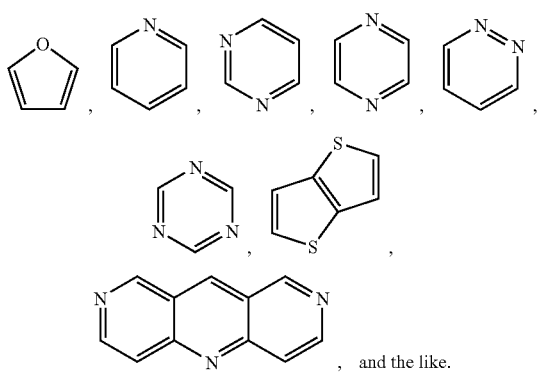

, and the like.

As used herein, the term "cycloalkyl" refers to a saturated or partially saturated, monocyclic or fused or spiro polycyclic, carbocycle having from 3 to 12 ring atoms per ring. Illustrative examples of cycloalkyl groups include the following moieties:

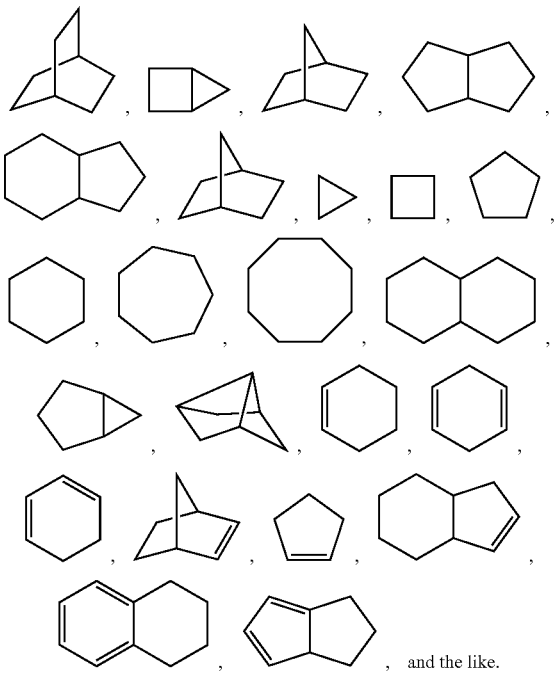

, and the like.

As used herein, the term "heterocycloalkyl" refers to a monocyclic, or fused or spiro polycyclic, ring structure that is saturated or partially saturated and has from 3 to 12 ring atoms per ring selected from C atoms and N, O, and S heteroatoms. Illustrative examples of heterocycloalkyl groups include:

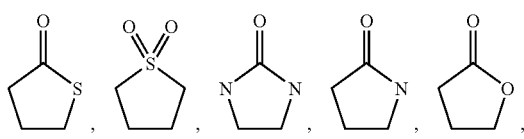

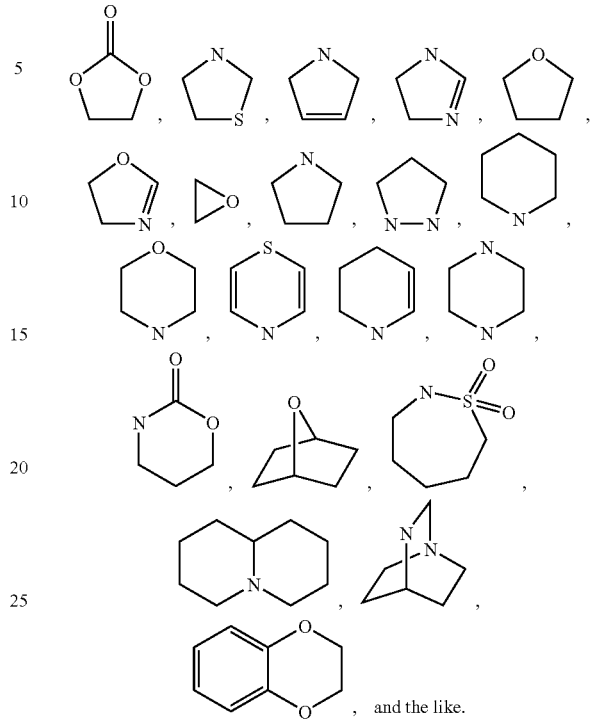

, and the like.

As used herein, "aryloxy" includes —O-aryl group, wherein aryl is as defined above. An aryloxy group can be unsubstituted or substituted.

As used herein, "arylalkyl" includes -(alkyl)-(aryl), wherein alkyl and aryl are defined above.

As used herein, "arylalkyloxy" includes —O-(alkyl)-(aryl), wherein alkyl and aryl are defined above.

As used herein, "cycloalkyl" includes a monocyclic or polycyclic saturated ring comprising carbon and hydrogen atoms and having no carbon-carbon multiple bonds. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

As used herein, "cycloalkyloxy" includes —O-(cycloalkyl), wherein cycloalkyl is defined above.

As used herein, "cycloalkylalkyloxy" includes —O-(alkyl)-(cycloalkyl), wherein cycloalkyl and alkyl are defined above.

As used herein, the term "alkylidene" includes the divalent radical —$C_nH_{2n}$—, wherein n is an integer from 1 to 8, such as —CH$_2$—, —CH$_2$CH$_2$—, —CH$_2$—CH$_2$—CH$_2$—, —CH$_2$CH$_2$CH$_2$CH$_2$—, —CH$_2$CH$_2$CH$_2$CH$_2$CH$_2$—, and the like, unsubstituted or substituted with one or more alkyl groups.

As used herein, "heteroatom-containing alkylidene" includes an alkylidene wherein at least one carbon atom is replaced by a heteroatom selected from nitrogen, oxygen, or sulfur, such as —CH$_2$CH$_2$OCH$_2$CH$_2$—, and the like, unsubstituted or substituted with one or more alkyl groups.

As used herein, "aminoalkoxy" includes —O-(alkyl)-NH$_2$, wherein alkyl is defined above.

As used herein, "mono-alkylamino" includes —NH(alkyl), wherein alkyl is defined above.

As used herein, "di-alkylamino" includes —N(alkyl) (alkyl), wherein each "alkyl" is independently an alkyl group defined above.

As used herein, "mono-alkylaminoalkoxy" includes —O-(alkyl)-NH(alkyl), wherein each "alkyl" is independently an alkyl group defined above.

As used herein, "di-alkylaminoalkoxy" includes —O-(alkyl)N(alkyl)(alkyl), wherein each "alkyl" is independently an alkyl group defined above.

As used herein, "arylamino" includes —NH(aryl), wherein aryl is defined above.

As used herein, "arylalkylamino" includes —NH-(alkyl)-(aryl), wherein alkyl and aryl are defined above.

As used herein, "alkylamino" includes —NH(alkyl), wherein alkyl is defined above.

As used herein, "cycloalkylamino" includes —NH-(cycloalkyl), wherein cyclohexyl is defined above.

As used herein, "cycloalkylalkylamino" includes —NH-(alkyl)-(cycloalkyl), wherein alkyl and cycloalkyl are defined above.

As used herein, "aminoalkyl" includes -(alkyl)-$NH_2$, wherein alkyl is defined above.

As used herein, "mono-alkylaminoalkyl" includes -(alkyl)-NH(alkyl), wherein each "alkyl" is independently an alkyl group defined above.

As used herein, "di-alkylaminoalkyl" includes -(alkyl)-N(alkyl)(alkyl), wherein each "alkyl" is independently an alkyl group defined above.

The term "whole integer" is intended to include whole numbers. For example, a whole integer from 0 to 4 would include 0, 1, 2, 3, and 4.

Sulfonyl refers to the presence of a sulfur atom, which is optionally linked to another moiety such as an aliphatic group, an aromatic group, an aryl group, an alicyclic group, or a heterocyclic group. Aryl or alkyl sulfonyl moieties have the formula —$SO_2R_d$, and alkoxy moieties have the formula —O—$R_d$, wherein $R_d$ is alkyl, as defined above, or is aryl wherein aryl is phenyl, optionally substituted with 1-3 substituents independently selected from halo (fluoro, chloro, bromo or iodo), lower alkyl ($C_{1-6}$) and lower alkoxy ($C_{1-6}$).

As used herein, the term "substituted" means that the specified group or moiety bears one or more suitable substituents.

As used herein, the term "unsubstituted" means that the specified group bears no substituents.

As used herein, the term "optionally substituted" means that the specified group is unsubstituted or substituted by one or more substituents.

Molecular embodiments of the present invention may possess one or more chiral centers and each center may exist in the R or S configuration. The present invention includes all diastereomeric, enantiomeric, and epimeric forms as well as the appropriate mixtures thereof. Stereoisomers may be obtained, if desired, by methods known in the art as, for example, the separation of stereoisomers by chiral chromatographic columns. Additionally, the compounds of the present invention may exist as geometric isomers. The present invention includes all cis, trans, syn, anti, entgegen (E), and zusammen (Z) isomers as well as the appropriate mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., Chem, Rev, 1996, 96, 3147-3176 and references cited therein.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

To more readily facilitate an understanding of the invention and its preferred embodiments, the meanings of terms used herein will become apparent from the context of this specification in view of common usage of various terms and the explicit definitions of other terms provided in the glossary below or in the ensuing description.

Compounds

In one aspect, the present invention is directed to compounds, compositions, and methods for treating conditions associated with abnormal kinase activity. In one embodiment, compounds useful in the invention are derivatives of isoxazoles, pyrazoles and isothiazoles. When the compounds of the invention contain one or more chiral centers, the invention includes optically pure forms as well as mixtures of stereoisomers or enantiomers.

Thus, the invention provides methods for modulating various kinases by providing an effective amount of a compound of the formulas described herein.

Salts of the compounds may be used for therapeutic and prophylactic purposes, where the salt is preferably a pharmaceutically acceptable salt. Examples of pharmaceutically acceptable salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycolic, gluconic, succinic and methanesulphonic and arylsulphonic, for example Q-toluenesulphonic, acids.

A "prodrug" refers to a drug or compound in which the pharmacological action results from conversion by metabolic processes within the body. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs may be designed as reversible drug derivatives, for use as modifiers to enhance drug transport to site-specific tissues. Additionally, prodrugs can increase the effective water solubility of the therapeutic compound for targeting to regions where water is the principal solvent. See, e.g., Fedorak et al., Am. J. Physiol., 269:G210-218 (1995); McLoed et al., Gastroenterol, 106:405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987. Prodrug forms of the above described compounds, wherein the prodrug is metabolized in vivo to produce a derivative as set forth above are included within the scope of the claims. Indeed, some of the above-described derivatives may be a prodrug for another derivative or active compound. The invention further provides for the optical isomers of the compounds disclosed herein, especially those resulting from the chiral carbon atoms in the molecule. In additional embodiments of the invention, mixtures of enantiomers and/or diastereoisomers, resulting from a single preparative step, combination, or interconversion may also be useful for the applications described herein.

In another aspect, compositions containing the above described analogs and derivatives are provided. Preferably, the compositions are formulated to be suitable for pharmaceutical or clinical use by the inclusion of appropriate carriers or excipients.

Groups such as carbonyl, carboxyl, alkoxy, amino, and cyano groups, etc., as shown in the formula above, need not be directly bound to the para position; they may be included elsewhere in the alkyl, alkenyl or alkynyl substituent. Thus, also acceptable substituents are the following representative forms:

—CH$_2$NHCH$_3$; —CH$_2$OCH$_3$; —CH$_2$SCH$_3$; —NHCH$_3$; —CH$_2$CH$_3$; —OCH$_2$CH$_3$; —SCH$_2$CH$_2$CH$_3$; —CH=CHCH$_2$NH$_2$; —CH$_2$CH$_2$OH;

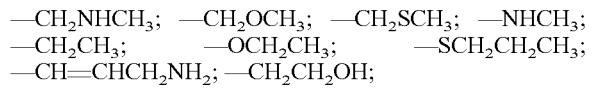

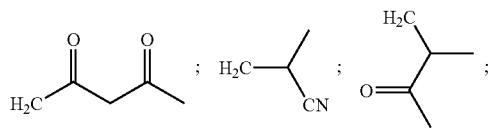

—CH$_2$CH$_2$CH$_2$SH; —CH$_2$OC(O)CH$_3$; —CH$_2$NHC(O) CH$_2$C(O)CH$_3$; —NHC(O)CH$_2$CH$_2$CH$_3$ each of which may further be substituted with a cycloalkyl, heterocycloalkyl, aryl or heteroaryl group.

It will also be evident that these substituents include, for example, trifluoromethyl, difluoromethyl and fluoromethyl (alkyl substituted by halo) and trifluoromethoxy, difluoromethoxy and fluoromethoxy (alkyl where one carbon is replaced by O and is further substituted by halo).

Compounds of the invention which contain carboxyl groups or which contain amino groups may be supplied in the forms of their pharmaceutically acceptable salts. Pharmaceutically acceptable salts of carboxylic acids include inorganic salts such as salts of sodium, potassium, calcium, magnesium and the like or salts formed with organic bases such as caffeine. Salts of amines are acid addition salts formed from inorganic acids such as hydrochloric, sulfuric, phosphoric acids or may be salts of organic acids such as acetates, maleates, propionates, and the like.

The invention also provides prodrug forms of the compounds described herein, wherein the prodrug is metabolized in vivo to produce a derivative as set forth above. Indeed, some of the above described derivatives may be a prodrug for another derivative or active compound. The invention further provides for the optical isomers of the compounds disclosed herein, especially those resulting from the chiral carbon atoms in the molecule. In additional embodiments of the invention, mixtures of enantiomers and/or diastereoisomers, resulting from a single preparative step, combination, or interconversion are provided.

In another aspect of the invention, compositions containing the above described analogs and derivatives are provided. Preferably, the compositions are formulated to be suitable for pharmaceutical or clinical use by the inclusion of appropriate carriers or excipients.

In yet another aspect of the invention, pharmaceutical formulations are provided comprising at least one compound described above, or a pharmaceutically acceptable salt or solvate thereof, together with one or more pharmaceutically acceptable carriers, diluents or excipients.

The compounds of the invention, especially when used in the invention methods and compositions, may be "conjugated"—that is they may be coupled to additional moieties that do not destroy their ability to modulate kinases. For example, the compounds might be coupled to a label such as a radioactive label, a fluorescent label and the like, or may be coupled to targeting agents such as antibodies or fragments, or to fragments to aid purification such as FLAG or a histidine tag. The compounds may also be coupled to specific binding partners such as biotin for use in assay procedures or to moieties that alter their biological half-lives such as polyethylene glycol. Thus, the methods of the invention employ the invention compounds per se as well as conjugates thereof.

Synthesis of Compounds

Compounds of the present invention may be synthesized using standard synthetic techniques known to those of skill in the art or using methods known in the art in combination with methods described herein. See, e.g., March, Advanced Organic Chemistry 4$^{th}$ Ed., (Wiley 1992); Carey and Sundberg, Advanced Organic Chemistry 3$^{rd}$ Ed., Vols. A and B (Plenum 1992), and Green and Wuts, Protective Groups in Organic Synthesis 2$^{nd}$ Ed. (Wiley 1991). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The compounds of the invention are synthesized by methods well known in the art. The compounds of the invention are ureas or cyclic forms thereof and can be synthesized using generally known procedures for urea synthesis.

In one group of methods, an amine is reacted with an isocyanate in an aprotic solvent.

Typically, in some embodiments, a molar excess of the amine is used in the presence of an aprotic solvent and the reaction is conducted at room temperature. The reaction mixture is then poured into water and precipitated with salt to recover the crude product which is then purified according to standard methods.

In alternative methods, the ureas are formed from two separate amine reactants in the presence of a condensing agent such as 1,1, carbonyldiimidazole (CDI) in the presence of an inert nonpolar solvent such as dichloromethane. One of the amines is first added to a solution of CDI in solvent under cooling conditions and then stirred at room temperature with the other amine. After removal of solvent, the crude product can be purified using standard procedures.

In still another method, one of the amines is added in an aprotic solvent to a solution of triphosgene and then treated with the other amine reactant dissolved in an inert solvent in the presence of base such as triethylamine. After reaction at room temperature, the mixture may be diluted with, for example, ethylacetate and washed with water and brine, dried and purified.

In still another method, one of the amine components is treated with 4-nitrophenylchloroformate in the presence of mild base in a solvent such as N-methylpyrrolidone (NMP). The other amine is then added and the reaction mixture heated, then cooled, poured into water, extracted into chloroform and further purified.

Alternatively, the urea may be formed by the reaction of an amine with the counterpart halo acylamine which is formed from the parent amine by treatment with phosgene and base in an inert solvent such as methylene dichloride or by reacting an amine with its counterpart amine with an acyl amine containing an alternate leaving group formed by reaction of that amine with 4-nitrophenylchloroformate in the presence of an amine base and in an inert solvent.

Details of these methods can be found in Matsuno et al. *J. Med. Chem.* 45:3057-66 (2002); Matsuno et al. *J. Med. Chem.* 45:4513-23 (2002); and Pandley et al., *J. Med. Chem.* 45:3772-93 (2002).

Cyclized forms of the ureas may be obtained by treating the formed urea with dibromo derivatives of the bridge, typically in the presence of a strong base and in an inert aprotic polar solvent.

The ureas may be converted to thioureas by treating with Lawesson's reagent in the presence of toluene.

For compounds having the moiety $Ar^1$-L-$Ar^2$ is obtained by first protecting the amino group of p-hydroxy aniline destined to become $Ar^1$ with a protecting agent such as Boc and then coupling the hydroxy group of $Ar^1$ to an aryl alkyl halide. This coupling is conducted in the presence of strong base and in an aprotic solvent. After deprotection, the urea is formed by reaction with the isoxazole isocyanate. These techniques are exemplified below.

Selected examples of covalent linkages and precursor functional groups which yield them are given in the Table entitled "Examples of Covalent Linkages and Precursors Thereof." Precursor functional groups are shown as electrophilic groups and nucleophilic groups. The functional group on the organic substance may be attached directly, or attached via any useful spacer or linker as defined below.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In general, carbon electrophiles are susceptible to attack by complementary nucleophiles, including carbon nucleophiles, wherein an attacking nucleophile brings an electron pair to the carbon electrophile in order to form a new bond between the nucleophile and the carbon electrophile.

Suitable carbon nucleophiles include, but are not limited to alkyl, alkenyl, aryl and alkynyl Grignard, organolithium, organozinc, alkyl-, alkenyl, aryl- and alkynyl-tin reagents (organostannanes), alkyl-, alkenyl-, aryl- and alkynyl-borane reagents (organoboranes and organoboronates); these carbon nucleophiles have the advantage of being kinetically stable in water or polar organic solvents. Other carbon nucleophiles include phosphorus ylids, enol and enolate reagents; these carbon nucleophiles have the advantage of being relatively easy to generate from precursors well known to those skilled in the art of synthetic organic chemistry. Carbon nucleophiles, when used in conjunction with carbon electrophiles, engender new carbon-carbon bonds between the carbon nucleophile and carbon electrophile.

Non-carbon nucleophiles suitable for coupling to carbon electrophiles include but are not limited to primary and secondary amines, thiols, thiolates, and thioethers, alcohols, alkoxides, azides, semicarbazides, and the like. These non-carbon nucleophiles, when used in conjunction with carbon electrophiles, typically generate heteroatom linkages (C—X—C), wherein X is a heteroatom, e.g, oxygen or nitrogen.

The term "protecting group" refers to chemical moieties that block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester derivatives as exemplified herein, or they may be blocked with oxidativelyremovable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a $Pd_0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

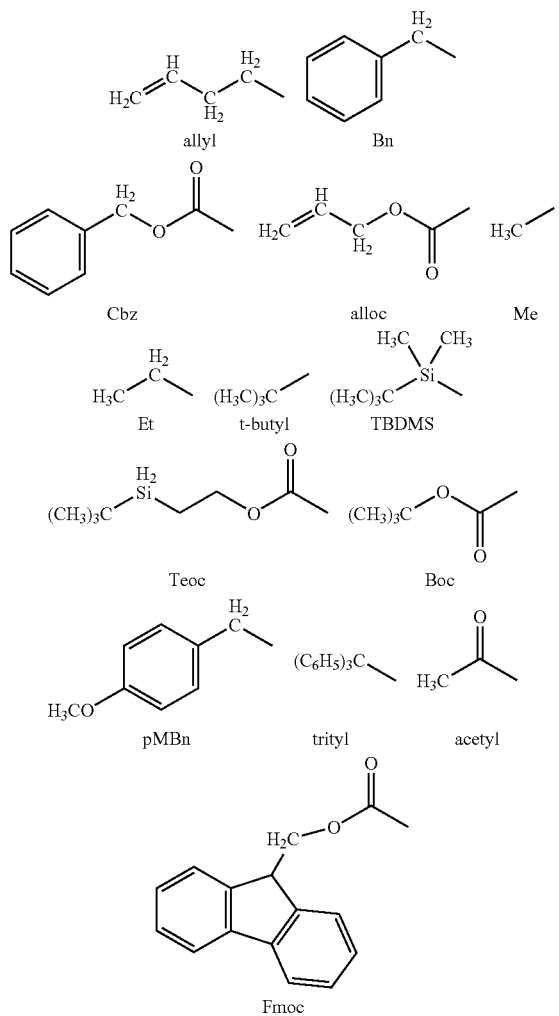

Other protecting groups are described in Greene and Wuts, Protective Groups in Organic Synthesis, 3rd Ed., John Wiley & Sons, New York, N.Y., 1999, which is incorporated herein by reference in its entirety.

Biological Activity

Protein kinases (PKs) play a role in signal transduction pathways regulating a number of cellular functions, such as cell growth, differentiation, and cell death. PKs are enzymes that catalyze the phosphorylation of hydroxy groups on tyrosine, serine and threonine residues of proteins. Abnormal PK activity has been related to disorders ranging from relatively non life threatening diseases such as psoriasis to extremely virulent diseases such as glioblastoma (brain cancer). In addition, a variety of tumor types have dysfunctional growth factor receptor tyrosine kinases, resulting in inappropriate mitogenic signaling. Protein kinases are believed to be involved in many different cellular signal transduction pathways. In particular, protein tyrosine kinases (PTK) are attractive targets in the search for therapeutic agents, not only for cancer, but also against many other diseases. Blocking or regulating the kinase phosphorylation process in a signaling cascade may help treat conditions such as cancer or inflammatory processes.

Protein tyrosine kinases are a family of tightly regulated enzymes, and the aberrant activation of various members of the family is one of the hallmarks of cancer. The protein-tyrosine kinase family includes Bcr-Abl tyrosine kinase, and can be divided into subgroups that have similar structural organization and sequence similarity within the kinase domain. The members of the type III group of receptor tyrosine kinases include the platelet-derived growth factor (PDGF) receptors (PDGF receptors α and β), colony-stimulating factor (CSF-1) receptor (CSF-1R, c-Fms), FLT-3, and stem cell or steel factor receptor (c-kit).

The compounds, compositions, and methods provided herein are useful to modulate the activity of kinases including, but not limited to, ERBB2, ABL1, AURKA, CDK2, EGFR, FGFR1, LCK, MAPK14, PDGFR, KDR, ABL1, BRAF, ERBB4, FLT3, KIT, and RAF1. In some embodiments, the compositions and methods provided herein modulate the activity of a mutant kinase.

Inhibition by the compounds provided herein can be determined using any suitable assay. In one embodiment, inhibition is determined in vitro. In a specific embodiment, inhibition is assessed by phosphorylation assays. Any suitable phosphorylation assay can be employed. For example, membrane autophosphorylation assays, receptor autophosphorylation assays in intact cells, and ELISA's can be employed. See, e.g., Gazit, et al., J. Med. Chem. (1996) 39:2170-2177, Chapter 18 in CURRENT PROTOCOLS IN MOLECULAR BIOLOGY (Ausubel, et al., eds. 2001). Cells useful in such assays include cells with wildtype or mutated forms. In one embodiment, the wildtype is a kinase that is not constitutively active, but is activated with upon dimerization. For example, the mutant FLT3 kinase is constitutively active via internal tandem duplication mutations or point mutations in the activation domain. Suitable cells include those derived through cell culture from patient samples as well as cells derived using routine molecular biology techniques, e.g., retroviral transduction, transfection, mutagenesis, etc. Exemplary cells include Ba/F3 or 32Dc13 cells transduced with, e.g., MSCV retroviral constructs FLT3-ITD (Kelly et al., 2002); Molm-13 and Molm14 cell line (Fujisaki Cell Center, Okayama, Japan); HL60 (AML-M3), AML193 (AML-M5), KG-1, KG-1a, CRL-1873, CRL-9591, and THP-1 (American Tissue Culture Collection, Bethesda, Md.); or any suitable cell line derived from a patient with a hematopoietic malignancy.

In some embodiments, the compounds described herein significantly inhibit receptor tyrosine kinases. A significant inhibition of a receptor tyrosine kinase activity refers to an $IC_{50}$ of less than or equal to 100 μM. Preferably, the compound can inhibit activity with an $IC_{50}$ of less than or equal to 50 μM, more preferably less than or equal to 10 μM, more preferably less than 1 μM, or less than 100 nM, most preferably less than 50 nM. Lower $IC_{50}$'s are preferred because the $IC_{50}$ provides an indication as to the in vivo effectiveness of the compound. Other factors known in the art, such as compound half-life, biodistribution, and toxicity should also be considered for therapeutic uses. Such factors may enable a compound with a lower $IC_{50}$ to have greater in vivo efficacy than a compound having a higher $IC_{50}$. Preferably, a compound that inhibits activity is administered at a dose where the effective tyrosine phosphorylation, i.e., $IC_{50}$, is less than its cytotoxic effects, $LD_{50}$.

In some embodiments, the compounds selectively inhibit one or more kinases. Selective inhibition of a kinase, such as FLT3, p38 kinase, STK10, MKNK2, Bcr-Abl, c-kit, or PDGFR, is achieved by inhibiting activity of one kinase, while having an insignificant effect on other members of the superfamily.

c-kit

The Stem Cell Factor (SCF) receptor c-kit is a receptor protein tyrosine kinase that initiates cell growth and proliferation signal transduction cascades in response to SCF binding. c-kit is a 145-kD transmembrane glycoprotein and is the normal cellular homolog of the v-kit retroviral oncogene, It is also a member of the Type III transmembrane receptor protein tyrosine kinase subfamily, which includes the macrophage colony-stimulating factor-1 receptor, also known as the FMS receptor, the related FLT-3 receptor, and the platelet-derived growth factor (PDGF) α and β receptors. The c-kit gene product is expressed in hematopoietic progenitor cells, mast cells, germ cells, interstitial cells of Cajal (ICC), and some human tumors. Inactivating mutations of c-kit or its ligand, Steel factor (SLF), have demonstrated that the normal functional activity of the c-kit gene product is essential for maintenance of normal hematopoeisis, melanogenesis, genetogensis, and growth and differentiation of mast cells and ICC. SLF is produce by human and murine hematopoietic stromal cells, including endothelial cells, fibroblasts, and bone marrow-derived stromal cells.

In addition to its importance in normal cellular physiologic activities, c-kit plays a role in the biological aspects of certain human cancers, including germ cell tumors, mast cell tumors, gastrointestinal stromal tumors (GIST), small-cell lung cancer, melanoma, breast cancer, acute myelogenous leukemia (AML), and neuroblastoma. Proliferation of tumor cell growth mediated by c-kit can occur by a specific mutation of the c-kit polypeptide that results in ligand independent activation or by autocrine stimulation of the receptor. In the former case, mutations that cause constitutive activation of c-kit kinase activity in the absence of SCF binding are implicated in malignant human cancers, including gastrointestinal stromal tumors, germ cell tumors, mast cell tumors, and myeloid leukemia's and in mastocytosis.

The activity of the c-kit receptor protein tyrosine kinase is regulated in normal cells, and as discussed the deregulated c-kit kinase activity is implicated in the pathogenesis of human cancers. In some types of tumors, inhibition of c-kit activity reduces cellular proliferation, suggesting a role for use of pharmacologic inhibitors of c-kit in the treatment of c-kit dependent malignancies.

In one embodiment, compositions and methods provided herein are effective to modulate the activity of c-kit. In other embodiments, compositions and methods provided herein are effective to selectively modulate the activity of c-kit.

Bcr-Abl c-Abl is a nonreceptor tyrosine kinase that contributes to several leukogenic fusion proteins, including the deregulated tyrosine kinase, Bcr-Abl. Chronic myeloid leukemia (CML) is a clonal disease involving the pluripotent hematopoietic stem cell compartment and is associated with the Philadelphia chromosome [Nowell P. C. and Hungerford D. A., Science 132,1497 (1960)], a reciprocal translocation between chromosomes 9 and 22 ([(9:22) (q34; q11)]) [Rowley J. D., Nature 243, 290-293 (1973)]. The translocation links the c-Abl tyrosine kinase oncogene on chromosome 9 to the 5, half of the bcr (breakpoint cluster region) gene on chromosome 22 and creates the fusion gene bcr/abl. The fusion gene produces a chimeric 8.5 kB transcript that codes for a 210-kD fusion protein ($p210^{bcr-abl}$), and this gene product is an activated protein tyrosine kinase. Thus, the Abelson tyrosine kinase is improperly activated by accidental fusion of the bcr gene with the gene encoding the intracellular non-receptor tyrosine kinase, c-Abl.

The Bcr domain interferes with the intramolecular Abl inhibitory loop and unveils a constitutive kinase activity that is absent in the normal Abl protein. Bcr-Abl tyrosine kinase is a potent inhibitor of apoptosis, and it is well accepted that the oncoprotein expresses a constitutive tyrosine kinase activity that is necessary for its cellular transforming activity. Constitutive activity of the fusion tyrosine kinase Bcr-Abl has been established as the characteristic molecular abnormality present in virtually all cases of chronic myeloid leukemia (CML) and up to 20 percent of adult acute lymphoblastic leukemia (ALL) [Faderl S. et al., N Engl J Med 341, 164-172 (1999); Sawyers C. L., N Engl J Med 340, 1330-1340 (1999)]. Mutations present in the kinase domain of the Bcr-Abl gene of patients suffering from CML or Ph+ALL account for the biological resistance of these patients towards STI571 treatment in that said mutations lead to resistance of the Bcr-Abl tyrosine kinase towards inhibition by STI571. Novel therapies for CML need to address this emerging problem of clinical resistance to STI571 (Gleevec). Because tumor progression in patients receiving STI571 seem to be mediated by amplification of or mutation in the Bcr-Abl gene that causes the tyrosine kinase to be less efficiently inhibited by the drug, newer tyrosine kinase inhibitors may be susceptible to the same mechanisms of resistance. None the less, these findings are extremely valuable in the development of new compounds or combinations of compounds which are capable to overcome resistance towards treatment with STI571. Furthermore, in view of the large number of protein kinase inhibitors and the multitude of proliferative and other PK-related diseases, there is an ever-existing need to provide novel classes of compounds that are useful as PK inhibitors and thus in the treatment of these PTK related diseases.

In one embodiment, compositions and methods provided herein are effective to modulate the activity of Bcr-Abl. In other embodiments, compositions and methods provided herein are effective to selectively modulate the activity of Bcr-Abl. In a further embodiment, compositions of Formula G, e.g., compounds described in Examples M and O, inhibit the protein tyrosine kinase associated with mutated bcr-abl, which gives rise to observed clinical resistance towards treatment with STI571.

PDGFR

Platelet-Derived Growth factor Receptors (PDGFR's) are receptor tyrosine kinases that regulate proliferative and chemotatic responses. PDGFR's have two forms-PDGFR-α (CD140a) and PDGFR-β (CD140b). PDGFRs are normally found in connective tissue and glia but are lacking in most epithelia, and PDGF expression has been shown in a number of different solid tumors, from glioblastomas to prostate carcinomas. For instance, PDGFR kinases are involved in various cancers such as T-cell lymphoma, acute lymphoblastic leukemia (ALL), acute myeloid leukemia (AML), melanoma, glioblastoma and others (see Bellamy W. T. et al., Cancer Res. 1999, 59, 728-733). In these various tumor types, the biological role of PDGF signaling can vary from autocrine stimulation of cancer cell growth to more subtle paracrine interactions involving adjacent stroma and angiogenesis. Furthermore, PDGF has been implicated in the pathogenesis of several nonmalignant proliferation diseases, including atherosclerosis, restenosis following vascular angioplasty and fibroproliferative disorders such as obliterative bronchiolitis. Therefore, inhibiting the PDGFR kinase activity with small molecules may interfere with tumor growth and angiogenesis.

The binding of PDGFR to its receptor activates the intracellular tyrosine kinase, resulting in the autophorylation of the receptor as well as other intracellular substrates such as Src, GTPase Activating Protein (GAP), and phosphatidylinositol-3-phosphate. Upon autophorylation the PDGFR also forms complexes with other signaling moieties including phospholipase C-γ (PLC-γ), phosphatidylinositol-3-kinase (PI3K), and raf-1. It appears to be involved in communication between endothelial cells and pericytes, a communication that is essential for normal blood vessel development.

It has been found previously that the disruption of the PDGFR-β in mice oblates neovascular pericytes that from part of the capillary wall. See Lindahl, P., et al., *Science* (1997) 227:242-245; Hellstrom, M., . . . , et al., *Development* (1999) 126:3047-3055. A recent study by Bergers, G., et al., *J. Clin. Invest.* (2003) 111:1287-1295 has suggested that inhibition of PDGFR kinase activity by certain compounds such as SU6668 or ST1571/Gleevec inhibits tumor growth and that these compounds combined with VEGFR inhibitor SU5416 were very effective in reducing tumor growth. Further, inhibition of PDGFR-β by Gleevec enhanced tumor chemotherapeutic efficacy in mice. Pietras, K., et al., *Cancer Res.* (2002) 62:5476-5484. A review of PDGFR receptors as cancer drug targets by Pietras, K., et al., appears in *Cancer Cell.* (2003) 3:439-443. Inhibition of this kinase activity is also effective where abnormal forms of PDGFR, such as the TEL/PDGFR-β fusion protein associated with chronic myelomonocytic leukemia (CMML) is produced. See also, Grisolano, J. L., et al., *Proc. Natl. Acad. Sci. USA.* (2003) 100:9506-9511.

Inhibitors of PDGFR-β frequently also inhibit additional kinases involved in tumor growth such as BCR-ABL, TEL-ABL, and PDGFR-α. See, Carroll, M., et al., *Blood* (1997) 90:4947-4952 and Cools, J., et al., *Cancer Cell* (2003) 3:450-469. One class of established inhibitors of PDGFR kinase activity includes quinazoline derivatives which comprise piperazine substitutions. Such compounds are disclosed in Yu, J-C., et al., *J. Pharmacol. Exp. Ther.* (2001) 298:1172-1178; Pandey, A., et al., *J. Med. Chem.* (2002) 45:3772-3793 Matsuno, K., et al., *J. Med. Chem.* (2002) 45: 4413-4523 and Matsuno, K., et al., ibid., 3057-3066. Still another class is represented by 2-phenyl pyrimidines as disclosed by Buchdunger, E., et al., *Proc. Natl. Acad. Sci. USA.* (1995) 92:2558-2562. However, there remains a need for additional compounds that are effective in inhibiting PDGFR kinase activity. Given the complexities of signal transduction with the redundancy and crosstalk between various pathways, the identification of specific PDGFR tyrosine kinase inhibitors permits accurate targeting with limited or no unwanted inhibition of the pathways, thus reducing the toxicity of such inhibitory compounds.

In one embodiment, compositions and methods provided herein are effective to modulate the activity of PDGFR. In other embodiments, compositions and methods provided herein are effective to selectively modulate the activity of PDGFR.

FLT-3

FLT3 kinase is a tyrosine kinase receptor involved in the regulation and stimulation of cellular proliferation. See e.g., Gilliland et al., *Blood* 100:1532-42 (2002). The FLT3 kinase is a member of the class III receptor tyrosine kinase (RTKIII) receptor family and belongs to the same subfamily of tyrosine kinases as c-kit, c-fms, and the platelet-derived growth factor α and β receptors. See e.g., Lyman et al., *FLT3 Ligand in* THE CYTOKINE HANDBOOK 989 (Thomson et al., eds. 4th Ed.) (2003). The FLT3 kinase has five immunoglobulin-like domains in its extracellular region as well as an insert region of 75-100 amino acids in the middle of its cytoplasmic domain. FLT3 kinase is activated upon the binding of the FLT3 ligand, which causes receptor dimerization. Dimerization of the FLT3 kinase by FLT3 ligand activates the intracellular kinase activity as well as a cascade of downstream substrates including Stat5, Ras, phosphatidylinositol-3-kinase (PI3K), PLCγ, Erk2, Akt, MAPK, SHC, SHP2, and SHIP. See e.g., Rosnet et al., *Acta Haematol.* 95:218 (1996); Hayakawa et al., *Oncogene* 19:624 (2000); Mizuki et al., *Blood* 96:3907 (2000); and Gilliland et al., *Curr. Opin. Hematol.* 9: 274-81 (2002). Both membrane-bound and soluble FLT3 ligand bind, dimerize, and subsequently activate the FLT3 kinase.

In normal cells, immature hematopoietic cells, typically CD34+ cells, placenta, gonads, and brain express FLT3 kinase. See, e.g., Rosnet, et al., *Blood* 82:1110-19 (1993); Small et al., *Proc. Natl. Acad. Sci. U.S.A.* 91:459-63 (1994); and Rosnet et al., *Leukemia* 10:238-48 (1996). However, efficient stimulation of proliferation via FLT3 kinase typically requires other hematopoietic growth factors or interleukins. FLT3 kinase also plays a critical role in immune function through its regulation of dendritic cell proliferation and differentiation. See e.g., McKenna et al., *Blood* 95:3489-97 (2000).

Numerous hematologic malignancies express FLT3 kinase, the most prominent of which is AML. See e.g., Yokota et al., *Leukemia* 11:1605-09 (1997). Other FLT3 expressing malignancies include B-precursor cell acute lymphoblastic leukemias, myelodysplastic leukemias, T-cell acute lymphoblastic leukemias, and chronic myelogenous leukemias. See e.g., Rasko et al., *Leukemia* 9:2058-66 (1995).

FLT3 kinase mutations associated with hematologic malignancies are activating mutations. In other words, the FLT3 kinase is constitutively activated without the need for binding and dimerization by FLT3 ligand, and therefore stimulates the cell to grow continuously.

Several studies have identified inhibitors of FLT3 kinase activity that also inhibit the kinase activity of related receptors, e.g., VEGF receptor (VEGFR), PDGF receptor (PDGFR), and kit receptor kinases. See e.g., Mendel et al., *Clin. Cancer Res.* 9:327-37 (2003); O'Farrell et al., *Blood* 101:3597-605 (2003); and Sun et al., *J. Med. Chem.* 46:1116-19 (2003). Such compounds effectively inhibit FLT3 kinase-mediated phosphorylation, cytokine production, cellular proliferation, resulting in the induction of apoptosis. See e.g., Spiekermann et al., *Blood* 101:1494-1504 (2003). Moreover, such compounds have potent antitumor activity in vitro and in vivo.

In some embodiments, the kinase is a class III receptor tyrosine kinase (RTKIII). In other embodiments, the kinase is a tyrosine kinase receptor intimately involved in the regulation and stimulation of cellular proliferation. In still other embodiments, the kinase is a fms-like tyrosine kinase 3 receptor (FLT-3 kinase). In this context, inhibition and reduction of the activity of FLT-3 kinase refers to a lower level of measured activity relative to a control experiment in which the protein, cell, or subject is not treated with the test compound, whereas an increase in the activity of FLT-3 kinase refers to a higher level of measured activity relative to a control experiment. In particular embodiments, the reduction or increase is at least 10%. One of skill in the art will appreciate that reduction or increase in the activity of FLT-3 kinase of at least 20%, 50%, 75%, 90% or 100% or any integer between 10% and 100% may be preferred for particular applications.

Compounds provided herein are useful in treating conditions characterized by inappropriate FLT3 activity such as proliferative disorders. FLT3 activity includes, but is not limited to, enhanced FLT3 activity resulting from increased or de novo expression of FLT3 in cells, increased FLT3 expression or activity, and FLT3 mutations resulting in constitutive activation. The existence of inappropriate or abnormal FLT3 ligand and FLT3 levels or activity can be determined using well known methods in the art. For example, abnormally high FLT3 levels can be determined using commercially available ELISA kits. FLT3 levels can be determined using flow cytometric analysis, immunohistochemical analysis, and in situ hybridization techniques.

An inappropriate activation of the FLT3 can be determined by an increase in one or more of the activities occurring subsequent to FLT3 binding: (1) phosphorylation or autophosphorylation of FLT3; (2) phosphorylation of a FLT3 substrate, e.g., Stat5, Ras; (3) activation of a related complex, e.g., PI3K; (4) activation of an adaptor molecule; and (5) cellular proliferation. These activities are readily measured by well known methods in the art.

Formulations

The compounds described herein can be used to prepare a medicament, such as by formulation into pharmaceutical compositions for administration to a subject using techniques generally known in the art. A summary of such pharmaceutical compositions may be found, for example, in Remington's Pharmaceutical Sciences, Mack Publishing Co., Easton, Pa. The compounds of the invention can be used singly or as components of mixtures. Preferred forms of the compounds are those for systemic administration as well as those for topical or transdermal administration. Formulations designed for timed release are also within the scope of the invention. Formulation in unit dosage form is also preferred for the practice of the invention.

In unit dosage form, the formulation is divided into unit doses containing appropriate quantities of one or more compounds. The unit dosage may be in the form of a package containing discrete quantities of the formulation. Non-limiting examples are packeted tablets or capsules, and powders in vials or ampoules.

The compounds described herein may be labeled isotopically (e.g. with a radioisotope) or by any other means, including, but not limited to, the use of chromophores or fluorescent moieties, bioluminescent labels, or chemiluminescent labels. The compositions may be in conventional forms, either as liquid solutions or suspensions, solid forms suitable for solution or suspension in a liquid prior to use, or as emulsions. Suitable excipients or carriers are, for example, water, saline, dextrose, glycerol, alcohols, aloe vera gel, allantoin, glycerin, vitamin A and E oils, mineral oil, propylene glycol, PPG-2 myristyl propionate, and the like. Of course, these compositions may also contain minor amounts of nontoxic, auxiliary substances, such as wetting or emulsifying agents, pH buffering agents, and so forth.

Methods for the preparation of compositions comprising the compounds described herein include formulating the derivatives with one or more inert, pharmaceutically acceptable carriers to form either a solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein.

A carrier of the invention can be one or more substances which also serve to act as a diluent, flavoring agent, solubilizer, lubricant, suspending agent, binder, or tablet disintegrating agent. A carrier can also be an encapsulating material.

In powder forms of the compositions, the carrier is preferably a finely divided solid in powder form which is interdispersed as a mixture with a finely divided powder from of one or more compound. In tablet forms of the compositions, one or more compounds is intermixed with a carrier with appropriate binding properties in suitable proportions followed by compaction into the shape and size desired. Powder and tablet form compositions preferably contain between about 5 to about 70% by weight of one or more compound. Carriers that may be used in the practice of the invention include, but are not limited to, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The compounds of the invention may also be encapsulated or microencapsulated by an encapsulating material, which may thus serve as a carrier, to provide a capsule in which the derivatives, with or without other carriers, is surrounded by the encapsulating material. In an analogous manner, cachets comprising one or more compounds are also provided by the instant invention. Tablet, powder, capsule, and cachet forms of the invention can be formulated as single or unit dosage forms suitable for administration, optionally conducted orally.

In suppository forms of the compositions, a low-melting wax such as, but not limited to, a mixture of fatty acid glycerides, optionally in combination with cocoa butter is first melted. One or more compounds are then dispersed into the melted material by, as a non-limiting example, stirring. The non-solid mixture is then placed into molds as desired and allowed to cool and solidify.

Non-limiting compositions in liquid form include solutions suitable for oral or parenteral administration, as well as suspensions and emulsions suitable for oral administration. Sterile aqueous based solutions of one or more compounds, optionally in the presence of an agent to increase solubility of the derivative(s), are also provided. Non-limiting examples of sterile solutions include those comprising water, ethanol, and/or propylene glycol in forms suitable for parenteral administration. A sterile solution of the invention may be prepared by dissolving one or more compounds in a desired solvent followed by sterilization, such as by filtration through a sterilizing membrane filter as a non-limiting example. In another embodiment, one or more compounds are dissolved into a previously sterilized solvent under sterile conditions.

A water based solution suitable for oral administration can be prepared by dissolving one or more compounds in water and adding suitable flavoring agents, coloring agents, stabilizers, and thickening agents as desired. Water based suspensions for oral use can be made by dispersing one or more compounds in water together with a viscous material such as, but not limited to, natural or synthetic gums, resins, methyl cellulose, sodium carboxymethyl cellulose, polyvinylpyrrolidone, and other suspending agents known to the pharmaceutical field.

In therapeutic use, the compounds of the invention are administered to a subject at dosage levels of from about 0.5 mg/kg to about 8.0 mg/kg of body weight per day. For example, a human subject of approximately 70 kg, this is a dosage of from 35 mg to 560 mg per day. Such dosages, however, may be altered depending on a number of variables, not limited to the activity of the compound used, the condition to be treated, the mode of administration, the requirements of the individual subject, the severity of the condition being treated, and the judgment of the practitioner.

The foregoing ranges are merely suggestive, as the number of variables in regard to an individual treatment regime is large, and considerable excursions from these recommended values are not uncommon.

Methods of Use

By modulating kinase activity, the compounds disclosed herein can be used to treat a variety of diseases. Suitable conditions characterized by undesirable protein-kinase activity can be treated by the compounds presented herein. As used herein, the term "condition" refers to a disease, disorder, or related symptom where inappropriate kinase activity is present. In some embodiments, these conditions are characterized by aggressive neovasculaturization including tumors, especially acute myelogenous leukemia (AML), B-precursor cell acute lymphoblastic leukemias, myelodysplastic leukemias, T-cell acute lymphoblastic leukemias, and chronic myelogenous leukemias (CMLs). In some embodiments, a FLT3 modulating compounds may be used to treat tumors. The ability of compounds that inhibit FLT3 kinase activity to treat tumors has been established. Compounds having this property include SU5416 (Sugen), PKC412 (Novartis), GTP-14564 and CT53518 (Millennium). See e.g., Giles et al., Blood 102:795-801 (2003); Weisberg et al., Cancer Cell 1:433-43 (2002); Murata et al., J. Biol. Chem. 278:32892-98 (2003); and Kelly et al., Cancer Cell 1:421-32 (2002).

Compounds presented herein are useful in the treatment of a variety of biologically aberrant conditions or disorders related to tyrosine kinase signal transduction. Such disorders pertain to abnormal cell proliferation, differentiation, and/or metabolism. Abnormal cell proliferation may result in a wide array of diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis).

In various embodiments, compounds presented herein regulate, modulate, and/or inhibit disorders associated with abnormal cell proliferation by affecting the enzymatic activity of one or more tyrosine kinases and interfering with the signal transduced by said kinase. More particularly, the present invention is directed to compounds which regulate, modulate said kinase mediated signal transduction pathways as a therapeutic approach to cure leukemia and many kinds of solid tumors, including but not limited to carcinoma, sarcoma, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

In other embodiments, compounds herein are useful in the treatment of cell proliferative disorders including cancers, blood vessel proliferative disorders, fibrotic disorders, and mesangial cell proliferative disorders. Blood vessel proliferation disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness. Conversely, disorders related to the shrinkage, contraction or closing of blood vessels, such as restenosis, are also implicated.

Fibrotic disorders refer to the abnormal formation of extracellular matrix. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Other fibrotic disorders implicated include atherosclerosis (see, below).

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. The cell proliferative disorders which are indications of the present invention are not necessarily independent. For example, fibrotic disorders may be related to, or overlap, with blood vessel proliferative disorders. For example, atherosclerosis results, in part, in the abnormal formation of fibrous tissue within blood vessels.

Compounds of the invention can be administered to a subject upon determination of the subject as having a disease or unwanted condition that would benefit by treatment with said derivative. The determination can be made by medical or clinical personnel as part of a diagnosis of a disease or condition in a subject. Non-limiting examples include determination of a risk of acute myelogenous leukemia (AML), B-precursor cell acute lymphoblastic leukemias, myelodysplastic leukemias, T-cell acute lymphoblastic leukemias, and chronic myelogenous leukemias (CMLs).

The methods of the invention can comprise the administration of an effective amount of one or more compounds as disclosed herein, optionally in combination with one or more other active agents for the treatment of a disease or unwanted condition as disclosed herein. The subject is preferably human, and repeated administration over time is within the scope of the present invention.

The present invention thus also provides compounds described above and their salts or solvates and pharmaceutically acceptable salts or solvates thereof for use in the prevention or treatment of disorders mediated by aberrant protein tyrosine kinase activity such as human malignancies and the other disorders mentioned above. The compounds of the present invention are especially useful for the treatment of disorders caused by aberrant kinase activity such as breast, ovarian, gastric, pancreatic, non-small cell lung, bladder, head and neck cancers, and psoriasis. The cancers include hematologic cancers, for example, acute myelogenous leukemia (AML), B-precursor cell acute lymphoblastic leukemias, myelodysplastic leukemias, T-cell acute lymphoblastic leukemias, and chronic myelogenous leukemias (CMLs).

A further aspect of the invention provides a method of treatment of a human or animal subject suffering from a disorder mediated by aberrant protein tyrosine kinase activity, including susceptible malignancies, which comprises administering to the subject an effective amount of a compound described above or a pharmaceutically acceptable salt or solvate thereof.

A further aspect of the present invention provides the use of a compound described above, or a pharmaceutically acceptable salt or solvate thereof, in the preparation of a medicament for the treatment of cancer and malignant tumors. The cancer can be stomach, gastric, bone, ovary, colon, lung, brain, larynx, lymphatic system, genitourinary tract, ovarian, squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, leukemia, acute myelogenous leukemia (AML), B-precursor cell acute lymphoblastic leukemias, myelodysplastic leukemias, T-cell acute lymphoblastic leukemias, and chronic myelogenous leukemias (CMLs), glioma, colorectal cancer, genitourinary cancer gastrointestinal cancer, or pancreatic cancer.

In accordance with the present invention, compounds provided herein are useful for preventing and treating conditions associated with ischemic cell death, such as myocardial infarction, stroke, glaucoma, and other neurodegenerative conditions. Various neurodegenerative conditions which may involve apoptotic cell death, include, but are not limited to, Alzheimer's Disease, ALS and motor neuron degeneration, Parkinson's disease, peripheral neuropathies, Down's Syndrome, age related macular degeneration (ARMD), traumatic brain injury, spinal cord injury, Huntington's Disease, spinal muscular atrophy, and HIV encephalitis. The compounds described in detail above can be used in methods and compositions for imparting neuroprotection and for treating neurodegenerative diseases.

The compounds described herein, can be used in a pharmaceutical composition for the prevention and/or the treatment of a condition selected from the group consisting of arthritis (including osteoarthritis, degenerative joint disease, spondyloarthropathies, gouty arthritis, systemic lupus erythematosus, juvenile arthritis and rheumatoid arthritis), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neurodegenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders, and septic shock, arthritis, fever, common cold, pain and cancer in a mammal, preferably a human, cat, livestock or a dog, comprising an amount of a compound described herein or a pharmaceutically acceptable salt thereof effective in such prevention and/or treatment optionally with a pharmaceutically acceptable carrier.

A further aspect of the present invention provides the use of a compound described above, or a pharmaceutically acceptable salt thereof, in the preparation of a medicament for the treatment of psoriasis.

As one of skill in the art will recognize, the compounds can be administered before, during or after the occurrence of a condition or a disease, and the timing of administering the composition containing a compound can vary. Thus, for example, the compounds can be used as a prophylactic and can be administered continuously to subjects with a propensity to conditions and diseases in order to prevent the occurrence of the disorder. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 min. to about 5 hours, a pill, a capsule, transdermal patch, buccal delivery, and the like, or a combination thereof. A compound is preferably administered as soon as is practicable after the onset of a condition or a disease is detected or suspected, and for a length of time necessary for the treatment of the disease, such as, for example, from about 1 month to about 3 months. As one of skill in the art will recognize, the length of treatment can vary for each subject, and the length can be determined using the known criteria. For example, the compound or a formulation containing the compound can be administered for at least 2 weeks, preferably about 1 month to about 5 years, and more preferably from about 1 month to about 3 years.

Kits/Articles of Manufacture

For use in the therapeutic applications described herein, kits and articles of manufacture are also within the scope of the invention. Such kits can comprise a carrier, package, or container that is compartmentalized to receive one or more containers such as vials, tubes, and the like, each of the container(s) comprising one of the separate elements to be used in a method of the invention. Suitable containers include, for example, bottles, vials, syringes, and test tubes. The containers can be formed from a variety of materials such as glass or plastic.

For example, the container(s) can comprise one or more compounds of the invention, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods of the present invention.

A kit of the invention will typically may comprise one or more additional containers, each with one or more of various materials (such as reagents, optionally in concentrated form, and/or devices) desirable from a commercial and user standpoint for use of a compound of the invention. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

The terms "kit" and "article of manufacture" may be used as synonyms.

EXAMPLES

The present invention is further illustrated by the following examples, which should not be construed as limiting in any way. The experimental procedures to generate the data shown are discussed in more detail below. For all formulations herein, multiple doses may be proportionally compounded as is known in the art. The coatings, layers and encapsulations are applied in conventional ways using equipment customary for these purposes.

The invention has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the following examples may be substituted with other suitable reagents. See, e.g., Smith & March, *Advanced Organic Chemistry*, 5$^{th}$ ed. (2001).

Example A

Synthesis of Isoxazole-Ureas

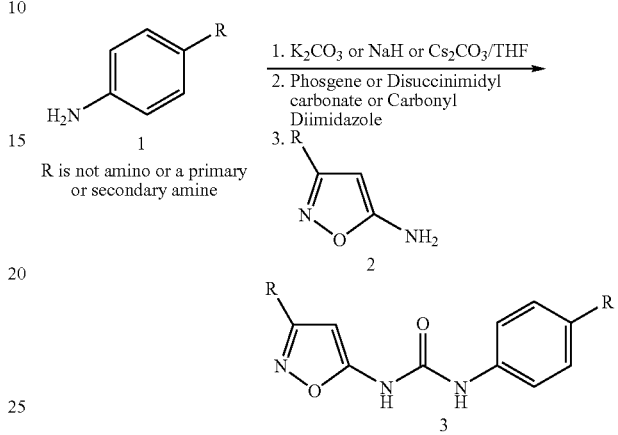

A mixture of amine 1 (1 eq) in dry THF is stirred at room temperature under argon for an hour. Then the stirred suspension is cooled to 0° C. and to it is added dropwise a solution of phosgene or disuccinimidyl carbonate or carbonyl diimidazole (1.2 eq). The reaction is stirred at 0° C. for half an hour. An isoxazol amine 2 in THF is added dropwise and the reaction is allowed to warm to room temperature and stirred overnight. The solvent is removed and extracted with ethyl acetate and water. The organic layer is dried over magnesium sulfate and solvent removed, and the product 3 purified by HPLC.

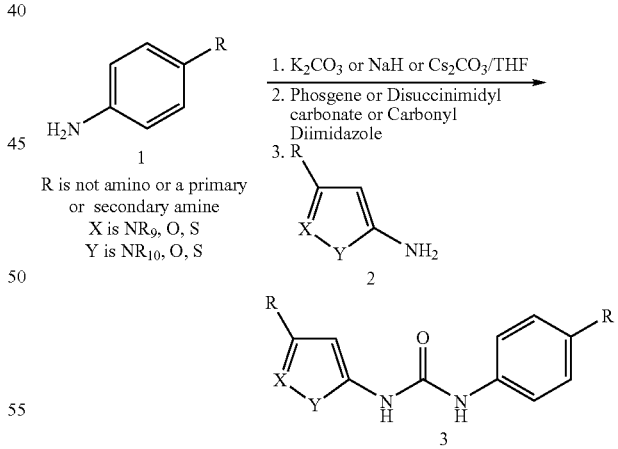

$R_9$ is hydrogen; or alkyl, alkenyl, alkynyl, aryl, cycloalkyl, heterocycloalkyl, or heteroaryl unsubstituted or substituted with one, two or three suitable substituents
$R_{10}$ is hydrogen; or alkyl, alkenyl, alkynyl aryl, cycloalkyl, heterocycloalkyl, or heteroaryl unsubstituted or substituted with one, two or three suitable substituents Alternatively, to a stirring solution of an isoxazol-amine 2 (1 eq) in THF, a mixture of 4-nitrophenyl chloroformate (1.2 eq) and triethyl amine (1.2 eq) is added dropwise at 0° C. The reaction is stirred for two hours at room temperature and the aniline 1 is added. The reaction is refluxed to 80° C. for six hours. The mixture is cooled to room temperature and poured into water and extracted with ethyl acetate and dried over magnesium sulfate, and the product 3 purified by HPLC.

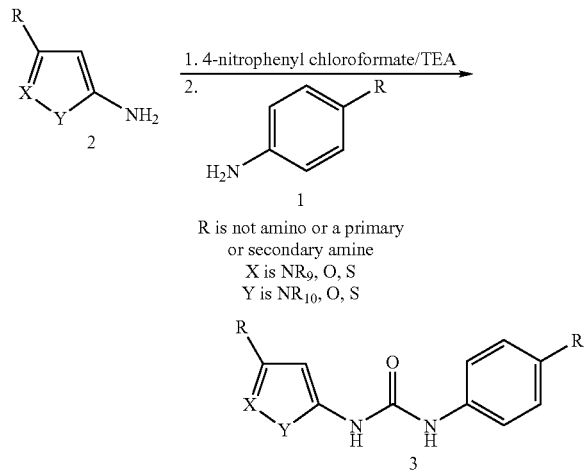

R is not amino or a primary or secondary amine
X is NR$_9$, O, S
Y is NR$_{10}$, O, S R$_9$ is hydrogen; or alkyl, alkenyl, alkynyl, aryl, cycloalkyl, heterocycloalkyl, or heteroaryl unsubstituted or substituted with one, two or three suitable substituents
R$_{10}$ is hydrogen; or alkyl, alkenyl, alkynyl, aryl, cycloalkyl, heterocycloalkyl, or heteroaryl unsubstituted or substituted with one, two or three suitable substituents Alternatively, amine 1 (1 eq) is dissolved in toluene at room temperature and stirred for 10 minutes. Then 3-tert-butyl-isoxazol-5-yl isocyanate 4 in toluene is added and heated at 80° C. for 4 hours. The solvent is removed and the crude mixture is purified by HPLC to obtain 5.

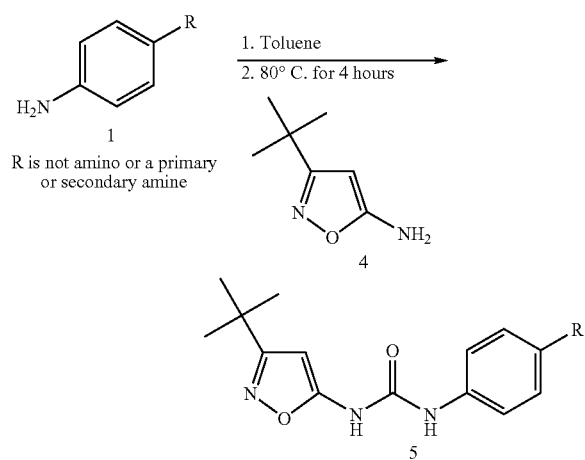

R is not amino or a primary or secondary amine

Synthesis of Compound A1: 1-(5-tert-butylisoxazol-3-yl)-3-(4-chloro-3-(trifluoromethyl)phenyl)urea

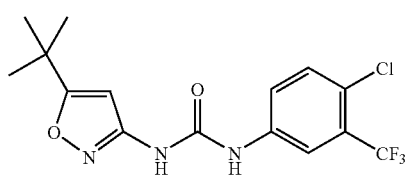

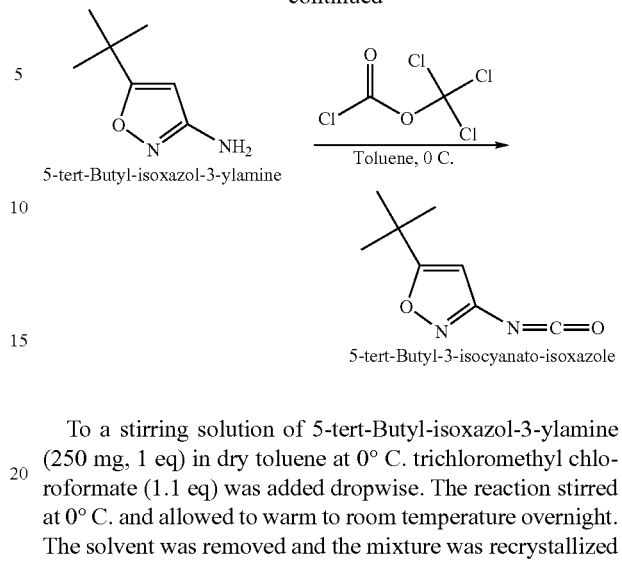

To a stirring solution of 5-tert-Butyl-isoxazol-3-ylamine (250 mg, 1 eq) in dry toluene at 0° C. trichloromethyl chloroformate (1.1 eq) was added dropwise. The reaction stirred at 0° C. and allowed to warm to room temperature overnight. The solvent was removed and the mixture was recrystallized in ethyl acetate. The solid was filtered off and washed with cold ethyl acetate. Yield: 242 mg (83%).

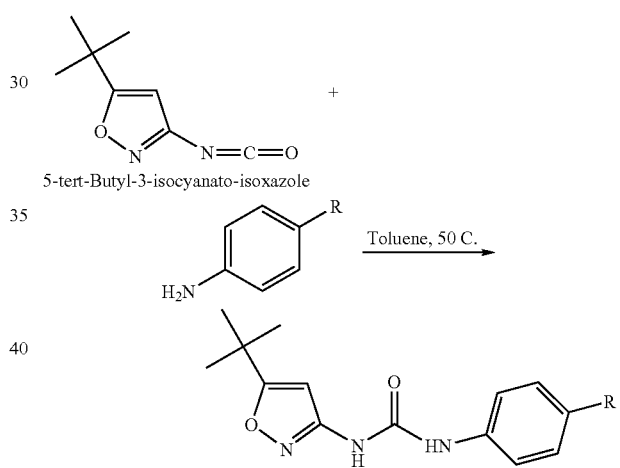

To a flask 5-tert-Butyl-3-isocyanato-isoxazole (242 mg, 1 eq) and substituted aniline (159 mg, 1 eq) was added and dissolved in toluene. The reaction was allowed to stir at 50° C. for three hours. The solvent was removed and the mixture was purified by HPLC. Yield: 188 mg (47%).

Compounds A2 through A57 were synthesized in a manner analogous to Compound A1 using similar starting materials and reagents. The structures are shown below in Table A:

TABLE A

| NO. | CHEMICAL STRUCTURE |
|---|---|
| A1 | 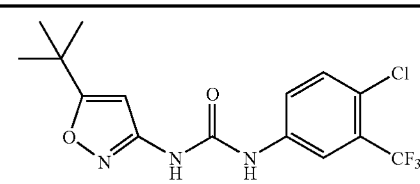 |

TABLE A-continued

| NO. | CHEMICAL STRUCTURE |
|---|---|
| A2 | 5-tert-butyl-isoxazol-3-yl urea with phenyl |
| A3 | 5-tert-butyl-isoxazol-3-yl urea with 4-(2-(4-aminophenyl)ethyl)phenyl |
| A4 | 3-methyl-4-chloro-isoxazol-5-yl urea with phenyl |
| A5 | 5-tert-butyl-isoxazol-3-yl urea with 2-methyl-3-chlorophenyl |
| A6 | 3-methyl-4-chloro-isoxazol-5-yl urea with phenyl |
| A7 | 5-tert-butyl-isoxazol-3-yl urea with 2,4-dichlorophenyl |
| A8 | 5-tert-butyl-isoxazol-3-yl urea with pyren-1-yl |
| A9 | 5-tert-butyl-isoxazol-3-yl urea with 2-(trifluoromethoxy)phenyl |
| A10 | 5-tert-butyl-isoxazol-3-yl urea with naphthalen-1-yl |
| A11 | 3-tert-butyl-isoxazol-5-yl urea with 4-isopropylphenyl |
| A12 | 5-tert-butyl-isoxazol-3-yl urea with 4-OCHF$_2$-phenyl |
| A13 | 3-tert-butyl-isoxazol-5-yl urea with 4-OCF$_3$-phenyl |
| A14 | 5-tert-butyl-isoxazol-3-yl urea with 2,4-difluorophenyl |
| A15 | 5-tert-butyl-isoxazol-3-yl urea with 4-(2-phenylethyl)phenyl |
| A16 | 3-tert-butyl-isoxazol-5-yl urea with 4-tert-butylphenyl |
| A17 | 5-tert-butyl-isoxazol-3-yl urea with 4-tert-butylphenyl |

TABLE A-continued
| NO. | CHEMICAL STRUCTURE |
|---|---|
| A18 | 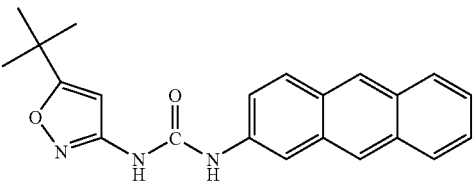 |
| A19 | 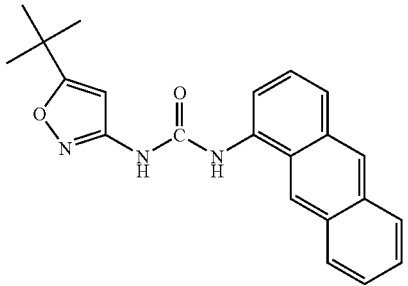 |
| A20 | 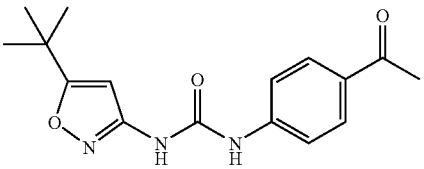 |
| A21 | 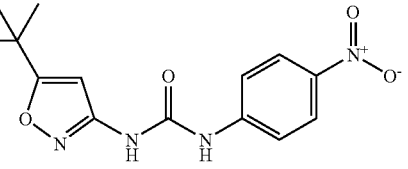 |
| A22 | 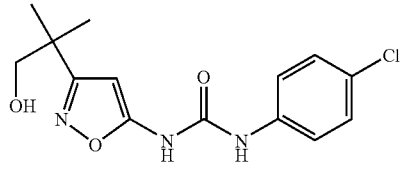 |
| A23 | 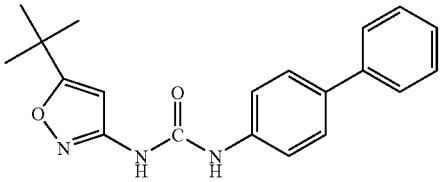 |
| A24 | 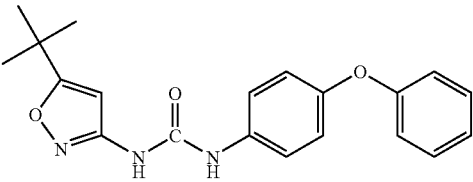 |
| A25 | 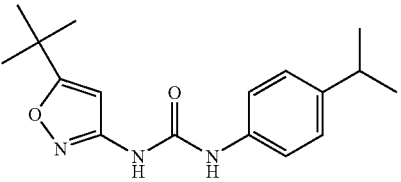 |
| A26 | 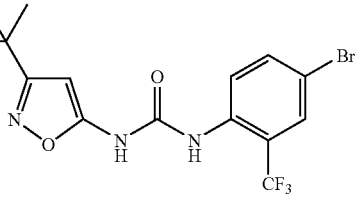 |
| A27 | 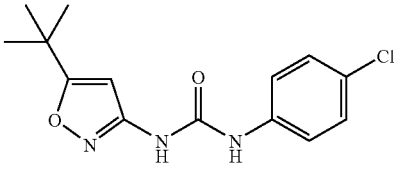 |
| A28 | 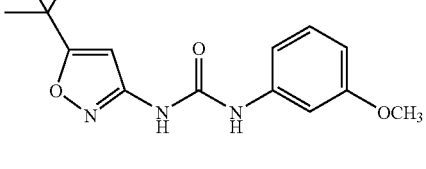 |
| A29 | 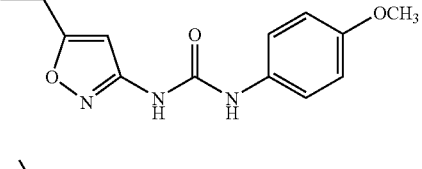 |
| A30 | 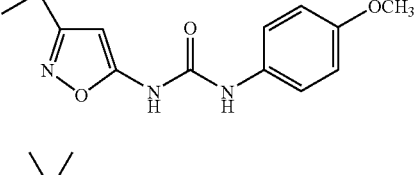 |
| A31 | 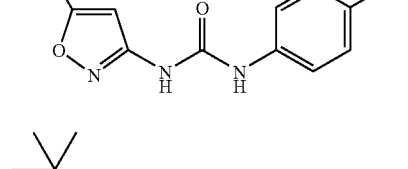 |
| A32 | 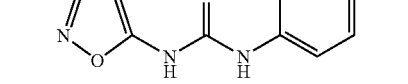 |

TABLE A-continued

| NO. | CHEMICAL STRUCTURE |
|---|---|
| A33 | 5-tert-butyl-N-(p-tolyl)isoxazole-3-urea |
| A34 | 5-tert-butyl-N-phenylisoxazole-3-urea |
| A35 | 5-tert-butyl-N-(2,4-dichlorophenyl)isoxazole-3-thiourea |
| A36 | 5-tert-butyl-N-(4-(2-morpholinoethoxy)naphthalen-1-yl)isoxazole-3-urea |
| A37 | 5-tert-butyl-N-(4-(methylthio)phenyl)isoxazole-3-urea |
| A38 | 5-tert-butyl-N-(4-(2-chloroethoxy)naphthalen-1-yl)isoxazole-3-urea |
| A39 | 3-tert-butyl-N-(4-(methylthio)phenyl)isoxazole-5-urea |
| A40 | 5-tert-butyl-N-(3,4-dimethylphenyl)isoxazole-3-urea |
| A41 | 5-tert-butyl-N-(4-bromo-2-(trifluoromethyl)phenyl)isoxazole-3-urea |
| A42 | 5-tert-butyl-N-(4-tert-butylphenyl)isoxazole-3-urea |
| A43 | 5-tert-butyl-N-(4-methoxyphenyl)isoxazole-3-thiourea |
| A44 | 5-tert-butyl-N-(4-(methylsulfonyl)phenyl)isoxazole-3-urea |
| A45 | 5-tert-butyl-N-(3-fluorophenyl)isoxazole-3-urea |
| A46 | 5-tert-butyl-N-(4-(methylsulfinyl)phenyl)isoxazole-3-urea |
| A47 | 5-tert-butyl-N-(4-fluorophenyl)isoxazole-3-urea |
| A48 | 5-tert-butyl-N-(3-chlorophenyl)isoxazole-3-urea |

TABLE A-continued

| NO. | CHEMICAL STRUCTURE |
|-----|-------------------|
| A49 | 5-tert-butylisoxazol-3-yl urea with 3,4,5-trimethoxyphenyl |
| A50 | 5-tert-butylisoxazol-3-yl urea with 4-chloro-3-trifluoromethylphenyl |
| A51 | 3-tert-butylisoxazol-5-yl urea with 3,4,5-trimethoxyphenyl |
| A52 | 5-tert-butylisoxazol-3-yl urea with 3-bromophenyl |
| A53 | 5-tert-butylisoxazol-3-yl urea with pyridin-4-yl |
| A54 | 5-tert-butylisoxazol-3-yl urea with 3-tert-butylisoxazol-5-yl |
| A55 | 5-tert-butylisoxazol-3-yl urea with 3,4-dimethoxyphenyl |
| A56 | 5-tert-butylisoxazol-3-yl urea with benzo[1,3]dioxol-5-yl |
| A57 | 5-tert-butylisoxazol-3-yl urea with 4-(1,3-dioxoisoindolin-2-yl)phenyl |

Example B

Synthesis of Alkyl-Ureas

Synthesis of Compound B1: 1-(4-methoxybenzyl)-3-(5-tert-butylisoxazol-3-yl)urea 5-tert-Butyl-3-isocyanato-isoxazole Toluene, 50 C.

To a flask 5-tert-Butyl-3-isocyanato-isoxazole (242 mg, 1 eq) and substituted benzylamine (1 eq) was added and dissolved in toluene. The reaction was allowed to stir at 50° C. for three hours. The solvent removed and the mixture was purified by HPLC. Yield: 188 mg (47%).

Compounds B2 through B8 were synthesized in a manner analogous to Compound B1 using similar starting materials and reagents. The structures are shown below in Table B:

TABLE B

| NO. | CHEMICAL STRUCTURE |
|---|---|
| B1 | 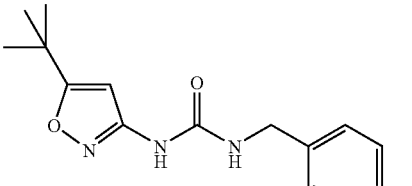 |
| B2 | 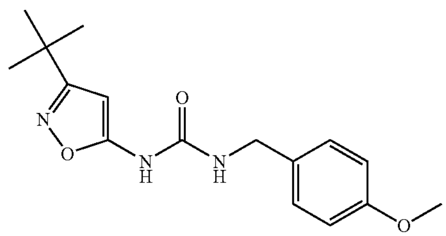 |
| B3 | 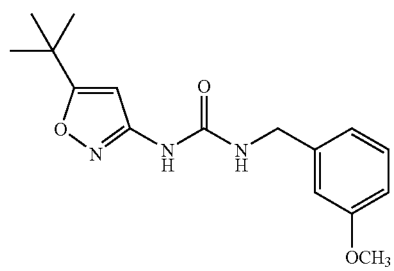 |
| B4 | 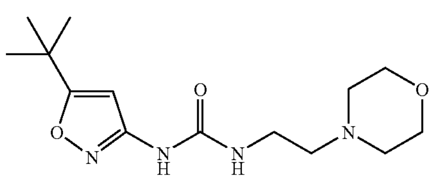 |
| B5 | 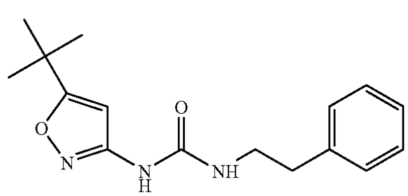 |
| B6 | 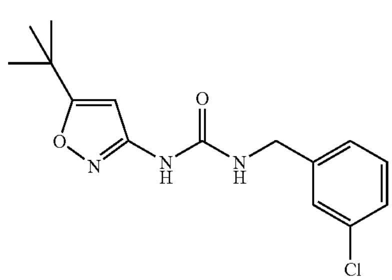 |

TABLE B-continued

| NO. | CHEMICAL STRUCTURE |
|---|---|
| B7 | 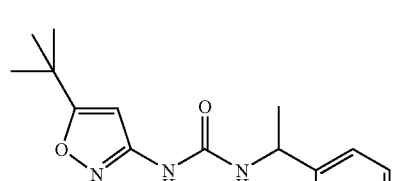 |
| B8 | 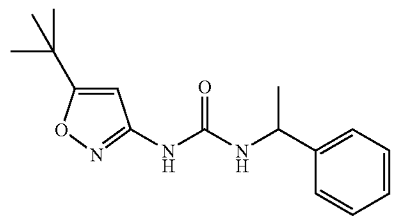 |

Example C

Synthesis of Reactive Ureas

Synthesis of Compound C1: 1-(5-tert-butylisoxazol-3-yl)-3-(4-aminophenyl)urea

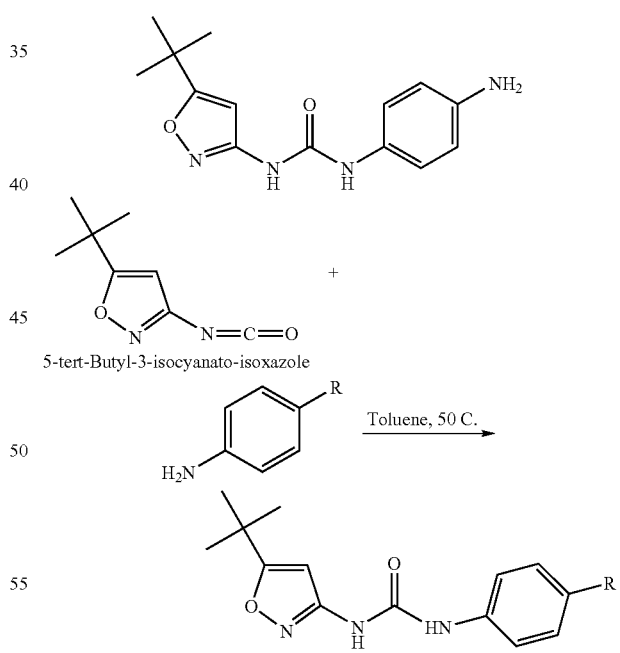

To a flask 5-tert-Butyl-3-isocyanato-isoxazole (242 mg, 1 eq) and substituted aniline (159 mg, 1 eq) was added and dissolved in toluene. The reaction was allowed to stir at 50° C. for three hours. The solvent removed and the mixture was purified by HPLC. Yield: 188 mg (47%).

Compounds C2 through C3 were synthesized in a manner analogous to Compound C1 using similar starting materials and reagents. The structures are shown below in Table C:

TABLE C

| NO. | CHEMICAL STRUCTURE |
|---|---|
| C1 | 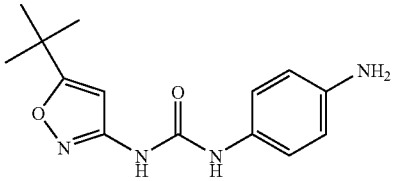 |
| C2 | 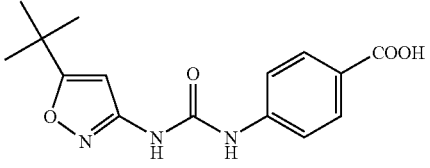 |
| C3 | 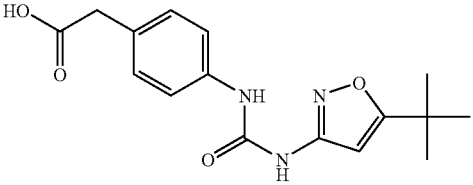 |

Example D

Synthesis of Substituted-Pyrazole Ureas

Synthesis of Compound D1: 1-(3-tert-butyl-1-p-tolyl-1H-pyrazol-5-yl)-3-(4-isopropylphenyl)urea

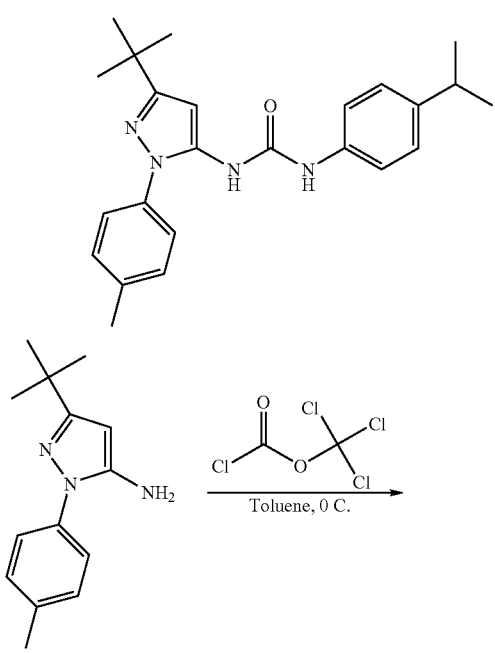

To a stirring solution of 5-tert-Butyl-2-p-tolyl-2H-pyrazol-3-ylamine (250 mg, 1 eq) in dry toluene at 0° C. trichloromethyl chloroformate (1.1 eq) was added dropwise. The reaction stirred at 0° C. and allowed to warm to room temperature overnight. The solvent was removed and the mixture was recrystallized in ethyl acetate. The solid was filtered off and washed with cold ethyl acetate. Yield: 242 mg (83%).

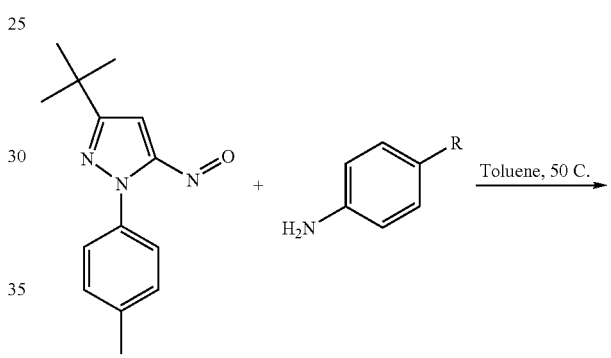

To a flask 3-tert-Butyl-5-isocyanato-1-p-tolyl-1H-pyrazole (242 mg, 1 eq) and substituted aniline (159 mg, 1 eq) was added and dissolved in toluene. The reaction was allowed to stir at 50° C. for three hours. The solvent was removed and the mixture was purified by HPLC. Yield: 188 mg (47%).

Compounds D2 through D22 were synthesized in a manner analogous to Compound D1 using similar starting materials and reagents. The structures are shown below in Table D:

TABLE D

| NO. | CHEMICAL STRUCTURE |
|---|---|
| D1 | 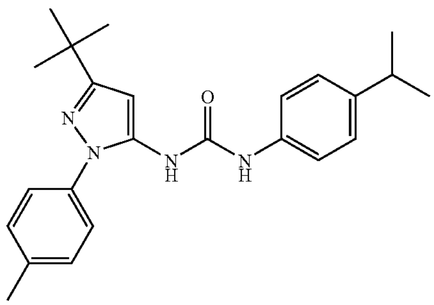 |
| D2 | 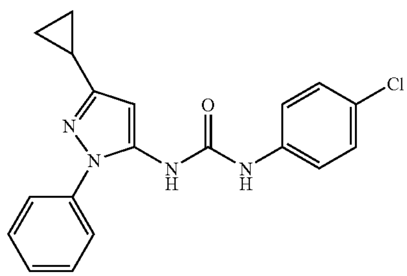 |
| D3 | 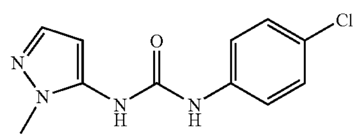 |
| D4 | 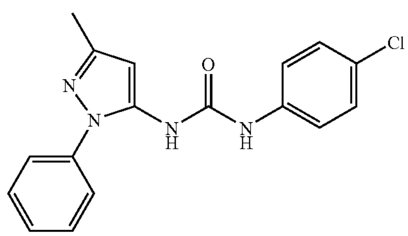 |
| D5 | 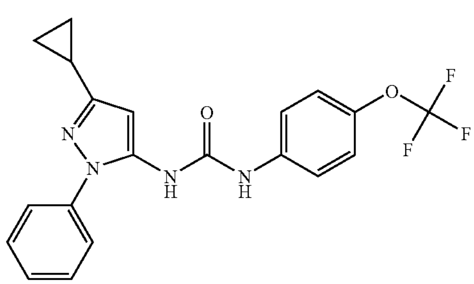 |
| D6 | 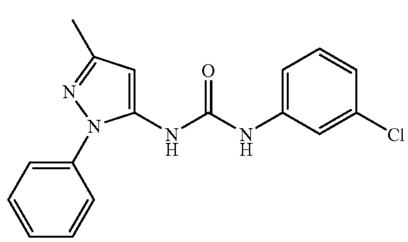 |

TABLE D-continued

| NO. | CHEMICAL STRUCTURE |
|---|---|
| D7 | 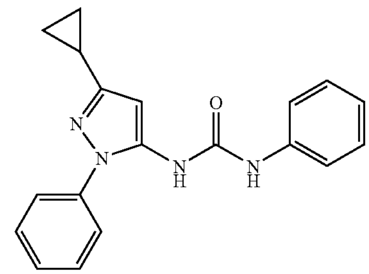 |
| D8 | 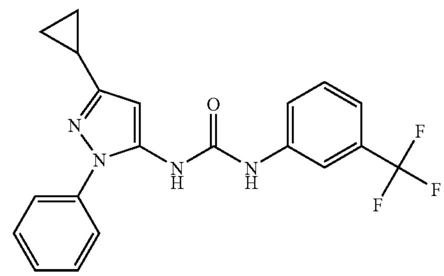 |
| D9 | 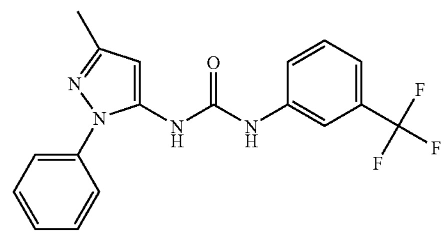 |
| D10 | 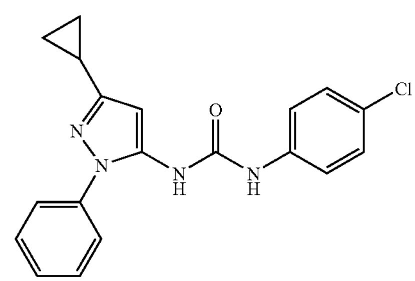 |
| D11 | 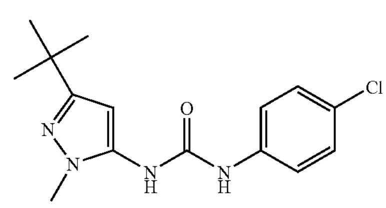 |
| D12 | 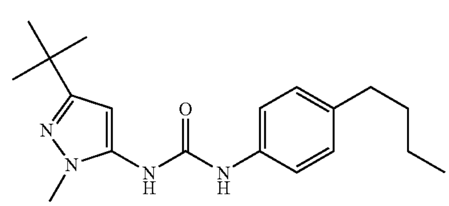 |

TABLE D-continued
| NO. | CHEMICAL STRUCTURE |
|-----|--------------------|
| D13 | 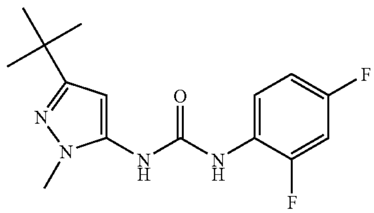 |
| D14 | 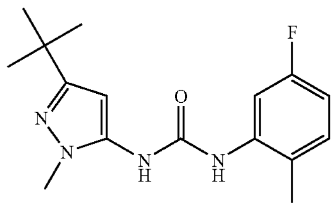 |
| D15 | 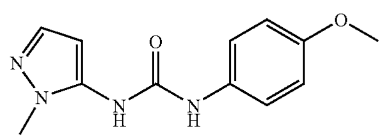 |
| D16 | 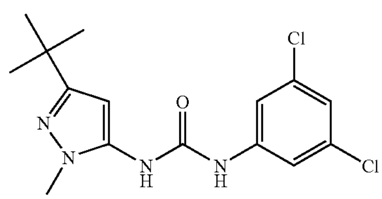 |
| D17 | 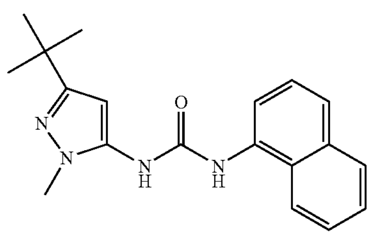 |
| D18 | 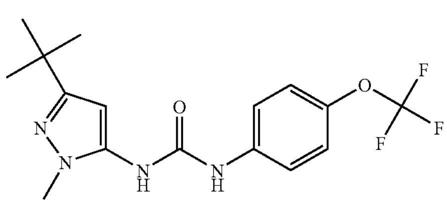 |
| D19 | 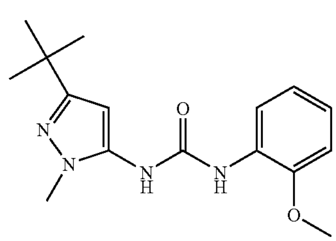 |
| D20 | 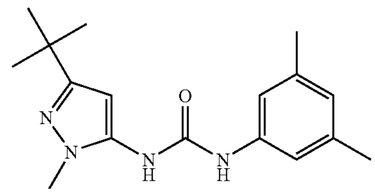 |
| D21 | 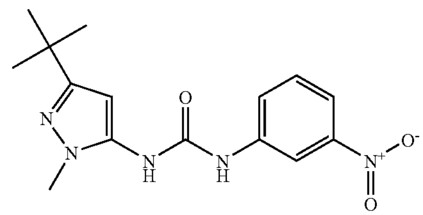 |
| D22 | 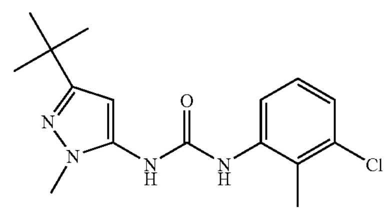 |
Example E
Exemplary Synthesis of Cyclic Ureas
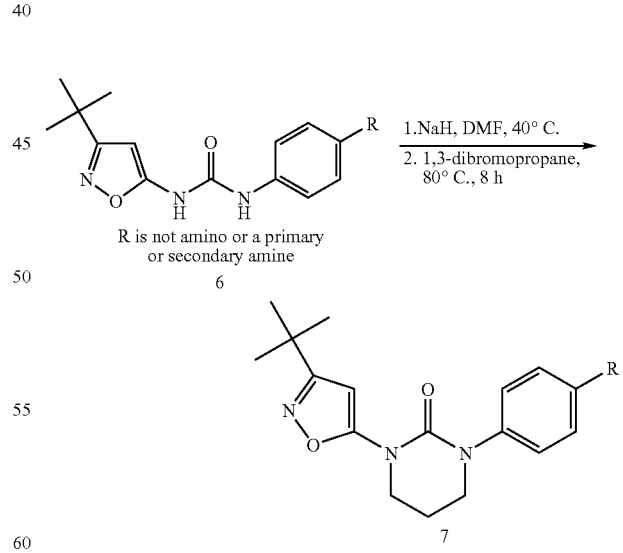
To the urea 6 is added NaH (2.5 eq) in DMF and the reaction is stirred at 40° C. for 1 hour. Then 1 eq of 1,3-dibromopropane is added and the reaction heated to 80° C. for 8 hours, then cooled, the solvent removed in vacuo and the product 7 purified by HPLC.

Synthesis of Compound E1: 3-(3-text-butyl-1-p-tolyl-1H-pyrazol-5-yl)-1-(4-(benzyloxy)phenyl)-tetrahydropyrimidin-2(1H)-one

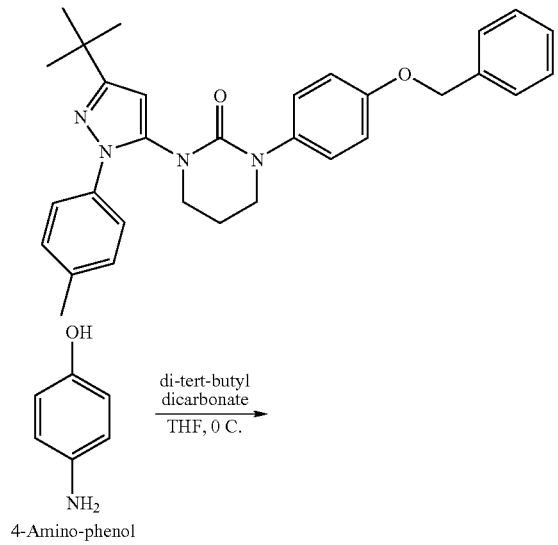

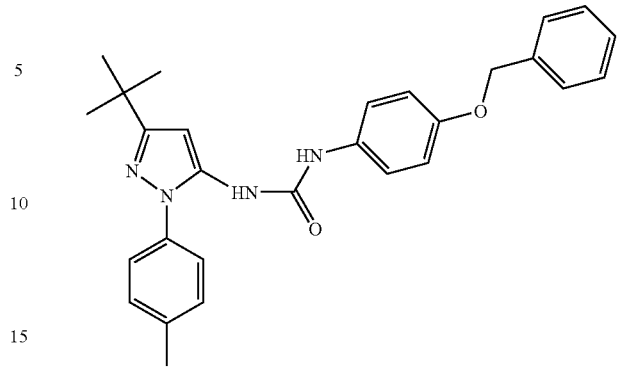

To a stirring solution of 4-aminophenol (1 g, 1 eq) in 20 mL THF at 0° C. di-tert-butyl dicarbonate (2 g, 1 eq) in 3 mL THF was slowly added dropwise over 30 minutes. The reaction stirred at 0° C. and allowed to warm to room temperature overnight. The solvent removed and diluted with ethyl acetate. It was then extracted with water three times, and the organic layer was dried over magnesium sulfate. It was recrystallized in dichloromethane. Yield: 1.5 g (79%).

Bocaminophenol (0.5 g, 1 eq), benzyl bromide (0.45 g, 1 eq), and cesium carbonate (1.94 g, 2.5 eq) was dissolved in 30 mL dimethylformamide. The reaction was allowed to stir at 45° C. overnight. The solvent was removed and dissolved in ethyl acetate and water. It was extracted with ethyl acetate three times. The organic layer was washed with 1N sodium hydroxide and dried with magnesium sulfate and solvent was removed. It was purified by column chromatography. Yield: 0.44 g (58%).

[4-(benzyloxy)-phenyl]-carbamic acid tea-butyl ester (0.44 g) was dissolved in 6 mL dichloromethane and 2 mL trifluoroacetic acid was added. The reaction stirred at room temperature for 1 hour. The excess trifluoroacetic acid was removed in vivo. Yield: 0.12 g (42%).

4-(benzyloxy)-phenylamine (0.12 g, 1 eq) was mixed with 5-tert-Butyl-2-p-tolyl-2H-pyrazole-3-carbonitrile N-oxide (0.9 g 1 eq) and dissolved in dry toluene. The reaction stirred at 80° C. overnight. The solvent was removed and purified by HPLC. Yield: 85 mg (31%)

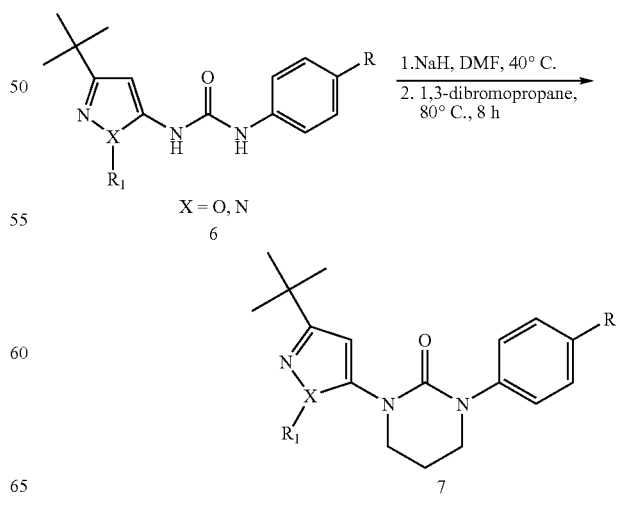

To 6 is added NaH (2.5 eq) in DMF and the reaction is stirred at 40° C. for 1 hour. Then 1 eq of 1,3-dibromopropane is added and the reaction heated to 80° C. for 8 hours, then cooled, the solvent removed in vacuo and the product 7 purified by HPLC.

Compounds E2 through E5 were synthesized in a manner analogous to Compound E1 using similar starting materials and reagents. The structures are shown below in Table E:

TABLE E

| NO. | CHEMICAL STRUCTURE |
|---|---|
| E1 | 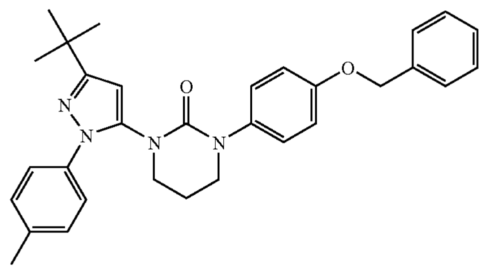 |
| E2 | 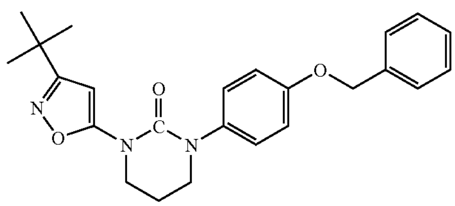 |
| E3 | 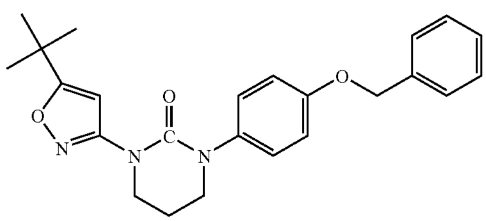 |
| E4 | 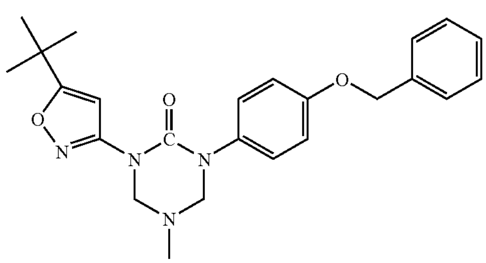 |
| E5 | 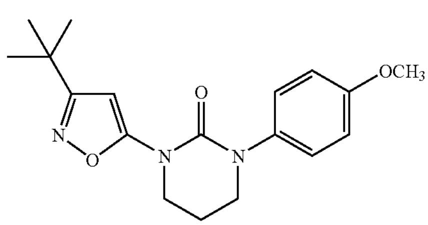 |

Example F

Conversion of Ureas to Thioureas

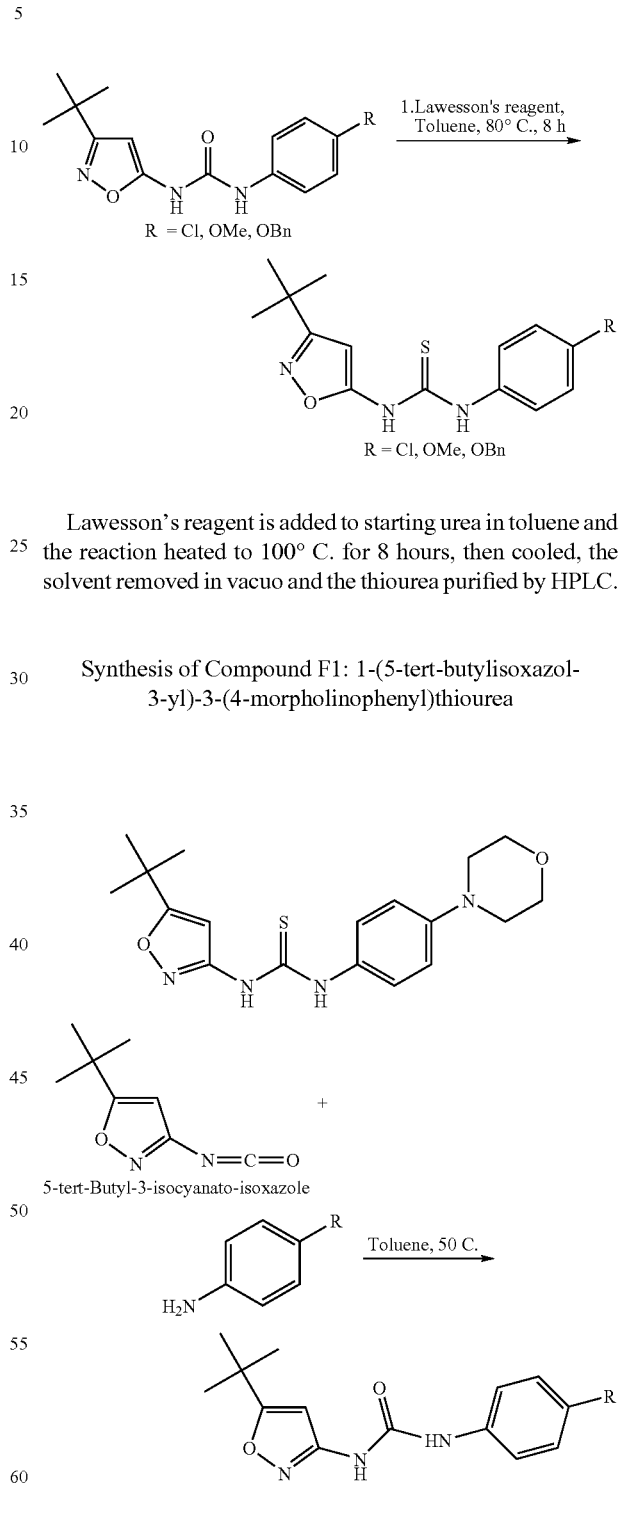

Lawesson's reagent is added to starting urea in toluene and the reaction heated to 100° C. for 8 hours, then cooled, the solvent removed in vacuo and the thiourea purified by HPLC.

Synthesis of Compound F1: 1-(5-tert-butylisoxazol-3-yl)-3-(4-morpholinophenyl)thiourea To a flask 5-tert-Butyl-3-isocyanato-isoxazole (242 mg, 1 eq) and substituted aniline (159 mg, 1 eq) was added and dissolved in toluene. The reaction was allowed to stir at 50° C. for three hours. The solvent removed and the mixture was purified by HPLC. Yield: 188 mg (47%)

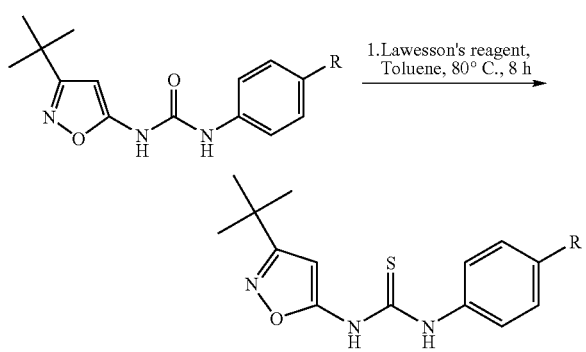
Lawesson's reagent is added to starting urea in toluene and the reaction heated to 100° C. for 8 hours, then cooled, the solvent removed in vacuo and the thiourea purified by HPLC.
Compounds F2 through F9 were synthesized in a manner analogous to Compound F1 using similar starting materials and reagents. The structures are shown below in Table F:

Example G

Exemplary Synthesis of Ureas with Ether Linkers

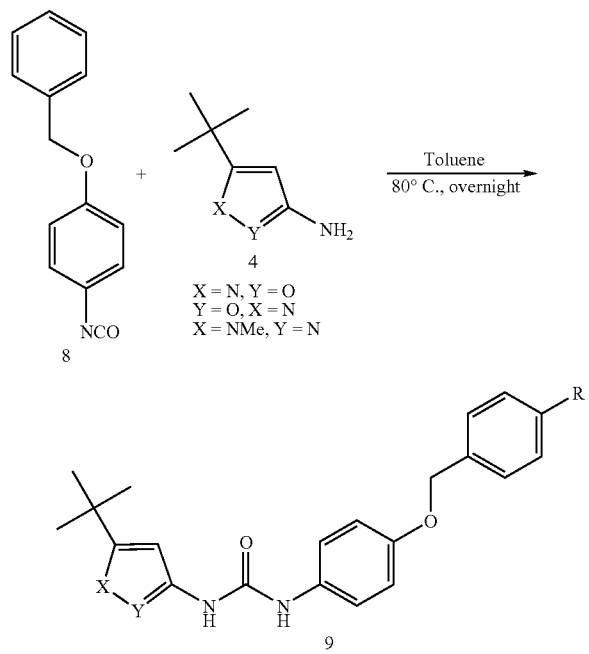

To a stirring solution of the amine 4 (1 eq) in toluene at room temperature is added the isocyanate 8 and heated at 80° C. overnight. The solvent is removed, and the product 9 is purified by HPLC. Compound C, compound A, compound B, compound D and other compounds in the benzoloxy series were made by the general method described above.

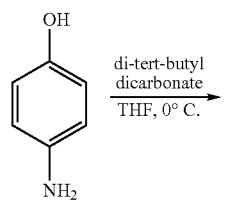

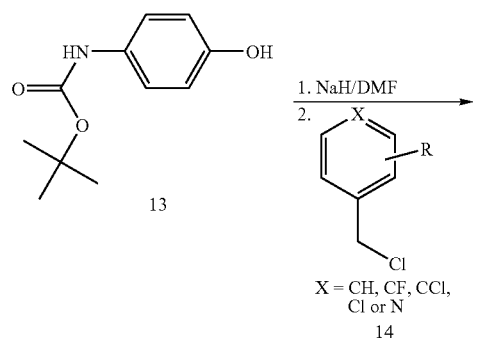

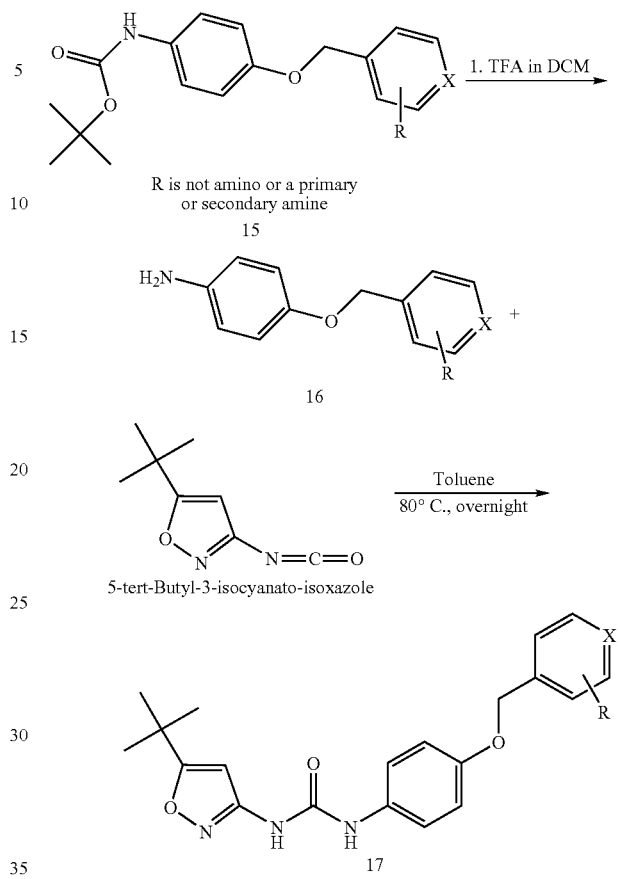

To a stirring solution of 4-aminophenol (1 eq) in THF at 0° C. di-tert-butyl dicarbonate (1 eq) in THF was slowly added dropwise over 30 minutes. The reaction stirred at 0° C. and allowed to warm to room temperature overnight. The solvent removed and diluted with ethyl acetate. It was then extracted with water three times, and the organic layer was dried over magnesium sulfate. It was recrystallized in dichloromethane.

To a stirring solution of sodium hydride (1.2 eq) in DMF, the Boc-aminophenol (1 eq) was added dropwise at 0° C. and stirred to room temperature for one hour. Then the substituted benzyl halide (1 eq) in THF was added dropwise at 0° C. The reaction was allowed to stir at 40° C. overnight. The solvent was removed and dissolved in ethyl acetate and water. It was extracted with ethyl acetate three times. The organic layer was washed with 1N sodium hydroxide and dried with magnesium sulfate and solvent was removed. It was purified by column chromatography.

The protected substituted benzyloxyaniline was dissolved in dichloromethane and trifluoroacetic acid was added. The reaction stirred at room temperature for 1 hour. The excess trifluoroacetic acid was removed in vivo.

The substituted benzyloxyaniline (1 eq) was mixed with 5-tert-Butyl-3-isocyanato-isoxazole (1 eq) and dissolved in dry toluene. The reaction stirred at 80° C. overnight. The solvent was removed and purified by HPLC.

Synthesis of Compound G1: 1-(4-(3-(pyridin-4-yl)propoxy)phenyl)-3-(5-tert-butylisoxazol-3-yl)urea

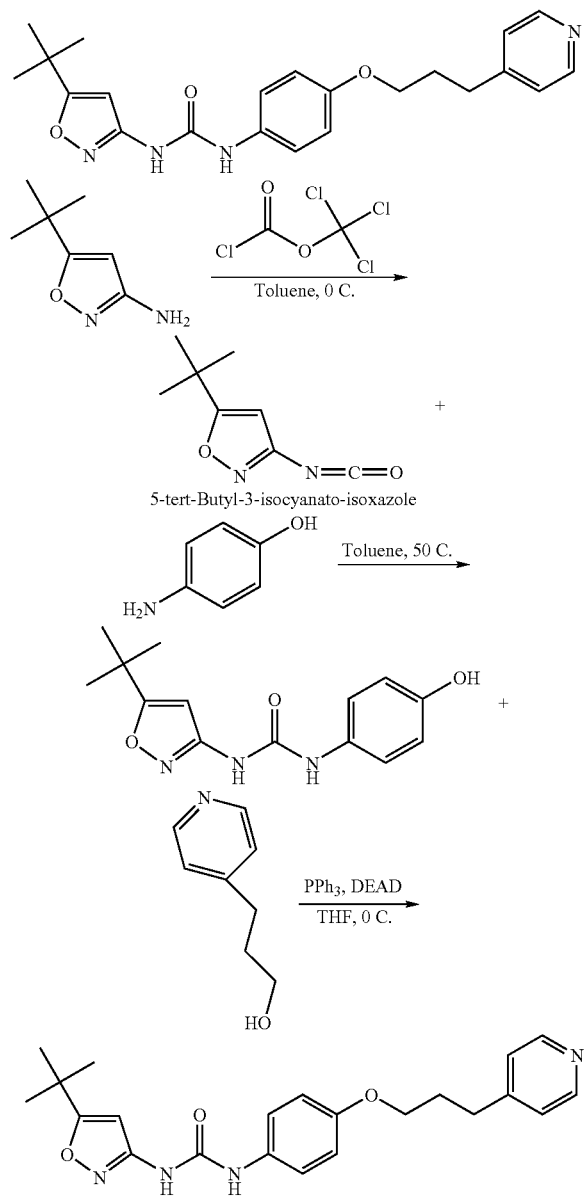

To a stirring solution of 5-tert-Butyl-isoxazol-3-ylamine (250 mg, 1 eq) in dry toluene at 0° C. trichloromethyl chloroformate (1.1 eq) was added dropwise. The reaction stirred at 0° C. and allowed to warm to room temperature overnight. The solvent was removed and the mixture was recrystallized in ethyl acetate. The solid was filtered off and washed with cold ethyl acetate. Yield: 242 mg (83%).

To a flask 5-tert-Butyl-3-isocyanato-isoxazole (242 mg, 1 eq) and 4-aminophenol (159 mg, 1 eq) was added and dissolved in toluene. The reaction was allowed to stir at 50° C. for three hours. The solvent removed and the mixture was purified by HPLC. Yield: 188 mg (47%), LC/MS [MH+] 276.

In a dry flask flushed with nitrogen gas 1-(5-tert-Butyl-isoxazol-3-yl)-3-(4-hydroxy-phenyl)-urea (100 mg, 1 eq), 3-Pyridin-4-yl-propan-1-ol (200 mg, 1 eq) and triphenylphosphine (143 mg, 1.5 eq) was added and then dissolved with THF. The flask was cooled to 0° C. and diethyl azodicarboxylate (95 mg, 1.5 eq) was added dropwise. The reaction stirred overnight at room temperature. The THF was removed and the mixture was purified by HPLC. Yield: 26 mg (18%), LC/MS [MH+] 395.

Synthesis of Compound G12: 1-(4-(2-fluorobenzyloxy)phenyl)-3-(5-tert-butylisoxazol-3-yl)urea

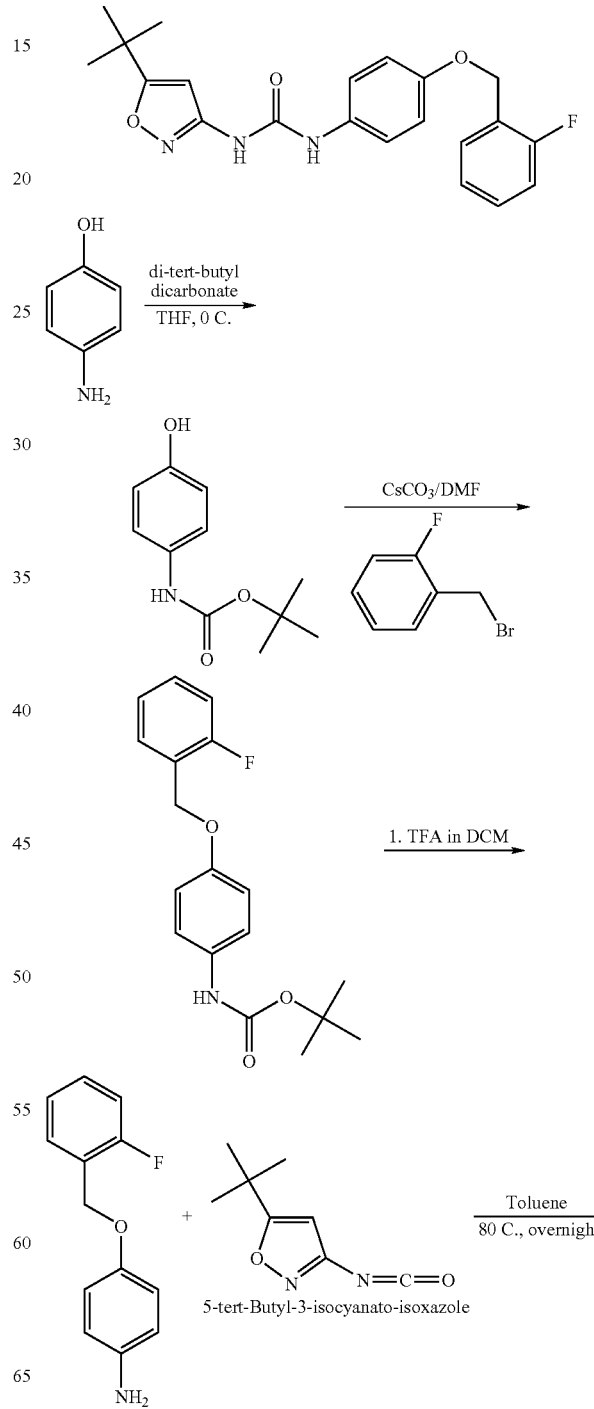

-continued

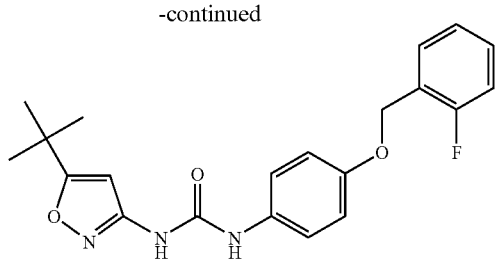

To a stirring solution of 4-aminophenol (1 g, 1 eq) in 20 mL THF at 0° C. di-tert-butyl dicarbonate (2 g, 1 eq) in 3 mL THF was slowly added dropwise over 30 minutes. The reaction stirred at 0° C. and allowed to warm to room temperature overnight. The solvent removed and diluted with ethyl acetate. It was then extracted with water three times, and the organic layer was dried over magnesium sulfate. It was recrystallized in dichloromethane. Yield: 1.5 g (79%).

Bocaminophenol (0.5 g, 1 eq), 2-fluorobenzyl bromide (0.45 g, 1 eq), and cesium carbonate (1.94 g, 2.5 eq) was dissolved in 30 mL dimethylformamide. The reaction was allowed to stir at 45° C. overnight. The solvent was removed and dissolved in ethyl acetate and water. It was extracted with ethyl acetate three times. The organic layer was washed with 1N sodium hydroxide and dried with magnesium sulfate and solvent was removed. It was purified by column chromatography. Yield: 0.44 g (58%).

[4-(2-Fluoro-benzyloxy)-phenyl]-carbamic acid tert-butyl ester (0.44 g) was dissolved in 6 mL dichloromethane and 2 mL trifluoroacetic acid was added. The reaction stirred at room temperature for 1 hour. The excess trifluoroacetic acid was removed in vivo. Yield: 0.12 g (42%), LC/MS [MH$^+$] 218.

4-(2-Fluoro-benzyloxy)-phenylamine (0.12 g, 1 eq) was mixed with 5-tert-Butyl-3-isocyanato-isoxazole (0.9 g 1 eq) and dissolved in dry toluene. The reaction stirred at 80° C. overnight. The solvent was removed and purified by HPLC. Yield: 85 mg (31%), LC/MS [MH$^+$] 384.

Compounds G2 through G57 were synthesized in a manner analogous to Compound G1 and G12 using similar starting materials and reagents. The structures are shown below in Table G:

TABLE G

| NO. | CHEMICAL STRUCTURE |
|---|---|
| G1 | 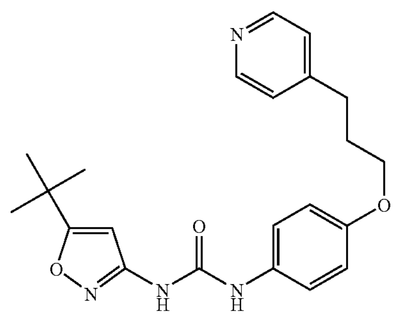 |
| G2 | 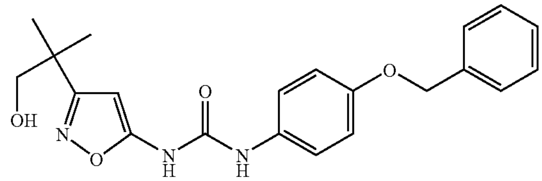 |
| G3 | 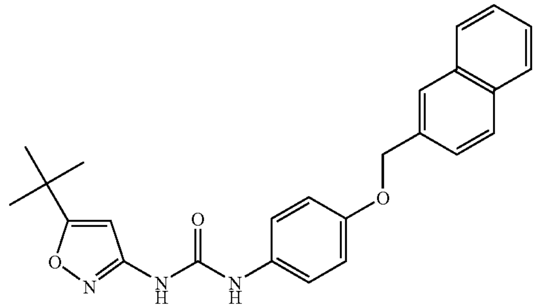 |

TABLE G-continued
| NO. | CHEMICAL STRUCTURE |
|---|---|
| G4 | 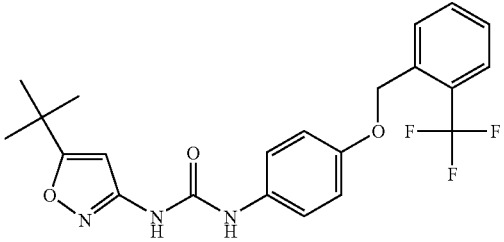 |
| G5 | 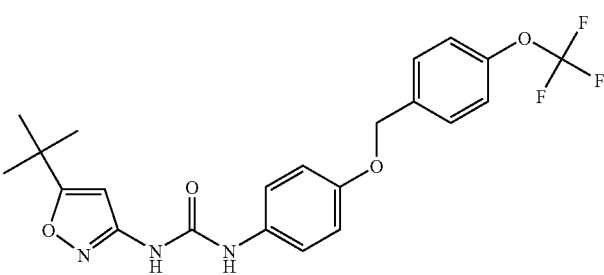 |
| G6 | 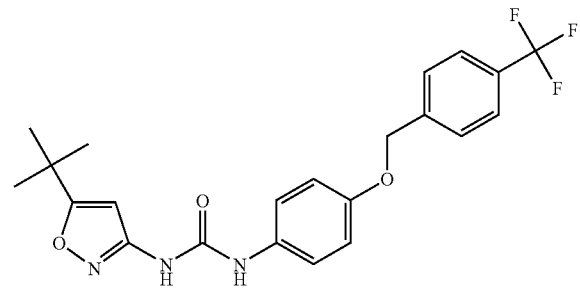 |
| G7 | 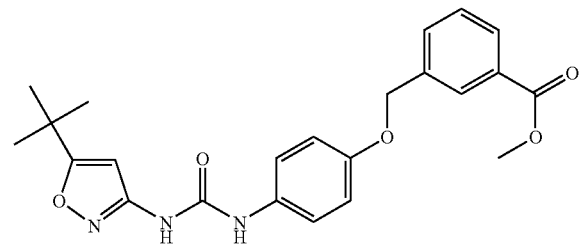 |
| G8 | 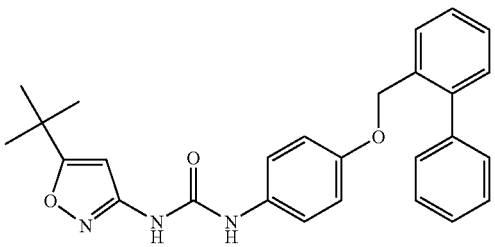 |

TABLE G-continued
| NO. | CHEMICAL STRUCTURE |
|---|---|
| G9 | 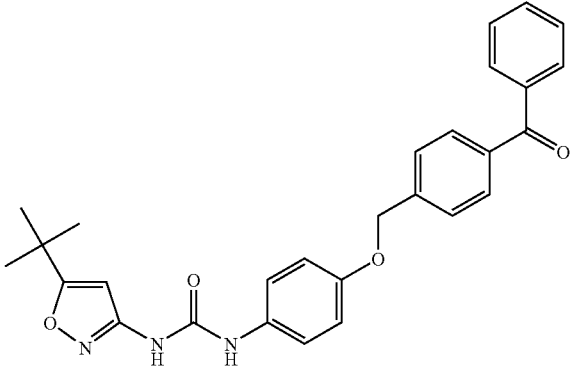 |
| G10 | 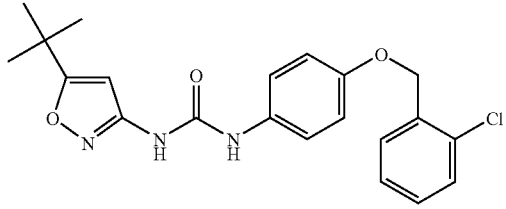 |
| G11 | 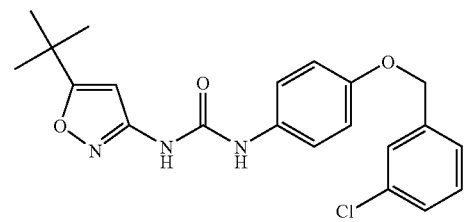 |
| G12 | 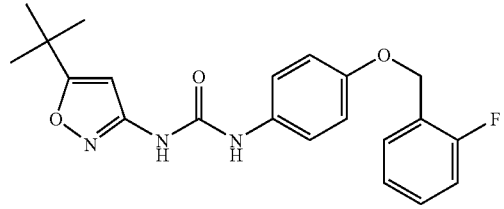 |
| G13 | 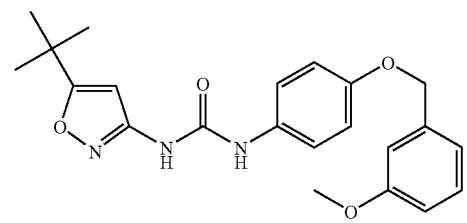 |
| G14 | 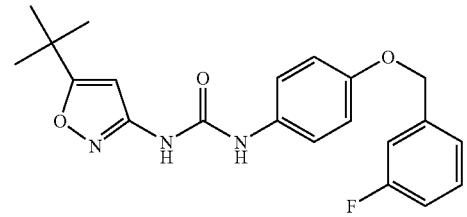 |

TABLE G-continued

| NO. | CHEMICAL STRUCTURE |
|---|---|
| G15 | 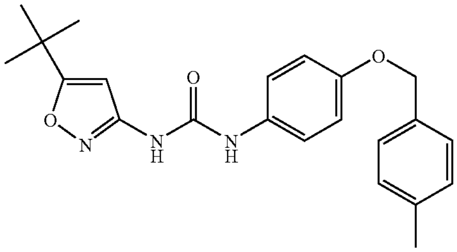 |
| G16 | 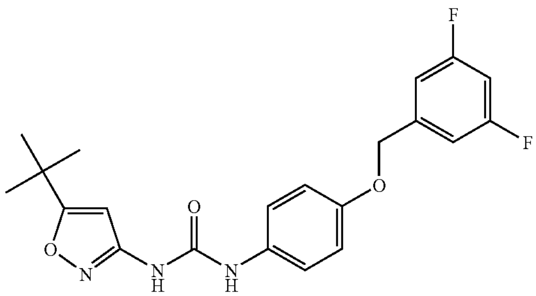 |
| G17 | 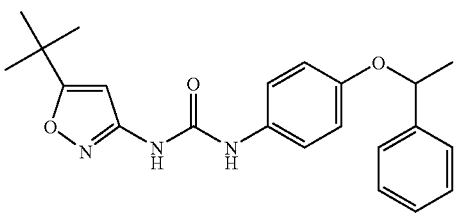 |
| G18 | 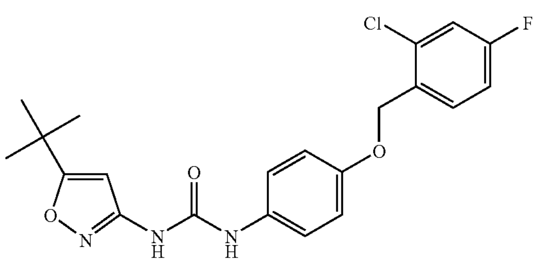 |
| G19 | 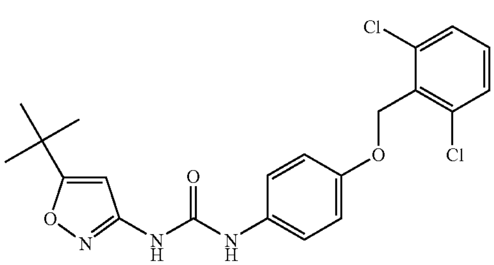 |
| G20 | 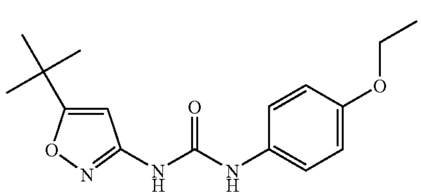 |

TABLE G-continued
| NO. | CHEMICAL STRUCTURE |
|---|---|
| G21 | 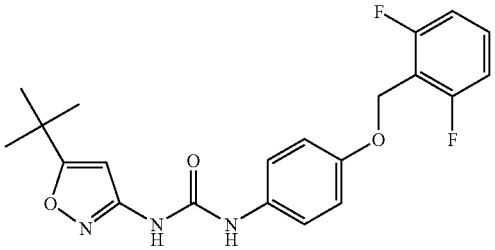 |
| G22 | 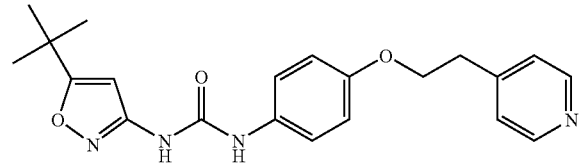 |
| G23 | 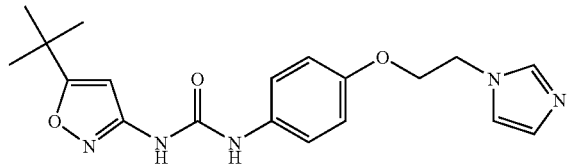 |
| G24 | 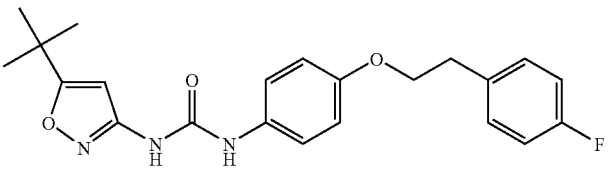 |
| G25 | 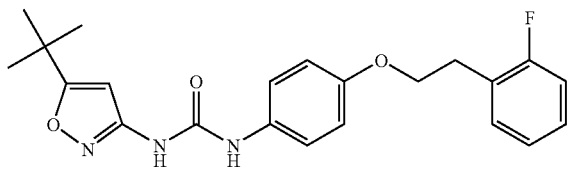 |
| G26 | 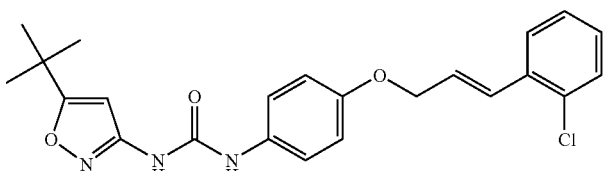 |
| G27 | 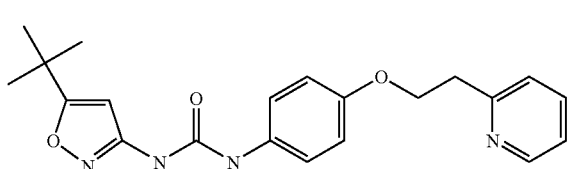 |
| G28 | 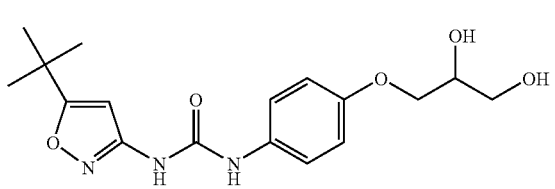 |

TABLE G-continued

| NO. | CHEMICAL STRUCTURE |
|---|---|
| G29 | 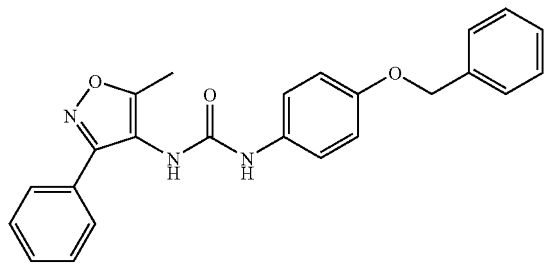 |
| G30 | 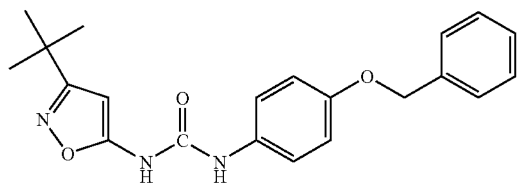 |
| G31 | 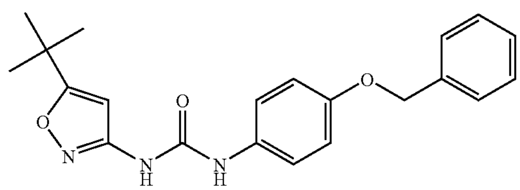 |
| G32 | 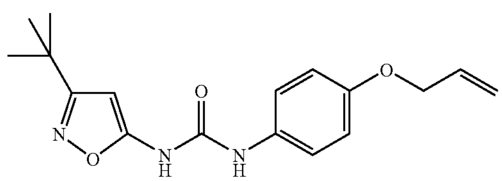 |
| G33 | 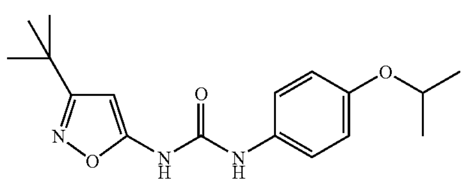 |
| G34 | 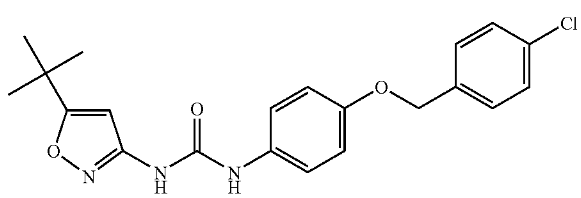 |
| G35 | 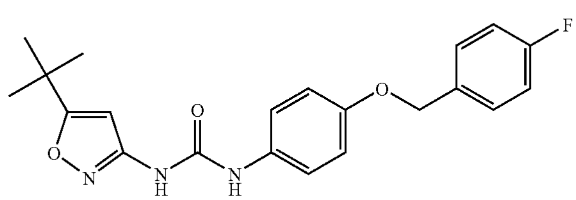 |

TABLE G-continued

| NO. | CHEMICAL STRUCTURE |
|---|---|
| G36 | 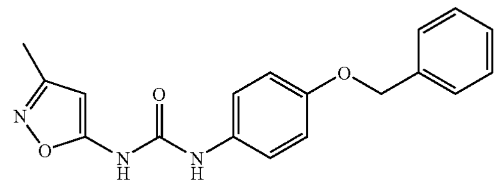 |
| G37 | 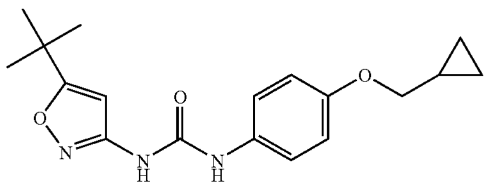 |
| G38 | 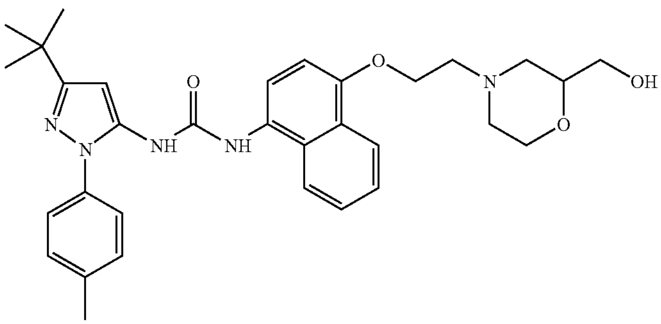 |
| G39 | 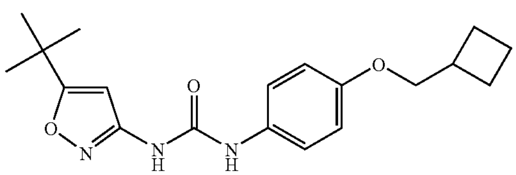 |
| G40 | 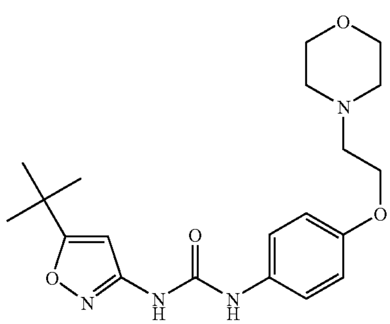 |
| G42 | 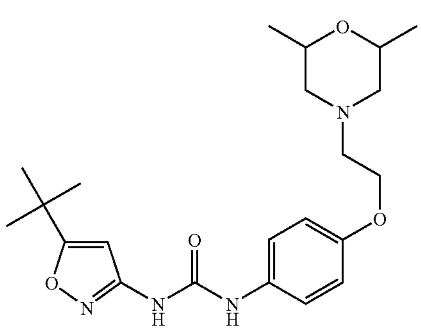 |

TABLE G-continued
| NO. | CHEMICAL STRUCTURE |
|---|---|
| G44 | 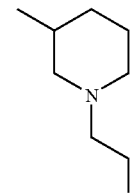 |
| G46 | 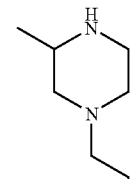 |
| G48 | 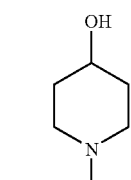 |
| G49 | 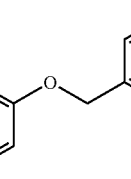 |
| G50 | 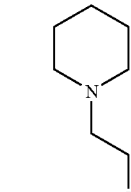 |

TABLE G-continued
| NO. | CHEMICAL STRUCTURE |
|---|---|
| G51 | 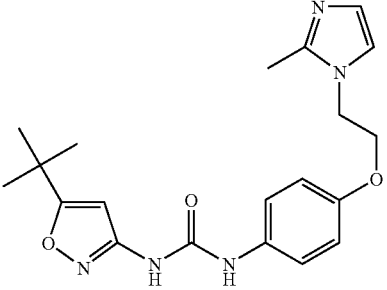 |
| G52 | 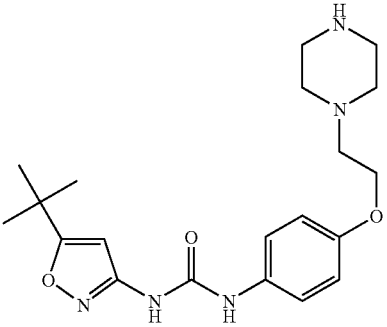 |
| G53 | 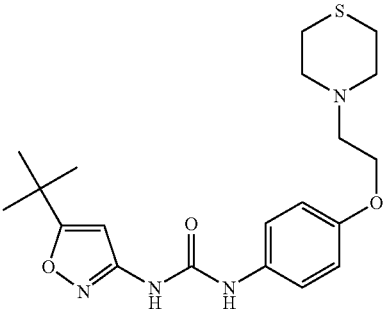 |
| G54 | 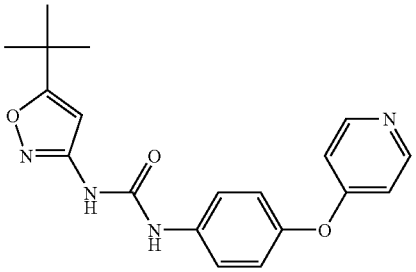 |
| G55 | 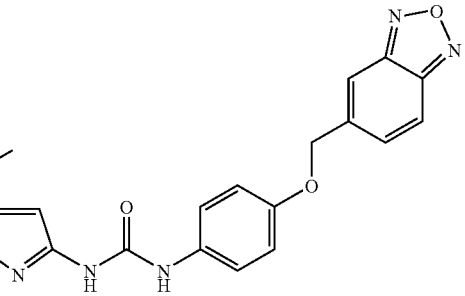 |

TABLE G-continued

| NO. | CHEMICAL STRUCTURE |
|---|---|
| G56 | 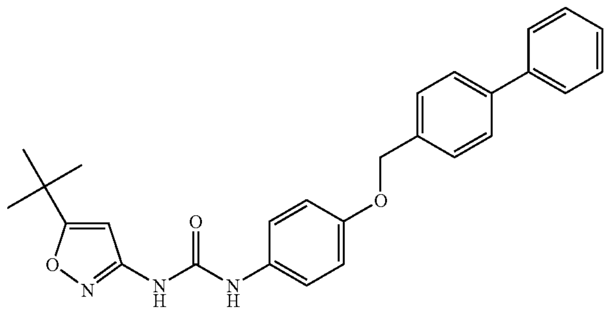 |
| G57 | 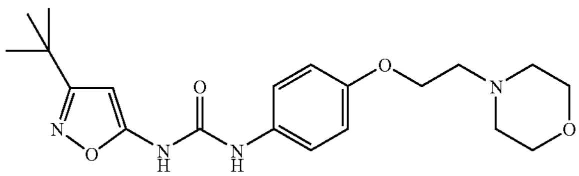 |

Example H

Exemplary Synthesis of Ureas with Ether Linkers

Synthesis of Compound H1: 1-(4-(benzyloxy)phenyl)-3-(1-phenyl-1H-pyrazol-5-yl)urea

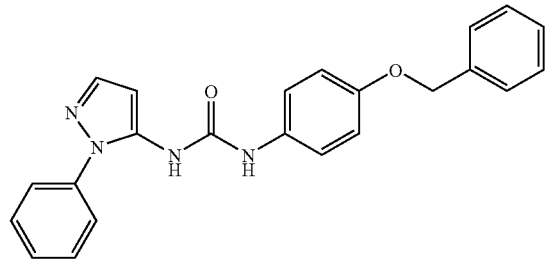

Compounds H1 through H10 were synthesized in a manner analogous to compound G1. Compounds H11 through H17 were synthesized in a manner analogous to Compound A1 using similar starting materials and reagents. The structures are shown below in Table H:

TABLE H

| NO. | CHEMICAL STRUCTURE |
|---|---|
| H1 | 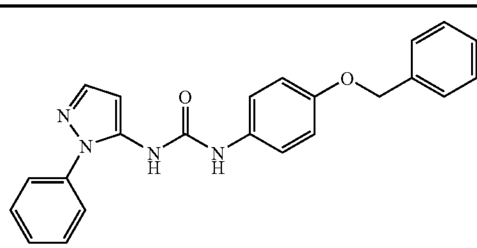 |

TABLE H-continued

| NO. | CHEMICAL STRUCTURE |
|---|---|
| H2 | 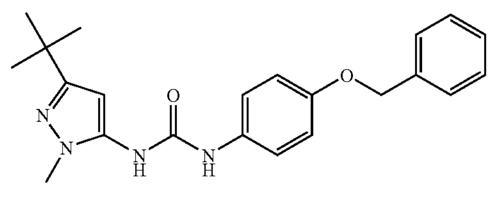 |
| H3 | 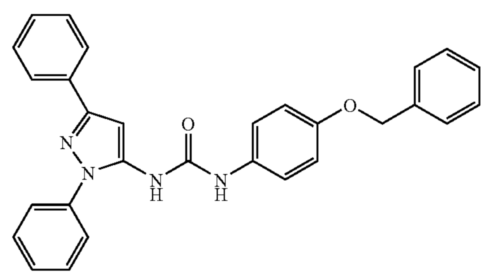 |
| H4 | 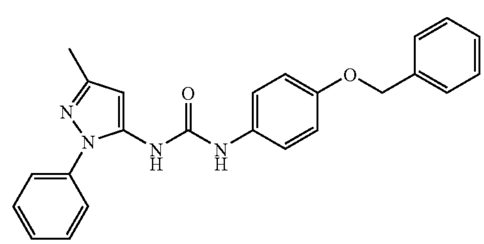 |

TABLE H-continued
| NO. | CHEMICAL STRUCTURE |
|---|---|
| H5 | 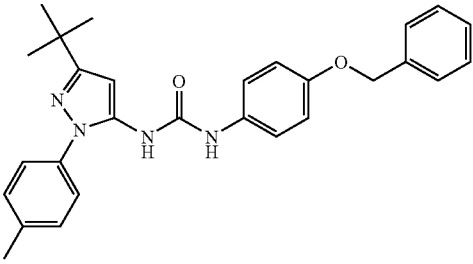 |
| H6 | 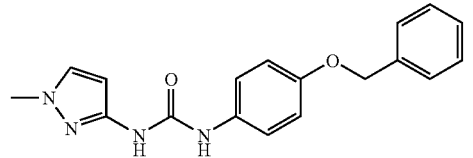 |
| H7 | 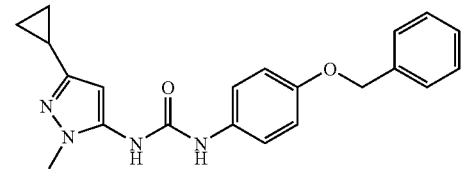 |
| H8 | 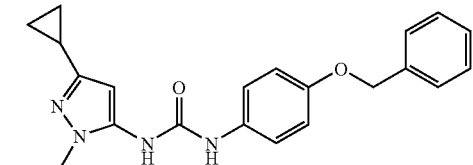 |
| H9 | 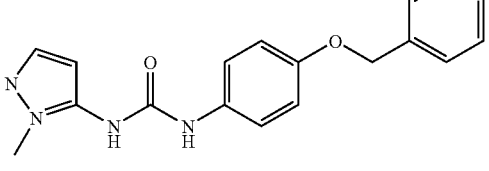 |
| H10 | 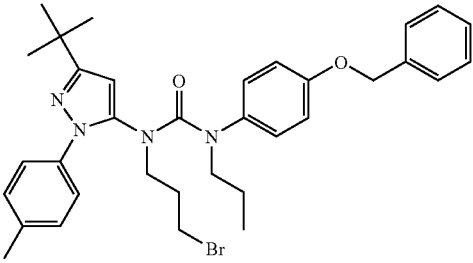 |
TABLE H-continued
| NO. | CHEMICAL STRUCTURE |
|---|---|
| H11 | 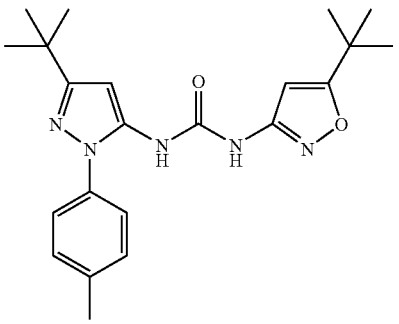 |
| H12 | 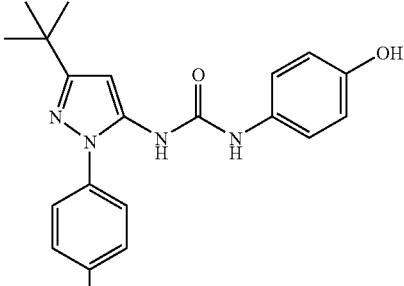 |
| H13 | 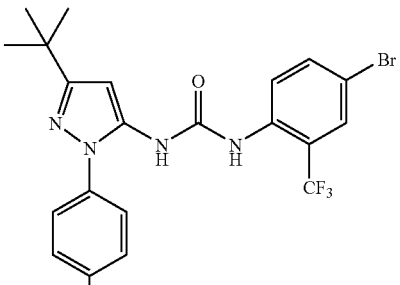 |
| H14 | 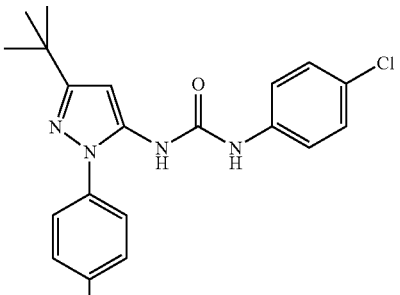 |

TABLE H-continued

| NO. | CHEMICAL STRUCTURE |
|-----|--------------------|
| H15 | 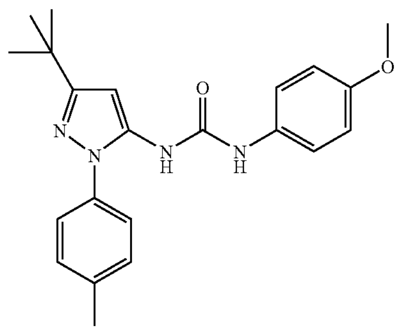 |
| H16 | 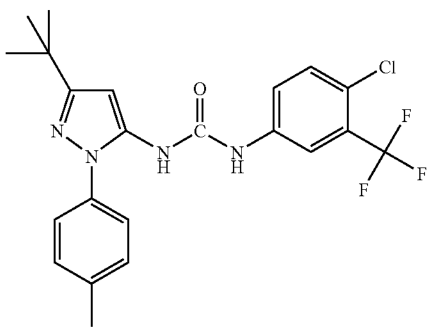 |
| H17 | 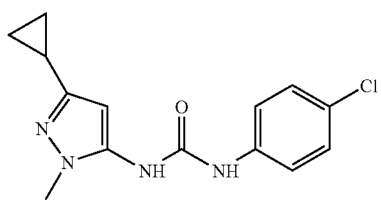 |

Example I

Exemplary Synthesis of Ureas with Ether Linkers

Synthesis of Compound I1: 1-(4-(benzyloxy)phenyl)-3-(4-methylthiazol-2-yl)urea

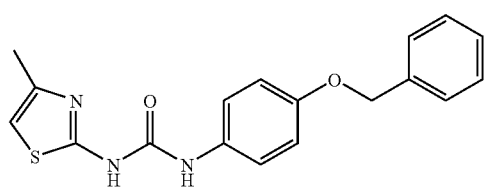

Compounds I1 through I4 were synthesized in a manner analogous to Compound G1 using similar starting materials and reagents. The structures are shown below in Table I:

TABLE I

| NO. | CHEMICAL STRUCTURE |
|-----|--------------------|
| I1  | 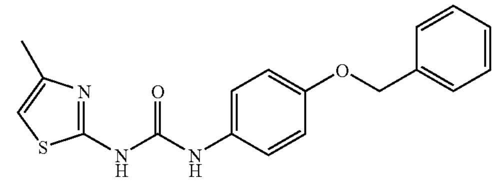 |
| I2  | 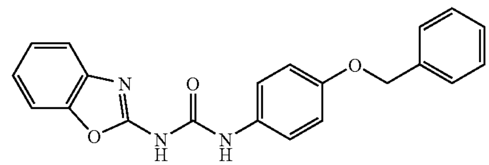 |
| I3  | 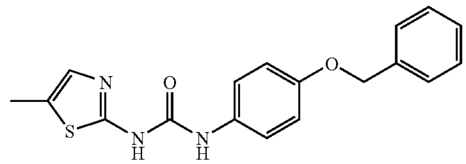 |
| I4  | 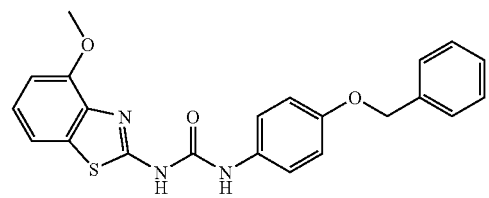 |

Example J

Synthesis of N-Substituted Ureas

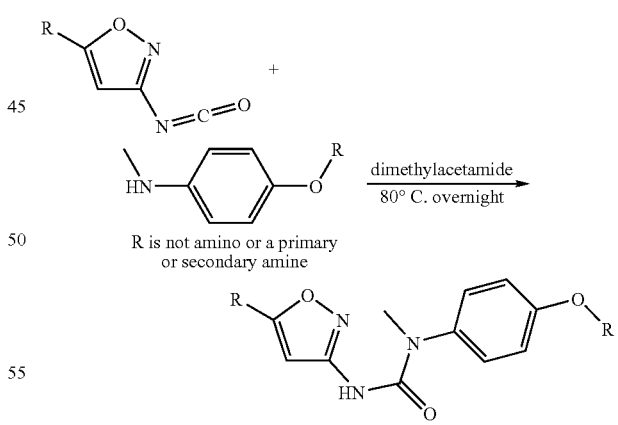

A solution of an isoxazole-3-isocyanate in dimethylacetamide is added to a solution of 4-alkoxy-N-alkylbenzenamine in dimethylacetamide, and the mixture is heated at 80° C. overnight. After cooling to room temperature, 20 ml water is added and the mixture is extracted with 3×30 ml EtOAc. The combined organic phases are washed with brine, dried over magnesium sulfate, and evaporated. Purification of the product is accomplished by flash chromatography (silica gel, hexanes, 0-50% EtOAc).

Synthesis of Compound J1: 1-(5-tert-butylisoxazol-3-yl)-3-(4-methoxyphenyl)-3-methylurea

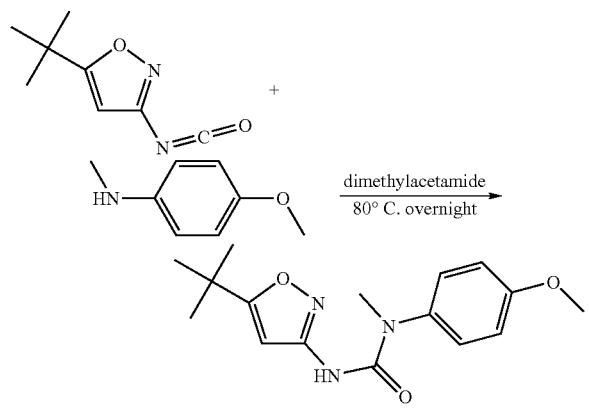

A solution of 5-tert-butyl-isoxazole-3-isocyanate (166 mg, 1 mmol) in 0.5 ml dimethylacetamide was added to a solution of 4-methoxy-N-methylaniline in 0.5 ml dimethylacetamide (137 mg, 1 mmol), and the mixture was heated at 80° C. overnight. After cooling to room temperature, 20 ml water was added and the mixture was extracted with 3×30 ml EtOAc. The combined organic phases were washed with brine, dried over magnesium sulfate, and evaporated. Purification of the product, N-(methyl)(4-methoxyphenyl)-N-(5-t-butyl-3-isoxazolyl)urea, was accomplished by flash chromatography (silica gel, hexanes, 0-50% EtOAc).

Compounds J2 through J15 were synthesized in a manner analogous to Compound J1 using similar starting materials and reagents. The structures are shown below in Table J:

TABLE J-continued

| NO. | CHEMICAL STRUCTURE |
|---|---|
| J11 | 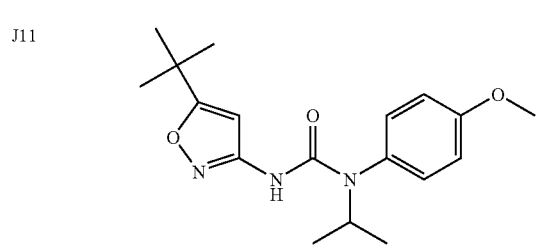 |
| J12 | 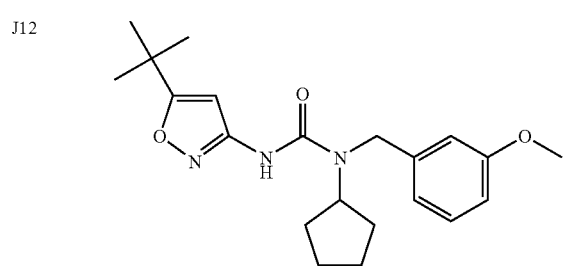 |
| J13 | 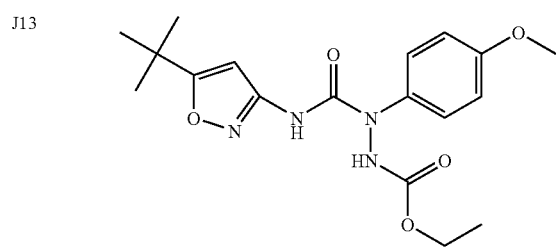 |
| J14 | 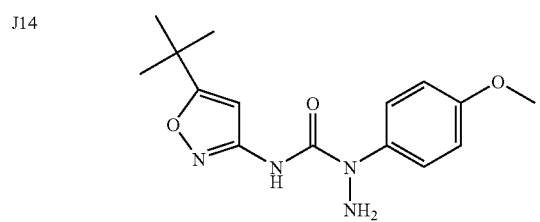 |
| J15 | 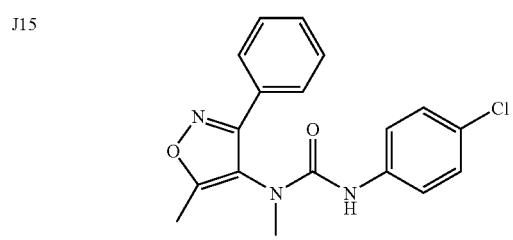 |

Example K

Synthesis of Compounds with Ether-Alkyl Chains

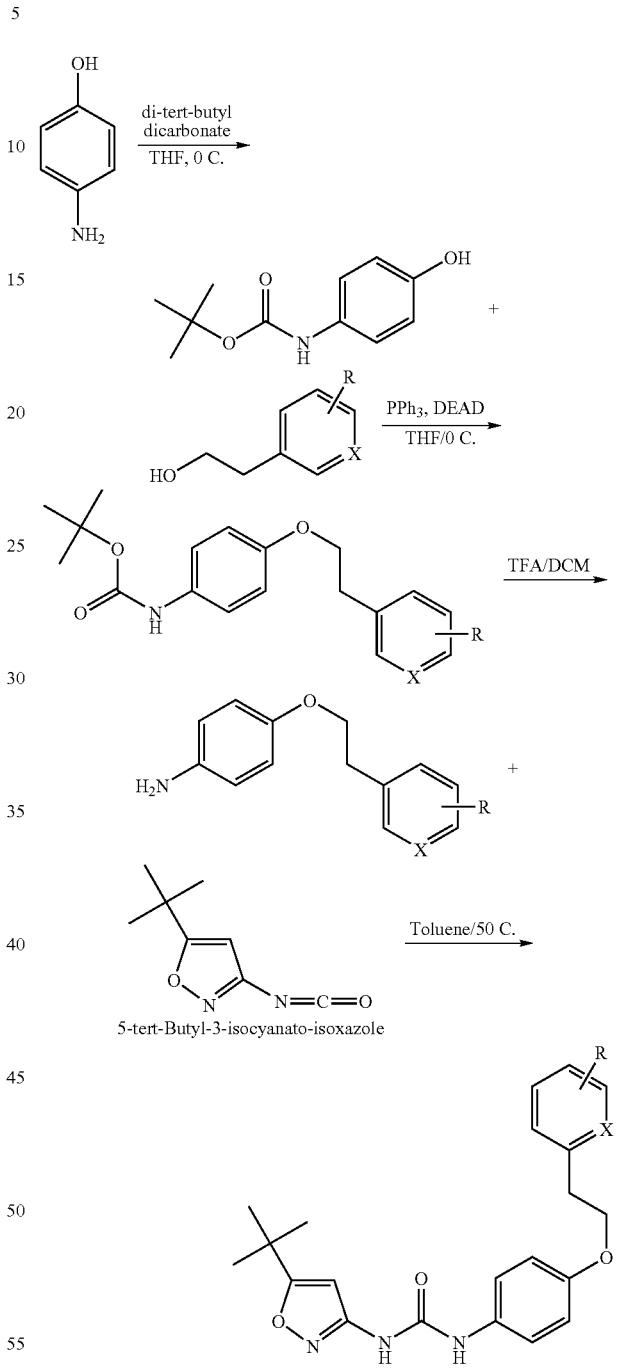

The following general procedure was used to synthesize compounds having the ethylene, propylene, or butylenes linkers. To a stirring solution of 4-aminophenol (1 eq) in THF at 0° C., di-tert-butyl dicarbonate (1 eq) in THF was slowly added dropwise over 30 minutes. The reaction was stirred at 0° C. and allowed to warm to room temperature overnight. The solvent removed and diluted with ethyl acetate. It was then extracted with water three times, and the organic layer was dried over magnesium sulfate. The solid was recrystallized from dichloromethane.

In a dry flask flushed with nitrogen gas bocaminophenol (1 eq), substituted alcohol (1 eq) and triphenylphosphine (1.5 eq) was added and then dissolved with THF. The flask was cooled to 0° C. and diethyl azodicarboxylate (1.5 eq) was added dropwise. The reaction stirred overnight at room temperature. THF was removed under vacuum and the mixture was purified by HPLC.

The protected substituted ethyloxyaniline was dissolved in dichloromethane and trifluoroacetic acid was added. The reaction stirred at room temperature for 1 hour. The excess trifluoroacetic acid was removed in vivo.

The substituted ethyloxyaniline (1 eq) was mixed with 5-tert-Butyl-3-isocyanato-isoxazole (1 eq) and dissolved in dry toluene. The reaction stirred at 50° C. overnight. The solvent was removed and purified by HPLC. Compound W, compound X, and others in the series were synthesized using the procedure described above.

Synthesis of Compound K1 : 1-(4-(2-morpholinoethoxy)naphthyl)-3-(3-tert-butylisoxazol-5-yl)urea

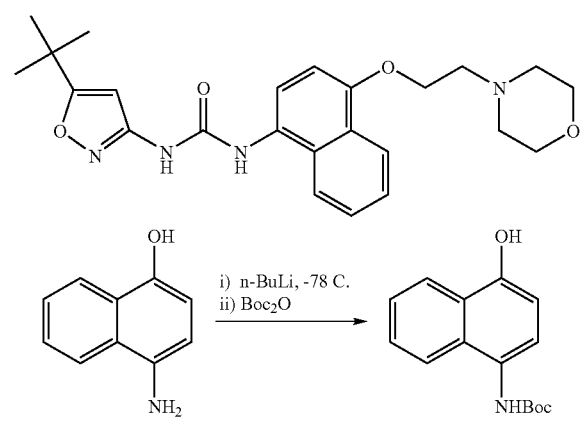

To a mixture of 4-amino-1-naphthol hydrochloride (15 g) in 100 mL dry THF at −78 C was added dropwise over 1 h n-BuLi (43 mL of a 1.6M solution in hexanes). After the addition was complete the mixture was allowed to warm to room temperature and then cooled to −78 C and di-tert-butyl dicarbonate (Boc₂O) (16.5 g in 100 mL THF was added over a period of 20 min). The mixture was slowly warmed to room temperature and stirred for 24 h and then most of the volatiles removed in vacuo. The residue was diluted with ethyl acetate and washed with water (3×100 mL) and brine (100 mL) and filtered through celite and dried over magnesium sulphate. Column chromatography (30% EtOAc/hexanes) gave 20 g of pure product.

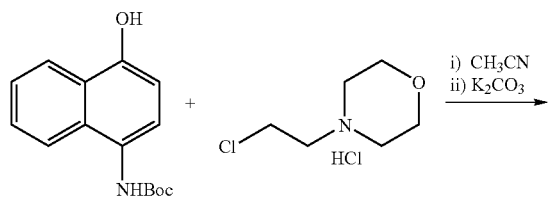

-continued

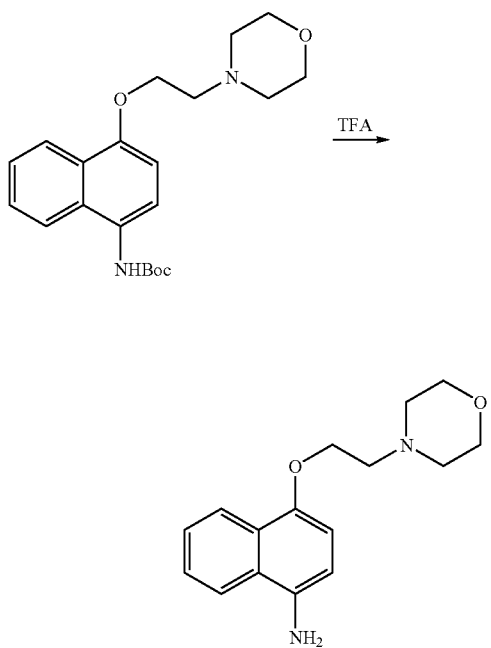

To a solution of (4-Hydroxy-naphthalen-1-yl)-carbamic acid tert-butyl ester (3 g) and 4-(2-Chloro-ethyl)-morpholine hydrochloride (2.22 g) in 25 mL of acetonitrile was added powdered potassium carbonate (6 g) and the solution heated overnight at 80 C. It was cooled, diluted with EtOAc and water. The organic layer was washed with water, brine and dried over anhydrous magnesium sulfate and the volatiles removed in vacuo. Purification by silica gel chromatography (10% EtOAc/hexanes) gave 2.3 g of pure product.

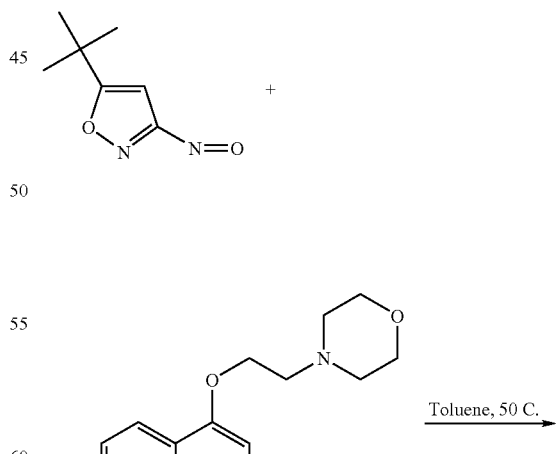

-continued

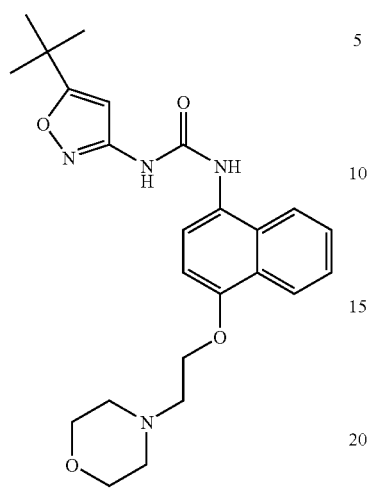

To a flask 5-tert-Butyl-3-isocyanato-isoxazole (242 mg, 1 eq) and substituted aniline (159 mg, 1 eq) was added and dissolved in toluene. The reaction was allowed to stir at 50° C. for three hours. The solvent removed and the mixture was purified by HPLC. Yield: 188 mg (47%)

Compound K2 was synthesized in a manner analogous to Compound K1 using similar starting materials and reagents. The structures are shown below in Table K:

TABLE K

| NO. | CHEMICAL STRUCTURE |
|---|---|
| K1 | 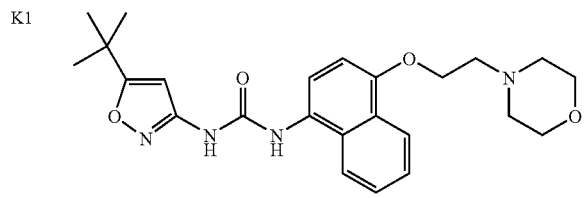 |
| K2 | 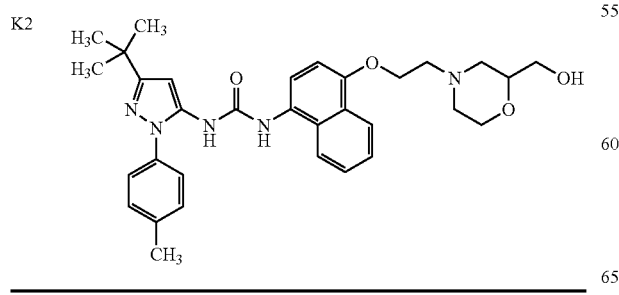 |

Example L

Exemplary Synthesis of Isoxazole-Urea

Synthesis of Compound L1:
1,3-bis(5-tert-butylisoxazol-3-yl)urea

A mixture of amine 5-tert-butyl-isoxazol-3-ylamine (1 eq) in dry THF is stirred at room temperature under argon for an hour. Then the stirred suspension is cooled to 0° C. and to it is added dropwise a solution of phosgene or disuccinimidyl carbonate or carbonyl diimidazole (1.2 eq). The reaction is stirred at 0° C. for half an hour. Then 5-tert-butyl-isoxazol-3-ylamine in THF is added dropwise and the reaction is allowed to warm to room temperature and stirred overnight. The solvent is removed and extracted with ethyl acetate and water. The organic layer is dried over magnesium sulfate and solvent removed, and the 1,3-bis(5-tert-butylisoxazol-3-yl)urea product purified by HPLC.

Example M

Exemplary Synthesis of Pyrimidine Containing Compounds

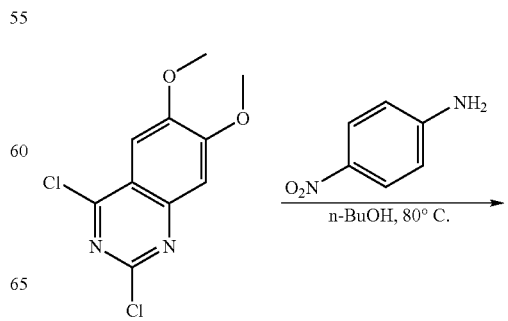

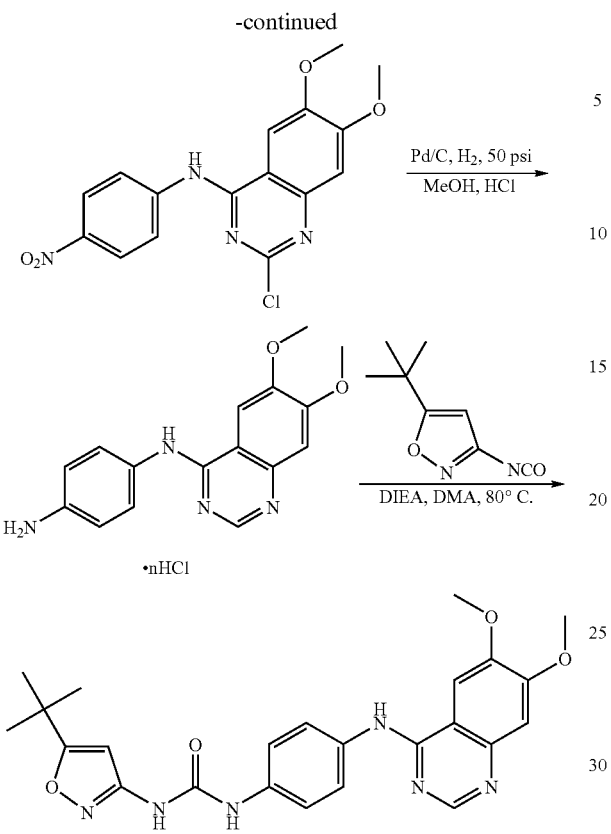

Dichloro-dimethoxyquinazoline was heated for 3 hours at 80° C. with one equivalent p-nitroaniline in n-butanol. After cooling to room temperature, isopropanol was added and the insoluble product was collected by filtration. Reduction was accomplished using 10% Pd/C in methanol at 50 psi in the presence of hydrochloric acid. The resulting aniline was reacted with the oxazole isocyanate in DMA at 80° C. in the presence of DIEA. The urea product was purified by HPLC.

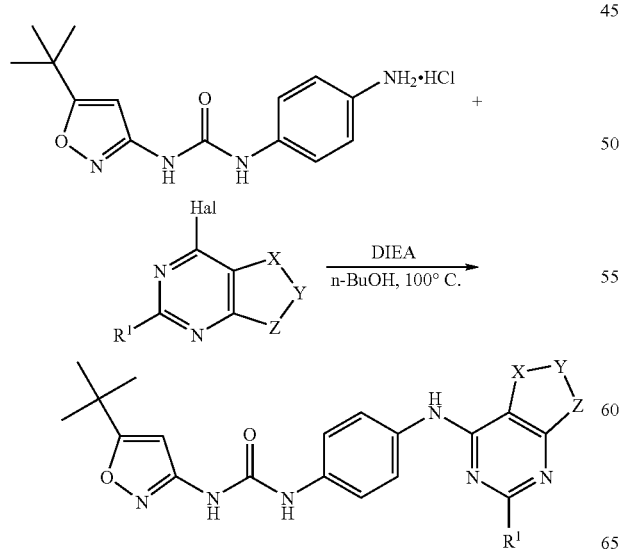

Hal: Cl, Br, I
X-Y-Z: N═CH—NR$^2$
CH═CH—NR$^2$,
CH═CR$^3$—CR$^4$═CH
R$^1$: H, Cl, Br, NR$^5$R$^6$
R$^2$: H, alkyl
R$^3$: O-alkyl
R$^4$: O-alkyl
R$^5$: H, alkyl
R$^6$: H, alkyl, alkylcarbonyl, arylcarbonyl

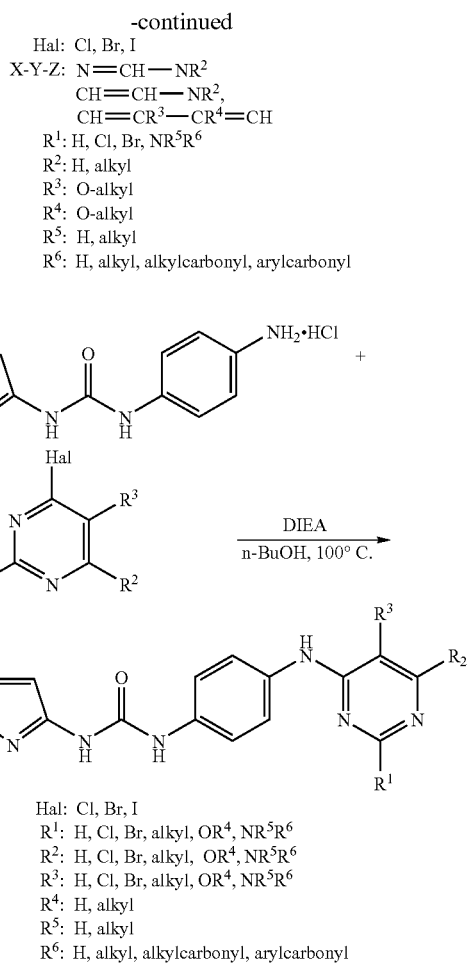

Hal: Cl, Br, I
R$^1$: H, Cl, Br, alkyl, OR$^4$, NR$^5$R$^6$
R$^2$: H, Cl, Br, alkyl, OR$^4$, NR$^5$R$^6$
R$^3$: H, Cl, Br, alkyl, OR$^4$, NR$^5$R$^6$
R$^4$: H, alkyl
R$^5$: H, alkyl
R$^6$: H, alkyl, alkylcarbonyl, arylcarbonyl A mixture of aminourea hydrochloride (155 mg, 0.5 mmol), halopurine/haloquinazoline/halopyrimidine (0.5 mmol), and DIEA (90 μl, 0.5 mmol) in n-butanol (2-5 ml) was heated at 100° C. for 1-16 h. The product was purified by HPLC.

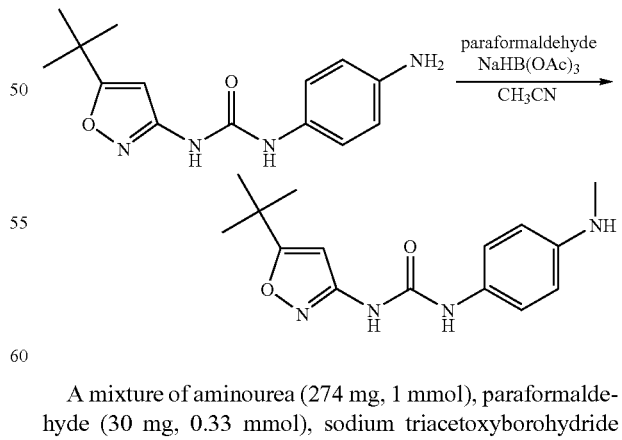

A mixture of aminourea (274 mg, 1 mmol), paraformaldehyde (30 mg, 0.33 mmol), sodium triacetoxyborohydride (636 mg, 3 mmol) and 10 drops glacial acetic acid was stirred at room temperature over night. The solvent was evaporated completely and the residue was treated with sat. aq. NaHCO$_3$. The solids were collected by filtration and purified via HPLC.

The resulting methylaniline was used in amide formations and aryl aminations as described above.

Example N

Exemplary Synthesis of Compounds Containing Amide Linkers

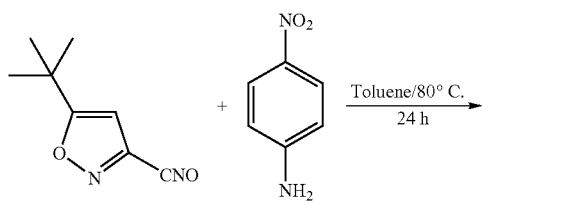

1 gm. (6 mmol) of 5-tert-butyl-isoxazole-3-isocyanate and 0.83 gm (6 mmol) 4-nitro-phenylamine were dissolved in 20 ml dry toluene and stirred at 80° C. for 24 h. The resulting suspension was cooled to room temperature and filtered off to give the title compound as a yellow solid. The product was used in the next step without further purification. Yield: 1.7 g (92%), LC/MS [MH⁺] 305.

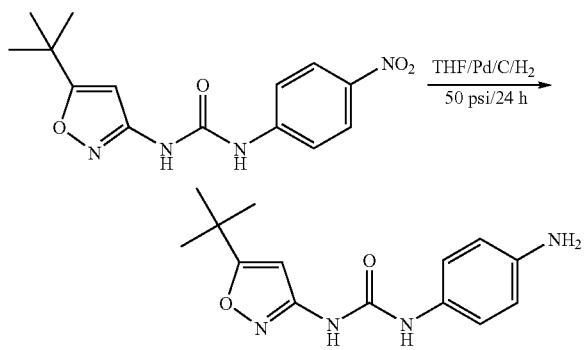

1.5 gm of 1-(5-tert-butyl-isoxazol-3-yl)-3-(4-nitro-phenyl)-urea was dissolved in 50 ml THF and 0.1 g of 10% Pd/C was added. The solution was stirred under hydrogen at 50 psi. for 24 h than filtered trough Celite pad. The organic solvent was evaporated under vacuum and the resulting residue was triturated with ethyl acetate. Yield: 1.3 g (96%), LC/MS [MH⁺] 275.

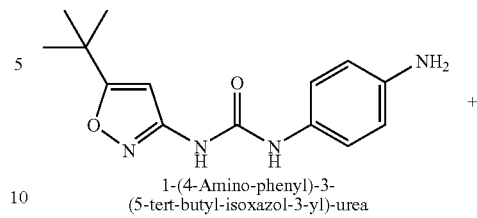

1-(4-Amino-phenyl)-3-(5-tert-butyl-isoxazol-3-yl)-urea

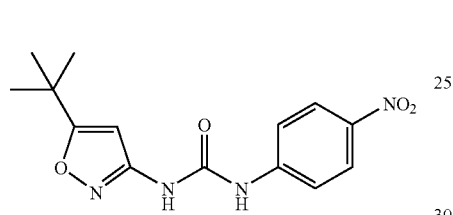

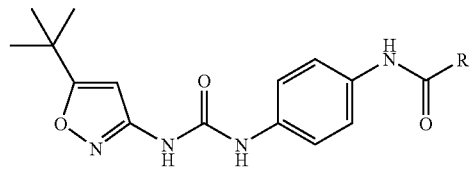

1 equivalent of the carboxylic acid and 1.1 equivalent of CDI were dissolved in dry DMF and stirred at 40° C. for 2 h, than 1 equivalent of aniline was added. The reaction mixture was stirred at 40° C. overnight and the final product was purified by preparative HPLC.

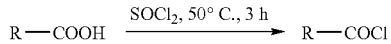

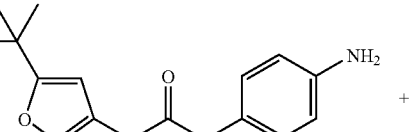

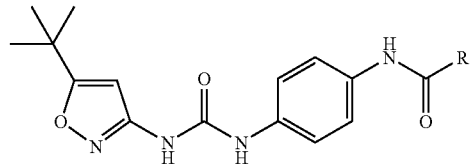

Alternatively, 1 equivalent of the carboxylic acid and 1.1 equivalent of thionyl chloride were heated in a sealed tube at 50° C. for 3 h. The excess thionyl chloride was evaporated, 1 equivalent of aniline in DMF was added, and the solution stirred at room temperature for 8 h. The final product was purified by preparative HPLC.

Compounds N1 through N189 were synthesized in a manner analogous to one of the above procedures using similar starting materials and reagents. The structures are shown below in Table N:

TABLE N

| NO. | CHEMICAL STRUCTURE |
|---|---|
| N1 | 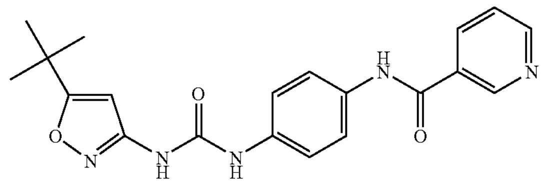 |
| N2 | 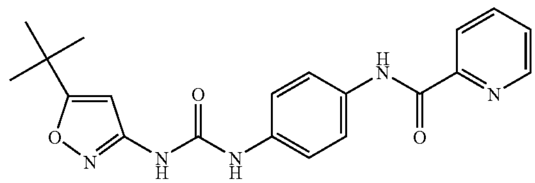 |
| N3 | 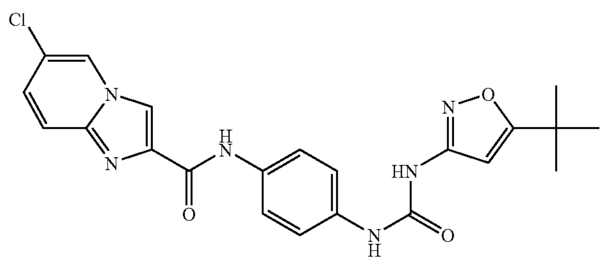 |
| N4 | 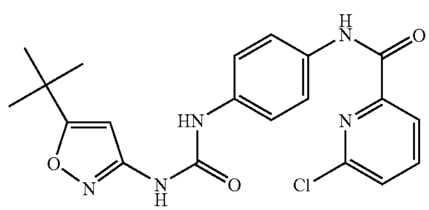 |
| N5 | 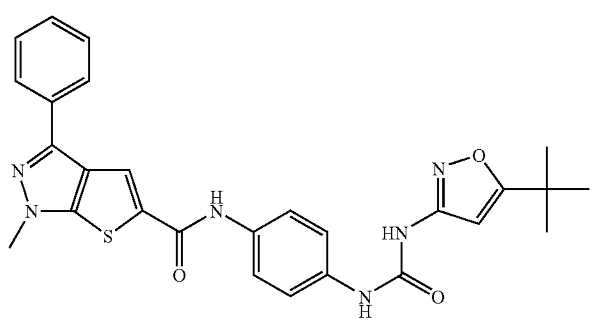 |
| N6 | 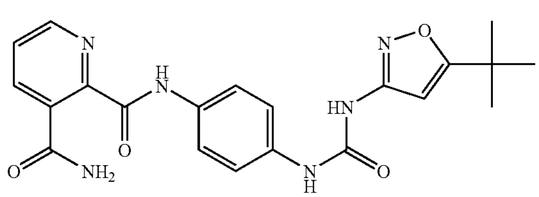 |

TABLE N-continued

| NO. | CHEMICAL STRUCTURE |
|---|---|
| N7 | 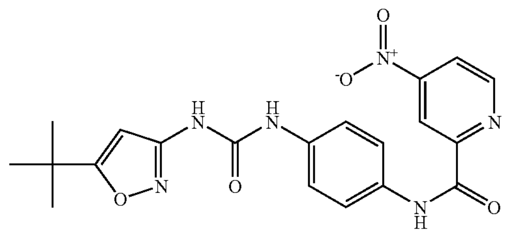 |
| N8 | 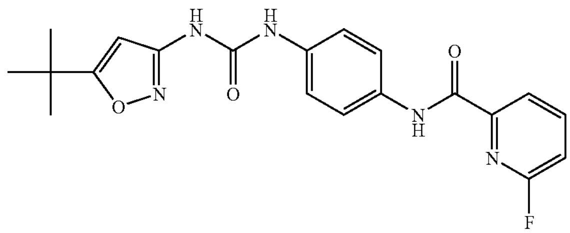 |
| N9 | 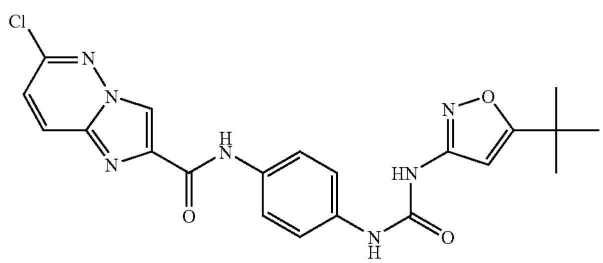 |
| N10 | 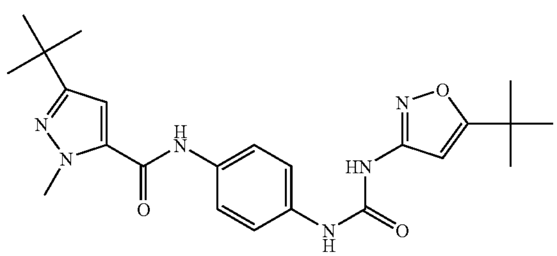 |
| N11 | 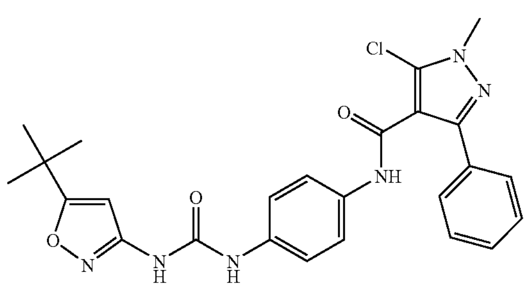 |
| N12 | 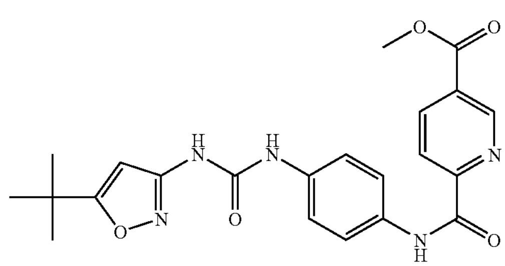 |

TABLE N-continued

| NO. | CHEMICAL STRUCTURE |
|---|---|
| N13 | 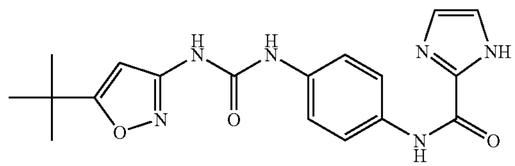 |
| N14 | 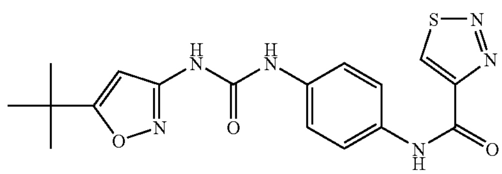 |
| N15 | 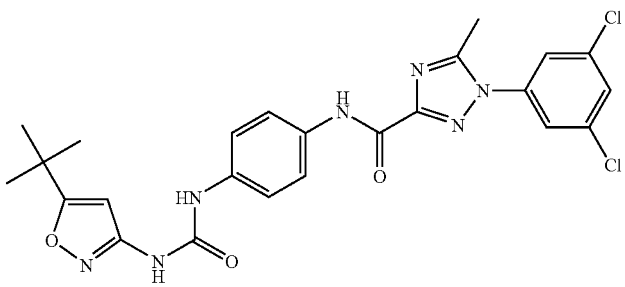 |
| N16 | 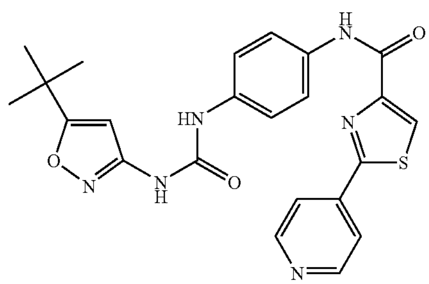 |
| N17 | 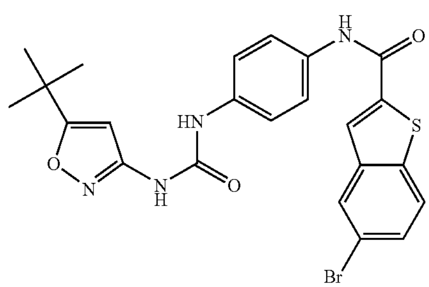 |
| N18 | 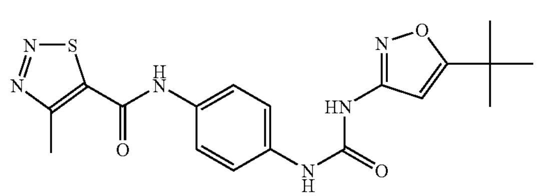 |

TABLE N-continued
| NO. | CHEMICAL STRUCTURE |
|---|---|
| N19 | 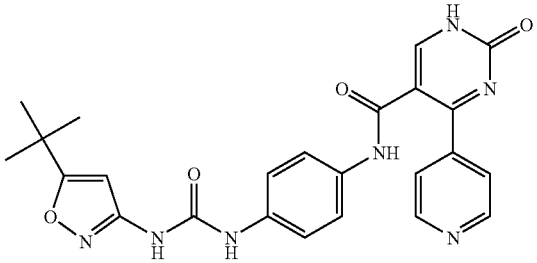 |
| N20 | 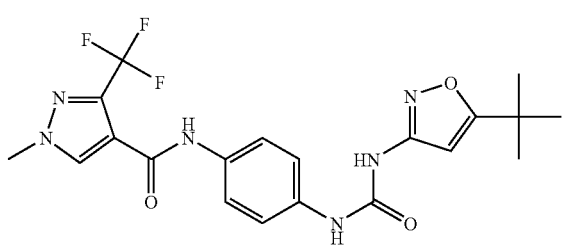 |
| N21 | 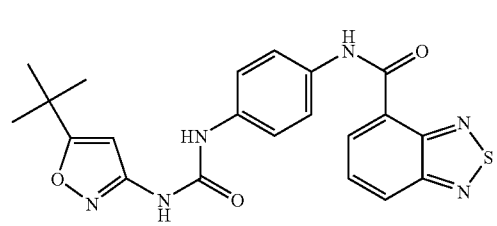 |
| N22 | 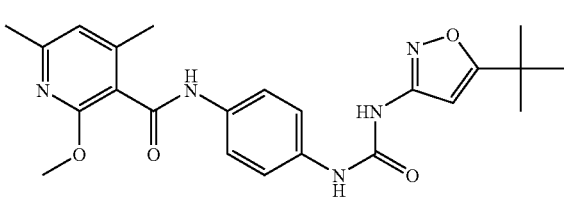 |
| N23 | 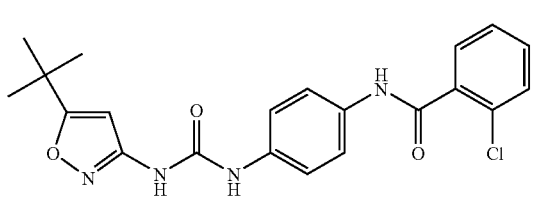 |
| N24 | 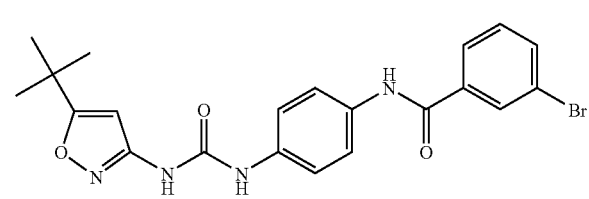 |
| N25 | 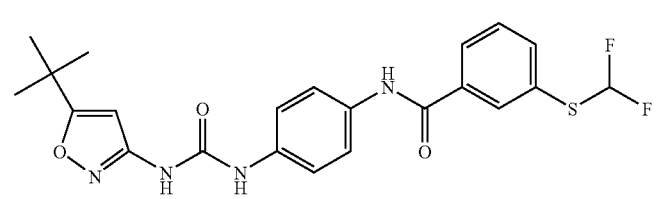 |

TABLE N-continued

| NO. | CHEMICAL STRUCTURE |
|---|---|
| N26 | 5-tert-butyl-isoxazol-3-yl urea linked to 4-(4-chlorobenzamido)phenyl |
| N27 | 5-tert-butyl-isoxazol-3-yl urea linked to 4-(4-bromobenzamido)phenyl |
| N28 | 5-tert-butyl-isoxazol-3-yl urea linked to 4-(naphthalene-2-carboxamido)phenyl |
| N29 | 5-tert-butyl-isoxazol-3-yl urea linked to 4-(3,5-dichlorobenzamido)phenyl |
| N30 | 5-tert-butyl-isoxazol-3-yl urea linked to 4-(4-trifluoromethoxybenzamido)phenyl |
| N31 | 5-tert-butyl-isoxazol-3-yl urea linked to 4-(2,4,6-trimethylbenzamido)phenyl |
| N32 | 5-tert-butyl-isoxazol-3-yl urea linked to 4-(4-ethylbenzamido)phenyl |

TABLE N-continued
| NO. | CHEMICAL STRUCTURE |
|---|---|
| N33 | 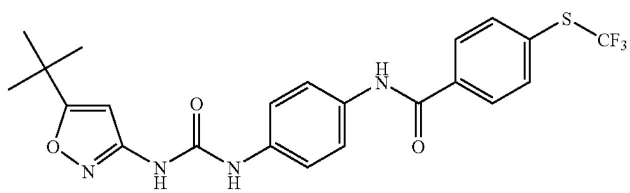 |
| N34 | 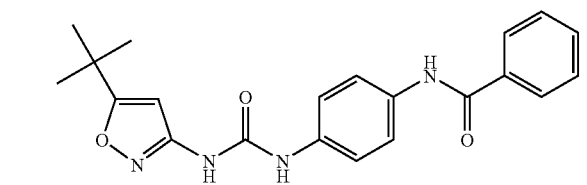 |
| N35 | 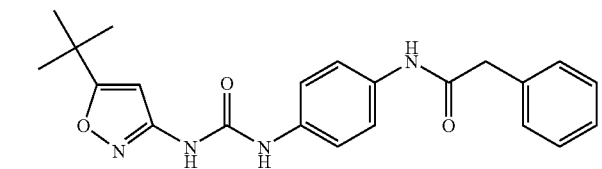 |
| N36 | 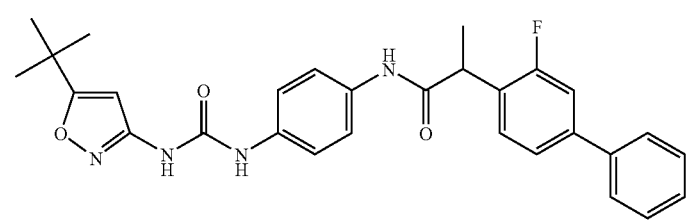 |
| N37 | 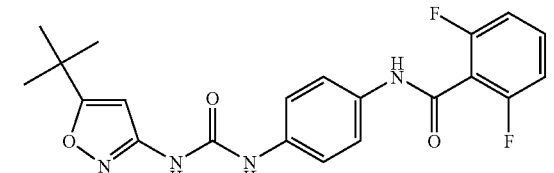 |
| N38 | 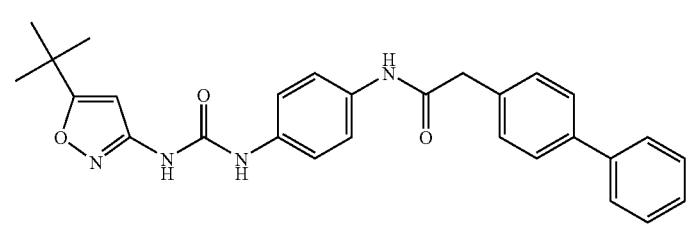 |

TABLE N-continued
| NO. | CHEMICAL STRUCTURE |
|---|---|
| N39 | 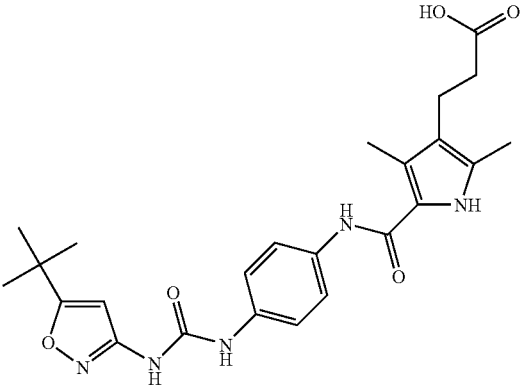 |
| N40 | 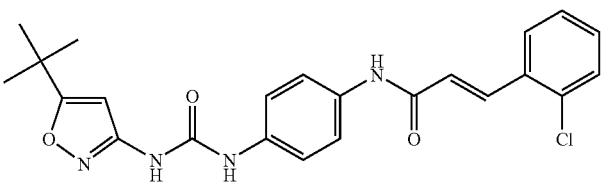 |
| N41 | 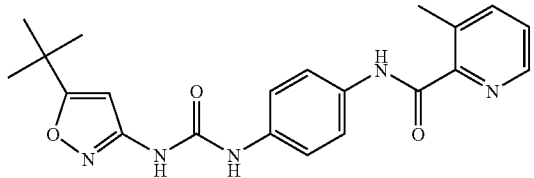 |
| N42 | 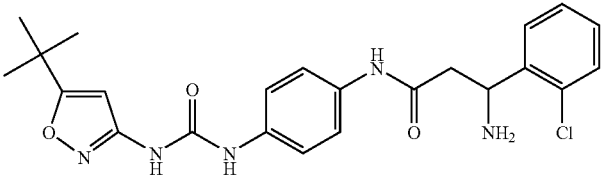 |
| N43 | 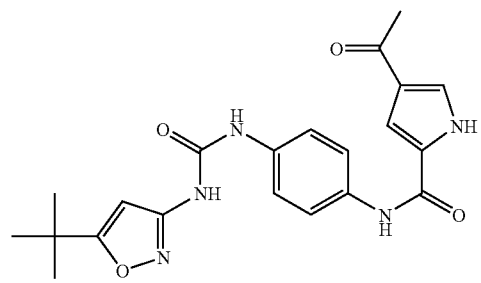 |
| N44 | 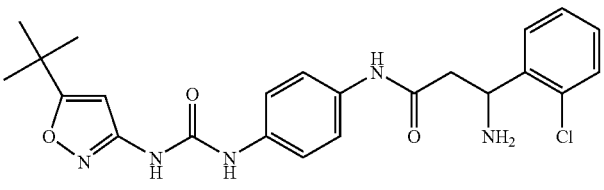 |

TABLE N-continued
| NO. | CHEMICAL STRUCTURE |
|---|---|
| N45 | 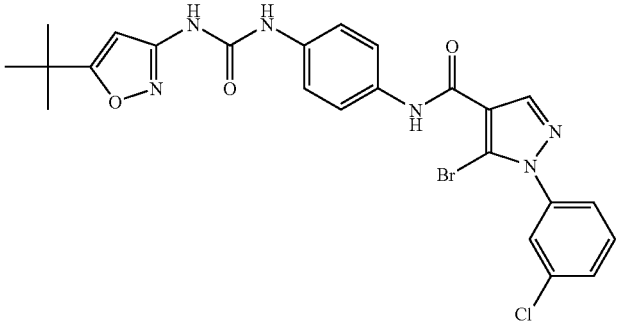 |
| N47 | 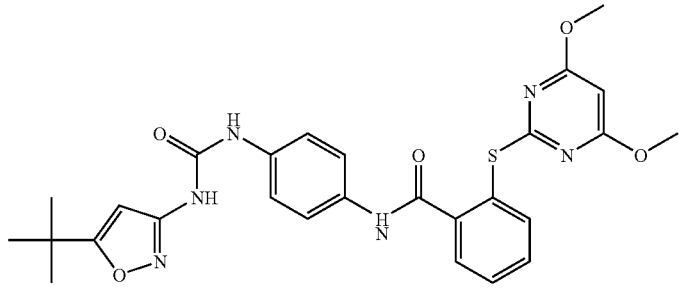 |
| N48 | 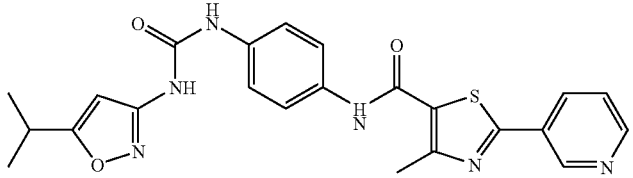 |
| N49 | 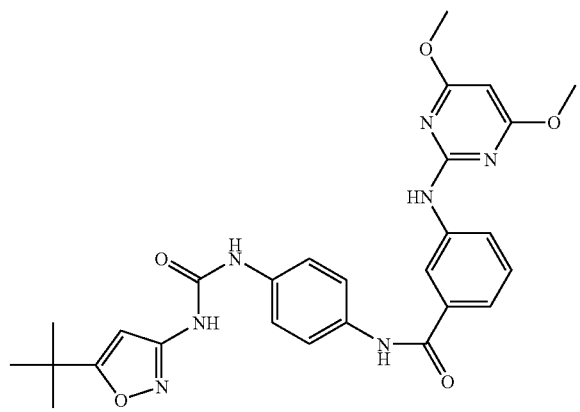 |

TABLE N-continued
| NO. | CHEMICAL STRUCTURE |
|---|---|
| N50 | 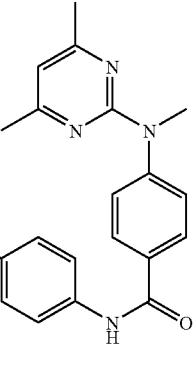 |
| N51 | 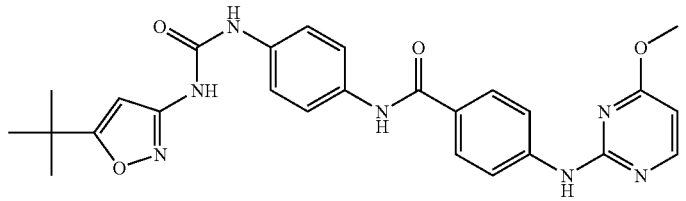 |
| N52 | 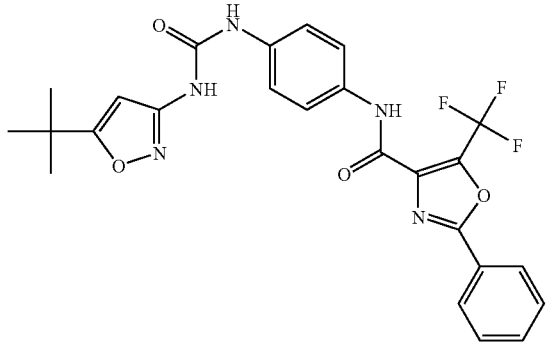 |
| N53 | 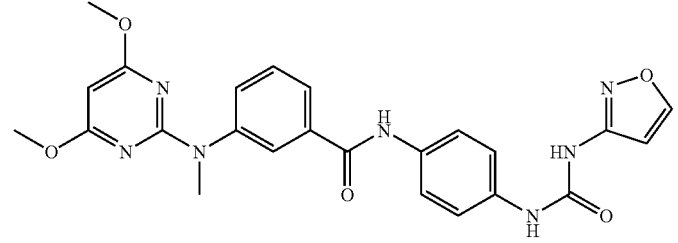 |
| N54 | 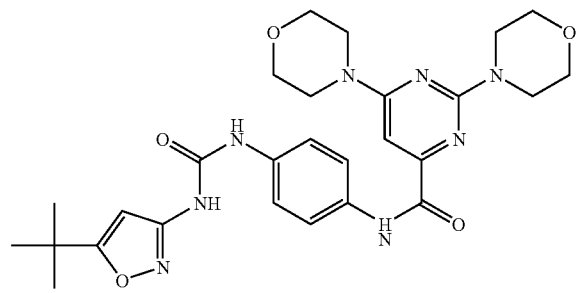 |

TABLE N-continued

| NO. | CHEMICAL STRUCTURE |
|---|---|
| N55 | 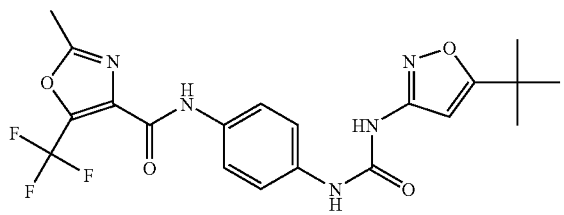 |
| N56 | 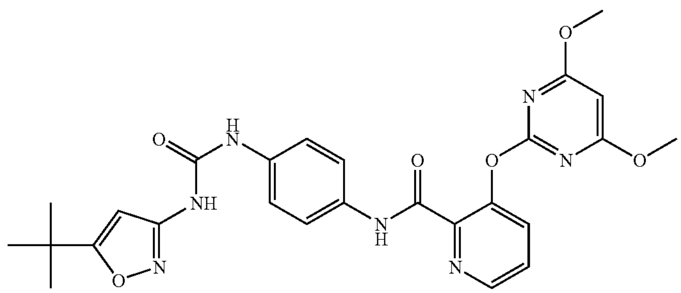 |
| N57 | 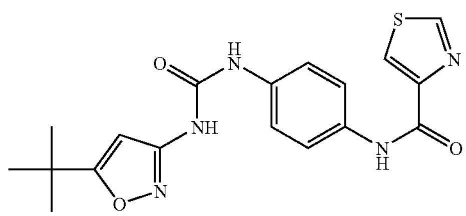 |
| N58 | 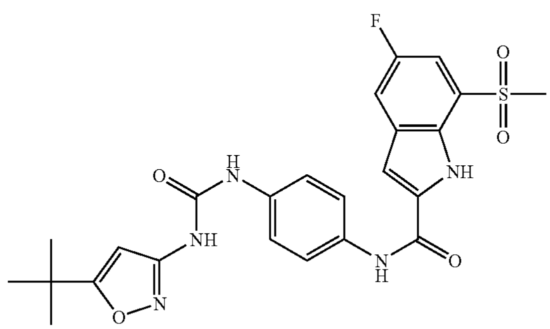 |
| N59 | 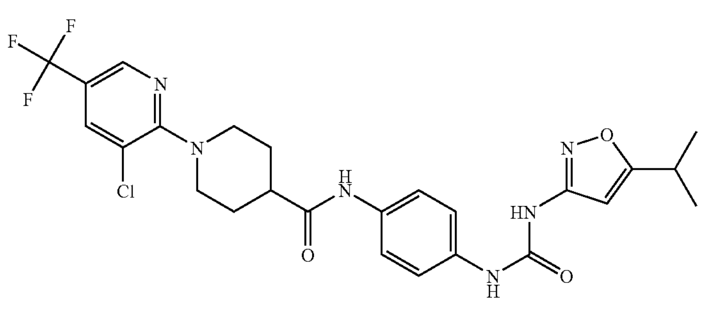 |

TABLE N-continued

| NO. | CHEMICAL STRUCTURE |
|---|---|
| N60 | 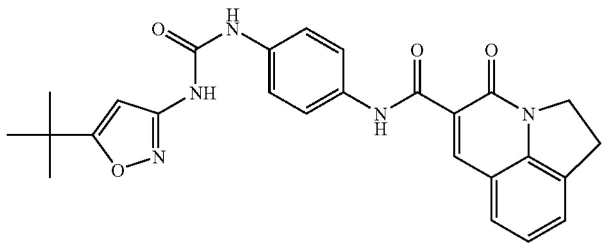 |
| N61 | 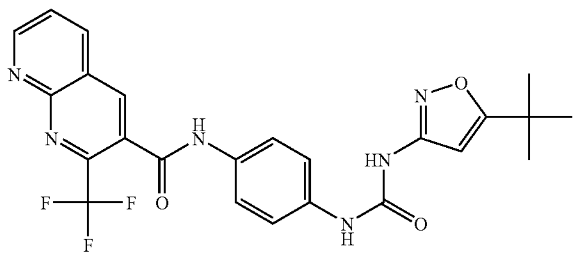 |
| N62 | 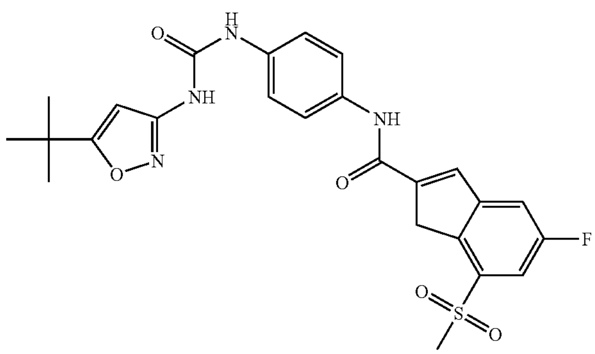 |
| N63 | 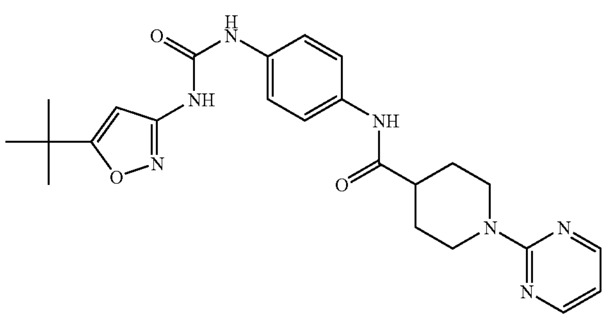 |
| N64 | 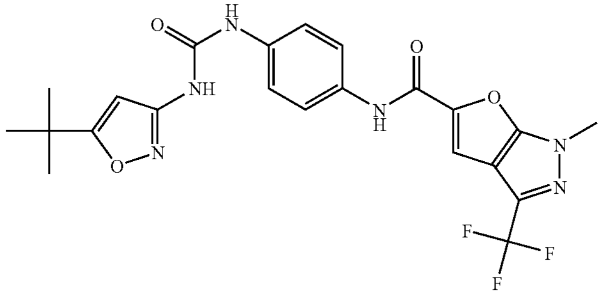 |

TABLE N-continued
| NO. | CHEMICAL STRUCTURE |
|---|---|
| N65 | 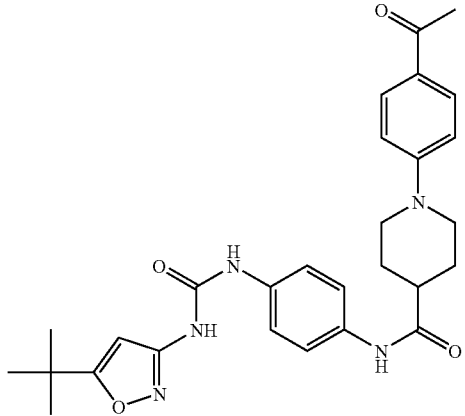 |
| N66 | 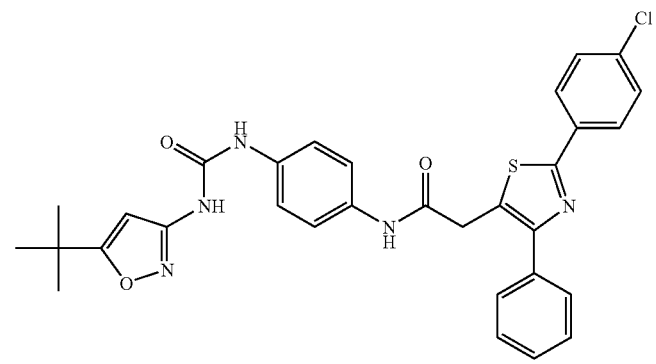 |
| N67 | 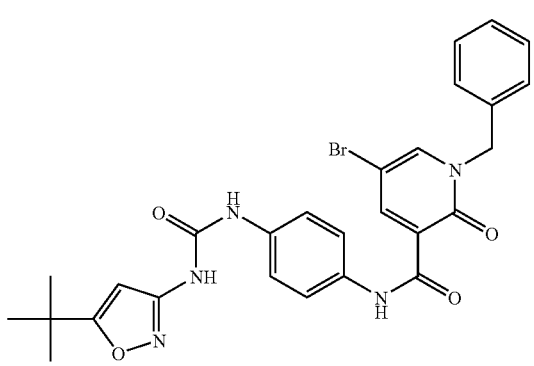 |
| N68 | 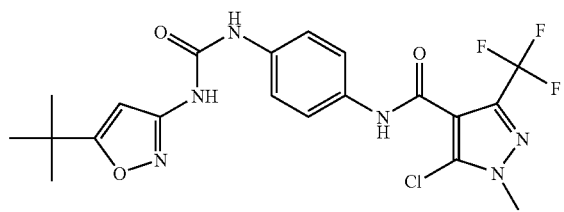 |

TABLE N-continued
| NO. | CHEMICAL STRUCTURE |
|---|---|
| N69 | 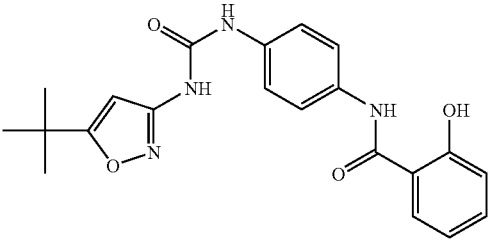 |
| N70 | 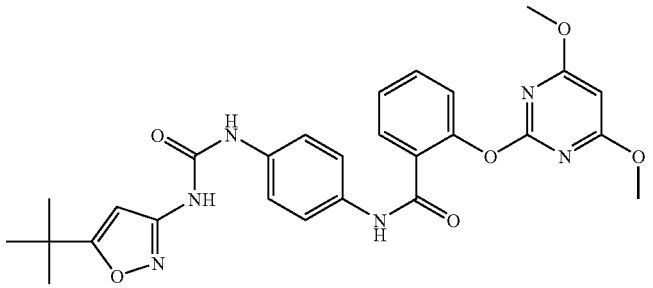 |
| N71 | 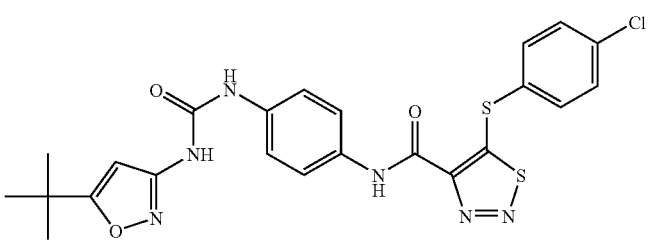 |
| N72 | 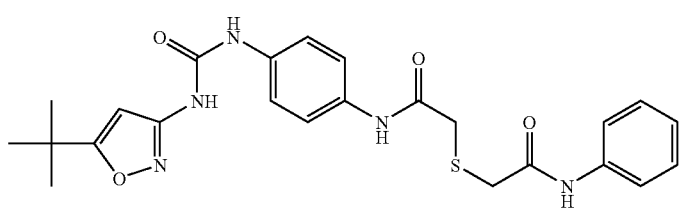 |
| N73 | 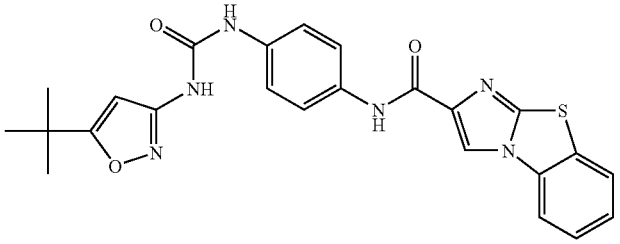 |
| N74 | 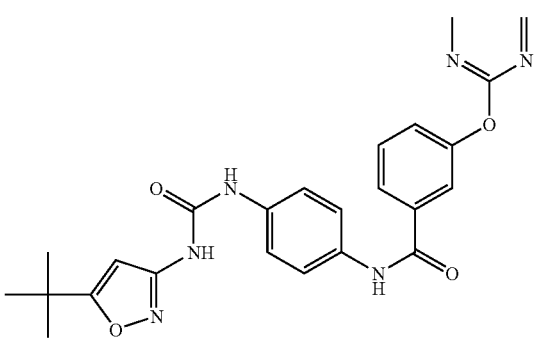 |

TABLE N-continued
| NO. | CHEMICAL STRUCTURE |
|---|---|
| N75 | 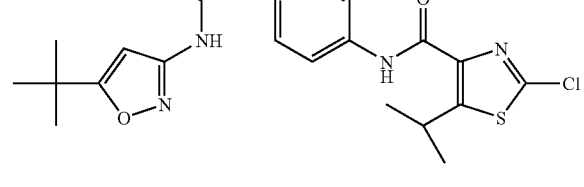 |
| N76 | 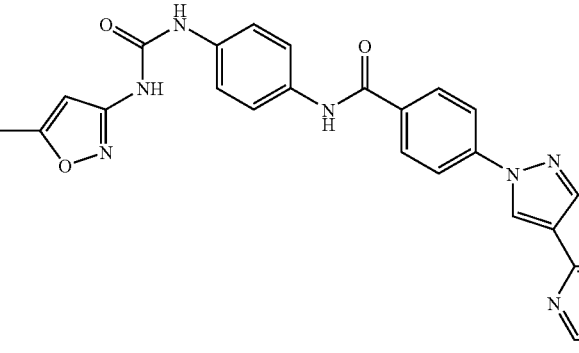 |
| N77 | 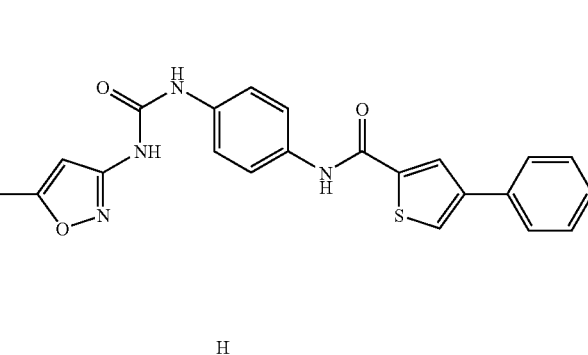 |
| N78 | 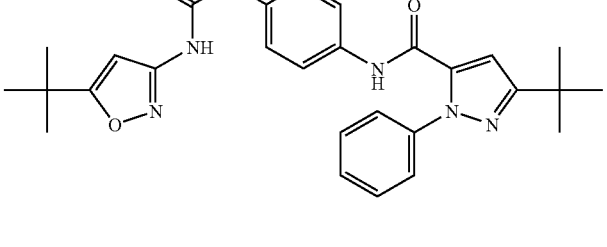 |
| N79 | 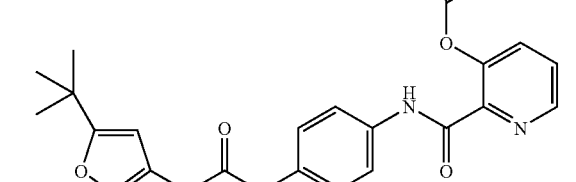 |

TABLE N-continued
| NO. | CHEMICAL STRUCTURE |
|---|---|
| N80 | 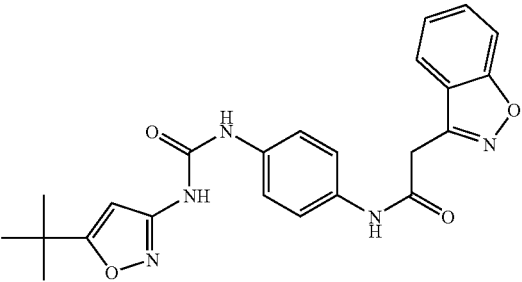 |
| N81 | 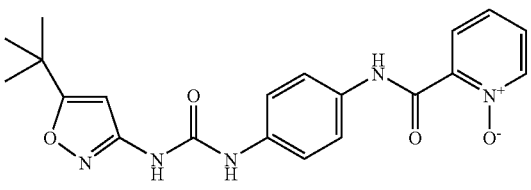 |
| N82 | 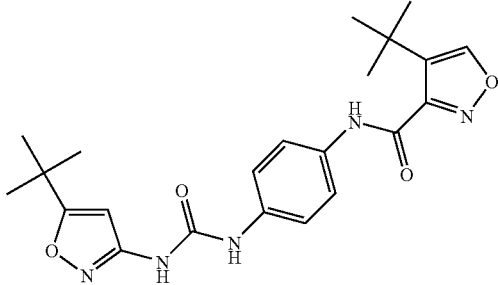 |
| N83 | 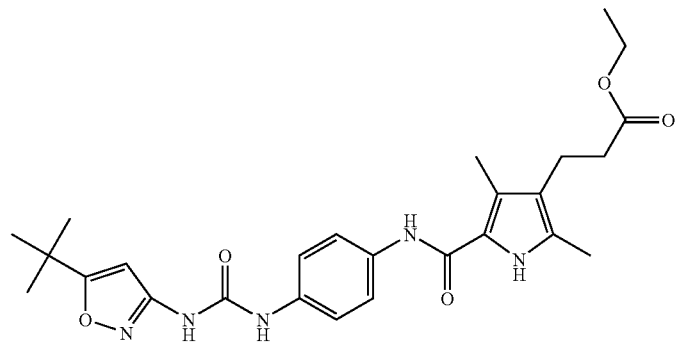 |
| N84 | 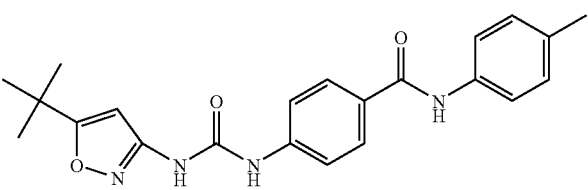 |
| N85 | 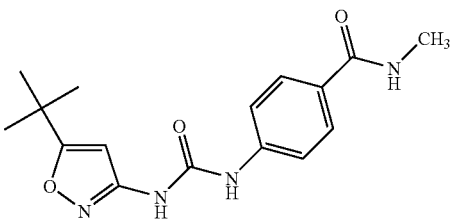 |

TABLE N-continued

| NO. | CHEMICAL STRUCTURE |
|---|---|
| N86 | 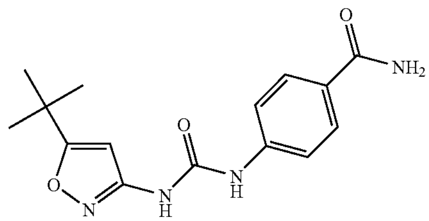 |
| N87 | 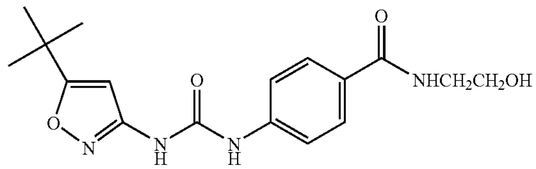 |
| N88 | 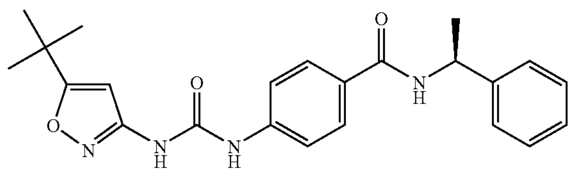 |
| N89 | 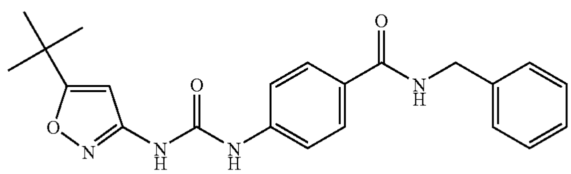 |
| N90 | 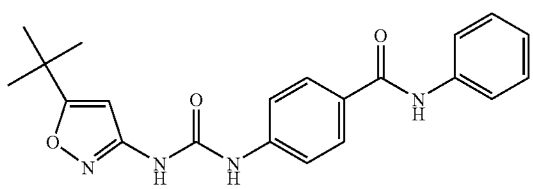 |
| N91 | 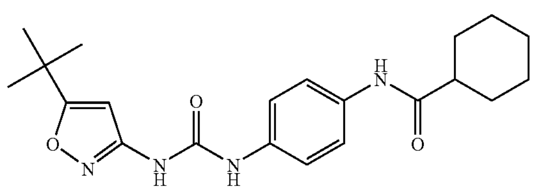 |
| N92 | 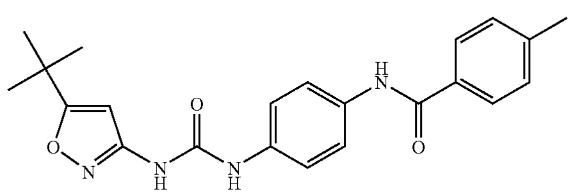 |
| N93 | 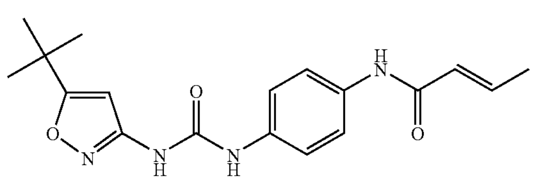 |

TABLE N-continued

| NO. | CHEMICAL STRUCTURE |
|---|---|
| N94 | 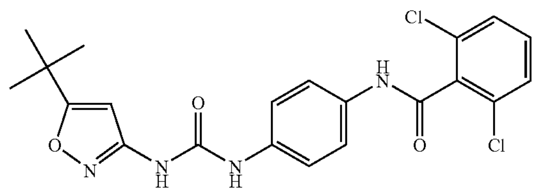 |
| N95 | 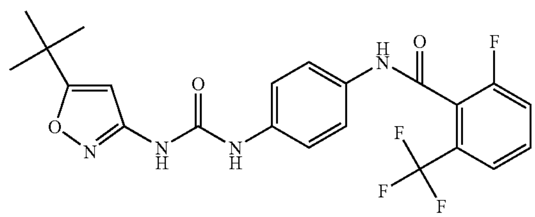 |
| N96 | 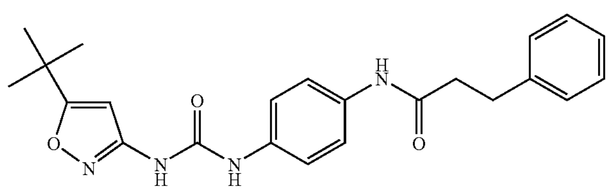 |
| N97 | 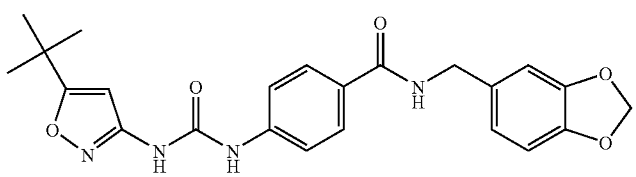 |
| N98 | 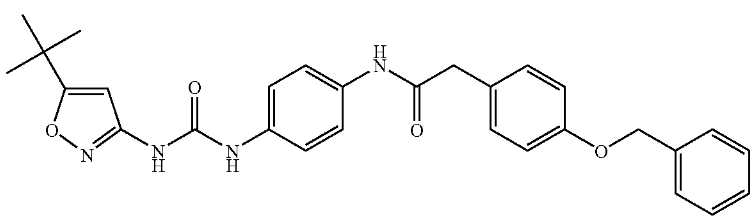 |
| N99 | 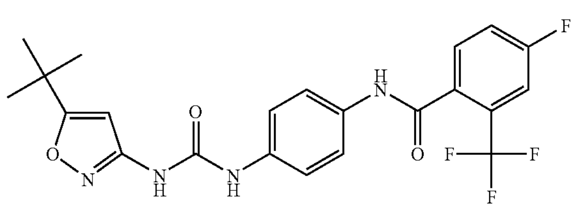 |
| N100 | 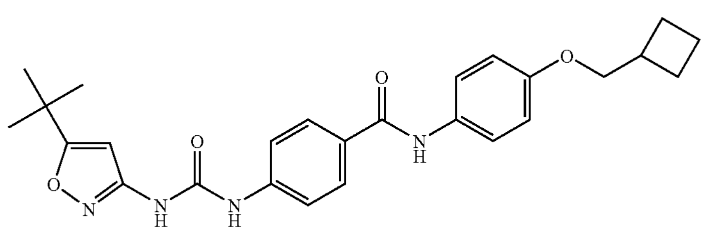 |

TABLE N-continued
| NO. | CHEMICAL STRUCTURE |
|---|---|
| N101 | 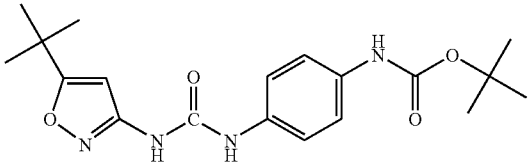 |
| N102 | 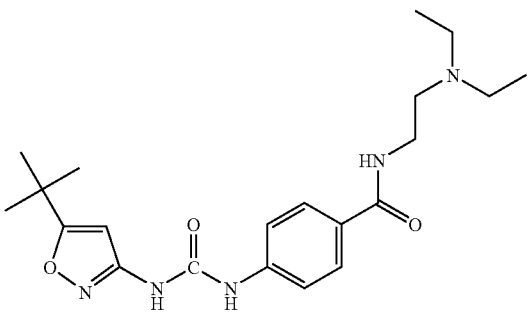 |
| N103 | 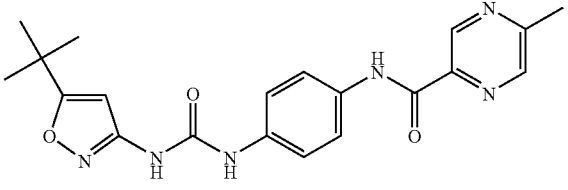 |
| N104 | 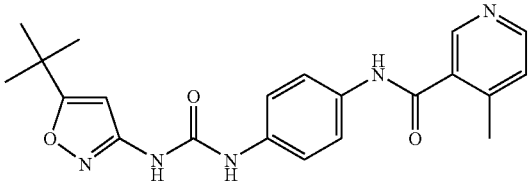 |
| N105 | 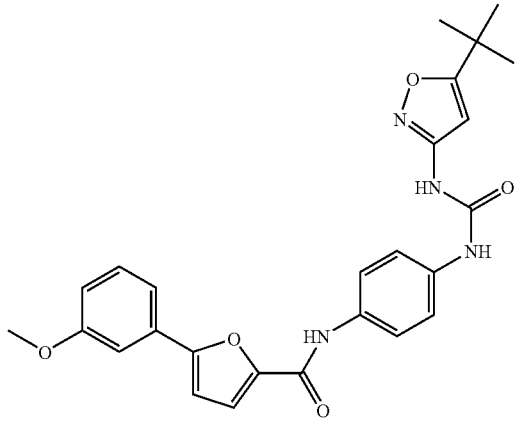 |
| N106 | 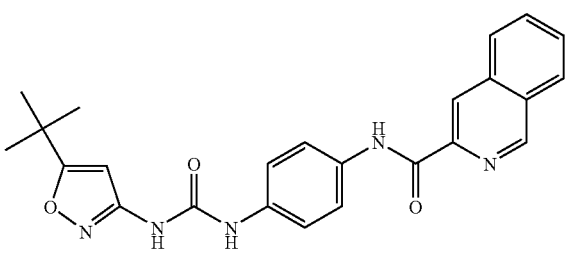 |

TABLE N-continued
| NO. | CHEMICAL STRUCTURE |
|---|---|
| N107 | 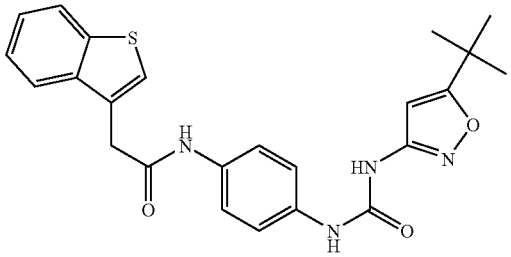 |
| N108 | 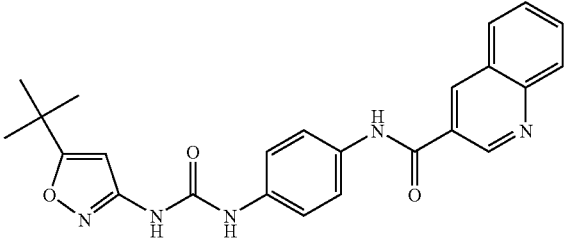 |
| N109 | 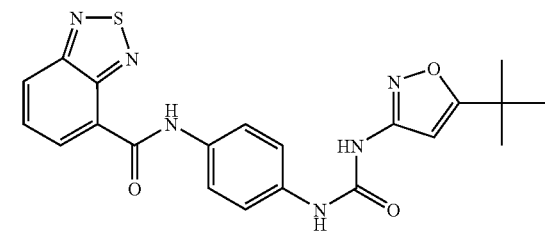 |
| N110 | 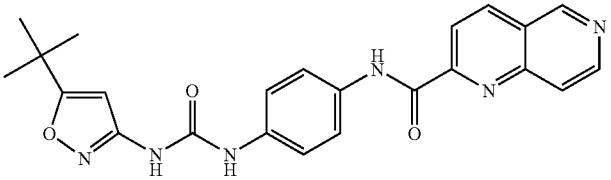 |
| N111 | 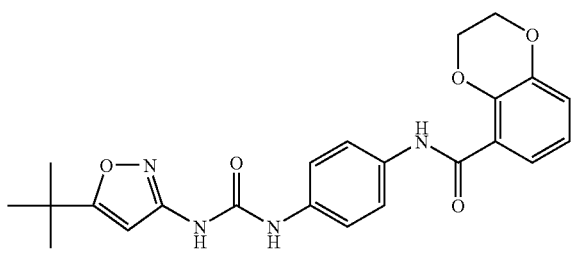 |
| N112 | 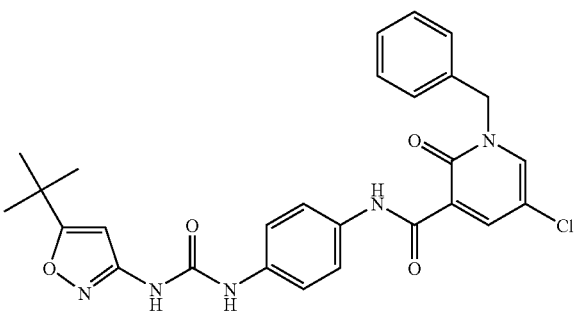 |

TABLE N-continued
| NO. | CHEMICAL STRUCTURE |
|---|---|
| N113 | 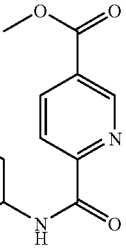 |
| N114 | 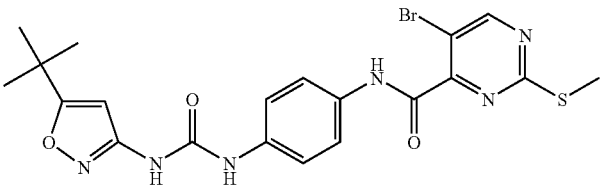 |
| N115 | 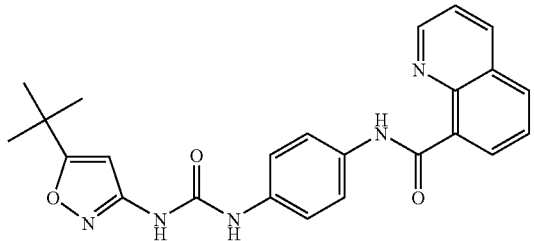 |
| N116 | 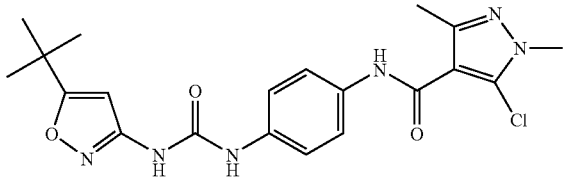 |
| N117 | 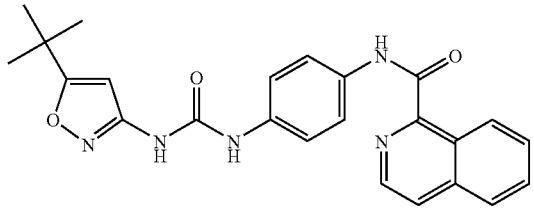 |
| N118 | 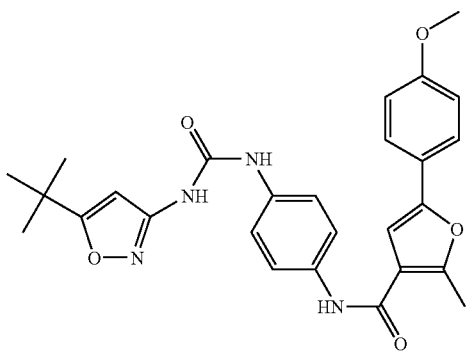 |

TABLE N-continued
| NO. | CHEMICAL STRUCTURE |
|---|---|
| N119 | 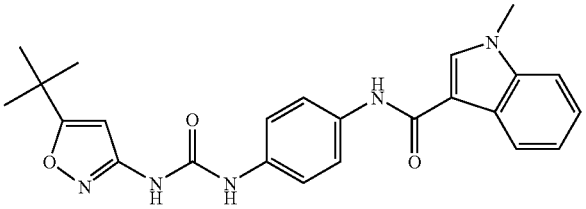 |
| N120 | 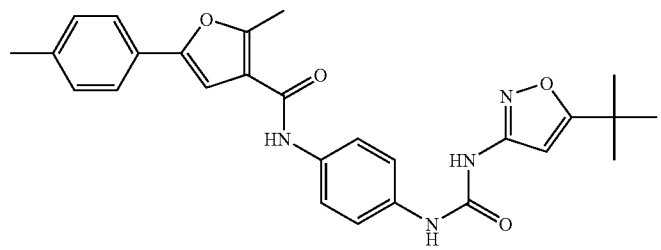 |
| N121 | 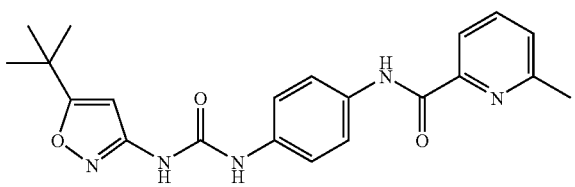 |
| N122 | 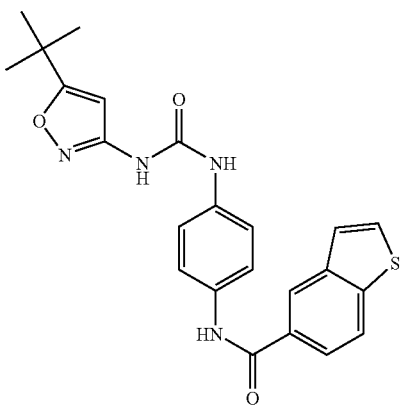 |
| N123 | 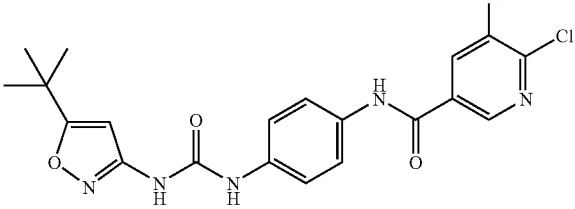 |

TABLE N-continued

| NO. | CHEMICAL STRUCTURE |
|---|---|
| N124 | 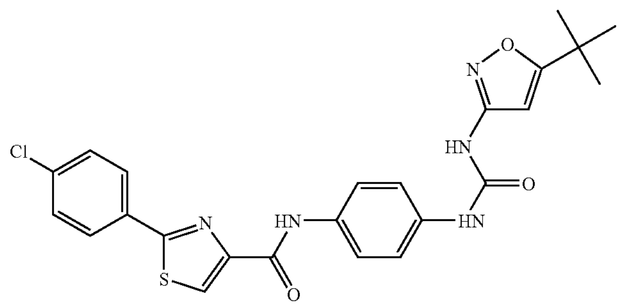 |
| N125 | 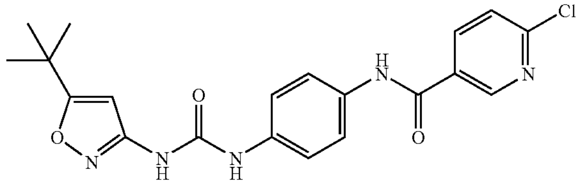 |
| N126 | 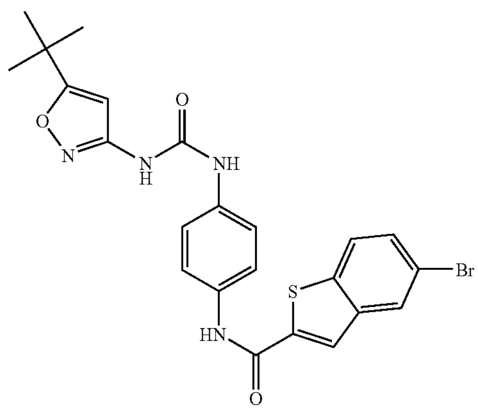 |
| N127 | 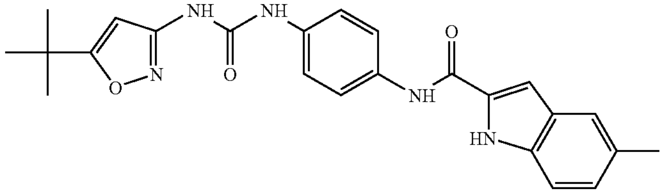 |
| N128 | 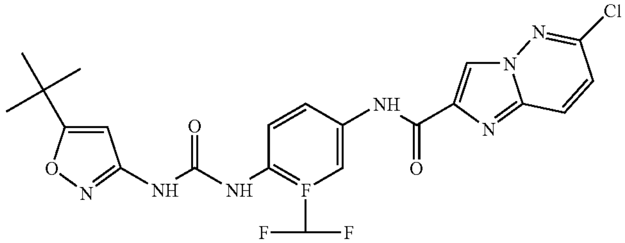 |

TABLE N-continued

| NO. | CHEMICAL STRUCTURE |
|---|---|
| N129 | 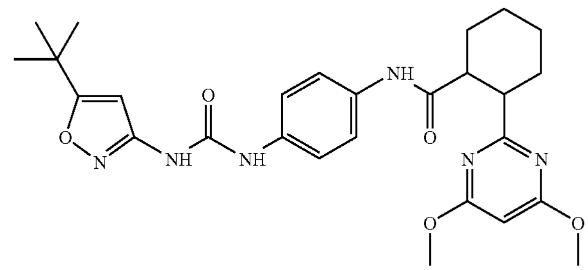 |
| N130 | 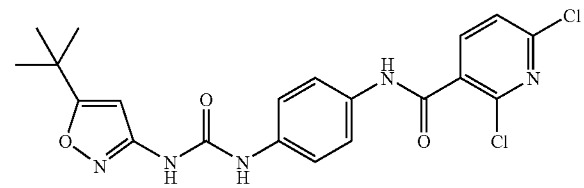 |
| N131 | 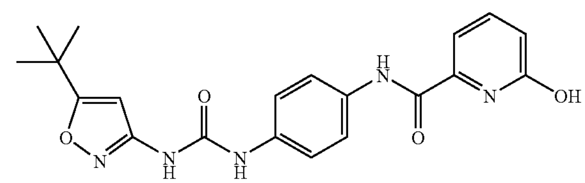 |
| N132 | 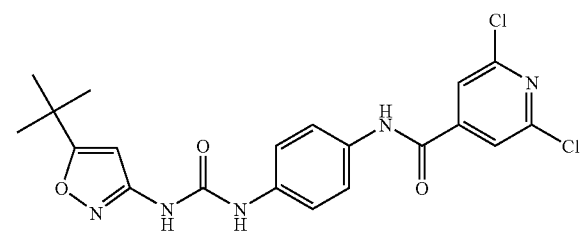 |
| N133 | 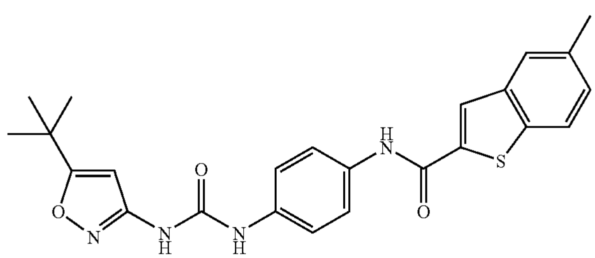 |
| N134 | 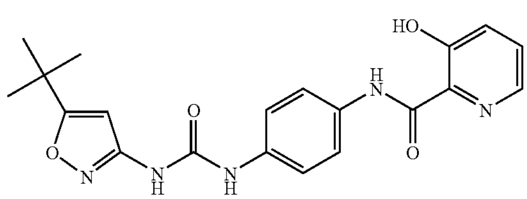 |
| N135 | 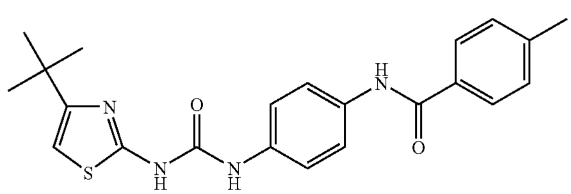 |

TABLE N-continued

| NO. | CHEMICAL STRUCTURE |
|---|---|
| N136 | 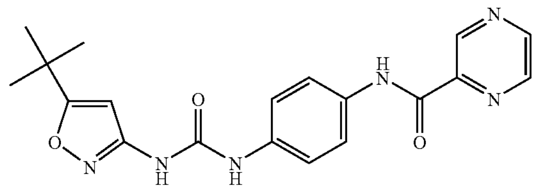 |
| N137 | 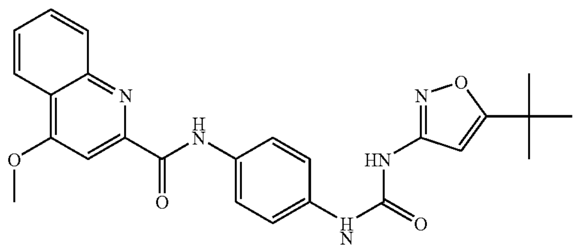 |
| N138 | 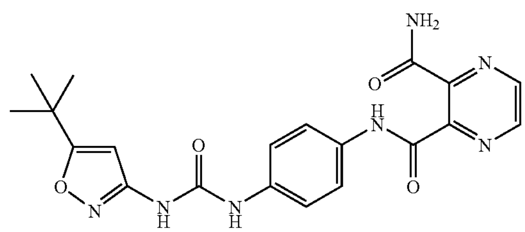 |
| N139 | 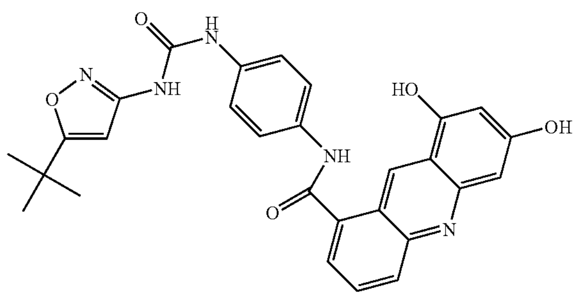 |
| N140 | 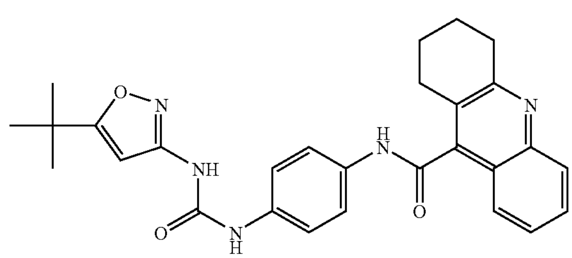 |
| N141 | 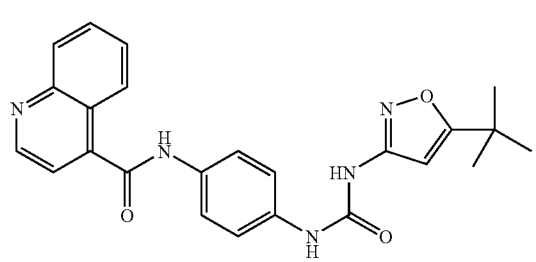 |

TABLE N-continued

| NO. | CHEMICAL STRUCTURE |
|---|---|
| N142 | 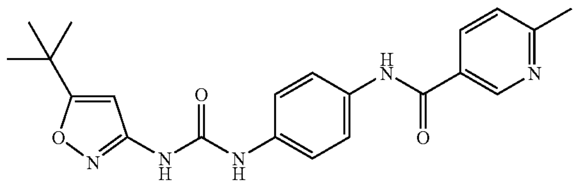 |
| N143 | 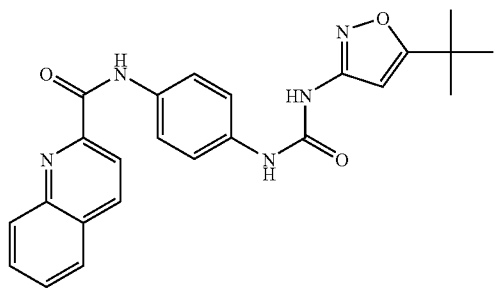 |
| N144 | 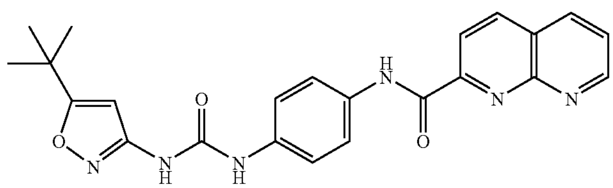 |
| N145 | 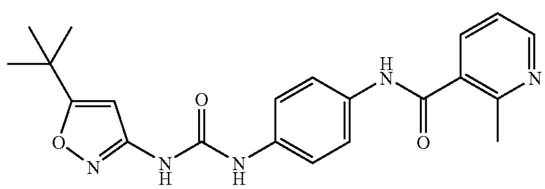 |
| N146 | 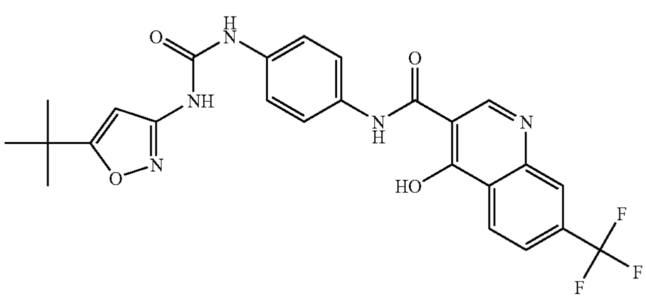 |
| N147 | 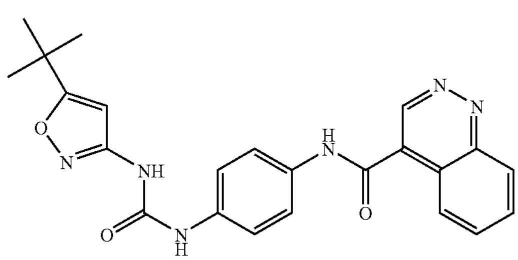 |

TABLE N-continued

| NO. | CHEMICAL STRUCTURE |
|---|---|
| N148 | 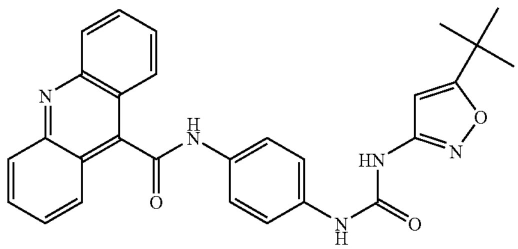 |
| N149 | 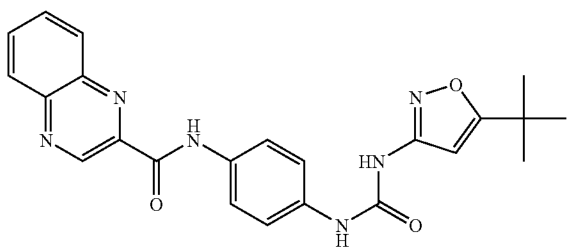 |
| N150 | 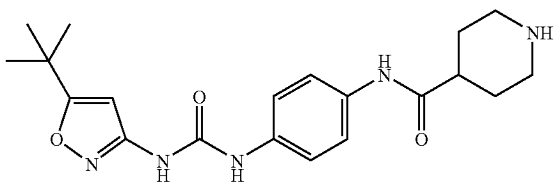 |
| N151 | 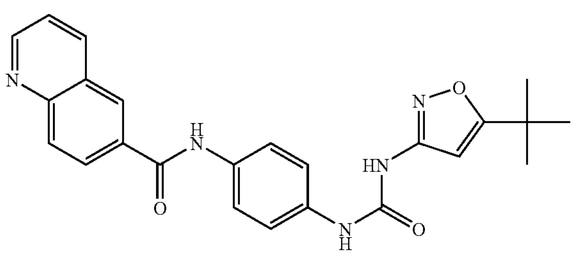 |
| N152 | 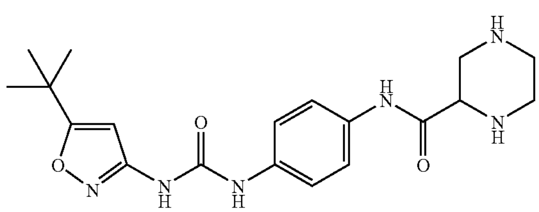 |
| N153 | 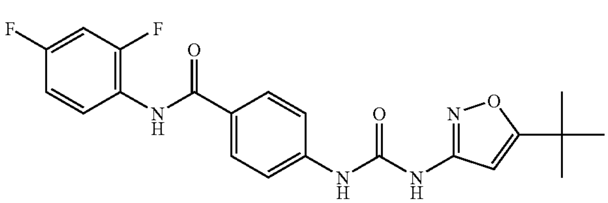 |

TABLE N-continued

| NO. | CHEMICAL STRUCTURE |
|---|---|
| N154 | 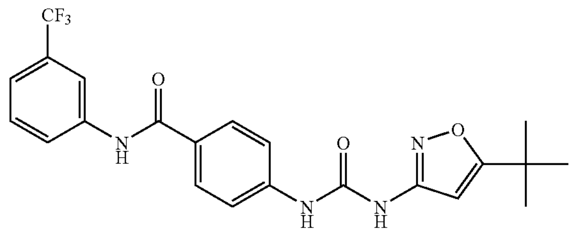 |
| N155 | 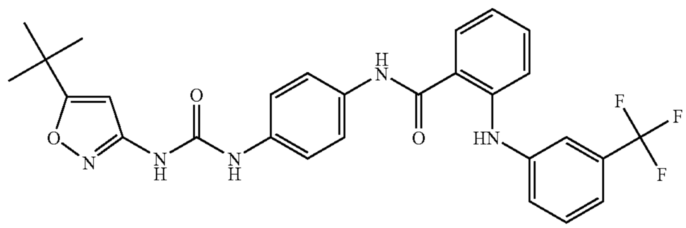 |
| N156 | 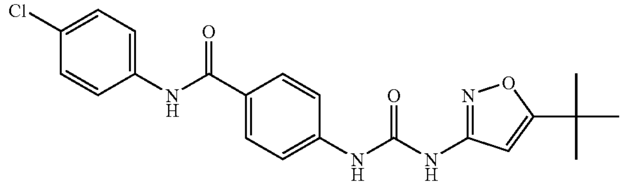 |
| N157 | 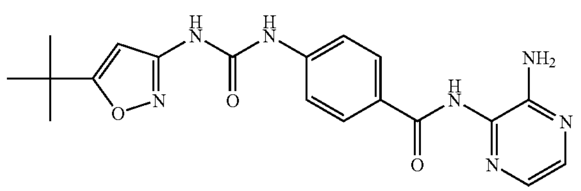 |
| N158 | 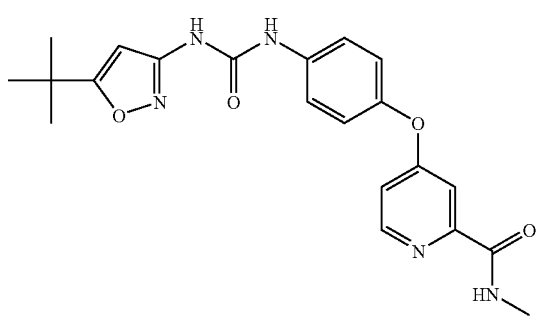 |
| N159 | 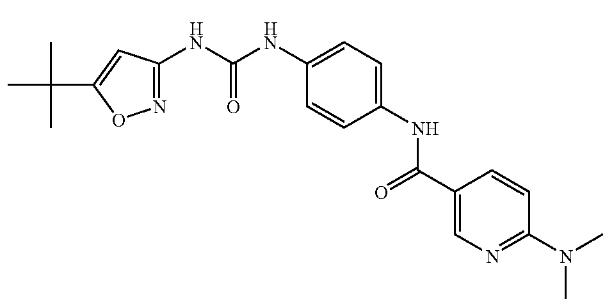 |

TABLE N-continued

| NO. | CHEMICAL STRUCTURE |
|-----|--------------------|
| N160 | 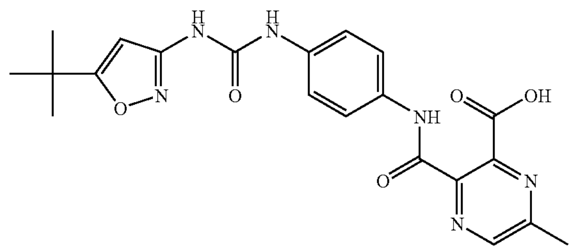 |
| N161 | 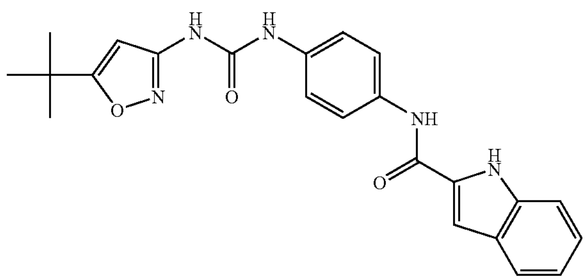 |
| N162 | 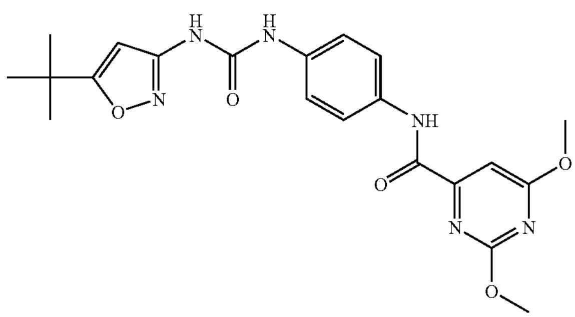 |
| N163 | 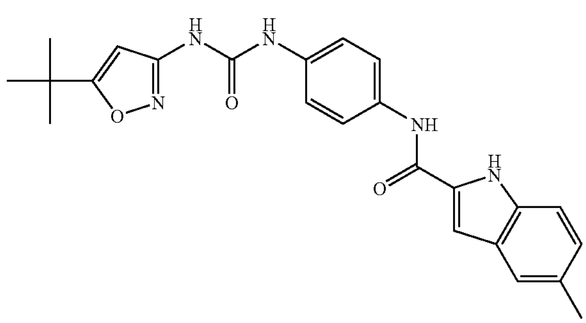 |
| N164 | 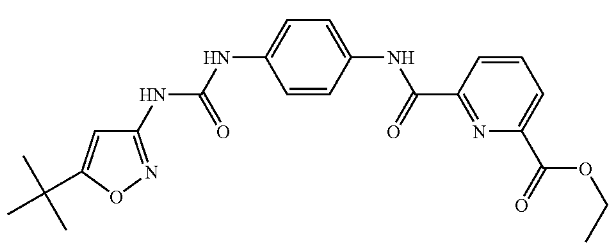 |

TABLE N-continued

| NO. | CHEMICAL STRUCTURE |
|---|---|
| N165 | 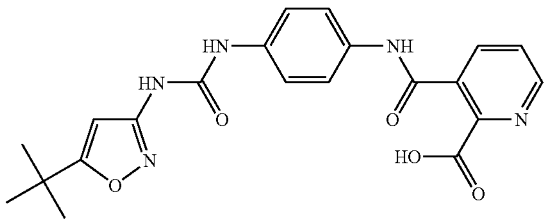 |
| N166 | 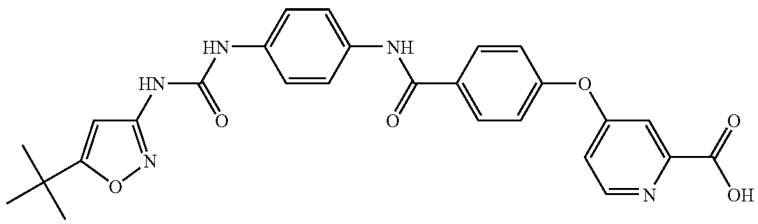 |
| N167 | 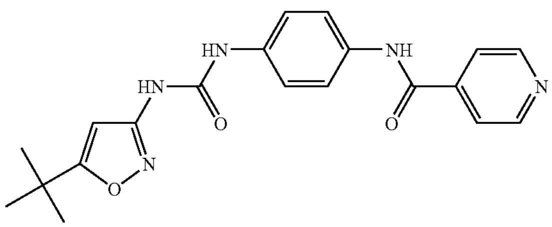 |
| N168 | 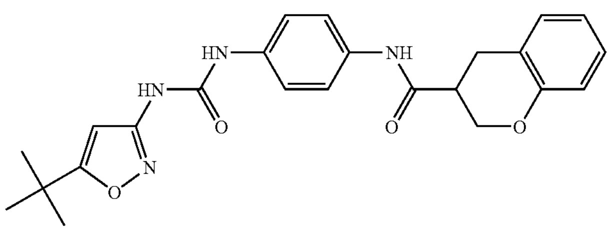 |
| N169 | 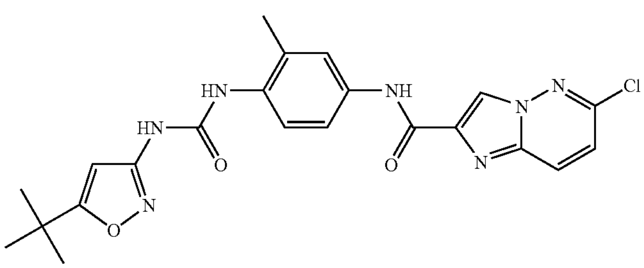 |
| N170 | 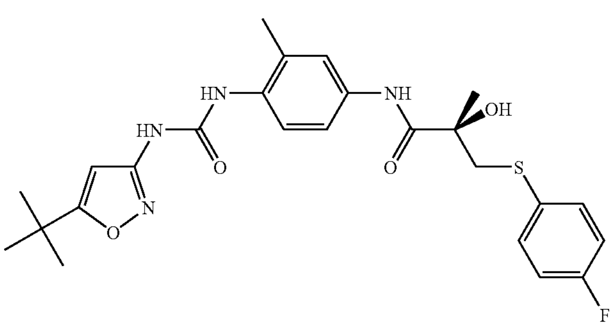 |

TABLE N-continued
| NO. | CHEMICAL STRUCTURE |
|---|---|
| N171 | 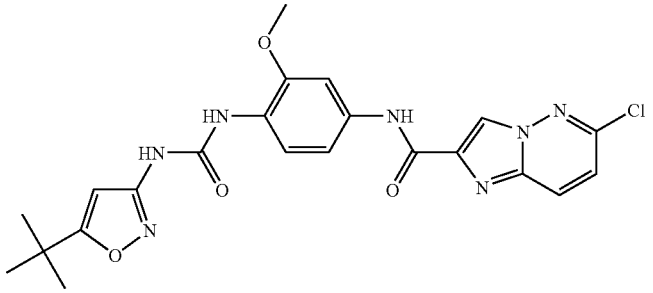 |
| N172 | 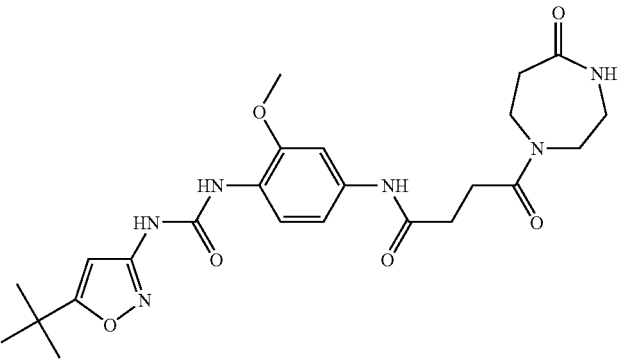 |
| N173 | 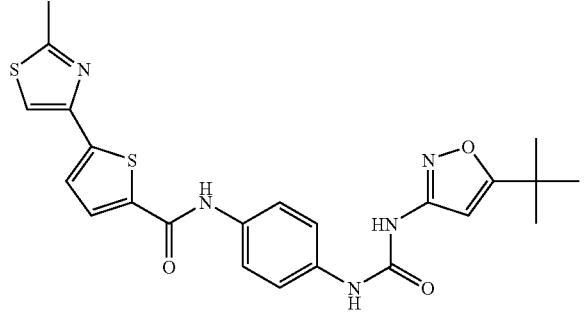 |
| N174 | 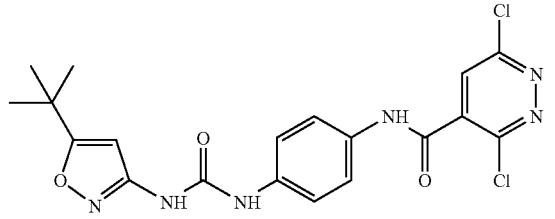 |
| N175 | 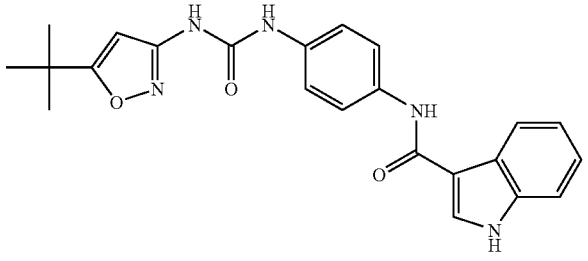 |

TABLE N-continued

| NO. | CHEMICAL STRUCTURE |
|---|---|
| N176 | 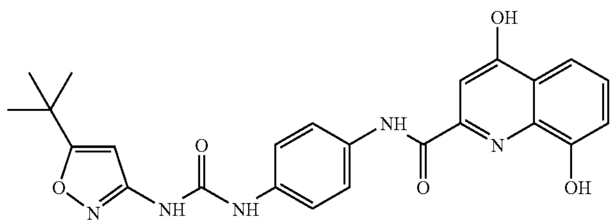 |
| N177 | 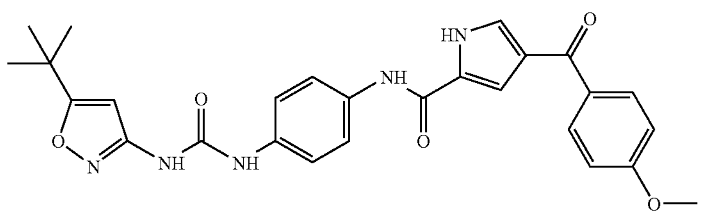 |
| N178 | 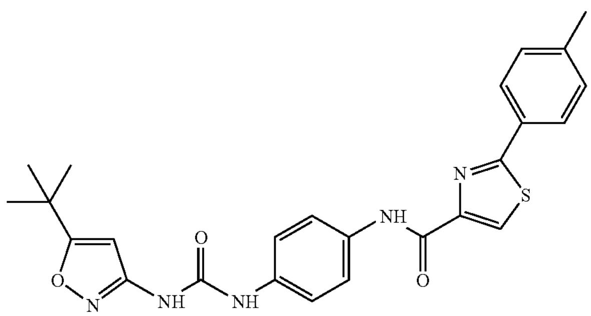 |
| N179 | 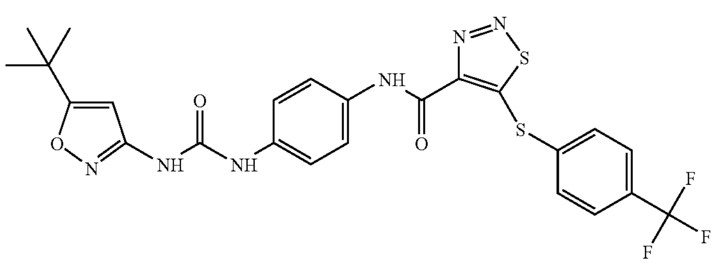 |
| N180 | 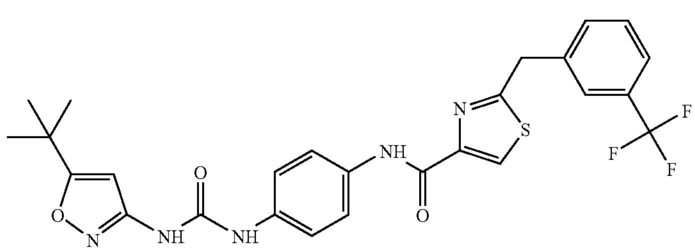 |
| N181 | 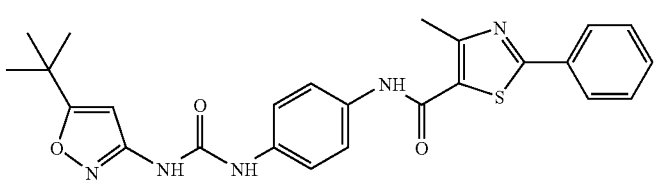 |

TABLE N-continued

| NO. | CHEMICAL STRUCTURE |
|---|---|
| N182 | 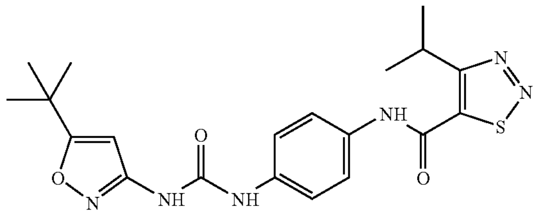 |
| N183 | 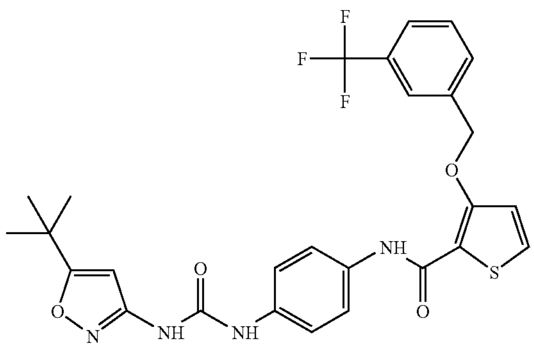 |
| N184 | 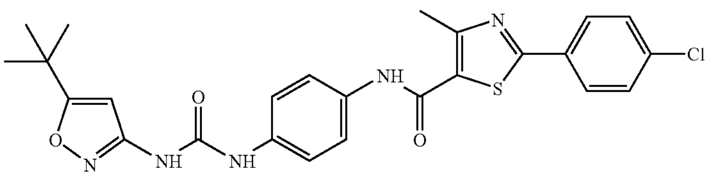 |
| N185 | 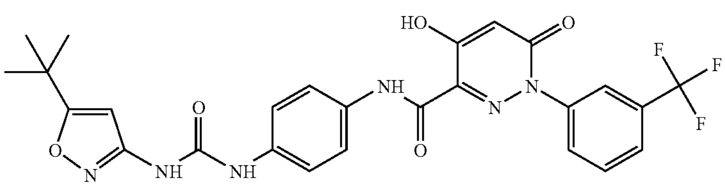 |
| N186 | 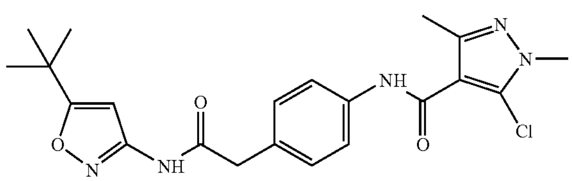 |
| N187 | 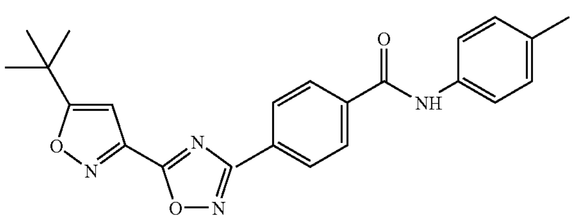 |
| N188 | 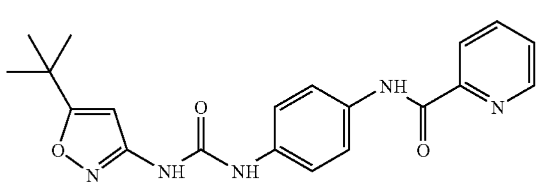 |

TABLE N-continued

| NO. | CHEMICAL STRUCTURE |
|---|---|
| N189 | 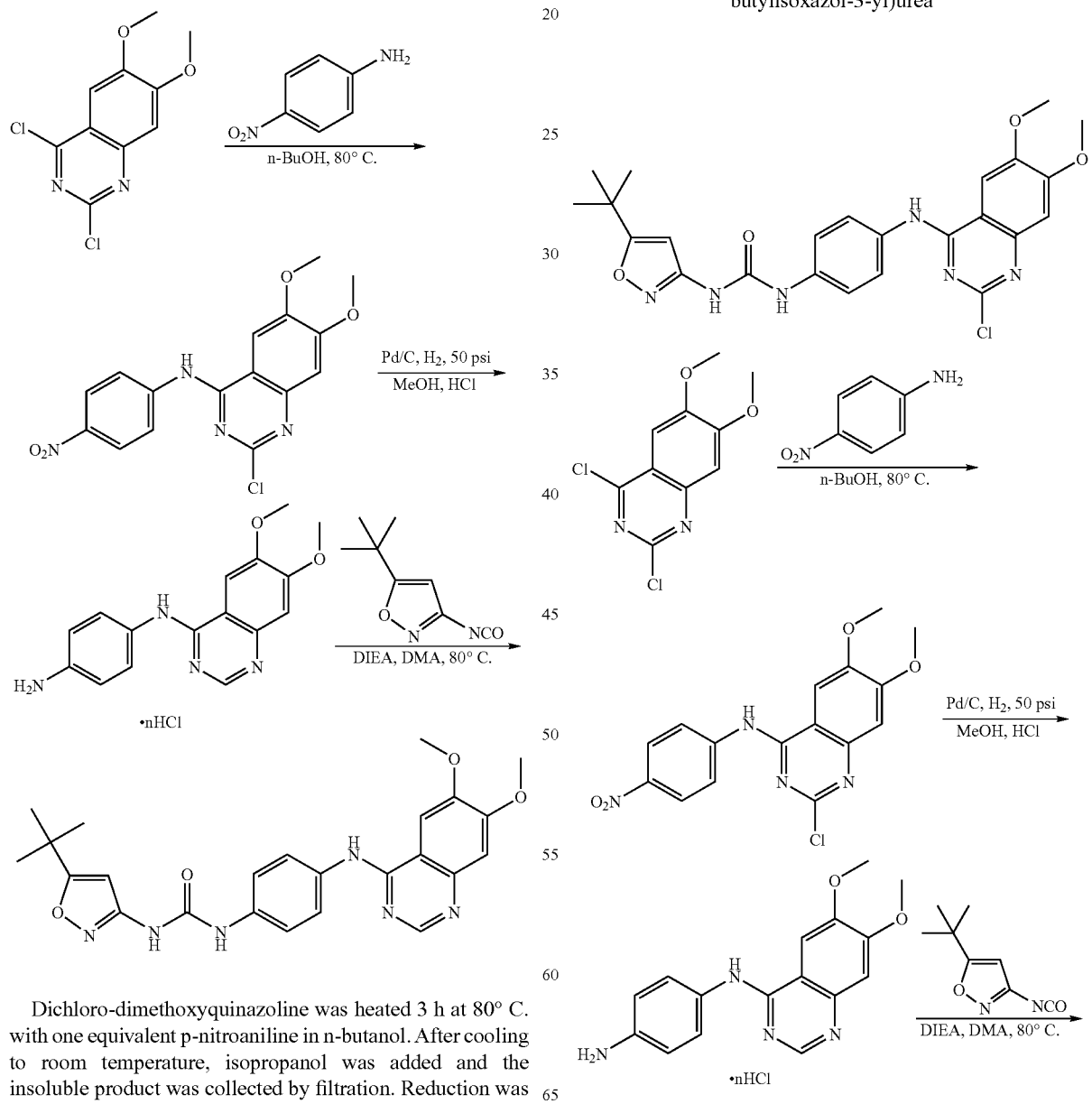 |

Example O

Synthesis of Compounds with Amine Linkers

Dichloro-dimethoxyquinazoline was heated 3 h at 80° C. with one equivalent p-nitroaniline in n-butanol. After cooling to room temperature, isopropanol was added and the insoluble product was collected by filtration. Reduction was accomplished using 10% Pd/C in methanol at 50 psi in the presence of hydrochloric acid. The resulting aniline was reacted with the oxazole isocyanate in DMA at 80° C. in the presence of DIEA. The urea product was purified by HPLC.

Synthesis of Compound O1: 1-(4-(2-chloro-6,7-dimethoxyquinazolin-4-ylamino)phenyl)-3-(5-tert-butylisoxazol-3-yl)urea -continued

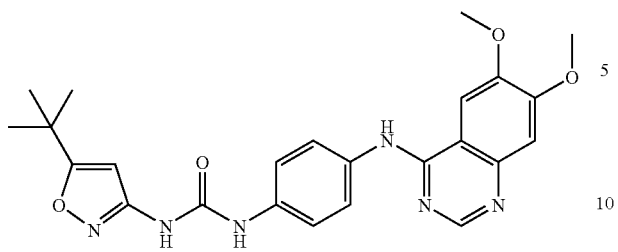

Dichloro-dimethoxyquinazoline was heated 3 h at 80° C. with one equivalent p-nitroaniline in n-butanol. After cooling to room temperature, isopropanol was added and the insoluble product was collected by filtration. Reduction was accomplished using 10% Pd/C in methanol at 50 psi in the presence of hydrochloric acid. The resulting aniline was reacted with the oxazole isocyanate in DMA at 80° C. in the presence of DIEA. The urea product was purified by HPLC.

Compounds O2 through O10 were synthesized in a manner analogous to Compound O1 using similar starting materials and reagents. The structures are shown below in Table O:

Example P

Synthesis of Chalcones

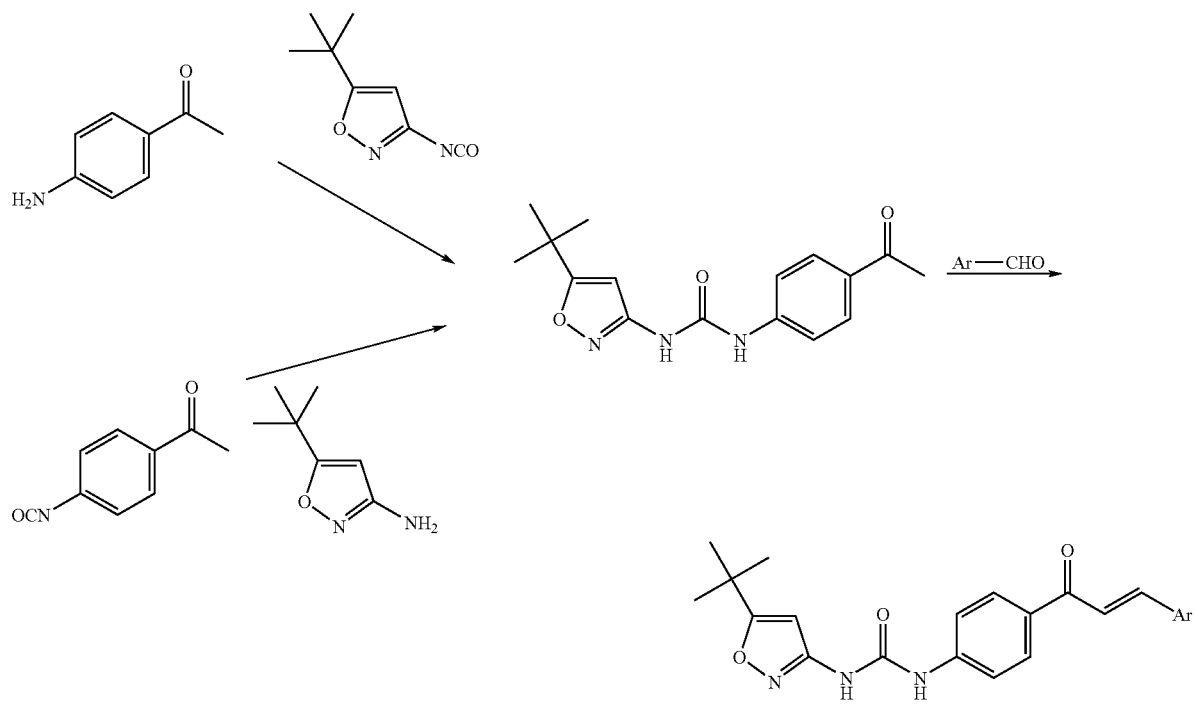

Acetylphenylurea (obtained from either reacting p-aminoacetophenone with oxazole isocyanate in toluene or reacting p-acetylphenyl isocyanate with oxazole amine in toluene) was reacted with e.g. 4-pyridine carboxaldehyde analogous to a literature procedure (Zhang et al., *Chem. Lett.* 2003, 32, 966-967).

Chalcone intermediates were further modified according to procedures described in the literature. See Powers et al., *Tetrahedron,* 1998, 54, 4085-4096; Katritzky et al. *Org. Lett.* 2000, 2, 429-431.

Compound P1: 1-(5-isopropylisoxazol-3-yl)-3-(4-((E)-3-(pyridin-4-yl)acryloyl)phenyl)urea

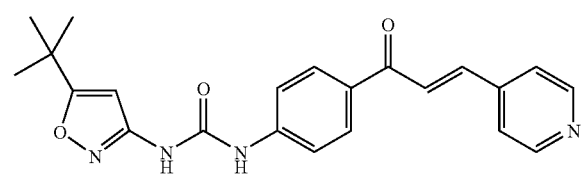

Compound P1 was synthesized in the manner outlined above.

Synthesis of Chalcone Derivatives

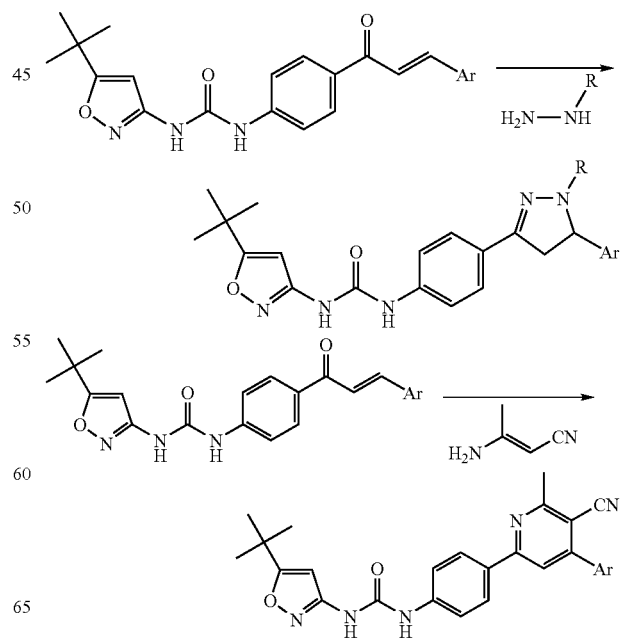

191

-continued

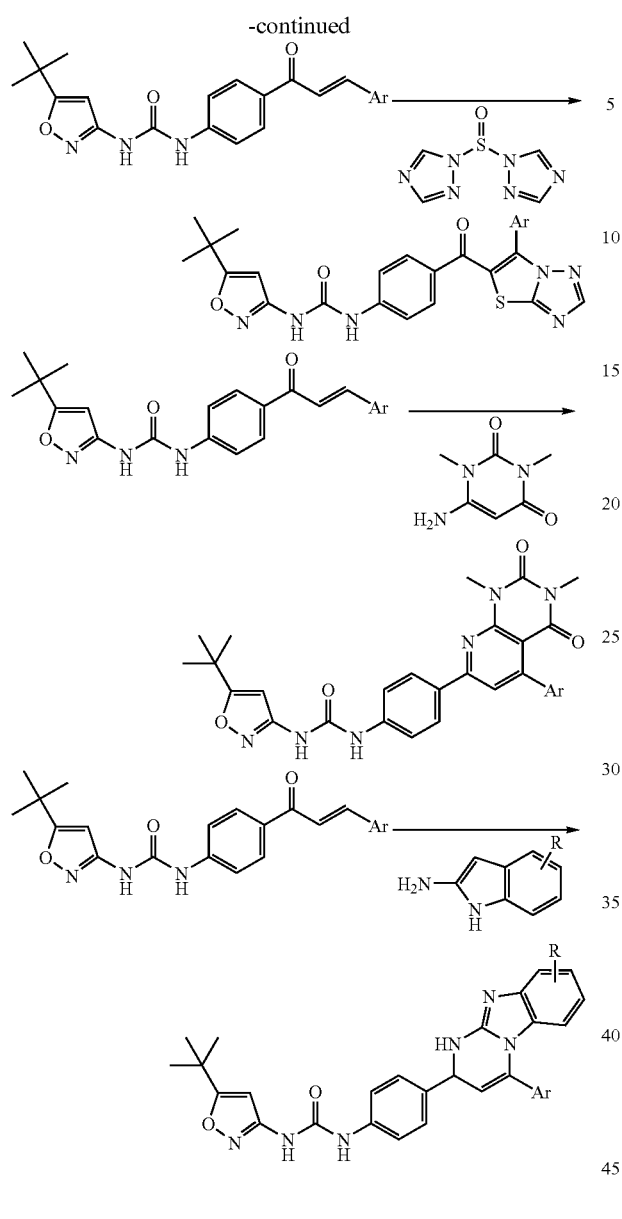

Synthesis of Compound P2: 1-(5-text-butylisoxazol-3-yl)-3-(4-(3-(1-methoxynaphthalen-4-yl)-1,2,4-oxadiazol-5-yl)phenyl)urea

192

-continued

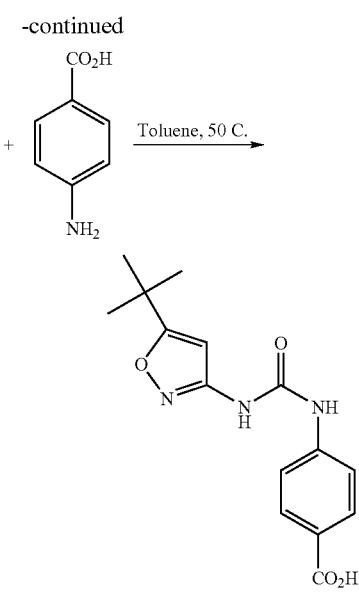

To a flask 5-tert-Butyl-3-isocyanato-isoxazole (242 mg, 1 eq) 4-aminobenzoic acid (159 mg, 1 eq) was added and dissolved in toluene. The reaction was allowed to stir at 50° C. for three hours. The solvent removed and the mixture was purified by HPLC. Yield: 188 mg (47%)

N-Hydroxy-4-methoxy-naphthalene-1-carboxamidine (1 g) and 4-[3-(5-tert-Butyl-isoxazol-3-yl)-ureido]-benzoic acid (1 eq) were refluxed in diglyme (5 mL) for 24 h and then purified to give 100 mg of 1-(5-tert-Butyl-isoxazol-3-yl)-3-{4-[3-(4-methoxy-naphthalen-1-yl)-[1,2,4]oxadiazol-5-yl]-phenyl}-urea.

Compounds P3 through P9 were synthesized in a manner analogous to Compound P2 using similar starting materials and reagents. The structures are shown below in Table P:

TABLE P

| NO. | CHEMICAL STRUCTURE |
|---|---|
| P2 | 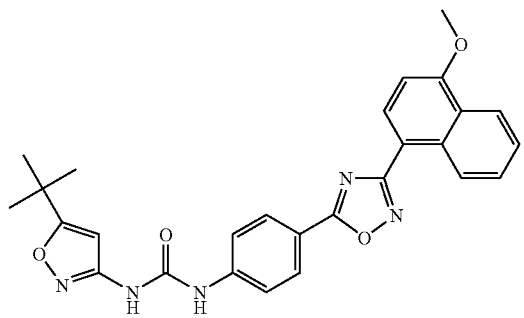 |
| P3 | 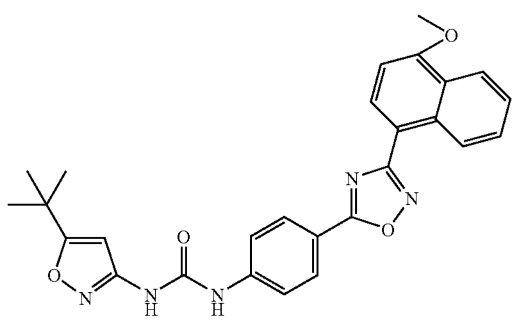 |
| P4 | 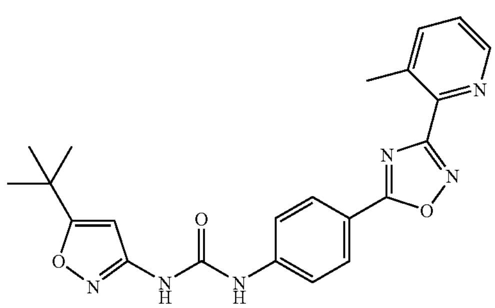 |
| P5 | 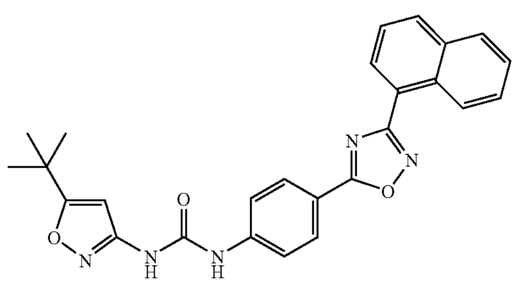 |

TABLE P-continued

| NO. | CHEMICAL STRUCTURE |
|---|---|
| P6 | 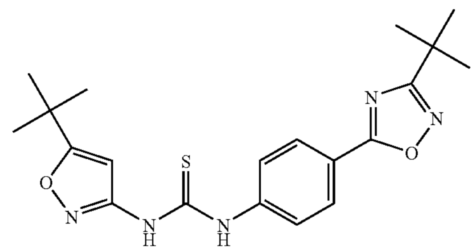 |
| P7 | 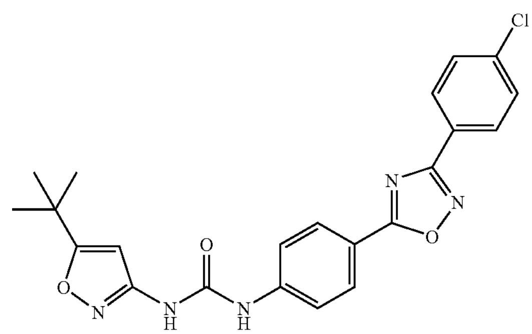 |
| P8 | 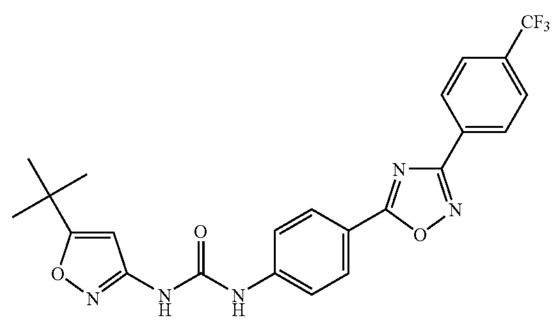 |
| P9 | 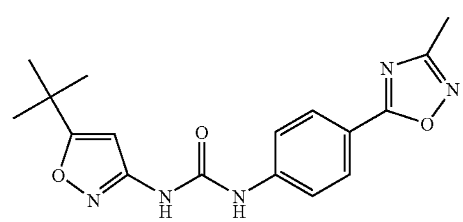 |

Example Q

Synthesis of Compounds Containing Heterocycloalkyl Groups

Synthesis of Compound Q1 : 4-(3-methoxyphenyl)-N-(4-methoxyphenyl)piperazine-1-carboxamide

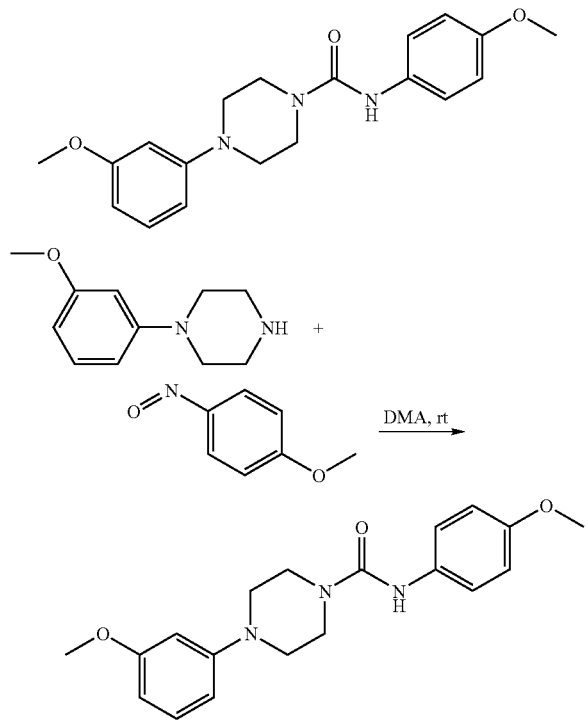

Commercially available isocyanides were reacted with a secondary amine in toluene or DMA (1 ml) with triethyl amine (0.2 mL) at room temperature or 50 C overnight. The solvent was removed and the compound purified by HPLC.

Compounds Q2 through Q27 were synthesized in a manner analogous to Compound Q1 using similar starting materials and reagents. The structures are shown below in Table Q:

TABLE Q-continued

| NO. | CHEMICAL STRUCTURE |
|-----|--------------------|
| Q9  | 4-methylpiperazine-N-(4-chlorophenyl)carboxamide |
| Q10 | morpholine-N-(4-chlorophenyl)carboxamide |
| Q11 | piperidine-N-(4-methoxyphenyl)carboxamide |
| Q12 | piperidine-N-(4-benzyloxyphenyl)carboxamide |
| Q13 | 4-methylpiperazine-N-(4-methoxyphenyl)carboxamide |
| Q30 | 4-(4-chlorophenyl)piperazine-N-(4-methoxyphenyl)carboxamide |
| Q31 | 4-(3-chlorophenyl)piperazine-N-(4-methoxyphenyl)carboxamide |

TABLE Q-continued

| NO. | CHEMICAL STRUCTURE |
|-----|--------------------|
| Q32 | 4-(2-methoxyphenyl)piperazine-N-(4-methoxyphenyl)carboxamide |
| Q17 | 4-benzylpiperidine-N-(4-chlorophenyl)carboxamide |
| Q18 | 4-phenylpiperazine-N-(4-chlorophenyl)carboxamide |
| Q19 | 4-(4-hydroxyphenyl)piperidine-N-(4-chlorophenyl)carboxamide |
| Q20 | 4-(2-chlorophenyl)piperazine-N-(4-chlorophenyl)carboxamide |
| Q21 | 4-(3-chlorophenyl)piperazine-N-(4-chlorophenyl)carboxamide |

TABLE Q-continued

| NO. | CHEMICAL STRUCTURE |
|---|---|
| Q22 | 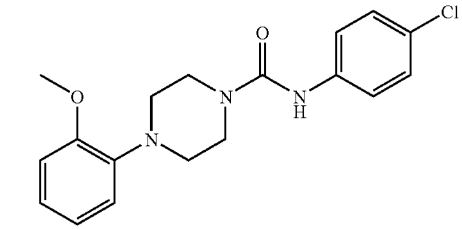 |
| Q23 | 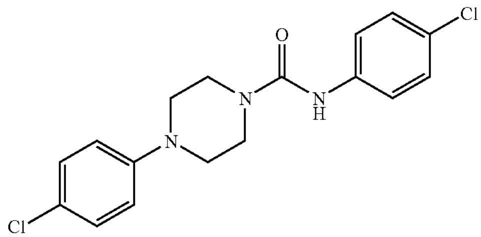 |
| Q24 | 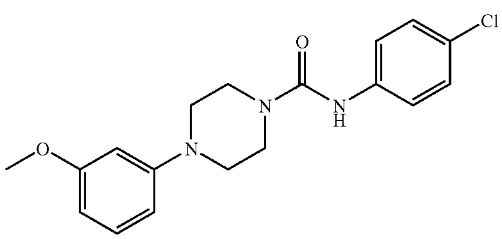 |
| Q25 | 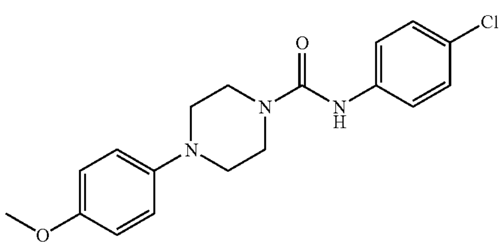 |
| Q26 | 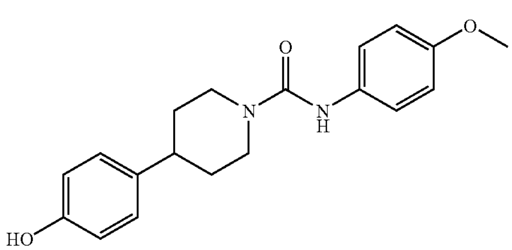 |
| Q27 | 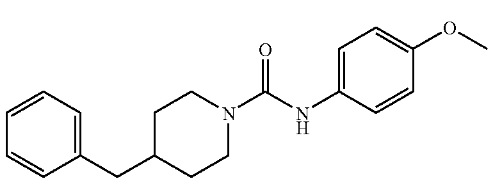 |

Example R

Synthesis of Compounds Containing Heterocycloalkyl Groups with Ether Linkers Synthesis of Compound S1: N-(4-(benzyloxy)phenyl)-4-(4-hydroxyphenyl)piperidine-1-carboxamide

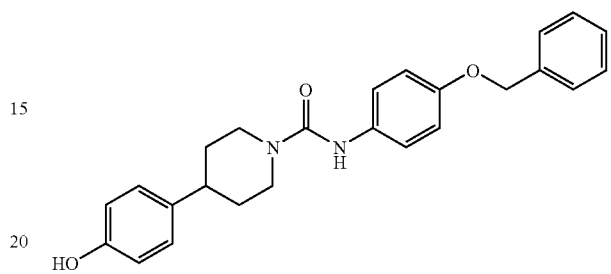

Commercially available isocyanides were reacted with a secondary amine in toluene or DMA (1 ml) with triethyl amine (0.2 mL) at room temperature or 50 C overnight. The solvent was removed and the compound purified by HPLC.

Compounds R2 through R9 were synthesized in a manner analogous to Compound R1 using similar starting materials and reagents. The structures are shown below in Table R:

TABLE R
| NO. | CHEMICAL STRUCTURE |
|---|---|
| R1 | 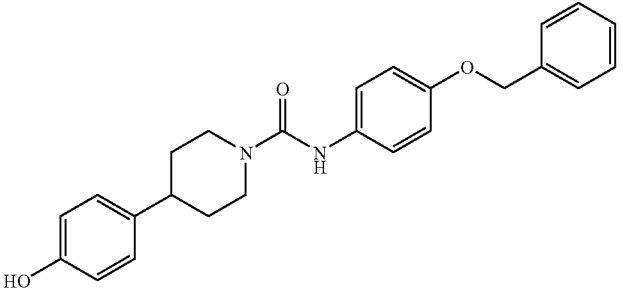 |
| R2 | 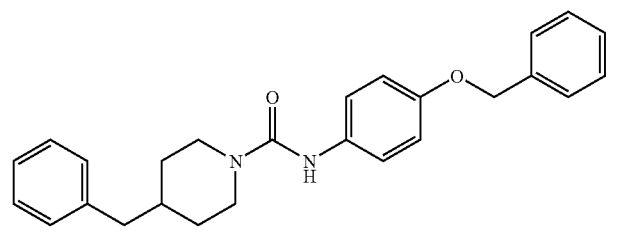 |
| R3 | 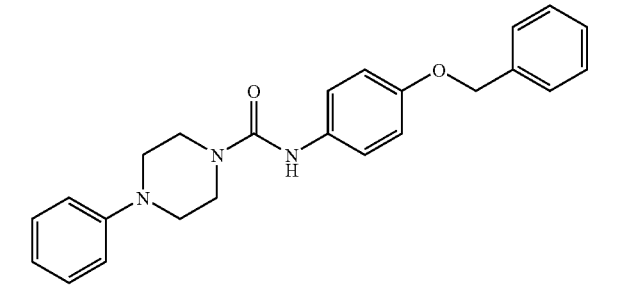 |
| R4 | 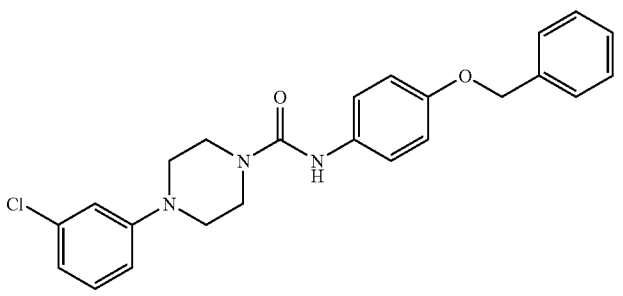 |
| R5 | 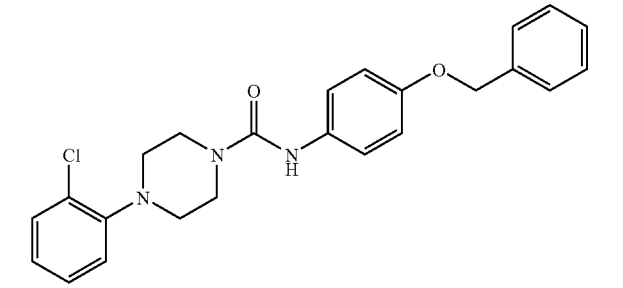 |

TABLE R-continued
| NO. | CHEMICAL STRUCTURE |
|---|---|
| R6 | 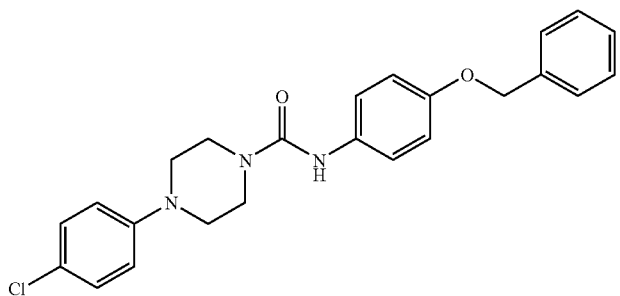 |
| R7 | 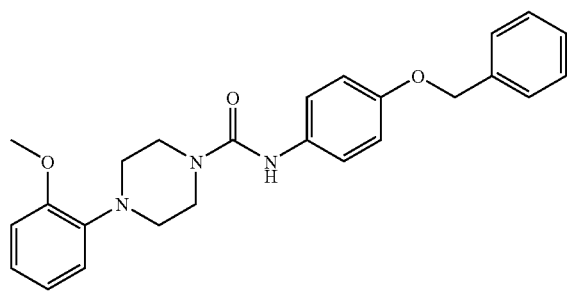 |
| R8 | 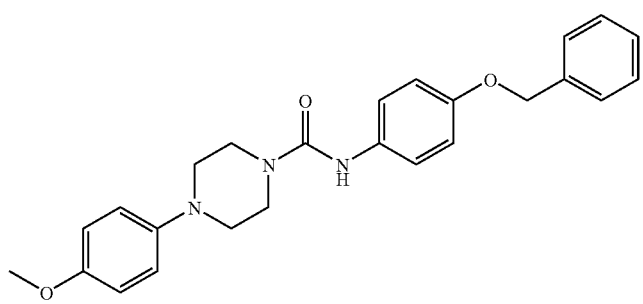 |
| R9 | 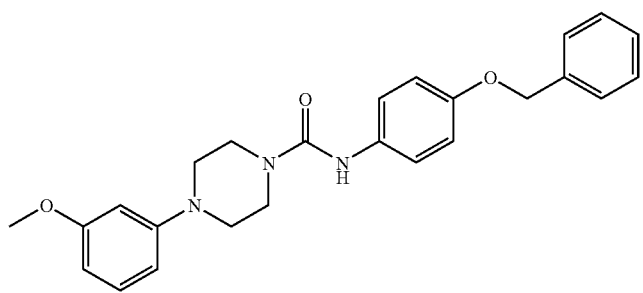 |

Example S

Synthesis of Carbamothioates

Synthesis of Compound S1: S-4-methoxyphenyl N-5-tert-butylisoxazol-3-ylcarbamothioate

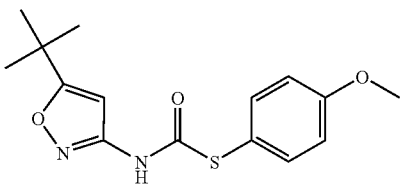

Synthesis of (3-tert-Butyl-isoxazol-5-yl)-thiocarbamic acid S-(4-methoxy-phenyl) ester

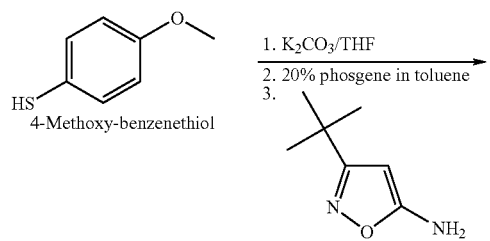

(3-tert-Butyl-isoxazol-5-yl)-thiocarbamic acid S-(4-methoxy-phenyl) ester

A mixture of 4-Methoxy-benzenethiol (0.20 g, 1 eq) and potassium carbonate (0.47 g, 2.5 eq) in dry THF was allowed to stir at room temperature under argon for an hour. Then the stirred suspension was cooled to 0° C. and to it was added drop wise a solution of phosgene (0.17 g 1.2 eq). The reaction stirred at 0° C. for half an hour. Then 3-tert-Butyl-isoxazol-5-ylamine (0.20 g, 1 eq) in THF was added dropwise. The reaction was allowed to warm to room temperature and stirred overnight. The solvent was removed and extracted with ethyl acetate and water. The organic layer was dried over magnesium sulfate and solvent removed. It was purified by HPLC. Yield: 157 mg (36%), LC/MS [MH$^+$] 307.

Compounds S2 through S3 were synthesized in a mariner analogous to Compound S1 using similar starting materials and reagents. The structures are shown below in Table S:

TABLE S

| NO. | CHEMICAL STRUCTURE |
|-----|-------------------|
| S1  | 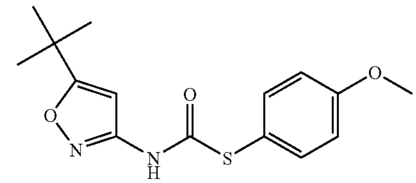 |
| S2  | 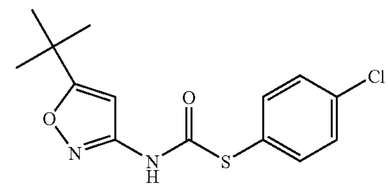 |
| S3  | 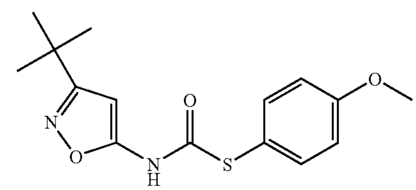 |

Example T

Synthesis of Carbamothioates

Synthesis of Compound T1: S-4-methoxyphenyl N-5-tert-butylisoxazol-3-ylcarbamothioate

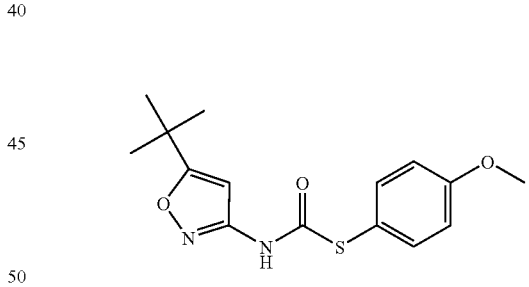

Synthesis of (3-tert-Butyl-isoxazol-5-yl)-thiocarbamic acid S-(4-methoxy-phenyl)ester

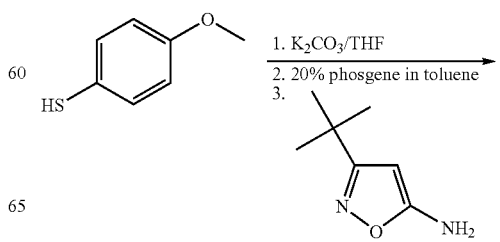

-continued

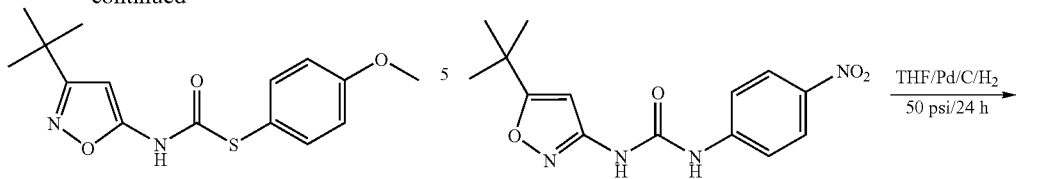

A mixture of 4-Methoxy-benzenethiol (0.20 g, 1 eq) and potassium carbonate (0.47 g, 2.5 eq) in dry THF was allowed to stir at room temperature under argon for an hour. Then the stirred suspension was cooled to 0° C. and to it was added dropwise a solution of phosgene (0.17 g 1.2 eq). The reaction stirred at 0° C. for half an hour. Then 3-tert-Butyl-isoxazol-5-ylamine (0.20 g, 1 eq) in THF was added dropwise. The reaction was allowed to warm to room temperature and stirred overnight. The solvent was removed and extracted with ethyl acetate and water. The organic layer was dried over magnesium sulfate and solvent removed. It was purified by HPLC. Yield: 157 mg (36%), LC/MS [MH$^+$] 307.

Example V

Synthesis of Ureas

Synthesis of Compound V1

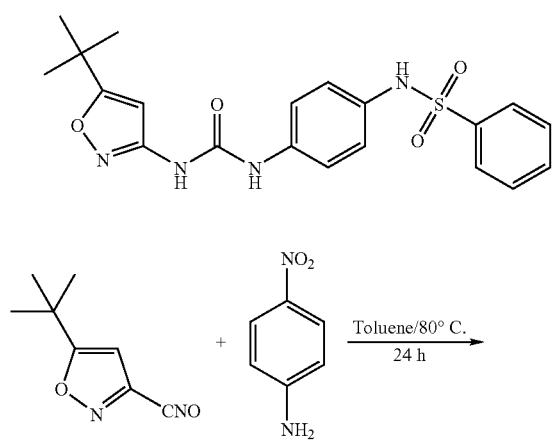

1 gm. (6 mmol) of 5-tert-butyl-isoxazole-3-isocyanate and 0.83 gm (6 mmol) 4-nitro-phenylamine were dissolved in 20 ml dry toluene and stirred at 80° C. for 24 h. The resulting suspension was cooled to room temperature and filtered off to give the title compound as a yellow solid. The product was used in the next step without further purification. Yield: 1.7 g (92%), LC/MS [MH$^+$] 305.

1.5 gm of 1-(5-tert-butyl-isoxazol-3-yl)-3-(4-nitro-phenyl)-urea was dissolved in 50 ml THF and 0.1 g of 10% Pd/C was added. The solution was stirred under hydrogen at 50 psi. for 24 h than filtered trough Celite pad. The organic solvent was evaporated under vacuum and the resulting residue was triturated with ethyl acetate. Yield: 1.3 g (96%), LC/MS [MH$^+$] 275.

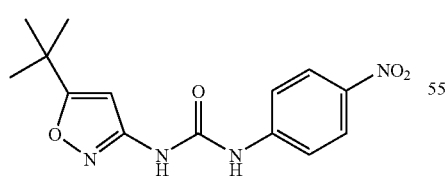

1-(4-Amino-phenyl)-3-(5-tert-butyl-isoxazol-3-yl)-urea 1 equivalent of the substituted sulfonyl chloride and 1 equivalent of the substituted aniline in DMF were added, and the solution stirred at room temperature for 8 h. The final product was purified by preparative HPLC.

Compounds V2 through V4 were synthesized in a manner analogous to Compound VI using similar starting materials and reagents. The structures are shown below in Table V:

TABLE V

| NO. | CHEMICAL STRUCTURE |
|---|---|
| V1 | 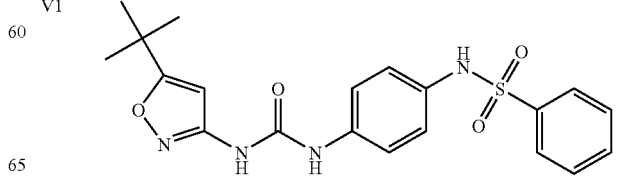 |

TABLE V-continued

| NO. | CHEMICAL STRUCTURE |
|---|---|
| V2 | 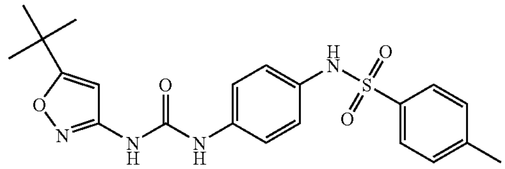 |
| V3 | 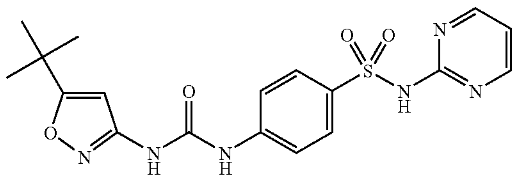 |
| V4 | 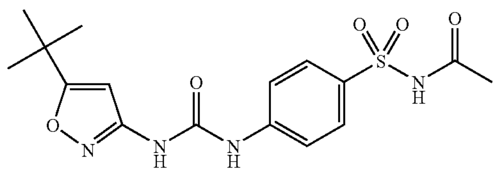 |

Example W

Compounds W1 and W2 were made by procedures know in the art or described herein.

TABLE W

| NO. | CHEMICAL STRUCTURE |
|---|---|
| W1 | 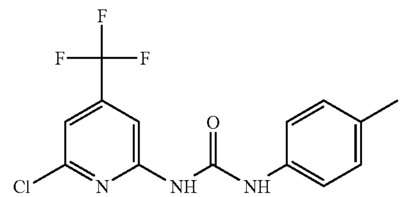 |
| W2 | 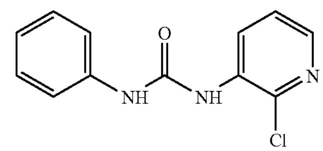 |

Example Z

Commercially Available Ureas

Compounds Z1-Z93 as shown in Table Z are commercially available:

TABLE Z

| NO. | CHEMICAL STRUCTURE |
|---|---|
| Z1 | 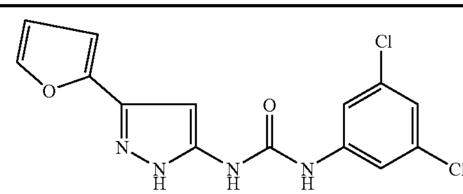 |
| Z2 | 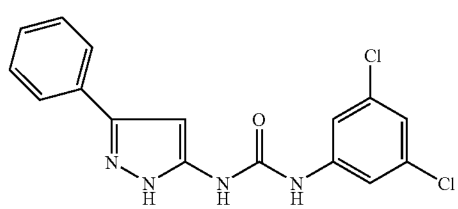 |
| Z3 | 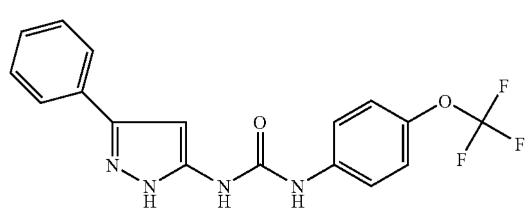 |
| Z4 | 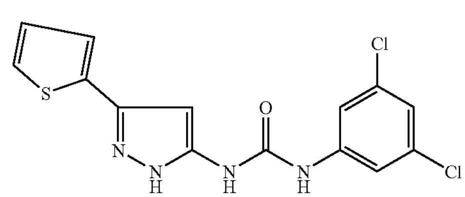 |

TABLE Z-continued

| NO. | CHEMICAL STRUCTURE |
|---|---|
| Z5 | (thiophene-pyrazole-urea-phenyl-OCF3) |
| Z6 | (phenyl-pyrazole-urea-phenyl) |
| Z7 | (furan-pyrazole-urea-phenyl-OCF3) |
| Z8 | (phenyl-urea-pyrazole with SMe and 4-chlorophenylsulfonyl substituents) |
| Z9 | (4-chlorophenyl-urea-pyrazole with SMe and 4-chlorophenylsulfonyl substituents) |
| Z10 | (phenyl-CF3-thiophene-pyrazole-urea-4-chlorophenyl) |
| Z11 | (isoxazole-urea-phenyl) |
| Z12 | (isoxazole-urea-2,4-dichlorophenyl) |

TABLE Z-continued

| NO. | CHEMICAL STRUCTURE |
|---|---|
| Z13 | isoxazol-5-yl-NH-C(=O)-NH-(4-methylphenyl) |
| Z14 | 3-methyl-isoxazol-5-yl-NH-C(=O)-NH-(3,5-dichlorophenyl) |
| Z15 | 3-methyl-isoxazol-5-yl-NH-C(=O)-NH-(4-chlorophenyl) |
| Z16 | ethyl 1-phenyl-5-[3-(3-chlorophenyl)ureido]-1H-pyrazole-4-carboxylate |
| Z17 | 1-(3,4-dichlorophenyl)-3-(4-methoxyphenyl)-5-[3-(2-cyanophenyl)ureido]-1H-pyrazole |
| Z18 | 3-(4-chlorophenyl)-1-(4-fluorophenyl)-5-[3-(4-trifluoromethoxyphenyl)ureido]-1H-pyrazole |

TABLE Z-continued
| NO. | CHEMICAL STRUCTURE |
|---|---|
| Z19 | 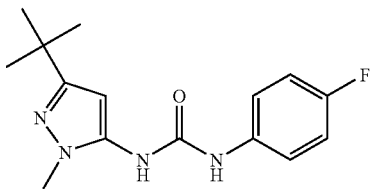 |
| Z20 | 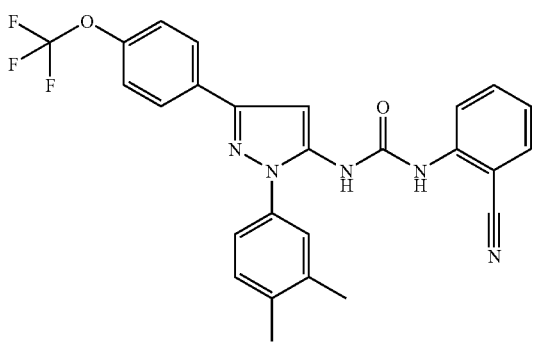 |
| Z21 | 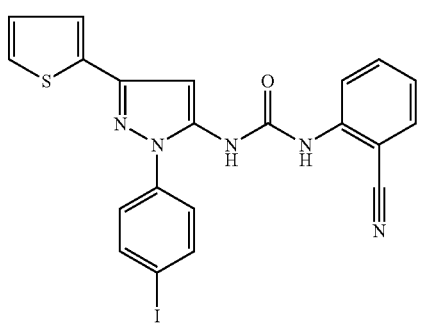 |
| Z22 | 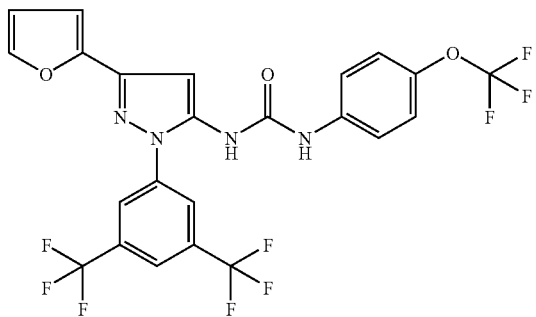 |
| Z23 | 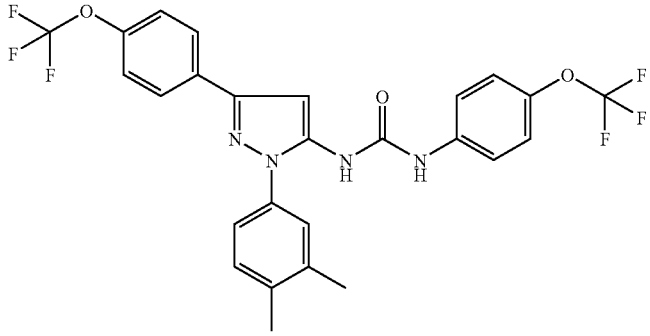 |

TABLE Z-continued

| NO. | CHEMICAL STRUCTURE |
|-----|--------------------|
| Z24 | 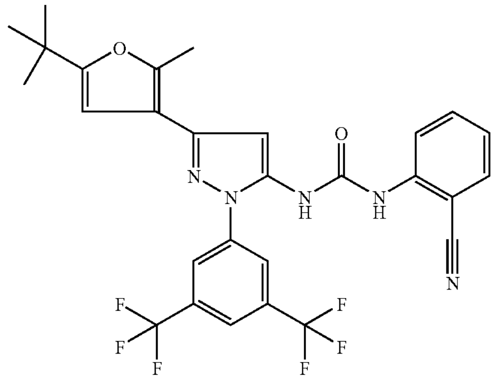 |
| Z25 | 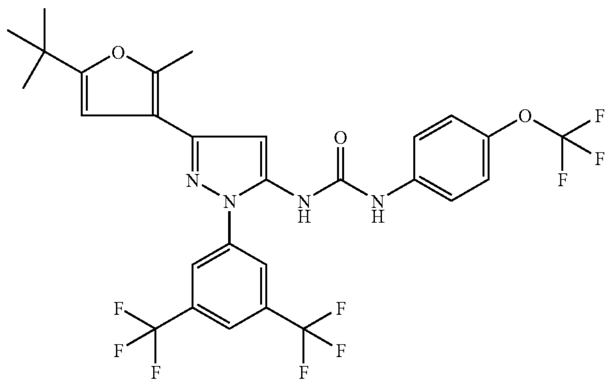 |
| Z26 | 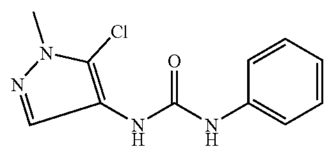 |
| Z27 | 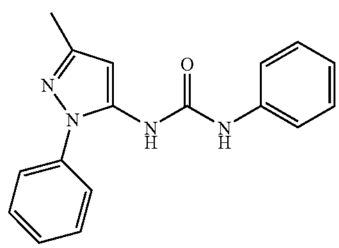 |
| Z28 | 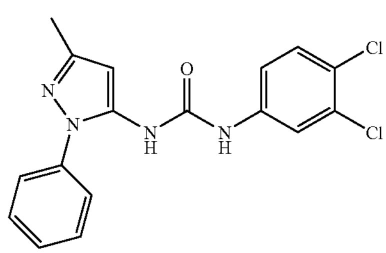 |
| Z29 | 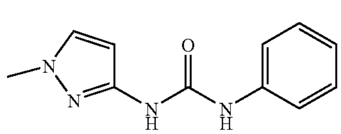 |

TABLE Z-continued

| NO. | CHEMICAL STRUCTURE |
|---|---|
| Z30 | 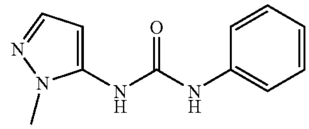 |
| Z31 | 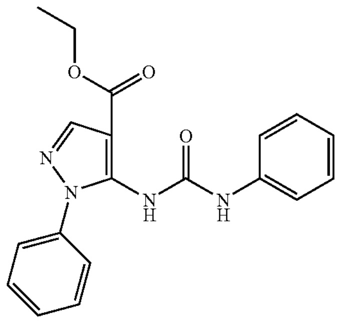 |
| Z32 | 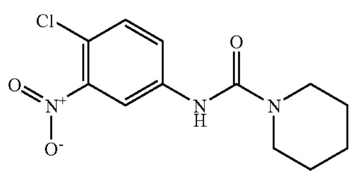 |
| Z33 | 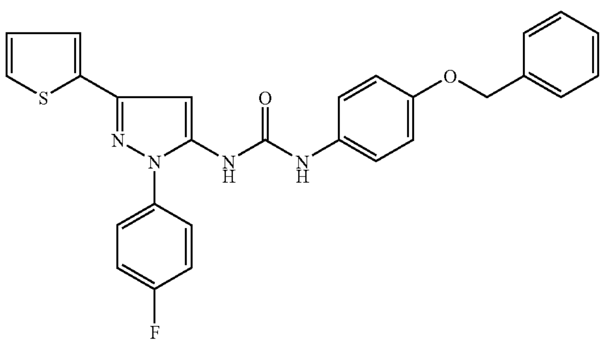 |
| Z34 | 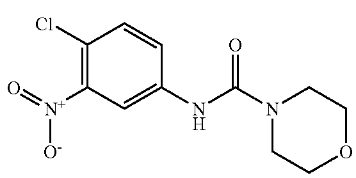 |
| Z35 | 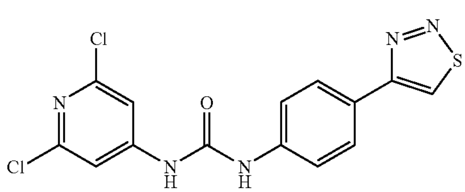 |

TABLE Z-continued

| NO. | CHEMICAL STRUCTURE |
| --- | --- |
| Z36 | 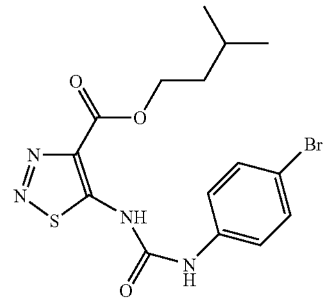 |
| Z38 | 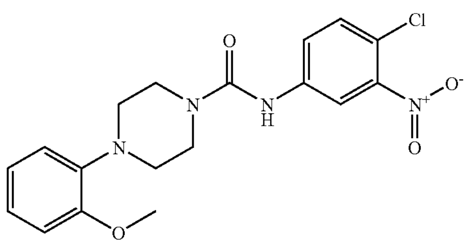 |
| Z39 | 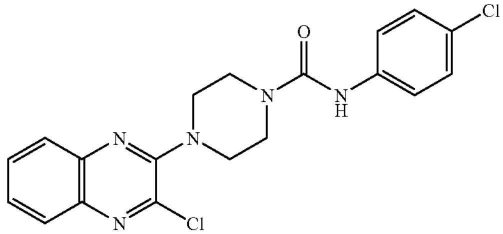 |
| Z40 | 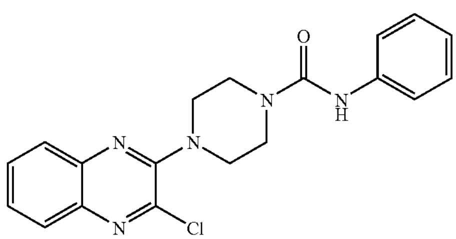 |
| Z43 | 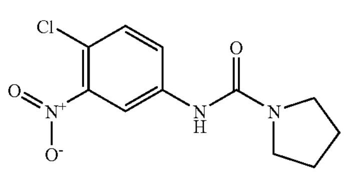 |
| Z44 | 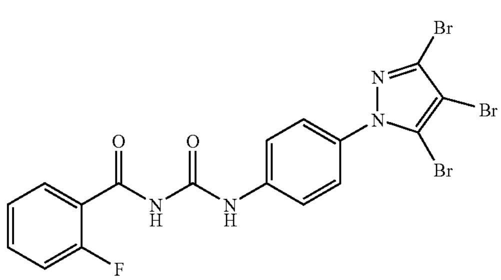 |

TABLE Z-continued
| NO. | CHEMICAL STRUCTURE |
|---|---|
| Z45 | 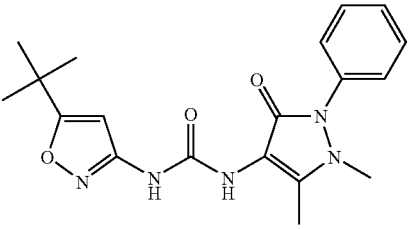 |
| Z46 | 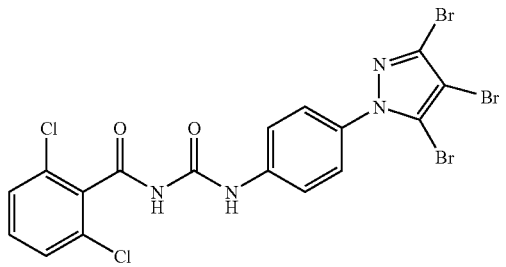 |
| Z47 | 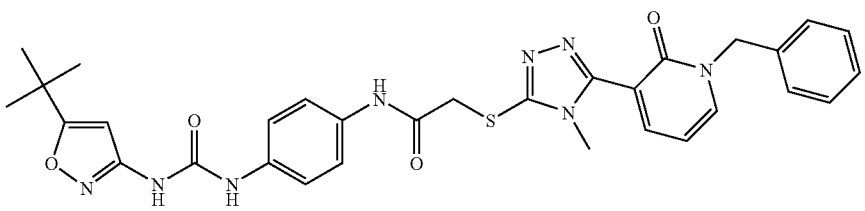 |
| Z48 | 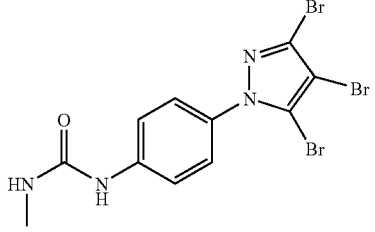 |
| Z49 | 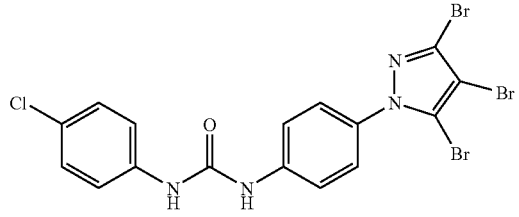 |
| Z50 | 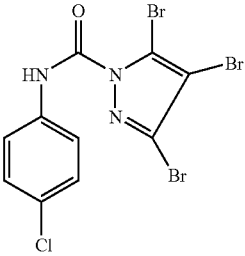 |

TABLE Z-continued
| NO. | CHEMICAL STRUCTURE |
|---|---|
| Z51 | 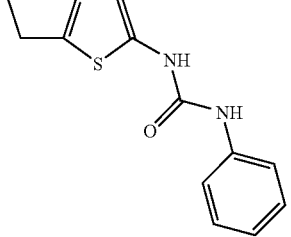 |
| Z52 | 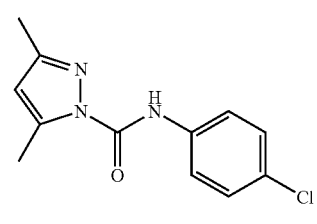 |
| Z53 | 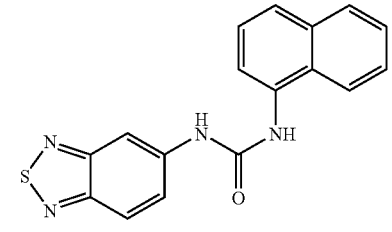 |
| Z54 | 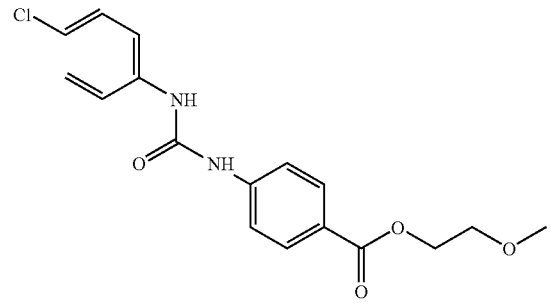 |
| Z55 | 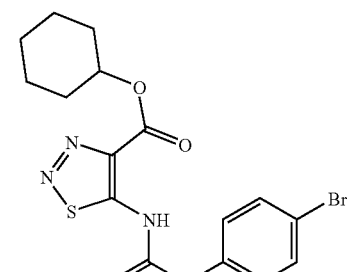 |

TABLE Z-continued

| NO. | CHEMICAL STRUCTURE |
|---|---|
| Z56 | 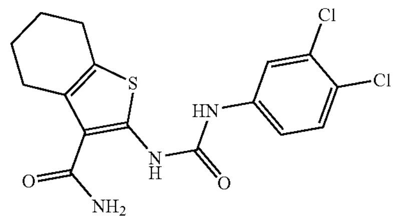 |
| Z57 | 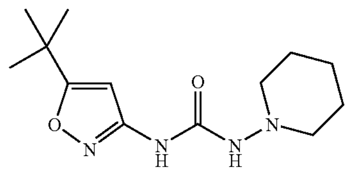 |
| Z58 | 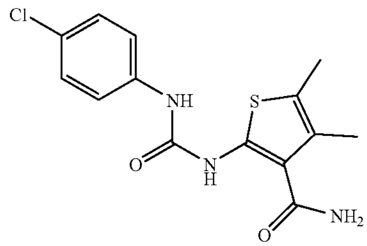 |
| Z59 | 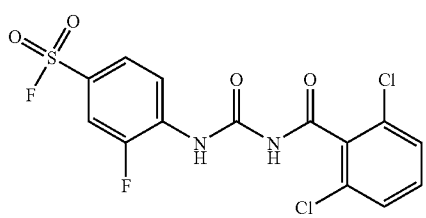 |
| Z60 | 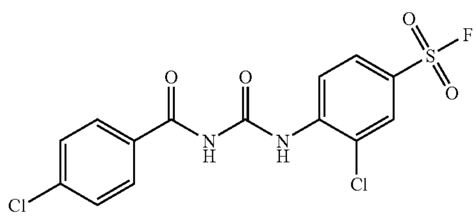 |
| Z61 | 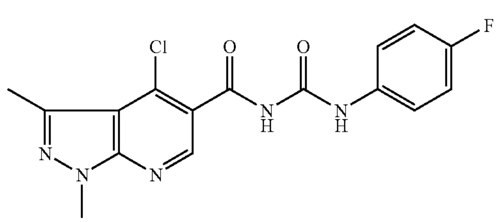 |
| Z62 | 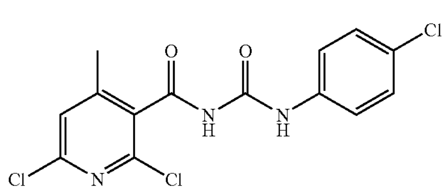 |

TABLE Z-continued
| NO. | CHEMICAL STRUCTURE |
|---|---|
| Z63 | 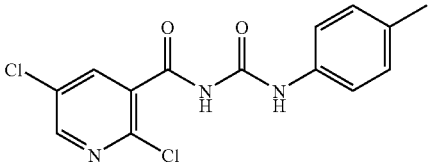 |
| Z64 | 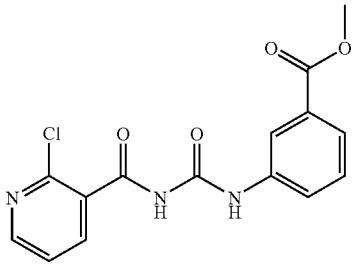 |
| Z65 | 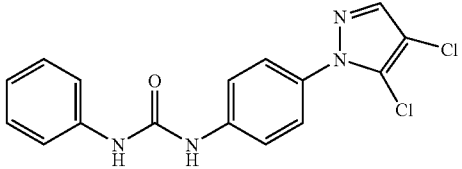 |
| Z66 | 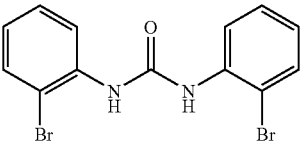 |
| Z67 | 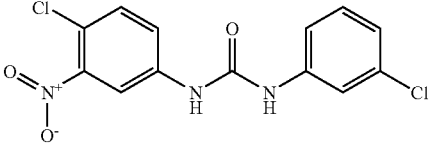 |
| Z68 | 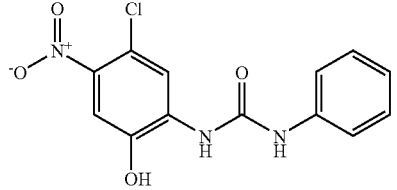 |
| Z69 | 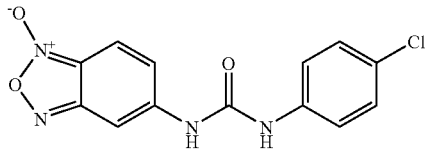 |
| Z70 | 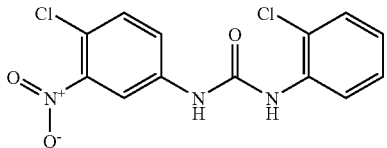 |

TABLE Z-continued
| NO. | CHEMICAL STRUCTURE |
|---|---|
| Z71 | 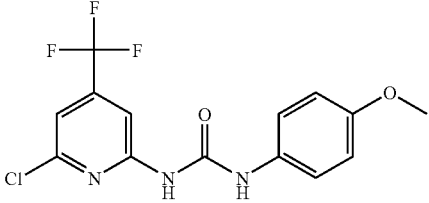 |
| Z72 | 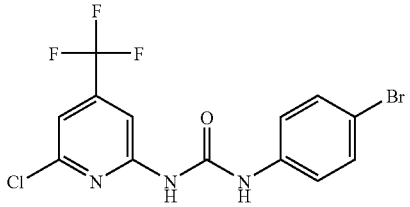 |
| Z73 | 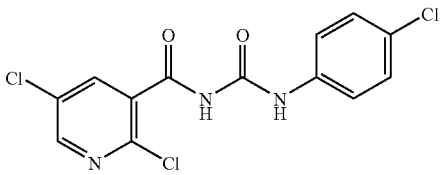 |
| Z74 | 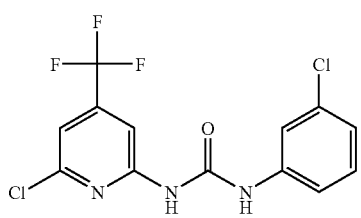 |
| Z75 | 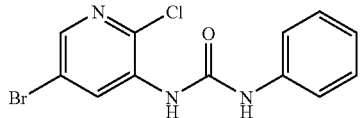 |
| Z76 | 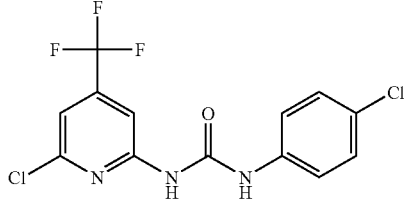 |
| Z77 | 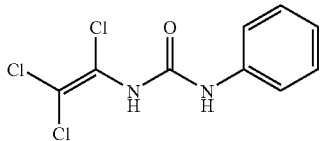 |

TABLE Z-continued

| NO. | CHEMICAL STRUCTURE |
|---|---|
| Z78 | 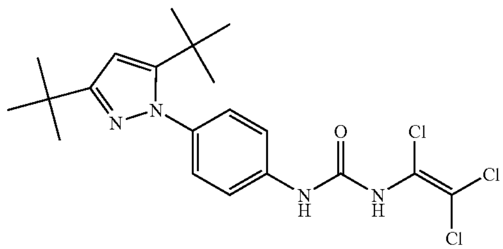 |
| Z79 | 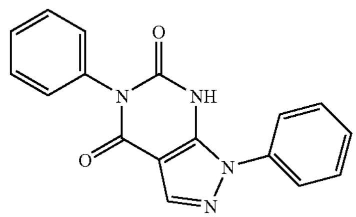 |
| Z80 | 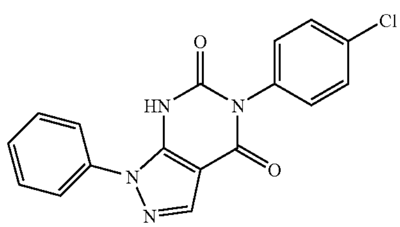 |
| Z81 | 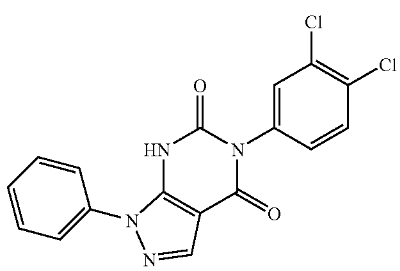 |
| Z82 | 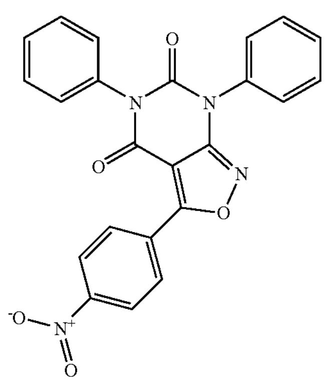 |

TABLE Z-continued

| NO. | CHEMICAL STRUCTURE |
|---|---|
| Z83 | 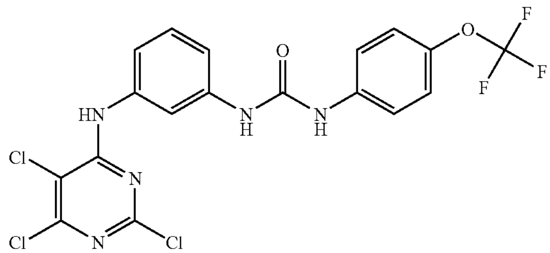 |
| Z84 | 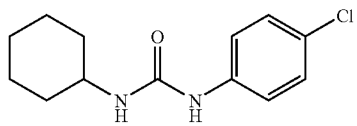 |
| Z85 | 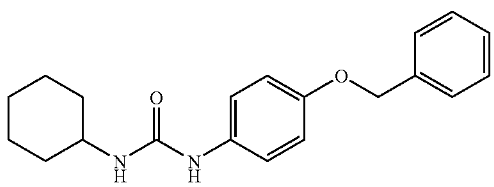 |
| Z86 | 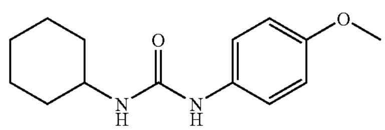 |
| Z87 | 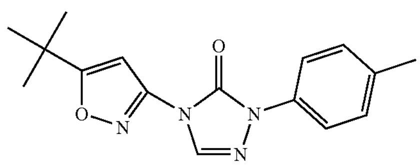 |
| Z88 | 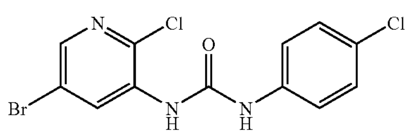 |
| Z89 | 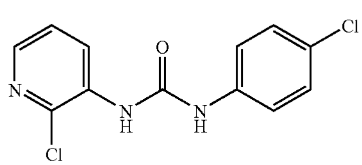 |
| Z90 | 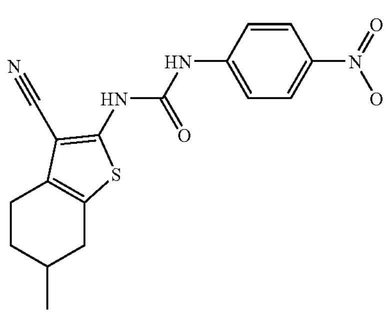 |

TABLE Z-continued

| NO. | CHEMICAL STRUCTURE |
|---|---|
| Z91 | 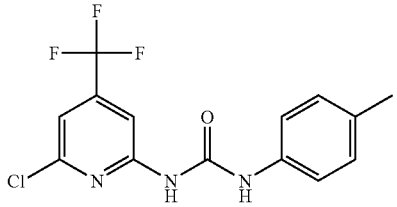 |
| Z92 | 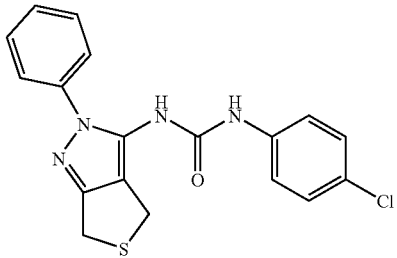 |
| Z93 | 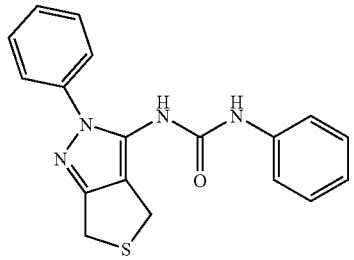 |

Binding Constant ($K_d$) Measurements for Small-Molecule-Kinase Interactions

Methods for measuring binding affinities for interactions between small molecules and kinases including FLT3, c-KIT, p38, STK-10, MKNK2, ABL(T334I) [a.k.a. ABL(T315I)], VEGFR2 (a.k.a. KDR), and EGFR are described in detail in U.S. application Ser. No. 10/873,835, which is incorporated by reference herein in its entirety. Components of the assays include human kinases expressed as fusions to T7 bacteriophage particles and immobilized ligands that bind to the ATP site of the kinases. For the assay, phage-displayed kinases and immobilized ATP site ligands are combined with the compound to be tested. If the test compound binds the kinase it competes with the immobilized ligand and prevents binding to the solid support. If the compound does not bind the kinase, phage-displayed proteins are free to bind to the solid support through the interaction between the kinase and the immobilized ligand. The results are read out by quantitating the amount of fusion protein bound to the solid support, which is accomplished by either traditional phage plaque assays or by quantitative PCR (qPCR) using the phage genome as a template. To determine the affinity of the interactions between a test molecule and a kinase, the amount of phage-displayed kinase bound to the solid support is quantitated as a function of test compound concentration. The concentration of test molecule that reduces the number of phage bound to the solid support by 50% is equal to the $K_d$ for the interaction between the kinase and the test molecule. Typically, data are collected for twelve concentrations of test compound and, the resultant binding curve is fit to a non-cooperative binding isotherm to calculate $K_d$.

Described in the exemplary assays below is data from binding with varying kinases. Binding values are reported as follows "+" for representative compounds exhibiting a binding dissociation constant (Kd) of 10,000 nM or higher; "++" for representative compounds exhibiting a Kd of 1,000 nM to 10,000 nM; "+++" for representative compounds exhibiting a Kd of 100 nM to 1,000 nM; and "++++" for representative compounds exhibiting a Kd of less than 100 nM. The term "ND" represents non-determined values.

Binding Constant ($K_d$) Measurements for Small-Molecule-p38 Interactions

| Compound No. | Binding Assay, p38-alpha(FKIN) |
|---|---|
| A33 | ++ |
| A31 | ++ |
| A29 | ++ |
| A27 | ++ |
| A36 | ++++ |
| A34 | ++ |
| A32 | ++ |
| A30 | ++ |
| A39 | ++ |
| A37 | ++ |
| H13 | +++ |
| H11 | +++ |
| H14 | ++++ |
| H12 | +++ |
| H15 | +++ |
| B6 | +++ |
| H16 | +++ |
| A46 | ++ |

-continued

| Compound No. | Binding Assay, p38-alpha(FKIN) |
|---|---|
| Z68 | +++ |
| A14 | ++ |
| A5 | +++ |
| G38 | ++++ |
| D17 | +++ |
| H5 | +++ |
| N1 | +++ |
| N134 | ND |
| N108 | ++ |
|  | +++ |

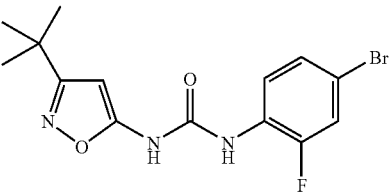

Binding Constant ($K_d$) Measurements for Small-Molecule-MKNK2 Interactions

| Compound No. | Binding Assay MKNK2(DKIN) |
|---|---|
| O2 | +++ |
| N151 | ++ |
| N147 | ++++ |
| N134 | ++++ |
| N108 | ++ |
| O4 | ++ |
| O1 | ++ |
| O3 | ++++ |
| N21 | ++ |
| N57 | +++ |
| O6 | ++++ |
| O5 | ++++ |
| N74 | +++ |
| N160 | ++ |
|  | +++ |

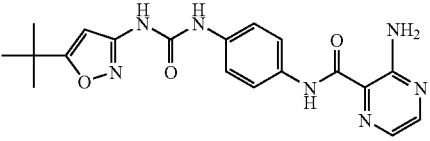

Binding Constant ($K_d$) Measurements for Small-Molecule-STK10 Interactions

| Compound No. | Binding Assay: STK10(DKIN) |
|---|---|
| N134 | +++ |
| O4 | +++ |
| O1 | ++++ |
| O3 | ++++ |
| O6 | +++ |
| O5 | ++++ |
| N74 | ++ |
| A57 | ++++ |

| Compound No. | Binding Assay: STK10(DKIN) |
|---|---|
|  | +++ |

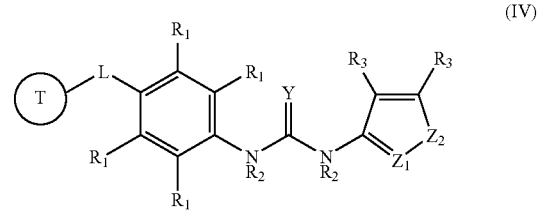

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A compound of Formula (IV):

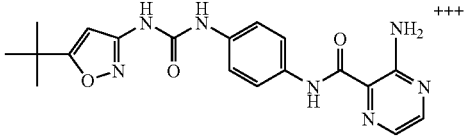

wherein:
$Z_1$ is N;
$Z_2$ is O;
each $R_3$ is H, alkyl, cycloalkyl, heteroaryl, or aryl;
each $R_2$ is independently H, alkyl, cycloalkyl, heterocyclyl, aryl, or heteroaryl; or wherein two $R_2$ groups are linked together by an alkylene;
each $R_1$ is independently H, halogen, alkyl, alkoxy, cycloalkyl, heterocyclyl, aryl, heteroaryl, —$OR_c$, —$OC(O)R_c$, —$NO_2$, —$N(R_c)_2$, —$SR_c$, $S(O)_jR_c$ where j is 1 or 2, —$NR_cC(O)R_c$, —$C(O)N(R_c)_2$, —$C(O)_2R_c$, or —$C(O)R_c$;
each $R_c$ is independently H, alkyl, cycloalkyl, aryl, or heteroaryl;
Y is O or S;
L is linker —C(O)NH—; and
T is a bi-, or tricyclic, cycloalkyl, heterocyclyl, aryl, or heteroaryl, or a stereoisomer or pharmaceutically acceptable salt thereof.

2. The compound of claim 1, wherein T corresponds to Formula (V):

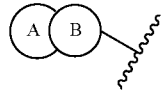
(V)

wherein A is a five or six-membered aryl, heterocyclyl or heteroaryl; and B is a five or six-membered arylene, heterocyclene or heteroarylene, wherein A and B together form a fused two-ring moiety.

3. The compound of claim 2, corresponding to Formula (VI):

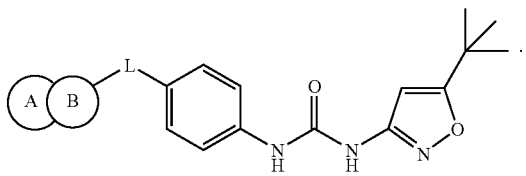
(VI)

4. The compound of claim 3, wherein L is —C(O)NH—.

5. The compound of claim 4, wherein B is phenylene, pyridinylene, pyrimidinylene, pyridazinylene, thiophenylene, imidazolylene, or pyrrolylene.

6. The compound of claim 5, selected from the group consisting of:

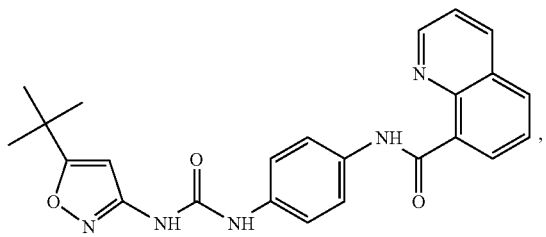

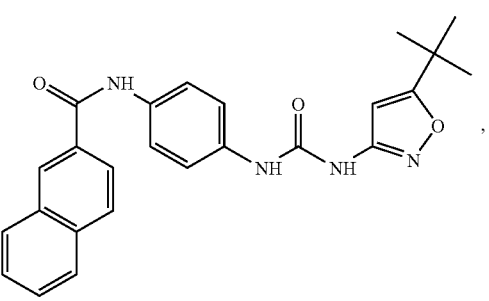

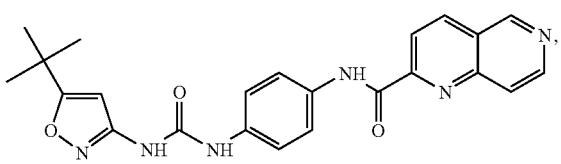

-continued

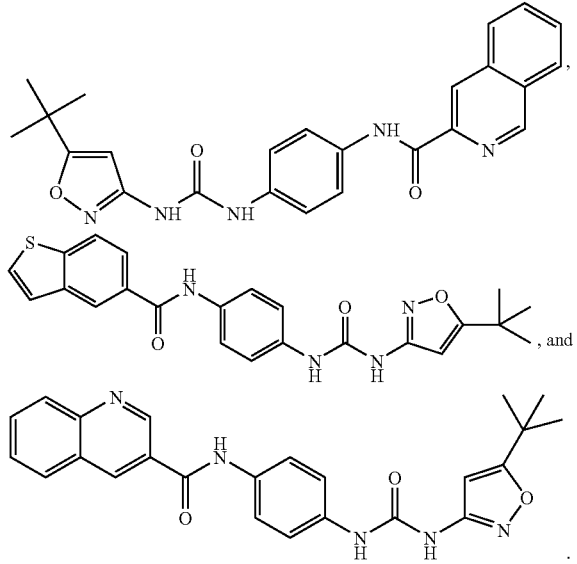
, and

7. The compound of claim 1, corresponding to:

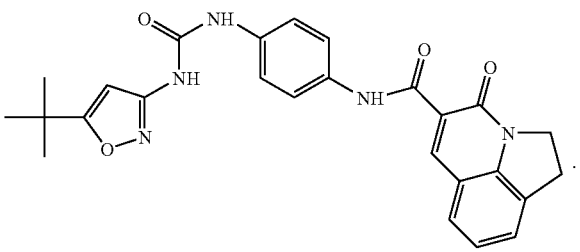

8. A compound of Formula (VII):

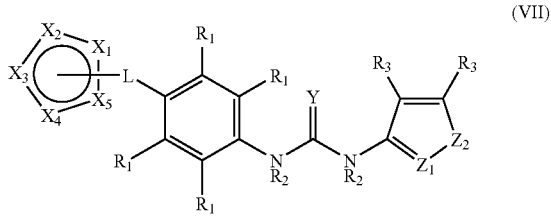
(VII)

wherein:
$Z_1$ is N;
$Z_2$ is O;
each $R_3$ is H, alkyl, cycloalkyl, heteroaryl, or aryl;
each $R_2$ is independently H, alkyl, cycloalkyl, heterocyclyl, aryl, or heteroaryl; or wherein two $R_2$ groups are linked together by an alkylene;
each $R_1$ is independently H, halogen, alkyl, alkoxy, cycloalkyl, heterocyclyl, aryl, heteroaryl, —$OR_c$, —$OC(O)R_c$, —$NO_2$, —$N(R_c)_2$, —$SR_c$, $S(O)_jR_c$ where j is 1 or 2, —$NR_cC(O)R_c$, —$C(O)N(R_c)_2$, —$C(O)_2R_c$, or —$C(O)R_c$;
each $R_c$ is independently H, alkyl, cycloalkyl, aryl, or heteroaryl;
Y is O or S;
L is —C(O)NH—;

each of $X_1, X_2, X_3, X_4$ and $X_5$ is independently C, CR, N, NR, S, or O, wherein no more than three of $X_1, X_2, X_3, X_4$ and $X_5$ is a heteroatom, and no two adjacent ring atoms are O or S; where each R is independently H, halogen, alkyl, —OH, alkoxy, —OC(O)$R_d$, —NO$_2$, —N($R_d$)$_2$, —S$R_d$, —S(O)$_j R_d$ where j is 1 or 2, —N$R_d$C(O)$R_d$, —C(O)$_2 R_d$, —C(O)N($R_d$)$_2$, or —C(O)$R_d$;

where each $R_d$ is independently H, alkyl, cycloalkyl, aryl, or heteroaryl, or stereoisomer or pharmaceutically acceptable salt thereof.

9. The compound of claim 8, corresponding to Formula (VIII):

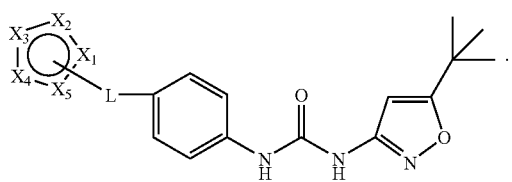

10. The compound of claim 9, wherein

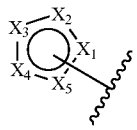

is selected from the group consisting of:

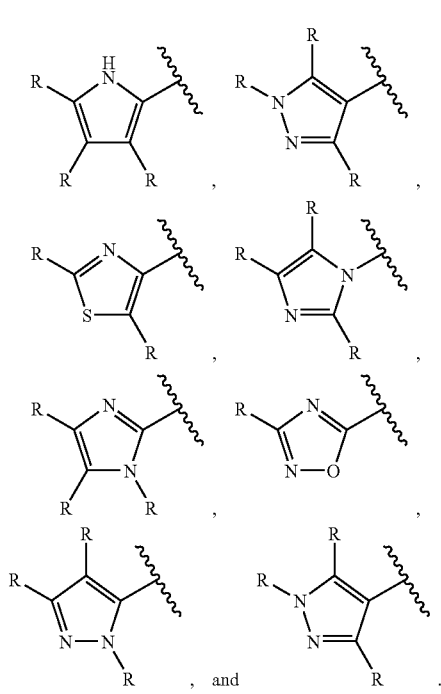

11. The compound of claim 10 selected from the group consisting of:

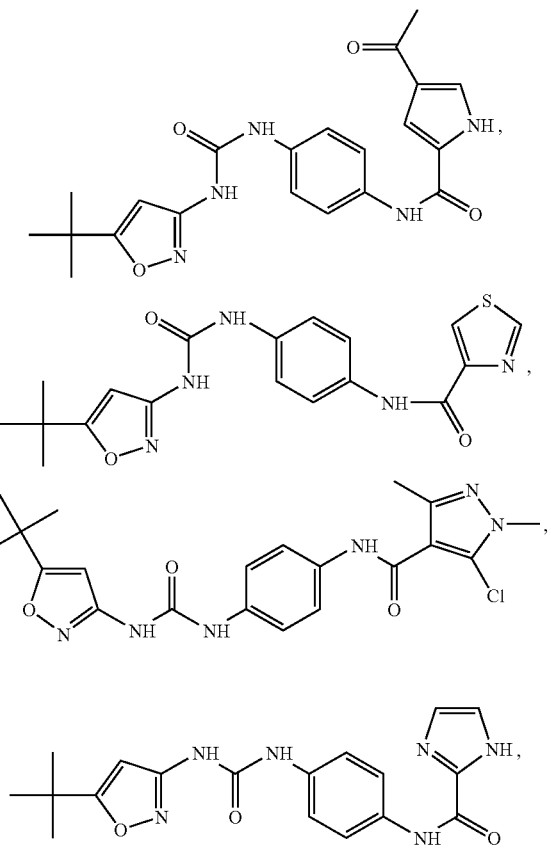

12. A compound of Formula (XI):

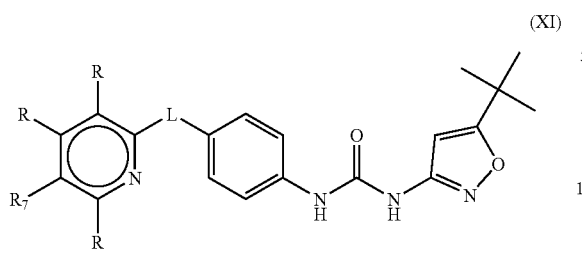

wherein:
L is —C(O)NH—;
R$_7$ is selected from the group consisting of H, halogen, alkyl, —OH, alkoxy, —C(O)R$_d$, —OC(O)R$_d$, —NO$_2$, —N(R$_d$)$_2$, —C(O)OR$_d$ and SR$_d$;
each R$_d$ is independently H, alkyl, cycloalkyl, aryl, or heteroaryl;
each R is independently H, halogen, alkyl, —OH, alkoxy, —OC(O)R$_d$, —NO$_2$, —N(R$_d$)$_2$, —S(O)$_j$R$_d$ where j is 1 or 2, —NR$_d$ C(O)R$_d$, —C(O)$_2$R$_d$, —C(O)N(R$_d$)$_2$, or —C(O)R$_d$;
or a stereoisomer or pharmaceutically acceptable salt thereof.

13. The compound of claim 12, selected from the group consisting of:

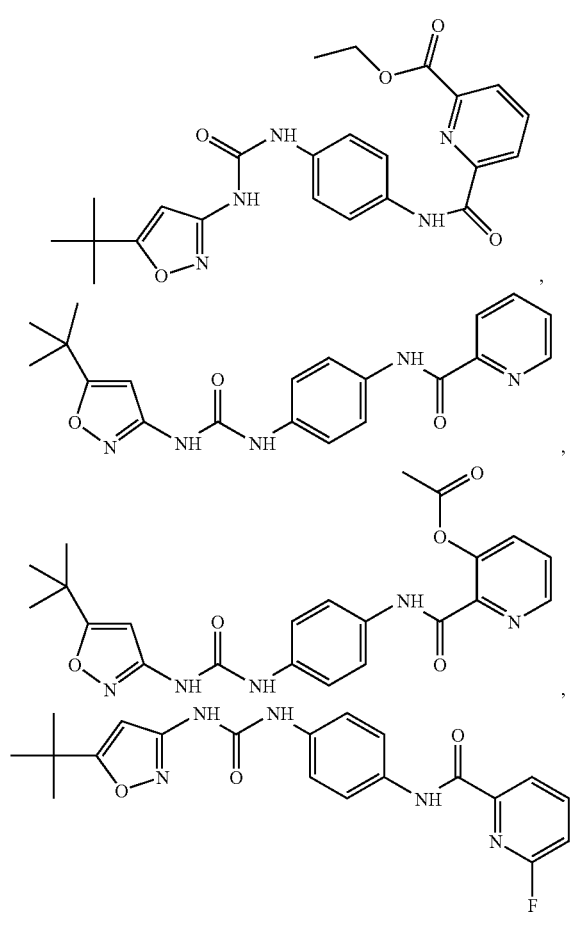

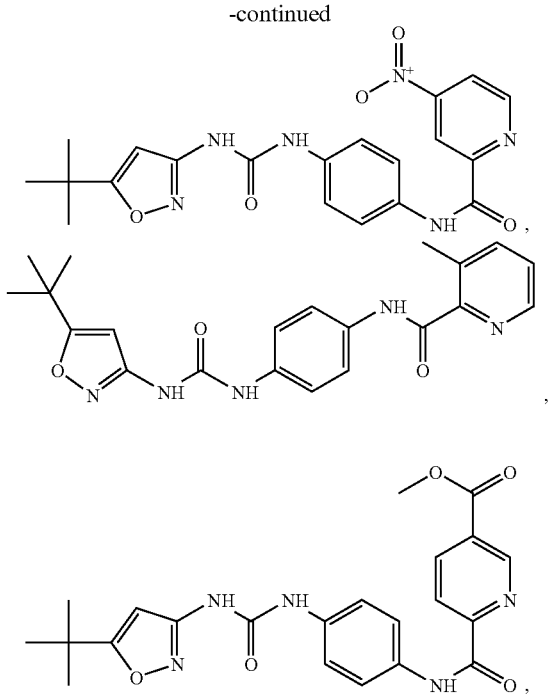

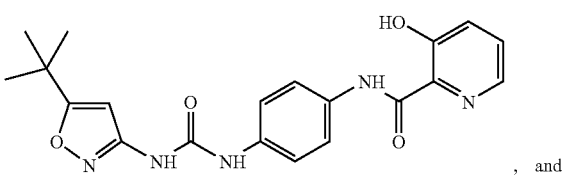

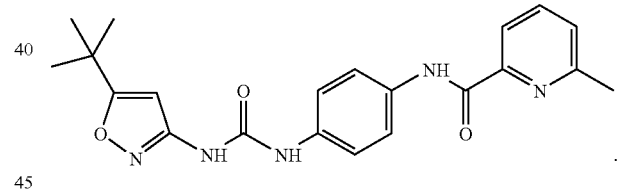

, and

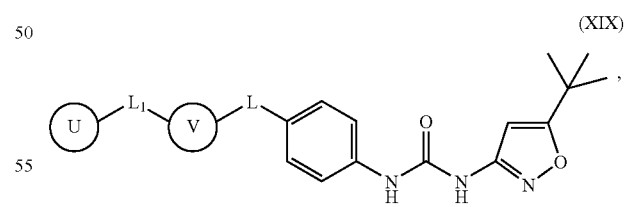

14. A compound corresponding to Formula (XIX):

(XIX)

wherein L$_1$ is a bond; and L is a bond or —C(O)NH—
U is selected from the group consisting of cycloalkyl, aryl, and heteroaryl; and
V is a cycloalkylene, heterocyclene, arylene, or heteroarylene.

15. The compound of claim 14, wherein U is phenyl, thiazolyl, or pyridinyl; and V is piperidinylene, thiazolylene, imidazolylene, or thiophenylene.

16. The compound of claim 15, wherein the compound is:

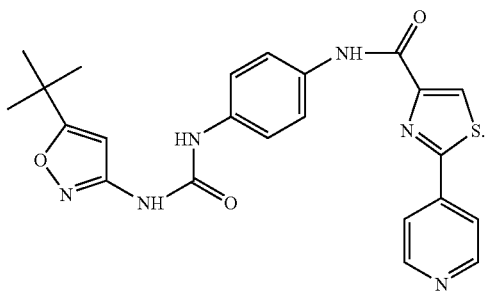

17. The compound of claim 14, corresponding to Formula (XX):

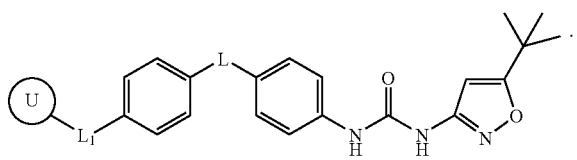
(XX)

18. The compound of claim 17, wherein U is phenyl, $C_3$-$C_6$ cycloalkyl, pyrimidine, or pyridine.

19. The compound of claim 14, corresponding to Formula (XXI):

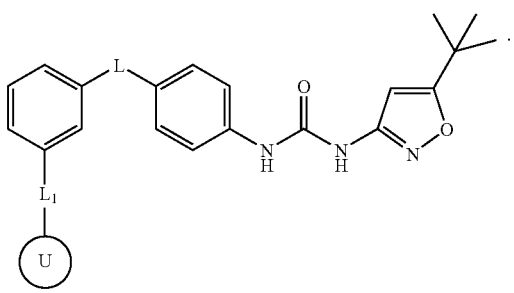
(XXI)

20. The compound of claim 19, wherein U is pyrimidinyl.

21. The compound of claim 1, corresponding to

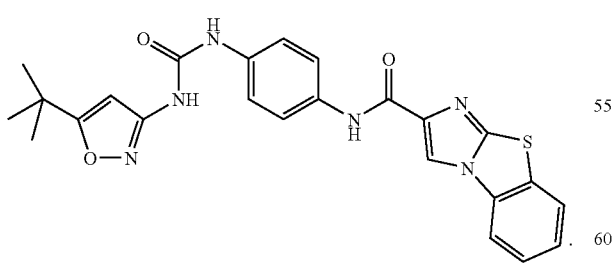

22. A method of modulating p38 kinase, said method comprising administering an effective amount of the compound of claim 14, or a pharmaceutically acceptable salt thereof.

23. A method of modulating MKNK2 kinase, said method comprising administering an effective amount of the compound of claim 8, or a pharmaceutically acceptable salt thereof.

24. A method of modulating MKNK2 kinase, said method comprising administering an effective amount of the compound of claim 12, or a pharmaceutically acceptable salt thereof.

25. A method of modulating MKNK2 kinase, said method comprising administering an effective amount of the compound of claim 14, or a pharmaceutically acceptable salt thereof.

26. A method of modulating STK10 kinase, said method comprising administering an effective amount of the compound of claim 8, or a pharmaceutically acceptable salt thereof.

27. A method of modulating STK10 kinase, said method comprising administering an effective amount of the compound of claim 12, or a pharmaceutically acceptable salt thereof.

28. A method of modulating STK10 kinase, said method comprising administering an effective amount of the compound of claim 14, or a pharmaceutically acceptable salt thereof.

29. A method of treating a cellular proliferative disorder, said method comprising administering a therapeutically effective amount of the compound of claim 8, or a pharmaceutically acceptable salt thereof, or a pharmaceutically acceptable salt thereof.

30. A method of treating a cellular proliferative disorder, said method comprising administering a therapeutically effective amount of the compound of claim 12, or a pharmaceutically acceptable salt thereof.

31. A method of treating a cellular proliferative disorder, said method comprising administering a therapeutically effective amount of the compound of claim 14, or a pharmaceutically acceptable salt thereof.

* * * * *